(12) United States Patent
LaFace et al.

(10) Patent No.: US 12,358,986 B2
(45) Date of Patent: Jul. 15, 2025

(54) ANTI-CANCER COMBINATION THERAPIES COMPRISING CTLA-4 AND PD-1 BLOCKING AGENTS

(71) Applicant: Merck Sharp & Dohme LLC, Rahway, NJ (US)

(72) Inventors: Drake LaFace, Half Moon Bay, CA (US); Juha Punnonen, Belmont, CA (US); Edward Bowman, Bowman, CA (US); David Bauche, San Mateo, CA (US); Alissa Chackerian, Sunnyvale, CA (US); Jeffery Grein, Sunnyvale, CA (US); Smita Mauze, Belmont, CA (US); Anandi Sawant, Sunnyvale, CA (US); Lakshmanan Annamalai, Dublin, CA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 982 days.

(21) Appl. No.: 17/436,857

(22) PCT Filed: Mar. 10, 2020

(86) PCT No.: PCT/US2020/021783
§ 371 (c)(1),
(2) Date: Sep. 7, 2021

(87) PCT Pub. No.: WO2020/185722
PCT Pub. Date: Sep. 17, 2020

(65) Prior Publication Data
US 2022/0411507 A1   Dec. 29, 2022

Related U.S. Application Data

(60) Provisional application No. 62/817,749, filed on Mar. 13, 2019.

(51) Int. Cl.
| | | |
|---|---|---|
| *C07K 16/28* | (2006.01) | |
| *A61K 39/00* | (2006.01) | |
| *A61P 35/00* | (2006.01) | |
| *C07K 16/00* | (2006.01) | |

(52) U.S. Cl.
CPC .......... *C07K 16/2818* (2013.01); *A61P 35/00* (2018.01); *A61K 39/00* (2013.01); *A61K 2039/507* (2013.01); *A61K 2039/545* (2013.01); *C07K 16/00* (2013.01); *C07K 16/2803* (2013.01); *C07K 2317/21* (2013.01); *C07K 2317/22* (2013.01); *C07K 2317/51* (2013.01); *C07K 2317/515* (2013.01); *C07K 2317/565* (2013.01); *C07K 2317/567* (2013.01); *C07K 2317/71* (2013.01); *C07K 2317/76* (2013.01)

(58) Field of Classification Search
CPC ............ C07K 16/2818; C07K 2317/22; C07K 2317/71; C07K 2317/76; C07K 16/18; C07K 2317/31; C07K 2317/524; C07K 2317/569; C07K 2317/41; C07K 2317/52; C07K 2317/73; C07K 16/2827; A61P 35/00; A61K 2039/507; A61K 2039/505
See application file for complete search history.

(56) References Cited

U.S. PATENT DOCUMENTS

| | | | |
|---|---|---|---|
| 4,816,567 | A | 3/1989 | Cabilly et al. |
| 6,984,720 | B1 | 1/2006 | Korman et al. |
| 8,008,449 | B2 | 8/2011 | Korman et al. |
| 8,354,509 | B2 | 1/2013 | Carven et al. |
| 8,491,895 | B2 | 7/2013 | Hanson et al. |
| 8,969,526 | B2 | 3/2015 | Baehner |
| 9,296,815 | B2 | 3/2016 | D'angelo |
| 9,708,406 | B2 | 7/2017 | Zhang |
| 9,987,500 | B2 | 6/2018 | Papadopoulos et al. |
| 10,196,445 | B1 | 2/2019 | Engelhardt et al. |
| 2006/0235208 | A1 | 10/2006 | Lazar et al. |
| 2017/0216433 | A1 | 8/2017 | Li et al. |
| 2018/0319892 | A1* | 11/2018 | Feltquate ................ A61P 37/04 |
| 2018/0333502 | A1 | 11/2018 | Lonberg |
| 2020/0262922 | A1* | 8/2020 | Bhattacharya .......... A61P 35/00 |
| 2021/0047409 | A1* | 2/2021 | Lala .................... C07K 16/2818 |

FOREIGN PATENT DOCUMENTS

| | | |
|---|---|---|
| JP | 2006512407 A | 4/2006 |
| JP | 2017515859 A | 6/2017 |
| WO | 199428027 A1 | 12/1994 |

(Continued)

OTHER PUBLICATIONS

Das R, et al. Combination therapy with anti-CTLA-4 and anti-PD-1 leads to distinct immunologic changes in vivo. J Immunol. Feb. 1, 2015;194(3):950-9. doi: 10.4049/jimmunol.1401686. Epub Dec. 24, 2014. PMID: 25539810; PMCID: PMC4380504. (Year: 2014).*

Schlothauer T, et al. Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016. PMID: 27578889. (Year: 2016).*

Hammers HJ, et al. Safety and Efficacy of Nivolumab in Combination With Ipilimumab in Metastatic Renal Cell Carcinoma: The CheckMate 016 Study. J Clin Oncol. Dec. 1, 2017;35(34):3851-3858. doi: 10.1200/JCO.2016.72.1985. Epub Jul. 5, 2017. PMID: 28678668; PMCID: PMC7587408. (Year: 2017).*

(Continued)

*Primary Examiner* — Maher M Haddad
*Assistant Examiner* — Alec Jon Peters
(74) *Attorney, Agent, or Firm* — John David Reilly; John C. Todaro

(57) ABSTRACT

Anti-cancer combination therapies comprising a CTLA-4 blocking agent and a PD-1 blocking agent are disclosed. In particular, combination therapies are disclosed wherein the CTLA-4 blocking agent is an effector-silent anti-CTLA-4 antibody or effector-silent anti-CTLA-4 antibody fragment and the PD-1 blocking agent is an anti-PD-1 or anti-PD-L1 antibody, or antibody fragment thereof.

5 Claims, 39 Drawing Sheets

Specification includes a Sequence Listing.

(56) References Cited

FOREIGN PATENT DOCUMENTS

| WO | 2004029207 | A2 | 4/2004 | |
|---|---|---|---|---|
| WO | 2004099249 | A2 | 11/2004 | |
| WO | 2006121168 | A1 | 11/2006 | |
| WO | 2008071447 | A2 | 6/2008 | |
| WO | 2009025846 | A2 | 2/2009 | |
| WO | 2009030285 | A1 | 3/2009 | |
| WO | 2009114335 | A2 | 9/2009 | |
| WO | 2010081173 | A2 | 7/2010 | |
| WO | 2012130831 | A1 | 10/2012 | |
| WO | 2014089113 | A1 | 12/2014 | |
| WO | 2015112800 | A1 | 7/2015 | |
| WO | 2015176033 | A1 | 11/2015 | |
| WO | 2016196237 | A1 | 12/2016 | |
| WO | 2017087587 | A1 | 5/2017 | |
| WO | 2017087588 | A1 | 5/2017 | |
| WO | 2017087589 | A2 | 5/2017 | |
| WO | WO-2017087870 | A1 * | 5/2017 | ............ A61P 35/00 |
| WO | 2017118675 | A1 | 7/2017 | |
| WO | 2018085555 | A1 | 5/2018 | |
| WO | 2018183408 | A1 | 10/2018 | |
| WO | 2018222949 | A1 | 12/2018 | |
| WO | 2019023482 | A1 | 1/2019 | |

OTHER PUBLICATIONS

Sozzi, G., et al. "MA04. 06 PD-1 Blockade Promotes Hyperprogressive Disease in NSCLC Through Macrophages Activation via Antibody-Fc/FcR Interaction." Journal of Thoracic Oncology 13.10 (2018): S368. (Year: 2018).*
Okan Cakir M, et al. Hyperprogression after immunotherapy: A comprehensive review. J Buon. Nov.-Dec. 2019;24(6):2232-2241. PMID: 31983088. (Year: 2019).*
Watanabe T, et al. Activated CTLA-4-independent immunosuppression of Treg cells disturbs CTLA-4 blockade-mediated antitumor immunity. Cancer Sci. May 2023; 114(5):1859-1870. doi: 10.1111/cas.15756. Epub Feb. 26, 2023. PMID: 36762794; PMCID: PMC10154808. (Year: 2023).*
Corraliza-Gorjón, Isabel et al., New Strategies Using Antibody Combinations to increase Cancer Treatment effectiveness, Frontiers in Immunology, vol. 8, Article 1804, 1-31, 2017.
Markham, Anthony et al., Cemiplimab: First Global Approval, Drugs, 78, 1841-1846, 2018.
Mould, Diane R. et al., Pharmacokinetics and Pharmacodynamics of Monoclonal Antibodies, BioDrugs, 24(1), 23-39, 2010.
Bauché, David et al., Antitumor efficacy of combined CTLA4/ PD-1 blockade without intestinal inflammation is achieved by elimination of FcγR interactions, J Immunother Cancer, 2020, 1-10, 8:e001584.
Deng, Rong et al., Preclinical pharmacokinetics, pharmacodynamics, tissue distribution, and tumor penetration of anti-PD-L1 monoclonal antibody, an immune checkpoint inhibitor, mAbs, 2016, 593-603, 8:3.
Schlothauer, Tilman et al., Novel human IgG1 and IgG4 Fc-engineered antibodies with completely abolished immune effector functions, Protein Engineering, Design & Selection, 2016, 457-466, 29(10).
Wang, Xinhua et al., IgG Fc engineering to modulate antibody effector functions, Protein Cell, 2018, 63-73, 9(1).
Madrenas, Joaquín et al., Conversion of CTLA-4 from Inhibitor to Activator of T Cells with a Bispecific Tandem Single-Chain Fv Ligand, J Immunol, 172(10), 5948-5956, 2004.
Bengsch, et al., Success of immune checkpoint blockade therapies—mechanisms and implications for hepatology, Z Gastroenterol, 57, pp. 74-86, 2019.
Topalian et al., Immune Checkpoint Blockade: A Common Denominator Approach to Cancer Therapy, Cancer Cell, vol. 27, pp. 450-461, 2015.
Wolchok et al., Nivolumab plus Ipilimumab in Advanced Melanoma, The New England Journal of Medicine, vol. 369(2), pp. 122-133, 2013.

Agata et al., Expression of the PD-1 antigen on the surface of stimulated mouse T and B lymphocytes, International Immunology, 1996, pp. 765-772, vol. 8, No. 5.
Angal et al., A Single Amino Acid Substitution Abolishes the Heterogeneity of Chimeric Mouse/Human (IgG4) Antibody, Molecular Immunology, 1993, pp. 105-108, vol. 30(1).
Armour et al., Recombinant Human IgG Molecules Lacking Fcγ receptor I Binding and Monocyte Triggering Activities, Eur. J. Immunol., 1999, pp. 2613-2624, 29.
Balzano, Christine et al., CTLA-4 and CD28: Similar Proteins, Neighbouring Genes, Int. J. Cancer, 1992, 28-32, Suppl. 7.
Beiboer, Sigrid H. W. et al., Guided Selection of a Pan Carcinoma Specific Antibody Reveals Similar Binding Characteristics yet Structural Divergence Between the Original Murine Antibody and its Human Equivalent, J. Mol. Biol., 2000, 833-849, 296.
Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses, The Journal of Immunology, 2003, pp. 711-718, vol. 170.
Bertrand, Anne et al., Immune related adverse events associated with anti-CTLA-4 antibodies: systematic review and meta-analysis, BMC Medicine, 2015, 1-14, 13:211.
Blank et al., Contribution of the PD-L1/PD-1 pathway to T-cell exhaustion: an update on implications for chronic infections, Cancer Immunol. Immunother., 2007, pp. 739-745, vol. 56(5).
Blank, Interaction of PD-L1 on tumor cells with PD-1 on tumor-specific T cells as a mechanism of immune evasion: Implications for tumor immunotherapy, Cancer Immunol. Immunother., 2005, pp. 307-314, 54.
Brown, Blockade of Programmed Death-1 Ligands on Dendritic Cells Enhances T Cell Activation and Cytokine Production, J. Immunol., 2003, pp. 1257-1266, vol. 170.
Béranger, et al., Ed. Ginetoux, Correspondence between the IMGT unique numbering for C-DOMAIN, the IMGT exon humbering, the Eu and Kabat numberings: Human IGHG, Created: May 17, 2001, Version: Aug. 6, 2016, which is accessible at ww.imgt.org/IMGTScientificChart/Numbering/Hu_IGHGnber.html#r). 7 pages.
Carter et al., PD-1:PD-L Inhibitory Pathway Affects Both CD4 Plus and CD8 Plus and CD8 Plus T Cells and is overcome by IL-2, Eur. J. Immunol., 2002, pp. 634-643, 32.
Cayatte, Corinne et al., Biomarkers of Therapeutic Response in the IL-23 Pathway in Inflammatory Bowel Disease, Clinical and Translational Gastroenterology, 2012, 1-10, 3:e10.
Chothia and Lesk et al., Canonical Structures for the Hypervariable Regions of Immunoglobins, J. Mol. Biol., 1987, 901-917, 196.
Chothia et al., Conformations of immunoglobin hypervariable regions, Nature, 1989, 877-883, 342.
Common Terminology Criteria for Adverse events (CTCAE) Version 5.0, published Nov. 27, 2017, by the U.S. Department of health and Human Services, 155 pages.
Dong et al., B7-H1 pathway and its role in the evasion of tumor immunity, J. Mol. Med., 2003, pp. 281-287, 81.
Edelman, Gerald M. et al., The Covalent Structure of an Entire gammaG Immunoglobulin Molecule, Proc. Natl. Acad. Sci. USA, 1969, 78-85, 63.
Freeman et al., Engagement of the PD-1 Immunoinhibitory Receptor by a Novel B7 Family Member Leads to Negative Regulation of Lymphocyte Activation, J. Exp. Med., 2000, pp. 1027-1034, vol. 192.
Hamid et al., Safety and Tumor Responses with Lambrolizumab (Anti-PD-1) in Melanoma, New Eng. J. Med., 2013, 134-144, 369(2).
Hui, Enfu et al., T cell costimulatory receptor CD28 is a primary target for PD-1-mediated inhibition, Science, 2017, 1428-1433, 355.
Ingram, Jessica R. et al., Anti-CTLA-4 therapy requires an Fc domain for efficacy, Proc. Natl. Acad. Sci. USA, 2018, 3912-3917, 115.
Ishida et al., Induced expression of PD-1, a novel member of the immunoglobulin gene superfamily, upon programmed cell death, The EMBO Journal, 1992, pp. 3887-3895, vol. 11(11).

(56) References Cited

OTHER PUBLICATIONS

Wai, Involvement of PD-L1 on tumor cells in the escape from host immune system and tumor immunotherapy by PD-L1 blockade, Proc. Natl. Acad. Sci. USA, 2002, pp. 12293-12297, vol. 99.
Kabat et al. (1991) Sequences of Proteins of Immunological Interest, 5th Ed. Public Health Service, National Institutes of Health, Bethesda, Md., 19 pages.
Kabat, The Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Kamphorst, Alice O., Rescue of exhaused CD8 T cells by PD-1 targeted therapies is CD28-dependent, Science, 2017, 1423-1427, 355(6332).
Klimka, A. et al., Human anti-CD30 recombinant antibodies by guided phage antibody selection using cell panning, British Journal of Cancer, 2000, 252-260, 83(2).
Konishi et al., B7-H1 Expression on Non-Small Cell Lung Cancer Cells and Its Relationship with Tumor-Infiltrating Lymphocytes and Their PD-1 Expression, Clin. Cancer Res., 2004, pp. 5094-5100, 10.
Konitzer, Jennifer D. et al., Reformatting Rituximab into Human IgG2 and IgG4 Isotypes Dramatically Improves Apoptosis Induction In Vitro, PLoS One, 2015, 1-20, 10:e0145633.
Korman, Alan J. et al., Abstract SY09-01: Next-generation anti-CTLA-4 antibodies, Cancer Research, 2017, 1-6, 77(13).
Morrison, Sherie L. et al., Chimeric human antibody molecules: Mouse antigen-binding domains with human constant region domains, Proc. Natl. Acad. Sci. USA, 1984, 6851-6855, 81.
Murata, Ken-Ya et al., Expression of the Costimulatory Molecule BB-1, the Ligands CTLA-4 and CD28, and their MRNA in Inflammatory Myopathies, American Journal of Pathology, 1999, 453-460, 155.
Nimmerjahn, FcγRIV: A Novel FcR with Distinct IgG Subclass Specificity, Immunity, 2005, pp. 41-51, 23.
Okazaki et al., New regulatory co-receptors: inducible co-stimulator and PD1, Curr. Opin. Immunol., 2002, pp. 779-782, 14.
Package Insert and Label for Yervoy (Jul. 2018), 52 pages.
Pai, Chien-Chun Steven et al., Tumon-conditional anti-CTLA4 uncouples antitumor efficacy from Immunotherapy-related toxicity, The Journal of Clinical Investigation, 2019, 349-363, 129.
Rader et al., A phage display approach for rapid antibody humanization: Designed combinatorial V gene libraries, Proc. Natl. Acad. Sci. USA, 1998, pp. 8910-8915, 95.
Ribas, Antoni et al., Tremelimumab (CP-675,206), a Cytotoxic T Lymphocyte-Associated Antigen 4 Blocking Monoclonal Antibody in Clinical Development for Patients with Cancer, The Oncologist, 2007, 873-993, 12.
Samaan, Mark A. et al., Gastrointestinal toxicity of immune checkpoint inhibitors: from mechanisms to management, Nature Reviews / Gastroenterology & Hepatology, 2018, 222-234, 15.
Schneider-Merck, Tanja et al., Human IgG2 Antibodies against Epidermal Growth Factor Receptor Effectively Trigger Antibody-Dependent Cellular Cytotoxicity but, in Contrast to IgG1, Only by Cells of Myeloid Lineage, The Journal of Immunology, 2010, 512-520, 184.
Schuurman et al., The inter-heavy chain disulfide bonds of IgG4 are in equilibrium with intra-chain disulfide bonds, Molecular Immunology, 2001, pp. 1-8, vol. 38.
Selby, Mark J. et al., Anti-CTLA-4 Antibodies of IgG2a Isotype Enhance Antitumor Activity through Reduction of Intratumoral Regulatory T Cells, Cancer Immunology Research, 2013, 32-42, 1.
Shields, Robert L. et al., High Resolution Mapping of the Bidning Site on Human IgG1 for FcγRI, FcγRII, FcγRIII, and ReRn and Design of IgG1 Variants with Improved Binding to the FcγR*, The Journal of Biological Chemistry, 2001, 6591-6604, 276(9).
Simpson, Tyler R. et al., Fc-dependent depletion of tumor-infiltrating regulatory T cells co-defines the efficacy of anti-CTLA-4 therapy against melanoma, The Journal of Experimental Medicine, 2013, 1695-1710, 210.
Sondermann et al., The 3.2-Angstrom Crystal Structure of the Human IgG1 Fc Fragment-Fc gamma RIII Complex, Nature, 2000, pp. 267-273, 406.
Vargas, Frederick Arce et al., Fc Effector Function Contributes to the Activity of Human Anti-CTLA-4 Antibodies, Cancer Cell, 2018, 649-663, 33.
Waight, Jeremy D. et al., Selective FcgR Co-engagement on APCs Modulates the Activity of Therapeutic Antibodies Targeting T Cell Antigens, Cancer Cell, 2018, 1033-1047, 33.
Xu, JL et al., Diversity in the CDR3 region of Vh is sufficient for most antibody specificities, Immunity, 2000, pp. 37-45, 13.

* cited by examiner

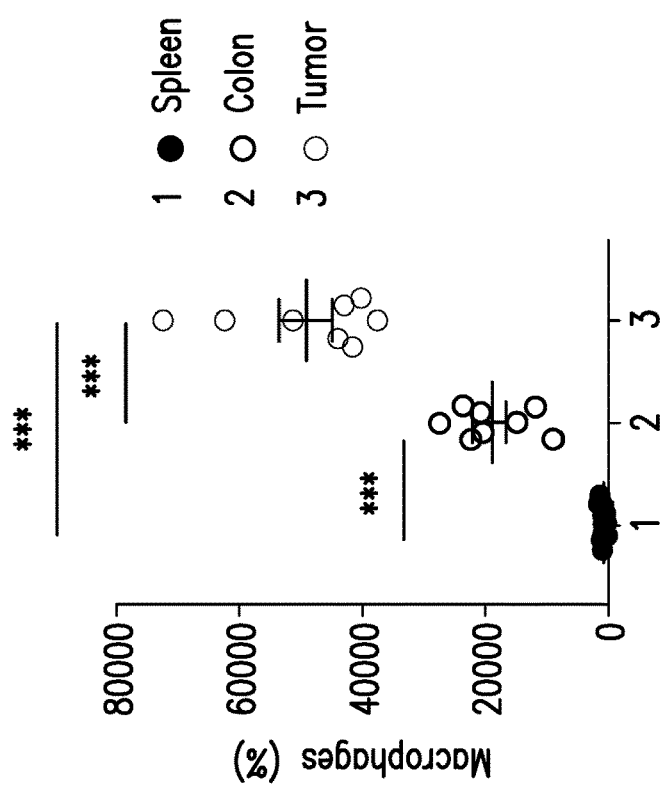
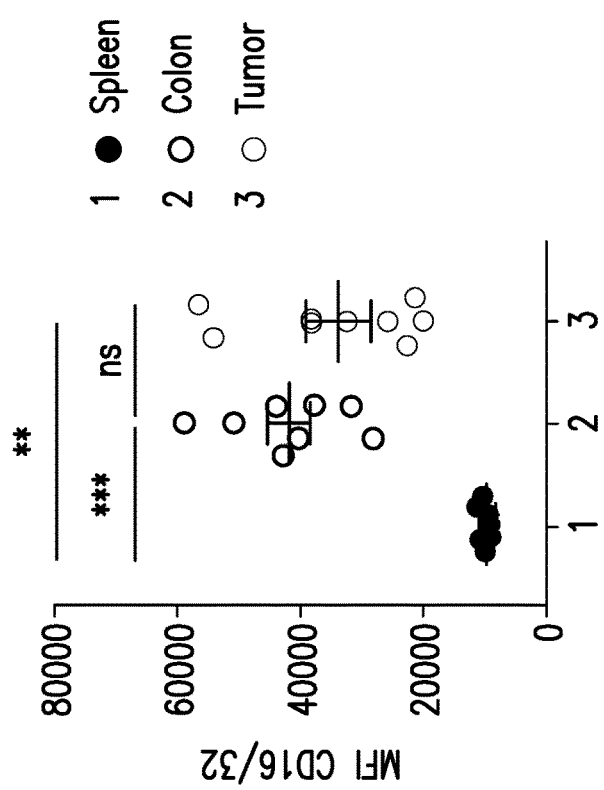
FIG. 8C
FIG. 8B

SEQUENCE LISTING

```
<160> NUMBER OF SEQ ID NOS: 117

<210> SEQ ID NO 1
<211> LENGTH: 12
<212> TYPE: PRT
<213> ORGANISM: Artificial Sequence
<220> FEATURE:
<223> OTHER INFORMATION: Ipilimumab LC-CDR1

<400> SEQUENCE: 1

Arg Ala Ser Gln Ser Val Gly Ser Ser Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Ipilimumab LC-CDR2

<400> SEQUENCE: 2

Gly Ala Phe Ser Arg Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Ipilimumab LC-CDR3

<400> SEQUENCE: 3

Gln Gln Tyr Gly Ser Ser Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Ipilimumab HC-CDR1
```

<400> SEQUENCE: 4

Ser Tyr Thr Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Ipilimumab HC-CDR2

<400> SEQUENCE: 5

Phe Ile Ser Tyr Asp Gly Asn Asn Lys Tyr Tyr Ala Asp Ser Val Lys
1               5                   10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: Ipilimumab HC-CDR3

<400> SEQUENCE: 6

Thr Gly Trp Leu Gly Pro Phe Asp Tyr
1               5

<210> SEQ ID NO 7
<211> LENGTH: 118
<212> TYPE: PRT
<213> ORGANISM: Artificial Sequence
<220> FEATURE:
<223> OTHER INFORMATION: Ipilimumab VH

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: Ipilimumab VL

```
<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
                100                 105

<210> SEQ ID NO 9
<211> LENGTH: 12
<212> TYPE: PRT
<213> ORGANISM: Artificial Sequence
<220> FEATURE:
<223> OTHER INFORMATION: Tremelimumab LC-CDR1

<400> SEQUENCE: 9

Arg Ala Ser Gln Ser Val Gly Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Tremelimumab LC-CDR2

<400> SEQUENCE: 10

Gly Ala Phe Ser Arg Ala Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Tremelimumab LC-CDR3

<400> SEQUENCE: 11

Gln Gln Tyr Gly Ser Ser Pro Trp Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Tremelimumab HC-CDR1

<400> SEQUENCE: 12

Ser Tyr Gly Met His
1               5

<210> SEQ ID NO 13
<211> LENGTH: 16
```

```
<212> TYPE: PRT
<213> ORGANISM: Artificial Sequence
<220> FEATURE:
<223> OTHER INFORMATION: Tremelimumab HC-CDR2

<400> SEQUENCE: 13

Ile Ser Tyr Asp Gly Asn Asn Lys Tyr Tyr Ala Asp Ser Val Lys Gly
1               5                   10                  15

<210> SEQ ID NO 14
<211> LENGTH: 5
<212> TYPE: PRT
<213> ORGANISM: Artificial Sequence
<220> FEATURE:
<223> OTHER INFORMATION: Tremelimumab HC-CDR3

<400> SEQUENCE: 14

Tyr Gly Ser Ser Pro
1               5

<210> SEQ ID NO 15
<211> LENGTH: 114
<212> TYPE: PRT
<213> ORGANISM: Artificial Sequence
<220> FEATURE:
<223> OTHER INFORMATION: Tremelimumab VH

<400> SEQUENCE: 15

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
                20                  25                  30

Gly Lys Gly Leu Glu Trp Val Ala Val Ile Trp Tyr Asp Gly Ser Asn
            35                  40                  45

Lys Tyr Tyr Ala Asp Ser Val Lys Gly Arg Phe Thr Ile Ser Arg Asp
50                  55                  60

Asn Ser Lys Asn Thr Leu Leu Gln Met Asn Ser Leu Arg Ala Glu Thr
65                  70                  75                  80

Ala Val Tyr Tyr Cys Ala Arg Asp Pro Arg Gly Ala Thr Leu Tyr Tyr
                85                  90                  95

Tyr Tyr Tyr Gly Met Asp Val Trp Gly Gln Gly Thr Thr Val Thr Val
            100                 105                 110

Ser Ser

<210> SEQ ID NO 16
<211> LENGTH: 100
<212> TYPE: PRT
<213> ORGANISM: Artificial Sequence
<220> FEATURE:
<223> OTHER INFORMATION: Tremelimumab VL

<400> SEQUENCE: 16

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
                20                  25                  30

Pro Gly Lys Ala Pro Lys Leu Leu Ile Tyr Ala Ala Ser Ser Leu Gln
            35                  40                  45

Ser Gly Val Pro Ser Arg Phe Ser Gly Ser Gly Ser Gly Thr Asp Phe
50                  55                  60
```

```
Thr Leu Thr Ile Ser Ser Leu Gln Pro Glu Asp Phe Ala Thr Tyr Tyr
 65                  70                  75                  80

Cys Gln Gln Tyr Tyr Ser Thr Pro Phe Thr Phe Gly Pro Gly Thr Lys
                 85                  90                  95

Val Glu Ile Lys
            100

<210> SEQ ID NO 17
<211> LENGTH: 5
<212> TYPE: PRT
<213> ORGANISM: Artificial Sequence
<220> FEATURE:
<223> OTHER INFORMATION: Nivolumab  HC-CDR1

<400> SEQUENCE: 17

Asn Ser Gly Met His
1               5

<210> SEQ ID NO 18
<211> LENGTH: 17
<212> TYPE: PRT
<213> ORGANISM: Artificial Sequence
<220> FEATURE:
<223> OTHER INFORMATION: Nivolumab HC-CDR2

<400> SEQUENCE: 18

Val Ile Trp Tyr Asp Gly Ser Lys Arg Tyr Tyr Ala Asp Ser Val Lys
1               5                   10                  15

Gly

<210> SEQ ID NO 19
<211> LENGTH: 4
<212> TYPE: PRT
<213> ORGANISM: Artificial Sequence
<220> FEATURE:
<223> OTHER INFORMATION: Nivolumab HC-CDR3

<400> SEQUENCE: 19

Asn Asp Asp Tyr
1

<210> SEQ ID NO 20
<211> LENGTH: 11
<212> TYPE: PRT
<213> ORGANISM: Artificial Sequence
<220> FEATURE:
<223> OTHER INFORMATION: Nivolumab LC-CDR1

<400> SEQUENCE: 20

Arg Ala Ser Gln Ser Val Ser Ser Tyr Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Nivolumab LC-CDR2

<400> SEQUENCE: 21

Asp Ala Ser Asn Arg Ala Thr
1               5

<210> SEQ ID NO 22
```

```
<211> LENGTH: 9
<212> TYPE: PRT
<213> ORGANISM: Artificial Sequence
<220> FEATURE:
<223> OTHER INFORMATION: Nivolumab LC-CDR3

<400> SEQUENCE: 22

Gln Gln Ser Ser Asn Trp Pro Arg Thr
1               5

<210> SEQ ID NO 23
<211> LENGTH: 113
<212> TYPE: PRT
<213> ORGANISM: Artificial Sequence
<220> FEATURE:
<223> OTHER INFORMATION: Nivolumab VH

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 24
<211> LENGTH: 107
<212> TYPE: PRT
<213> ORGANISM: Artificial Sequence
<220> FEATURE:
<223> OTHER INFORMATION: Nivolumab VL

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 25
<211> LENGTH: 440
<212> TYPE: PRT
```

<213> ORGANISM: Artificial Sequence
<220> FEATURE:
<223> OTHER INFORMATION: Nivolumab HC (IgG4 S228P)

<400> SEQUENCE: 25

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380
```

-continued

```
Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
        420                 425                 430

Ser Leu Ser Leu Ser Leu Gly Lys
        435                 440

<210> SEQ ID NO 26
<211> LENGTH: 214
<212> TYPE: PRT
<213> ORGANISM: Artificial Sequence
<220> FEATURE:
<223> OTHER INFORMATION: Nivolumab LC

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 447
<212> TYPE: PRT
<213> ORGANISM: Artificial Sequence
<220> FEATURE:
<223> OTHER INFORMATION: Pembrolizumab HC (IgG4 S228P)

<400> SEQUENCE: 27

Gln Val Gln Leu Val Gln Ser Gly Val Glu Val Lys Lys Pro Gly Ala
1               5                   10                  15
```

```
Ser Val Lys Val Ser Cys Lys Ala Ser Gly Tyr Thr Phe Thr Asn Tyr
            20                  25                  30
Tyr Met Tyr Trp Val Arg Gln Ala Pro Gly Gln Gly Leu Glu Trp Met
        35                  40                  45
Gly Gly Ile Asn Pro Ser Asn Gly Gly Thr Asn Phe Asn Glu Lys Phe
    50                  55                  60
Lys Asn Arg Val Thr Leu Thr Thr Asp Ser Ser Thr Thr Thr Ala Tyr
65                  70                  75                  80
Met Glu Leu Lys Ser Leu Gln Phe Asp Asp Thr Ala Val Tyr Tyr Cys
                85                  90                  95
Ala Arg Arg Asp Tyr Arg Phe Asp Met Gly Phe Asp Tyr Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
```

```
His Asn His Tyr Thr Gln Lys Ser Leu Ser Leu Ser Leu Gly Lys
            435                 440                 445
```

<210> SEQ ID NO 28
<211> LENGTH: 218
<212> TYPE: PRT
<213> ORGANISM: Artificial Sequence
<220> FEATURE:
<223> OTHER INFORMATION: Pembrolizumab LC

<400> SEQUENCE: 28

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 29
<211> LENGTH: 120
<212> TYPE: PRT
<213> ORGANISM: Artificial Sequence
<220> FEATURE:
<223> OTHER INFORMATION: Pembrolizumab VH

<400> SEQUENCE: 29

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80
```

Met Glu Leu Lys Ser Leu Gln Phe Asp Asp Thr Ala Val Tyr Tyr Cys
             85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 30
<211> LENGTH: 111
<212> TYPE: PRT
<213> ORGANISM: Artificial Sequence
<220> FEATURE:
<223> OTHER INFORMATION: Pembrolizumab VL

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 31
<211> LENGTH: 10
<212> TYPE: PRT
<213> ORGANISM: Artificial Sequence
<220> FEATURE:
<223> OTHER INFORMATION: Pembrolizumab HC-CDR1

<400> SEQUENCE: 31

Gly Tyr Thr Phe Thr Asn Tyr Tyr Met Tyr
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Pembrolizumab HC-CDR2

<400> SEQUENCE: 32

Asn Pro Ser Asn Gly Gly Thr Asn Phe Asn Glu Lys Phe Lys Asn
1               5                   10                  15

<210> SEQ ID NO 33
<211> LENGTH: 11
<212> TYPE: PRT
<213> ORGANISM: Artificial Sequence
<220> FEATURE:
<223> OTHER INFORMATION: Pembrolizumab HC-CDR3

<400> SEQUENCE: 33

Arg Asp Tyr Arg Phe Asp Met Gly Phe Asp Tyr
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Pembrolizumab LC-CDR1

<400> SEQUENCE: 34

Arg Ala Ser Lys Gly Val Ser Thr Ser Gly Tyr Ser Tyr Leu His
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Pembrolizumab LC-CDR2

<400> SEQUENCE: 35

Leu Ala Ser Tyr Leu Glu Ser
1               5

<210> SEQ ID NO 36
<211> LENGTH: 10
<212> TYPE: PRT
<213> ORGANISM: Artificial Sequence
<220> FEATURE:
<223> OTHER INFORMATION: Pembrolizumab LC-CDR3

<400> SEQUENCE: 36

Cys Gln His Ser Arg Asp Leu Pro Leu Thr
1               5                   10

<210> SEQ ID NO 37
<211> LENGTH: 330
<212> TYPE: PRT
<213> ORGANISM: Artificial Sequence
<220> FEATURE:
<223> OTHER INFORMATION: Human IgG1 HC constant domain

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

-continued

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 330
<212> TYPE: PRT
<213> ORGANISM: Artificial Sequence
<220> FEATURE:
<223> OTHER INFORMATION: Human IgG1 HC Constant domain (L234A L235A
      D265S)

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 39
<211> LENGTH: 330
<212> TYPE: PRT
<213> ORGANISM: Artificial Sequence
<220> FEATURE:
<223> OTHER INFORMATION: Human IgG1 HC Constant domain (L234A L235A
      P329G)

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: Artificial Sequence
<220> FEATURE:
<223> OTHER INFORMATION: Human IgG1 HC Constant domain (L235E)

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 41
<211> LENGTH: 330
<212> TYPE: PRT
<213> ORGANISM: Artificial Sequence
<220> FEATURE:
<223> OTHER INFORMATION: Human IgG1 HC Constant domain (D265A)

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 330
<212> TYPE: PRT
<213> ORGANISM: Artificial Sequence
<220> FEATURE:
<223> OTHER INFORMATION: Human IgG1 HC Constant domain (D265A N297G)

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 330
<212> TYPE: PRT
<213> ORGANISM: Artificial Sequence
<220> FEATURE:
<223> OTHER INFORMATION: Human IgG1 HC Constant domain (E233A/L235A)

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
                325                 330

<210> SEQ ID NO 44
<211> LENGTH: 330
<212> TYPE: PRT
<213> ORGANISM: Artificial Sequence
<220> FEATURE:
<223> OTHER INFORMATION: Human IgG1 HC Constant domain (N297X, wherein X
      is any amino acid other than N)
<220> FEATURE:
<221> NAME/KEY: misc_feature
<222> LOCATION: (180)..(180)
<223> OTHER INFORMATION: Xaa can be any naturally occurring amino acid

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Xaa Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
                325                 330

<210> SEQ ID NO 45
<211> LENGTH: 326
<212> TYPE: PRT
<213> ORGANISM: Artificial Sequence
<220> FEATURE:
<223> OTHER INFORMATION: Human IgG2 HC Constant domain

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 46
<211> LENGTH: 326

<212> TYPE: PRT
<213> ORGANISM: Artificial Sequence
<220> FEATURE:
<223> OTHER INFORMATION: Human IgG2 HC Constant domain (D265S)

<400> SEQUENCE: 46

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ser
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 47
<211> LENGTH: 326
<212> TYPE: PRT
<213> ORGANISM: Artificial Sequence
<220> FEATURE:
<223> OTHER INFORMATION: Human IgG2 HC Constant domain (P329G)

<400> SEQUENCE: 47

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65              70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Gly
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 48
<211> LENGTH: 326
<212> TYPE: PRT
<213> ORGANISM: Artificial Sequence
<220> FEATURE:
<223> OTHER INFORMATION: Human IgG2 HC Constant domain (D265A)

<400> SEQUENCE: 48

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 49
<211> LENGTH: 326
<212> TYPE: PRT
<213> ORGANISM: Artificial Sequence
<220> FEATURE:
<223> OTHER INFORMATION: Human IgG2 HC Constant domain (D265A N297G)

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Gly
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 50
<211> LENGTH: 326
<212> TYPE: PRT
<213> ORGANISM: Artificial Sequence
<220> FEATURE:
<223> OTHER INFORMATION: Human IgG2 HC Constant domain (N297X, wherein X
      is any amino acid other than N)
<220> FEATURE:
<221> NAME/KEY: misc_feature
<222> LOCATION: (176)..(176)
<223> OTHER INFORMATION: Xaa can be any naturally occurring amino acid

<400> SEQUENCE: 50

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                    85                  90                  95

Thr Val Glu Arg Lys Cys Cys Val Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Xaa
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 51
<211> LENGTH: 326
<212> TYPE: PRT
<213> ORGANISM: Artificial Sequence
<220> FEATURE:
<223> OTHER INFORMATION: Human IgG2 HC Constant domain (V234A G237A
      P238S H268A V309L A330S P331S X378S/A
<220> FEATURE:
<221> NAME/KEY: misc_feature
<222> LOCATION: (257)..(257)
<223> OTHER INFORMATION: Xaa can be any naturally occurring amino acid

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Ala Ala Ala Ser Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Ala Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Xaa Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 52
<211> LENGTH: 327
<212> TYPE: PRT
<213> ORGANISM: Artificial Sequence
<220> FEATURE:
<223> OTHER INFORMATION: Human IgG4 HC Constant domain (S228P)

<400> SEQUENCE: 52

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 53
<211> LENGTH: 327
<212> TYPE: PRT
<213> ORGANISM: Artificial Sequence
<220> FEATURE:
<223> OTHER INFORMATION: Human IgG4 HC Constant domain (S228P P329G)

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Leu Gly Gly Pro Ser Val Phe Leu Phe Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Gly Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 54
<211> LENGTH: 327
<212> TYPE: PRT
<213> ORGANISM: Artificial Sequence
<220> FEATURE:
<223> OTHER INFORMATION: Human IgG4 HC Constant domain (S228P D265A)

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Lys Pro Lys
        115                 120                 125

Asp Thr Leu Met Ile Ser Arg Thr Pro Glu Val Thr Cys Val Val Val
    130                 135                 140
```

```
Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 55
<211> LENGTH: 327
<212> TYPE: PRT
<213> ORGANISM: Artificial Sequence
<220> FEATURE:
<223> OTHER INFORMATION: Human IgG4 HC Constant domain (S228P D265A
      N297G)

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Gly Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 56
<211> LENGTH: 327
<212> TYPE: PRT
<213> ORGANISM: Artificial Sequence
<220> FEATURE:
<223> OTHER INFORMATION: Human IgG4 HC Constant domain (S228P N297X, wherein X is any amino acid other than N)
<220> FEATURE:
<221> NAME/KEY: misc_feature
<222> LOCATION: (177)..(177)
<223> OTHER INFORMATION: Xaa can be any naturally occurring amino acid

<400> SEQUENCE: 56

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175
```

```
Xaa Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 57
<211> LENGTH: 107
<212> TYPE: PRT
<213> ORGANISM: Artificial Sequence
<220> FEATURE:
<223> OTHER INFORMATION: Human LC Kappa  Constant domain

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 447
<212> TYPE: PRT
<213> ORGANISM: Artificial Sequence
<220> FEATURE:
<223> OTHER INFORMATION: Mouse anti-CTLA-4 IgG2 HC (Mouse Modified x
      [CTLA-4_M] mAb (9D9 Balb/c (Igh-1a) haplotype- main a allele)
      IgG2a / Kappa-Heavy Chain))

<400> SEQUENCE: 58

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30
```

```
Tyr Met Asn Trp Val Lys Gln Ser His Gly Lys Ser Leu Glu Trp Ile
            35                  40                  45

Gly Val Ile Asn Pro Tyr Asn Gly Asp Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Asn Ser Leu Thr Ser Glu Asp Ser Ala Val Tyr Tyr Cys
                 85                  90                  95

Ala Arg Tyr Tyr Gly Ser Trp Phe Ala Tyr Trp Gly Gln Gly Thr Leu
            100                 105                 110

Ile Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
            210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
            435                 440                 445
```

```
<210> SEQ ID NO 59
<211> LENGTH: 219
<212> TYPE: PRT
<213> ORGANISM: Artificial Sequence
<220> FEATURE:
<223> OTHER INFORMATION: Mouse anti-CTLA-4 kappa LC (12AIL_9D9_LC)

<400> SEQUENCE: 59

Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 60
<211> LENGTH: 441
<212> TYPE: PRT
<213> ORGANISM: Artificial Sequence
<220> FEATURE:
<223> OTHER INFORMATION: Mouse anti-CTLA-4 (D265A) HC (mouse x
      [CTLA-4_M] mAb (9D9 mutation D265A) IgG1 / Kappa-Heavy chain)

<400> SEQUENCE: 60

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95
```

```
Ala Arg Tyr Tyr Gly Ser Trp Phe Ala Tyr Trp Gln Gly Thr Leu
            100                 105                 110

Ile Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Ala Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 61
<211> LENGTH: 415
<212> TYPE: PRT
<213> ORGANISM: Artificial Sequence
<220> FEATURE:
<223> OTHER INFORMATION: Mouse anti-CTLA-4 ISVD (54BBI_Llama x [CTLA4_M]
      [ALB_H] VHH (F023700894) (PI))
```

<400> SEQUENCE: 61

Glu Val Gln Leu Val Glu Ser Gly Gly Leu Val Gln Ala Gly Gly
1               5                   10                  15

Ser Leu Arg Leu Ser Cys Ala Ala Ser Gly Ser Thr Pro Ser Ile Asn
            20                  25                  30

Tyr Met Gly Trp Tyr Arg Gln Ala Pro Gly Lys Gln Arg Glu Phe Val
        35                  40                  45

Ala Thr Ile Arg Ser Gly Gly Ala Thr Asn Tyr Ala Asp Ser Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Asp Cys Tyr
                85                  90                  95

Thr Gly Gly Gly Gly Tyr Glu Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Ala Gly Gly Ser Leu Arg Leu Ser Cys Ala Ala Ser Gly
                165                 170                 175

Ser Thr Pro Ser Ile Asn Tyr Met Gly Trp Tyr Arg Gln Ala Pro Gly
            180                 185                 190

Lys Gln Arg Glu Phe Val Ala Thr Ile Arg Ser Gly Gly Ala Thr Asn
        195                 200                 205

Tyr Ala Asp Ser Val Lys Gly Arg Phe Thr Ile Ser Arg Asp Asn Thr
    210                 215                 220

Lys Asn Thr Val Tyr Leu Gln Met Asn Ser Leu Lys Pro Glu Asp Thr
225                 230                 235                 240

Ala Val Tyr Asp Cys Tyr Thr Gly Gly Gly Gly Tyr Glu Tyr Trp Gly
                245                 250                 255

Gln Gly Thr Leu Val Thr Val Ser Ser Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Gly Gly Gly Gly Ser Gly Gly Gly Gly Ser Glu Val Gln Leu
    290                 295                 300

Val Glu Ser Gly Gly Gly Leu Val Gln Pro Gly Asn Ser Leu Arg Leu
305                 310                 315                 320

Ser Cys Ala Ala Ser Gly Phe Thr Phe Ser Ser Phe Gly Met Ser Trp
                325                 330                 335

Val Arg Gln Ala Pro Gly Lys Gly Leu Glu Trp Val Ser Ser Ile Ser
            340                 345                 350

Gly Ser Gly Ser Asp Thr Leu Tyr Ala Asp Ser Val Lys Gly Arg Phe
        355                 360                 365

Thr Ile Ser Arg Asp Asn Ala Lys Thr Thr Leu Tyr Leu Gln Met Asn
    370                 375                 380

Ser Leu Arg Pro Glu Asp Thr Ala Val Tyr Tyr Cys Thr Ile Gly Gly
385                 390                 395                 400

```
Ser Leu Ser Arg Ser Ser Gln Gly Thr Leu Val Thr Val Ser Ser
            405                 410                 415

<210> SEQ ID NO 62
<211> LENGTH: 436
<212> TYPE: PRT
<213> ORGANISM: Artificial Sequence
<220> FEATURE:
<223> OTHER INFORMATION: Mouse anti-PD-1 ISVD PF023700037

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr His
            20                  25                  30

Thr Met Gly Trp Phe Arg Gln Gly Pro Gly Lys Glu Arg Glu Phe Val
        35                  40                  45

Ala Thr Ile Asn Arg Leu Asp Tyr Thr Tyr Tyr Ala Asn Ser Val Arg
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Ala
            85                  90                  95

Ala Asp Ser Glu Arg Arg Leu Gly Val Ile Pro Gly Leu Tyr Asp Tyr
        100                 105                 110

Trp Gly Gln Gly Thr Leu Val Thr Val Ser Ser Gly Gly Gly Gly Ser
    115                 120                 125

Gly Gly Gly Gly Ser Gly Gly Gly Ser Gly Gly Gly Gly Ser Gly
130                 135                 140

Gly Gly Gly Ser Gly Gly Gly Ser Gly Gly Gly Gly Ser Glu Val
145                 150                 155                 160

Gln Leu Val Glu Ser Gly Gly Gly Leu Val Gln Pro Gly Gly Ser Leu
            165                 170                 175

Arg Leu Ser Cys Ala Ala Ser Gly Arg Thr Phe Ser Arg Leu Ala Met
        180                 185                 190

Gly Trp Phe Arg Gln Ala Pro Gly Lys Glu Arg Glu Phe Val Ala Ser
    195                 200                 205

Ile Ser Trp Ser Gly Gly Ser Thr Tyr Tyr Ala Asp Ser Val Lys Gly
    210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Val Tyr Tyr Cys Ala Ala
            245                 250                 255

Ser Arg Glu Tyr Ser Gly Ser Tyr Tyr Tyr Gly Leu Thr Leu Tyr Glu
        260                 265                 270

Tyr Asp Tyr Trp Gly Gln Gly Thr Leu Val Thr Val Ser Ser Gly Gly
    275                 280                 285

Gly Gly Ser Gly Gly Gly Gly Ser Gly Gly Gly Ser Gly Gly Gly
        290                 295                 300

Gly Ser Gly Gly Gly Gly Ser Gly Gly Gly Ser Gly Gly Gly Gly
305                 310                 315                 320

Ser Glu Val Gln Leu Val Glu Ser Gly Gly Gly Leu Val Gln Pro Gly
            325                 330                 335

Asn Ser Leu Arg Leu Ser Cys Ala Ala Ser Gly Phe Thr Phe Ser Ser
        340                 345                 350
```

-continued

```
Phe Gly Met Ser Trp Val Arg Gln Ala Pro Gly Lys Gly Leu Glu Trp
        355                 360                 365

Val Ser Ser Ile Ser Gly Ser Gly Ser Asp Thr Leu Tyr Ala Asp Ser
370                 375                 380

Val Lys Gly Arg Phe Thr Ile Ser Arg Asp Asn Ala Lys Thr Thr Leu
385                 390                 395                 400

Tyr Leu Gln Met Asn Ser Leu Arg Pro Glu Asp Thr Ala Val Tyr Tyr
                405                 410                 415

Cys Thr Ile Gly Gly Ser Leu Ser Arg Ser Ser Gln Gly Thr Leu Val
                420                 425                 430

Thr Val Ser Ser
        435

<210> SEQ ID NO 63
<211> LENGTH: 443
<212> TYPE: PRT
<213> ORGANISM: Artificial Sequence
<220> FEATURE:
<223> OTHER INFORMATION: Mouse anti-PD-1 antibody clone DX400 HC

<400> SEQUENCE: 63

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ser
            20                  25                  30

Gly Leu Ala Trp Val Arg Gln Ala Pro Glu Lys Gly Leu Glu Trp Val
        35                  40                  45

Ala Thr Ile Thr Tyr Asn Gly Thr Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Thr Tyr Tyr Cys
                85                  90                  95

Ala Arg Trp Val Pro Gly Ser Gly Asn Phe Asp Tyr Trp Gly Gln Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Ala Ile Ser Lys Asp Asp Pro Glu Val Gln Phe Ser
            260                 265                 270
```

```
Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
                355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 64
<211> LENGTH: 218
<212> TYPE: PRT
<213> ORGANISM: Artificial Sequence
<220> FEATURE:
<223> OTHER INFORMATION: Mouse anti-PD-1 antibody clone DX400 LC

<400> SEQUENCE: 64

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Thr Ile Ser
                20                  25                  30

Arg Tyr Thr Leu Met His Trp Tyr Gln Gln Lys Pro Gly Gln Pro Pro
            35                  40                  45

Lys Leu Leu Ile Tyr Arg Ala Ser Asn Leu Ala Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Asp Asp Ala Ala Thr Tyr Tyr Cys Gln Gln Ser Arg
                85                  90                  95

Glu Ser Pro Trp Thr Phe Gly Gly Gly Thr Lys Leu Glu Ile Lys Arg
                100                 105                 110

Ala Asp Ala Ala Pro Thr Val Ser Ile Phe Pro Pro Ser Ser Glu Gln
                115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
                180                 185                 190
```

```
His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 65
<211> LENGTH: 4
<212> TYPE: PRT
<213> ORGANISM: Artificial Sequence
<220> FEATURE:
<223> OTHER INFORMATION: Residues after LC-CDR3
<220> FEATURE:
<221> NAME/KEY: VARIANT
<222> LOCATION: (3)..(3)
<223> OTHER INFORMATION: Xaa = any amino acid

<400> SEQUENCE: 65

Phe Gly Xaa Gly
1

<210> SEQ ID NO 66
<211> LENGTH: 4
<212> TYPE: PRT
<213> ORGANISM: Artificial Sequence
<220> FEATURE:
<223> OTHER INFORMATION: Residues before HC-CDR1
<220> FEATURE:
<221> NAME/KEY: VARIANT
<222> LOCATION: (2)..(4)
<223> OTHER INFORMATION: Xaa = any amino acid

<400> SEQUENCE: 66

Cys Xaa Xaa Xaa
1

<210> SEQ ID NO 67
<211> LENGTH: 5
<212> TYPE: PRT
<213> ORGANISM: Artificial Sequence
<220> FEATURE:
<223> OTHER INFORMATION: Residues before HC-CDR2

<400> SEQUENCE: 67

Leu Glu Trp Ile Gly
1               5

<210> SEQ ID NO 68
<211> LENGTH: 4
<212> TYPE: PRT
<213> ORGANISM: Artificial Sequence
<220> FEATURE:
<223> OTHER INFORMATION: Residues after HC-CDR3
<220> FEATURE:
<221> NAME/KEY: VARIANT
<222> LOCATION: (3)..(3)
<223> OTHER INFORMATION: Xaa = any amino acid

<400> SEQUENCE: 68

Trp Gly Xaa Gly
1

<210> SEQ ID NO 69
<211> LENGTH: 5
<212> TYPE: PRT
<213> ORGANISM: Artificial Sequence
<220> FEATURE:
<223> OTHER INFORMATION: CDR-1 of anti-CTLA-4 ISVD
```

```
<400> SEQUENCE: 69

Phe Tyr Gly Met Gly
1               5

<210> SEQ ID NO 70
<211> LENGTH: 17
<212> TYPE: PRT
<213> ORGANISM: Artificial Sequence
<220> FEATURE:
<223> OTHER INFORMATION: CDR-2 of anti-CTLA-4 ISVD

<400> SEQUENCE: 70

Asp Ile Arg Thr Ser Ala Gly Arg Thr Thr Tyr Ala Asp Ser Val Lys
1               5                   10                  15

Gly

<210> SEQ ID NO 71
<211> LENGTH: 10
<212> TYPE: PRT
<213> ORGANISM: Artificial Sequence
<220> FEATURE:
<223> OTHER INFORMATION: CDR-3 of anti-CTLA-4 ISVD

<400> SEQUENCE: 71

Glu Met Ser Gly Ile Ser Gly Trp Asp Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: CDR-3 of anti-CTLA-4 ISVD variant

<400> SEQUENCE: 72

Glu Pro Ser Gly Ile Ser Gly Trp Asp Tyr
1               5                   10

<210> SEQ ID NO 73
<211> LENGTH: 115
<212> TYPE: PRT
<213> ORGANISM: Artificial Sequence
<220> FEATURE:
<223> OTHER INFORMATION: 8D2/8D2 (RE) VH

<400> SEQUENCE: 73

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Asn
                20                  25                  30

Trp Met Asn Trp Val Arg Gln Ser Pro Glu Lys Gly Leu Glu Trp Leu
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Gly Glu Asp Met Gly Ile Tyr
                85                  90                  95

Tyr Cys Thr Ala Gln Phe Ala Tyr Trp Gly Gln Gly Thr Leu Val Thr
                100                 105                 110

Val Ser Ala
        115
```

<210> SEQ ID NO 74
<211> LENGTH: 106
<212> TYPE: PRT
<213> ORGANISM: Artificial Sequence
<220> FEATURE:
<223> OTHER INFORMATION: 8D2/8D2 (RE) VL

<400> SEQUENCE: 74

Asp Ile Gln Met Thr Gln Ser Pro Ala Ser Leu Ser Ala Ser Val Gly
1               5                   10                  15

Glu Thr Val Thr Ile Thr Cys Gly Thr Ser Glu Asn Ile Tyr Gly Gly
            20                  25                  30

Leu Asn Trp Tyr Gln Arg Lys Gln Gly Lys Ser Pro Gln Leu Leu Ile
        35                  40                  45

Phe Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Arg Ser Pro Phe
                85                  90                  95

Thr Phe Gly Ser Gly Thr Lys Leu Glu Ile
            100                 105

<210> SEQ ID NO 75
<211> LENGTH: 115
<212> TYPE: PRT
<213> ORGANISM: Artificial Sequence
<220> FEATURE:
<223> OTHER INFORMATION: 8D2/8D2 RE VH VARIANT 1 M18I

<400> SEQUENCE: 75

Glu Val Lys Leu Asp Glu Thr Gly Gly Gly Leu Val Gln Pro Gly Arg
1               5                   10                  15

Pro Ile Lys Leu Ser Cys Val Ala Ser Gly Phe Thr Phe Ser Asp Asn
            20                  25                  30

Trp Met Asn Trp Val Arg Gln Ser Pro Glu Lys Gly Leu Glu Trp Leu
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Gly Glu Asp Met Gly Ile Tyr
                85                  90                  95

Tyr Cys Thr Ala Gln Phe Ala Tyr Trp Gly Gln Gly Thr Leu Val Thr
            100                 105                 110

Val Ser Ala
        115

<210> SEQ ID NO 76
<211> LENGTH: 106
<212> TYPE: PRT
<213> ORGANISM: Artificial Sequence
<220> FEATURE:
<223> OTHER INFORMATION: 8D2/8D2 RE VL VARIANT 1 M18I

<400> SEQUENCE: 76

Asp Ile Gln Met Thr Gln Ser Pro Ala Ser Leu Ser Ala Ser Val Gly
1               5                   10                  15

```
Glu Thr Val Thr Ile Thr Cys Gly Thr Ser Glu Asn Ile Tyr Gly Gly
            20                  25                  30

Leu Asn Trp Tyr Gln Arg Lys Gln Gly Lys Ser Pro Gln Leu Leu Ile
        35                  40                  45

Phe Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65              70                  75                  80

Asp Asp Val Ala Thr Tyr Tyr Cys Gln Asn Val Leu Arg Ser Pro Phe
                85                  90                  95

Thr Phe Gly Ser Gly Thr Lys Leu Glu Ile
            100                 105
```

<210> SEQ ID NO 77
<211> LENGTH: 115
<212> TYPE: PRT
<213> ORGANISM: Artificial Sequence
<220> FEATURE:
<223> OTHER INFORMATION: 8D2H1L1 VH

<400> SEQUENCE: 77

```
Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Asn Ser
65              70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115
```

<210> SEQ ID NO 78
<211> LENGTH: 107
<212> TYPE: PRT
<213> ORGANISM: Artificial Sequence
<220> FEATURE:
<223> OTHER INFORMATION: 8D2H1L1 VL

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Gln Gly Lys Ser Pro Lys Leu Leu Ile
        35                  40                  45

Tyr Gly Ala Thr Asn Leu Ala Ser Gly Met Ser Ser Arg Phe Ser Gly
    50                  55                  60

Ser Gly Ser Gly Thr Asp Tyr Thr Leu Lys Ile Ser Ser Leu His Pro
65              70                  75                  80

Asp Asp Val Ala Thr Tyr Tyr Cys Gln Asn Val Leu Arg Ser Pro Phe
                85                  90                  95
```

```
Thr Phe Gly Ser Gly Thr Lys Leu Glu Ile Lys
            100                 105
```

<210> SEQ ID NO 79
<211> LENGTH: 115
<212> TYPE: PRT
<213> ORGANISM: Artificial Sequence
<220> FEATURE:
<223> OTHER INFORMATION: 8D2H1L1 VH VARIANT 1 M18I

<400> SEQUENCE: 79

```
Glu Val Gln Leu Val Glu Ser Gly Gly Gly Leu Val Gln Pro Gly Gly
1               5                   10                  15

Ser Ile Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115
```

<210> SEQ ID NO 80
<211> LENGTH: 107
<212> TYPE: PRT
<213> ORGANISM: Artificial Sequence
<220> FEATURE:
<223> OTHER INFORMATION: 8D2H1L1 VL VARIANT 1 M18I

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Gln Gly Lys Ser Pro Lys Leu Leu Ile
        35                  40                  45

Tyr Gly Ala Thr Asn Leu Ala Ser Gly Met Ser Ser Arg Phe Ser Gly
    50                  55                  60

Ser Gly Ser Gly Thr Asp Tyr Thr Leu Lys Ile Ser Ser Leu His Pro
65                  70                  75                  80

Asp Asp Val Ala Thr Tyr Tyr Cys Gln Asn Val Leu Arg Ser Pro Phe
                85                  90                  95

Thr Phe Gly Ser Gly Thr Lys Leu Glu Ile Lys
            100                 105
```

<210> SEQ ID NO 81
<211> LENGTH: 115
<212> TYPE: PRT
<213> ORGANISM: Artificial Sequence
<220> FEATURE:
<223> OTHER INFORMATION: 8D2H2L2 VH

<400> SEQUENCE: 81

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115

<210> SEQ ID NO 82
<211> LENGTH: 107
<212> TYPE: PRT
<213> ORGANISM: Artificial Sequence
<220> FEATURE:
<223> OTHER INFORMATION: 8D2H2L2 VL

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Pro Gly Lys Ser Pro Lys Leu Leu Ile
        35                  40                  45

Tyr Gly Ala Thr Asn Leu Ala Ser Gly Val Ser Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Val Leu Arg Ser Pro Phe
                85                  90                  95

Thr Phe Gly Ser Gly Thr Lys Leu Glu Ile Lys
            100                 105

<210> SEQ ID NO 83
<211> LENGTH: 115
<212> TYPE: PRT
<213> ORGANISM: Artificial Sequence
<220> FEATURE:
<223> OTHER INFORMATION: 8D2H2L2 VH VARIANT 1 M18I

<400> SEQUENCE: 83

Glu Val Gln Leu Val Glu Ser Gly Gly Gly Leu Val Gln Pro Gly Gly
1               5                   10                  15

Ser Ile Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

```
Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Gly Val Tyr
                 85                  90                  95

Tyr Cys Thr Ala Gln Phe Ala Tyr Trp Gly Gln Gly Thr Leu Val Thr
            100                 105                 110

Val Ser Ser
        115
```

<210> SEQ ID NO 84
<211> LENGTH: 107
<212> TYPE: PRT
<213> ORGANISM: Artificial Sequence
<220> FEATURE:
<223> OTHER INFORMATION: 8D2H2L2 VL VARIANT 1 M18I

<400> SEQUENCE: 84

```
Asp Ile Gln Met Thr Gln Ser Pro Ser Ser Leu Ser Ala Ser Val Gly
  1               5                  10                  15

Asp Arg Val Thr Ile Thr Cys Arg Thr Ser Glu Asn Ile Tyr Gly Gly
                 20                  25                  30

Leu Asn Trp Tyr Gln Arg Lys Pro Gly Lys Ser Pro Lys Leu Leu Ile
             35                  40                  45

Tyr Gly Ala Thr Asn Leu Ala Ser Gly Val Ser Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Val Ala Thr Tyr Tyr Cys Gln Asn Val Leu Arg Ser Pro Phe
                 85                  90                  95

Thr Phe Gly Ser Gly Thr Lys Leu Glu Ile Lys
            100                 105
```

<210> SEQ ID NO 85
<211> LENGTH: 115
<212> TYPE: PRT
<213> ORGANISM: Artificial Sequence
<220> FEATURE:
<223> OTHER INFORMATION: 8D3H3L3 VH

<400> SEQUENCE: 85

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Asn
                 20                  25                  30

Trp Met Asn Trp Val Arg Gln Ala Pro Gly Lys Gly Leu Glu Trp Val
             35                  40                  45

Ala Gln Ile Arg Asn Lys Pro Tyr Asn Tyr Glu Thr Glu Tyr Ala Ala
     50                  55                  60

Ser Val Lys Gly Arg Phe Thr Ile Ser Arg Asp Asp Ser Lys Asn Ser
 65                  70                  75                  80

Ala Tyr Leu Gln Met Asn Ser Leu Lys Thr Glu Asp Thr Ala Val Tyr
                 85                  90                  95

Tyr Cys Thr Ala Gln Phe Ala Tyr Trp Gly Gln Gly Thr Leu Val Thr
            100                 105                 110

Val Ser Ser
        115
```

```
<210> SEQ ID NO 86
<211> LENGTH: 107
<212> TYPE: PRT
<213> ORGANISM: Artificial Sequence
<220> FEATURE:
<223> OTHER INFORMATION: 8D3H3L3 VL

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Gly Gly
            20                  25                  30

Leu Asn Trp Tyr Gln Gln Lys Pro Gly Lys Ala Pro Lys Leu Leu Ile
        35                  40                  45

Tyr Gly Ala Thr Ser Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Arg Ser Pro Phe
                85                  90                  95

Thr Phe Gly Ser Gly Thr Lys Leu Glu Ile Lys
            100                 105

<210> SEQ ID NO 87
<211> LENGTH: 115
<212> TYPE: PRT
<213> ORGANISM: Artificial Sequence
<220> FEATURE:
<223> OTHER INFORMATION: 8D2H2L15 VH

<400> SEQUENCE: 87

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115

<210> SEQ ID NO 88
<211> LENGTH: 107
<212> TYPE: PRT
<213> ORGANISM: Artificial Sequence
<220> FEATURE:
<223> OTHER INFORMATION: 8D2H2L15 VL

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30
```

Leu Asn Trp Tyr Gln Arg Lys Pro Gly Lys Ser Pro Lys Leu Leu Ile
            35                  40                  45

Tyr Gly Ala Thr Asn Leu Ala Ser Gly Val Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Val Leu Ser Arg His Pro
                85                  90                  95

Gly Phe Gly Ser Gly Thr Lys Leu Glu Ile Lys
            100                 105

<210> SEQ ID NO 89
<211> LENGTH: 115
<212> TYPE: PRT
<213> ORGANISM: Artificial Sequence
<220> FEATURE:
<223> OTHER INFORMATION: 8D2H2L15 VH VARIANT 1 M18I

<400> SEQUENCE: 89

Glu Val Gln Leu Val Glu Ser Gly Gly Gly Leu Val Gln Pro Gly Gly
1               5                   10                  15

Ser Ile Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115

<210> SEQ ID NO 90
<211> LENGTH: 107
<212> TYPE: PRT
<213> ORGANISM: Artificial Sequence
<220> FEATURE:
<223> OTHER INFORMATION: 8D2H2L15 VL VARIANT 1 M18I

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Pro Gly Lys Ser Pro Lys Leu Leu Ile
            35                  40                  45

Tyr Gly Ala Thr Asn Leu Ala Ser Gly Val Ser Arg Phe Ser Gly
        50                  55                  60

Ser Gly Ser Gly Thr Asp Tyr Thr Leu Thr Ile Ser Ser Leu Gln Pro
65                  70                  75                  80

```
Glu Asp Val Ala Thr Tyr Tyr Cys Gln Asn Val Leu Ser Arg His Pro
                85                  90                  95
Gly Phe Gly Ser Gly Thr Lys Leu Glu Ile Lys
            100                 105
```

<210> SEQ ID NO 91
<211> LENGTH: 115
<212> TYPE: PRT
<213> ORGANISM: Artificial Sequence
<220> FEATURE:
<223> OTHER INFORMATION: 8D2H2L17 VH

<400> SEQUENCE: 91

```
Glu Val Gln Leu Val Glu Ser Gly Gly Gly Leu Val Gln Pro Gly Gly
1               5                   10                  15
Ser Met Arg Leu Ser Cys Ala Ala Ser Gly Phe Thr Phe Ser Asp Asn
            20                  25                  30
Trp Met Asn Trp Val Arg Gln Ala Pro Gly Lys Gly Leu Glu Trp Leu
        35                  40                  45
Ala Gln Ile Arg Asn Lys Pro Tyr Asn Tyr Glu Thr Tyr Tyr Ser Ala
    50                  55                  60
Ser Val Lys Gly Arg Phe Thr Ile Ser Arg Asp Asp Ser Lys Asn Ser
65                  70                  75                  80
Val Tyr Leu Gln Met Asn Ser Leu Lys Thr Glu Asp Thr Gly Val Tyr
                85                  90                  95
Tyr Cys Thr Ala Gln Phe Ala Tyr Trp Gly Gln Gly Thr Leu Val Thr
            100                 105                 110
Val Ser Ser
        115
```

<210> SEQ ID NO 92
<211> LENGTH: 107
<212> TYPE: PRT
<213> ORGANISM: Artificial Sequence
<220> FEATURE:
<223> OTHER INFORMATION: 8D2H2L17 VL

<400> SEQUENCE: 92

```
Asp Ile Gln Met Thr Gln Ser Pro Ser Ser Leu Ser Ala Ser Val Gly
1               5                   10                  15
Asp Arg Val Thr Ile Thr Cys Arg Thr Ser Glu Asn Ile Tyr Gly Gly
            20                  25                  30
Leu Asn Trp Tyr Gln Arg Lys Pro Gly Lys Ser Pro Lys Leu Leu Ile
        35                  40                  45
Tyr Gly Ala Thr Asn Leu Ala Ser Gly Val Ser Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Val Ala Thr Tyr Tyr Cys Gln Asn Val Leu Ser Ser Arg Pro
                85                  90                  95
Gly Phe Gly Ser Gly Thr Lys Leu Glu Ile Lys
            100                 105
```

<210> SEQ ID NO 93
<211> LENGTH: 115
<212> TYPE: PRT
<213> ORGANISM: Artificial Sequence
<220> FEATURE:
<223> OTHER INFORMATION: 8D2H2L17 VH VARIANT 1 M18I

<400> SEQUENCE: 93

Glu Val Gln Leu Val Glu Ser Gly Gly Gly Leu Val Gln Pro Gly Gly
1               5                   10                  15

Ser Ile Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115

<210> SEQ ID NO 94
<211> LENGTH: 107
<212> TYPE: PRT
<213> ORGANISM: Artificial Sequence
<220> FEATURE:
<223> OTHER INFORMATION: 8D2H2L17 VL VARIANT 1 M18I

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Pro Gly Lys Ser Pro Lys Leu Leu Ile
        35                  40                  45

Tyr Gly Ala Thr Asn Leu Ala Ser Gly Val Ser Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Val Leu Ser Ser Arg Pro
                85                  90                  95

Gly Phe Gly Ser Gly Thr Lys Leu Glu Ile Lys
            100                 105

<210> SEQ ID NO 95
<211> LENGTH: 116
<212> TYPE: PRT
<213> ORGANISM: Artificial Sequence
<220> FEATURE:
<223> OTHER INFORMATION: REGN4659 VH WO2019023482

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ser Ser Ile Arg Thr Ser Gly Thr Thr Lys Tyr Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gly Gly Thr Phe Leu His Tyr Trp Gly Gln Gly Thr Leu Val
            100                 105                 110

Thr Val Ser Ser
        115

<210> SEQ ID NO 96
<211> LENGTH: 108
<212> TYPE: PRT
<213> ORGANISM: Artificial Sequence
<220> FEATURE:
<223> OTHER INFORMATION: REGN4659 VL

<400> SEQUENCE: 96

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ala Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Met
                85                  90                  95

Tyr Thr Phe Gly Gln Gly Thr Lys Leu Glu Ile Lys
            100                 105

<210> SEQ ID NO 97
<211> LENGTH: 118
<212> TYPE: PRT
<213> ORGANISM: Artificial Sequence
<220> FEATURE:
<223> OTHER INFORMATION: AGEN1884w VH

<400> SEQUENCE: 97

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115

```
<210> SEQ ID NO 98
<211> LENGTH: 107
<212> TYPE: PRT
<213> ORGANISM: Artificial Sequence
<220> FEATURE:
<223> OTHER INFORMATION: AGEN1884w VL

<400> SEQUENCE: 98

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 99
<211> LENGTH: 117
<212> TYPE: PRT
<213> ORGANISM: Artificial Sequence
<220> FEATURE:
<223> OTHER INFORMATION: Cemiplimab-rwlc VH

<400> SEQUENCE: 99

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 100
<211> LENGTH: 107
<212> TYPE: PRT
<213> ORGANISM: Artificial Sequence
<220> FEATURE:
<223> OTHER INFORMATION: Cemiplimab-rwlc VL

<400> SEQUENCE: 100

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30
```

```
Leu Asn Trp Tyr Gln Gln Lys Pro Gly Lys Ala Pro Asn Leu Leu Ile
             35                  40                  45

Tyr Ala Ala Ser Ser Leu His Gly Gly Val Pro Ser Arg Phe Ser Gly
 50                  55                  60

Ser Gly Ser Gly Thr Asp Phe Thr Leu Thr Ile Arg Thr Leu Gln Pro
 65                  70                  75                  80

Glu Asp Phe Ala Thr Tyr Tyr Cys Gln Gln Ser Ser Asn Thr Pro Phe
                 85                  90                  95

Thr Phe Gly Pro Gly Thr Val Val Asp Phe Arg
                100                 105

<210> SEQ ID NO 101
<211> LENGTH: 444
<212> TYPE: PRT
<213> ORGANISM: Artificial Sequence
<220> FEATURE:
<223> OTHER INFORMATION: Cemiplimab-rwlc HC (S228P)

<400> SEQUENCE: 101

Glu Val Gln Leu Leu Glu Ser Gly Gly Val Leu Val Gln Pro Gly Gly
 1               5                  10                  15

Ser Leu Arg Leu Ser Cys Ala Ala Ser Gly Phe Thr Phe Ser Asn Phe
             20                  25                  30

Gly Met Thr Trp Val Arg Gln Ala Pro Gly Lys Gly Leu Glu Trp Val
             35                  40                  45

Ser Gly Ile Ser Gly Gly Gly Arg Asp Thr Tyr Phe Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Gly Glu Asp Thr Ala Val Tyr Tyr Cys
                 85                  90                  95

Val Lys Trp Gly Asn Ile Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285
```

```
Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 102
<211> LENGTH: 214
<212> TYPE: PRT
<213> ORGANISM: Artificial Sequence
<220> FEATURE:
<223> OTHER INFORMATION: Cemiplimab-rwlc LC

<400> SEQUENCE: 102

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 103
<211> LENGTH: 121
<212> TYPE: PRT
<213> ORGANISM: Artificial Sequence
<220> FEATURE:
<223> OTHER INFORMATION: Durvalumab VH

<400> SEQUENCE: 103

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 104
<211> LENGTH: 108
<212> TYPE: PRT
<213> ORGANISM: Artificial Sequence
<220> FEATURE:
<223> OTHER INFORMATION: Durvalumab VL

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 105
<211> LENGTH: 80
<212> TYPE: PRT
<213> ORGANISM: Artificial Sequence
<220> FEATURE:
<223> OTHER INFORMATION: Avelumab VH

<400> SEQUENCE: 105

Gln Ala Pro Gly Lys Gly Leu Glu Trp Val Ser Ser Ile Tyr Pro Ser
1               5                   10                  15

Gly Gly Ile Thr Phe Tyr Ala Asp Lys Gly Arg Phe Thr Ile Ser Arg
            20                  25                  30

Asp Asn Ser Lys Asn Thr Leu Tyr Leu Gln Met Asn Ser Leu Arg Ala
        35                  40                  45

Glu Asp Thr Ala Val Tyr Tyr Cys Ala Arg Ile Lys Leu Gly Thr Val
50                  55                  60

Thr Thr Val Asp Tyr Trp Gly Gln Gly Thr Leu Val Thr Val Ser Ser
65                  70                  75                  80

<210> SEQ ID NO 106
<211> LENGTH: 110
<212> TYPE: PRT
<213> ORGANISM: Artificial Sequence
<220> FEATURE:
<223> OTHER INFORMATION: Avelumab VL

<400> SEQUENCE: 106

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 107
<211> LENGTH: 118
<212> TYPE: PRT
<213> ORGANISM: Artificial Sequence
<220> FEATURE:
<223> OTHER INFORMATION: Atezolizumab VH

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 108
<211> LENGTH: 107
<212> TYPE: PRT
<213> ORGANISM: Artificial Sequence
<220> FEATURE:
<223> OTHER INFORMATION: Atezolizumab VL

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 109
<211> LENGTH: 451
<212> TYPE: PRT
<213> ORGANISM: Artificial Sequence
<220> FEATURE:
<223> OTHER INFORMATION: Durvalumab HC (IgG1
      L234F/L235E/P331S/D356E/L358M)

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 110
<211> LENGTH: 215
<212> TYPE: PRT
<213> ORGANISM: Artificial Sequence
<220> FEATURE:
<223> OTHER INFORMATION: Durvalumab LC

<400> SEQUENCE: 110

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 111
<211> LENGTH: 450
<212> TYPE: PRT
<213> ORGANISM: Artificial Sequence
<220> FEATURE:
<223> OTHER INFORMATION: Avelumab HC (IgG1)

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 112
<211> LENGTH: 216
<212> TYPE: PRT
<213> ORGANISM: Artificial Sequence
<220> FEATURE:
<223> OTHER INFORMATION: Avelumab LC

<400> SEQUENCE: 112

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
            85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

```
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
            195                 200                 205
Thr Val Ala Pro Thr Glu Cys Ser
    210                 215
```

<210> SEQ ID NO 113
<211> LENGTH: 448
<212> TYPE: PRT
<213> ORGANISM: Artificial Sequence
<220> FEATURE:
<223> OTHER INFORMATION: Atezolizumab HC (IgG1 N297A/D235E/L358M)

<400> SEQUENCE: 113

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
                20                  25                  30
Trp Ile His Trp Val Arg Gln Ala Pro Gly Lys Gly Leu Glu Trp Val
            35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ser Ala Ser Thr Lys Gly Pro Ser Val Phe Pro
    115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
    195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 114
<211> LENGTH: 214
<212> TYPE: PRT
<213> ORGANISM: Artificial Sequence
<220> FEATURE:
<223> OTHER INFORMATION: Atezolizumab LC

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 115
<211> LENGTH: 330
<212> TYPE: PRT
<213> ORGANISM: Artificial Sequence
<220> FEATURE:
<223> OTHER INFORMATION: Human IgG1 HC Constant domain
      (N297A/D356E/L358M)

<400> SEQUENCE: 115

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 116
<211> LENGTH: 317
<212> TYPE: PRT
<213> ORGANISM: Artificial Sequence
<220> FEATURE:
<223> OTHER INFORMATION: Human IgG1 HC Constant domain
    (L234F/L235E/P331S/D356E/L358M)

<400> SEQUENCE: 116

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Leu Thr Cys Leu Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Tyr Ser Arg Leu Thr Val Asp Lys Ser Arg Trp Gln
        275                 280                 285

Glu Gly Asn Val Phe Ser Cys Ser Val Met His Glu Ala Leu His Asn
    290                 295                 300

His Tyr Thr Gln Lys Ser Leu Ser Leu Ser Leu Gly Lys
305                 310                 315
```

<210> SEQ ID NO 117
<211> LENGTH: 106
<212> TYPE: PRT
<213> ORGANISM: Artificial Sequence
<220> FEATURE:
<223> OTHER INFORMATION: Human LC lambda Constant domain

```
<400> SEQUENCE: 117

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

ANTI-CANCER COMBINATION THERAPIES COMPRISING CTLA-4 AND PD-1 BLOCKING AGENTS

CROSS-REFERENCE TO RELATED APPLICATIONS

This application is a National Stage application of International Patent Application No. PCT/US2020/021783, filed Mar. 10, 2020, which claims benefit of U.S. Provisional Patent Application No. 62/817,749, filed Mar. 13, 2019.

REFERENCE TO SEQUENCE LISTING SUBMITTED ELECTRONICALLY

The sequence listing of the present application is submitted electronically via EFS-Web as an ASCII formatted sequence listing with a file name "24702WOPCTSEQ-2.txt", creation date of Mar. 14, 2022, and a size of 173 Kb. This sequence listing submitted via EFS-Web is part of the specification and is herein incorporated by reference in its entirety.

BACKGROUND OF THE INVENTION

(1) Field of the Invention

The present invention relates to anti-cancer combination therapies comprising a CTLA-4 blocking agent and a PD-1 blocking agent. In particular, the present invention relates to combination therapies wherein the CTLA-4 blocking agent is an anti-CTLA-4 antibody with reduced or no measurable effector function or an anti-CTLA-4 antibody fragment that lacks an Fc domain, and the PD-1 blocking agent is an anti-PD-1 antibody, anti-PD-1 antibody fragment, anti-PD-L1 antibody, or anti-PD-L1 antibody fragment.

(2) Description of Related Art

Tumor immunotherapy has assumed a more prominent role for treatment of a variety of cancer indications. The clinical successes utilizing antibody blockade of immune checkpoint inhibitory receptors expressed on T cells such as cytotoxic T-lymphocyte antigen-4 (CTLA-4) and programmed death receptor-1 (PD-1) has galvanized the notable advancement of immunotherapy for cancer. CTLA-4 or PD-1 monotherapy blockade by monoclonal antibodies (mAbs) has resulted in enhanced anti-tumor responses and beneficial clinical outcomes in controlled randomized clinical trials.

A prominent feature of the immune checkpoint blockade for treating various cancers is the clinically validated benefit of combination therapies that include anti-PD-1 and anti-CTLA-4 antibodies. As more and more clinical data is released, it is becoming clear that anti-PD-1/CTLA-4 combination therapies may provide superior clinical efficacy when compared to targeting either checkpoint pathway alone. However, immune-related toxicities (irAEs) associated with anti-CTLA-4 antibodies have been significant in both monotherapy settings and in combination therapies with anti-PD-1 antibodies. For example, the anti-CTLA-4 antibody ipilimumab, which is marketed by Bristol-Myers Squibb under the tradename YERVOY and is the only anti-CTLA-4 antibody approved by the United States Food and Drug Administration (U.S. FDA), is subject to a Black Box warning due to its potential to induce severe and fatal immune-mediated adverse reactions such as inflammation of the intestines, liver, skin, hormone-producing glands, and/or eyes. Ipilimumab has also been approved for combination therapies with the anti-PD-1 antibody nivolumab (marketed by Bristol-Myers Squibb under the tradename OPDIVO) for advanced renal cell carcinoma and certain colorectal cancers but due to the risk for significant irAEs, ipilimumab is administered at a low or subtherapeutic dose of 1 mg/kg. The subtherapeutic dose for the combination therapy is significantly lower than the 3 mg/kg monotherapy dose for unresectable or metastatic melanoma or the 10 mg/kg monotherapy dose for adjuvant melanoma (see Package Insert and Label for YERVOY (July 2018)).

Both FDA-approved anti-PD1 mAbs, nivolumab and pembrolizumab, are humanized anti-PD1 IgG4 kappa antibodies, which are disclosed in U.S. Pat. Nos. 8,008,449 and 8,354,509, respectively. The IgG4 isotype Fc domain is generally recognized as having little detectable effector function.

Ipilimumab is a human anti-CTLA-4 IgG1 kappa antibody, which is disclosed in U.S. Pat. No. 6,984,720. The heavy chain (HC) constant domain of the IgG1 isotype has an Fc domain that is generally recognized as having high affinity for Fc receptors (FcR), which provides significant effector function to the antibody (e.g., inducing antibody-dependent cellular cytotoxicity (ADCC), antibody-dependent cellular phagocytosis (ADCP), and/or Complement-dependent cytotoxicity (CDC)). Research has shown that Fc effector function is required for efficacy of anti-CTLA-4 antibodies. For example, Ingram et al., Proc. Natl. Acad. Sci. USA 115:3912-3917 (2018) showed in a mouse model that an anti-CTLA-4 alpaca heavy chain-only antibody fragment (VHH) that lacks a heavy chain Fc domain and its attendant effector function had no anti-tumor efficacy; however, anti-tumor efficacy could be restored to the molecule by fusing it to a mouse IgG2 heavy chain Fc domain displaying effector function; and, Selby et al., Cancer Immunol. Res. 1:32-42 (2013) showed in a mouse model that anti-CTLA-4 antibodies fused or linked to an Fc domain mutated to eliminate effector function did not display any anti-tumor activity. See also Simpson et al., J. Exp. Med.; 210:1695-710 (2013) and International Patent Application No. WO2014089113.

Tremelizumab is a human anti-CTLA-4 human IgG2 antibody, which has been disclosed in U.S. Pat. No. 8,491,895. The human IgG2 isotype had been selected to minimize potential effector function activity and thereby potentially reduce irAEs. However, as shown in Vargas et al., Cancer Cell 33:649-663 (2018), tremelizumab retains effector function; and Bertrand et al, BMC Med. 13:211-214 (2015) showed that while tremelizumab could be administered at a dose higher than that for ipilimumab, it was still capable of inducing irAEs, in particular gut and skin inflammatory immune-mediated toxicities. See also Ribas et al., The Oncologist 12:873-993 (2007), Schneider-Merck et al., J. Immunol. 184:512-520 (2010) and Könitzer et al., PLOS One. 10: e0145633 (2015), which showed other human $IgG_2$ antibodies that induce ADCC and ADCP in vitro of similar equivalence to the human $IgG_1$ isoform.

Other attempts to reduce irAEs of ipilimumab include BMS-986249, a probody composed of ipilimumab linked to a proprietary masking peptide that covers the active antigen-binding site of the antibody through a protease-cleavable linker. The masking peptide may reduce irAEs by minimizing ipilimumab's ability to bind CTLA-4 in normal tissues (See, International patent Applications WO2009025846, WO2010081173, WO2018222949, WO2018085555, Pai et al., J. Clin. Invest. 129:349-363 (2019), and Korman et al., Abstract SY09-01, AACR Annual Meeting Vol 77, issue 13 (2017)).

In light of studies suggesting that the therapeutic efficacy of anti-CTLA-4 antibodies like ipilimumab may involve depletion of regulatory T cells (Tregs), it has been proposed that anti-CTLA-4 antibodies, such as ipilimumab, that have enhanced ADCC activity would provide more effective anti-tumor activity than current antibodies. U.S. Pat. No. 10,196,445 discloses several ipilimumab variants with enhanced ADCC activity.

The standard-of-care for some anti-cancer therapies comprises providing an anti-PD-1 antibody in combination with chemotherapy. The anti-tumor activity of an anti-CTLA-4 antibody may further enhance the efficacy of these therapies; however, because gastrointestinal toxicity is one of the most commonly encountered side effects experienced during chemotherapy, addition of an anti-CTLA-4 antibody to the therapy may instead exacerbate the gastrointestinal toxicity.

Clearly, anti-CTLA-4 antibodies that enabled dosing at higher, more optimal levels, without associated irAEs, in particular the skin and gut inflammatory immune-mediated toxicities associated with current anti-CTLA-4 antibodies, would likely allow for more effective therapies in combination with anti-PD-1 antagonists and, optionally, chemotherapies.

BRIEF SUMMARY OF THE INVENTION

The inventors have discovered that while certain CTLA-4 blocking agents that bind CTLA-4 have reduced or no measurable anti-tumor activity when administered as a monotherapy, they may display clinically relevant anti-tumor activity when used in combination therapies with a PD-1 blocking agent. The inventors have also discovered that these certain CTLA-4 blocking agents may exert anti-tumor activity in a CTLA-4/PD-1 blockade combination therapy without inducing the immune-mediated adverse reactions (irAEs), including the irAEs in the skin and gut, that have been associated with the currently approved CTLA-4/PD-1 blockade combination therapies. The CTLA-4/PD-1 blockade combinations disclosed herein enable therapies of increased therapeutic index over the current CTLA-4/PD-1 blockade combination therapies including combination therapies that include chemotherapy, which may lead to more efficacious cancer treatments with improved patient outcomes.

The certain CTLA-4 blocking agents used as part of CTLA-4/PD-1 blockade combination therapy of the present invention may be selected from the group consisting of (i) an effector-silent anti-CTLA-4 antibody and (ii) an effector-silent anti-CTLA-4 antibody fragment that either lacks a fragment crystallizable (Fc) domain or has an Fc domain that comprises deletions of those regions in the Fc domain that bind the Fc receptors (FcRs). An effector-silent antibody or antibody fragment displays either (i) no measurable binding to one or more FcRs, as may be measured in a Biacore assay wherein an association constant in the micromolar range indicates no measurable binding or (ii) measurable binding to one or more FcRs as may be measured in a Biacore assay that is reduced compared to the binding that is typical for an antibody of the same isotype. These certain CTLA-4 blocking agents are effector-silent CTLA-4 blocking agents.

In particular embodiments, these effector-silent anti-CTLA-4 antibodies and effector-silent anti-CTLA-4 antibody fragments may not display measurable anti-tumor activity in an anti-cancer monotherapy but will display measurable anti-tumor activity in a combination anti-cancer therapy with a PD-1 or PD-L1 blocking agent and without displaying the irAEs typically associated with CTLA-4/PD-1 blockade combination therapies, in particular skin or gut inflammatory immune-related toxicities.

The effector-silent anti-CTLA-4 antibodies or effector-silent anti-CTLA-4 antibody fragments disclosed herein may be used at higher doses and for longer time periods in combination with PD-1 or PD-L1 blocking agents without displaying the irAEs typically associated with CTLA-4/PD-1 blockade combination therapies, in particular skin or gut inflammatory immune-related toxicities. Currently, the anti-CTLA-4 antibody ipilimumab dose approved for use in anti-CTLA-4/PD-1 blockade combination therapies is 1 mg/kg compared to the 3 mg/kg or 10 mg/kg dose approved for use in monotherapies (See Package Insert and Label for YERVOY (July 2018)) or the 100 mg or less fixed dose contemplated for CTLA-4/PD-1 blockade combination therapies in International Patent Application WO2018183408. Thus, the CTLA-4/PD-1 blockade combination therapies of the present invention may use effector-silent anti-CTLA-4 antibodies or effector-silent anti-CTLA-4 antibody fragments at doses that are the same as or higher than the doses currently approved for anti-CTLA-4 antibodies in monotherapies. The effector-silent anti-CTLA-4 antibodies or anti-CTLA-4 antibody fragments disclosed herein may also be used in combination with anti-PD-1 or anti-PD-L1 antibodies at doses similar to those currently used in or contemplated for CTLA-4/PD-1 blockade combination therapies but for a longer duration of time than is currently obtainable for anti-CTLA-4 antibodies and without displaying the irAEs typically associated with CTLA-4/PD-1 blockade combination therapies, in particular skin or gut inflammatory immune-related toxicities.

Accordingly, the present invention provides a combination therapy for treating cancer in an individual in need of such treatment, the method comprising administering to an individual with a cancer (i) a therapeutic dose of a PD-1 or PD-L1 blocking agent and (ii) a therapeutic dose of an effector-silent CTLA-4 blocking agent, to treat the cancer, wherein the effector-silent CTLA-4 blocking agent displays anti-tumor activity in the combination therapy that it does not display when administered to an individual in a monotherapy without the PD-1 or PD-L1 blocking agent. In further embodiments, the combination therapy does not induce or has reduced risk of inducing immune-mediated adverse reactions (irAEs) in the gut or skin during the course of the combination therapy that is greater than Grade 2 as defined in Common Terminology Criteria for Adverse events (CTCAE) Version 5.0 compared to combination therapies comprising an anti-CTLA-4 antibody displaying effector function. In particular embodiments, the effector-silent CTLA-4 blocking agent used as part of the combination therapy does not induce irAEs in the skin or gut that is greater than Grade 2 for at least the first 10 weeks of combination therapy. In particular embodiments, the combination therapy does not result in detectable irAEs for at least the first four weeks of the combination therapy or irAE greater than Grade 1 for at least the first four weeks of the combination therapy.

In one embodiment, the effector-silent CTLA-4 blocking agent used as part of the combination therapy described herein is an effector-silent anti-CTLA-4 antibody or an effector-silent anti-CTLA-4 antibody fragment.

In another embodiment, the PD-1 blocking agent used as part of the combination therapy described herein is an anti-PD-1 or anti-PD-L1 antibody or an anti-PD-1 or an anti-PD-L1 antibody fragment. In particular embodiments, the anti-PD-1 or anti-PD-L1 antibody comprises an HC domain comprising one or more mutations in the Fc domain that render the antibody effector-silent. The PD-1 blocking agent may also be an anti-PD-1 or an anti-PD-L1 antibody fragment, each of which lacks an Fc domain or those regions of the Fc domain that bind one or more FcRs, which renders the antibody fragment effector-silent.

The present invention further provides anti-cancer combination therapies, which comprise, administering to an individual in need of a cancer therapy (i) a first formulation comprising a PD-1 blocking agent selected from the group consisting of an anti-PD-1 antibody having an $IgG_4$ or $IgG_2$ Fc domain, an effector-silent anti-PD-1 antibody, and effector-silent anti-PD-1 antibody fragment; and, (ii) a second formulation comprising an effector-silent CTLA-4 blocking agent selected from the group consisting of an effector-silent anti-CTLA-4 antibody and an effector-silent anti-CTLA-4 antibody fragment.

The present invention further provides an anti-cancer combination therapy, which comprises administering to an individual in need of a cancer therapy a formulation comprising (i) a PD-1 blocking agent selected from the group consisting of an anti-PD-1 antibody having an $IgG_4$ or $IgG_2$ Fc domain, an effector-silent anti-PD-1 antibody, and effector-silent anti-PD-1 antibody fragment; and, (ii) an effector-silent CTLA-4 blocking agent selected from the group consisting of an effector-silent anti-CTLA-4 antibody and an effector-silent anti-CTLA-4 antibody fragment.

The present invention further provides anti-cancer combination therapies, which comprise, administering to an individual in need of a cancer therapy (i) a first formulation comprising a PD-L1 blocking agent selected from the group consisting of an anti-PD-L1 antibody having an $IgG_4$ or $IgG_2$ Fc domain, an effector-silent anti-PD-L1 antibody, and effector-silent anti-PD-L1 antibody fragment; and, (ii) a second formulation comprising an effector-silent CTLA-4 blocking agent selected from the group consisting of an effector-silent anti-CTLA-4 antibody and an effector-silent anti-CTLA-4 antibody fragment.

The present invention further provides an anti-cancer combination therapy, which comprises administering to an individual in need of a cancer therapy a formulation comprising (i) a PD-L1 blocking agent selected from the group consisting of an anti-PD-L1 antibody having an $IgG_4$ or $IgG_2$ Fc domain, an effector-silent anti-PD-L1 antibody, and an effector-silent anti-PD-L1 antibody fragment; and, (ii) an effector-silent CTLA-4 blocking agent selected from the group consisting of an effector-silent anti-CTLA-4 antibody and an effector-silent anti-CTLA-4 antibody fragment.

In more specific embodiments of the combination therapy, the effector-silent anti-CTLA-4 antibody comprises an $IgG_1$ Fc domain having (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N297A, L234A/L235A/D265A, L234A/L235A/P329G, L235E, D265A, E233A/L235A,S267E/L328F, S2339D/A330L/1332E, L235G/G236R, N297A/D356E/L358M, L234F/L235E/P331S/D365E/L358M, and D265A/N297G or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of L234A/L235A/D265A, L234A/L235A/P329G, L235E, D265A, E233A/L235A,S267E/L328F, S2339D/A330L/1332E, L235G/G236R, D356E/L358M, L234F/L235E/P331S/D365E/L358M, and D265A or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In particular embodiments of the combination therapy, the effector-silent anti-CTLA-4 antibody comprises an $IgG_2$ Fc domain having (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N297A/D265S, D265A, P329G/D265A/N297G, or V234A/G237A/P238S/H268A/V309L/A330S/P331S or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of N297A/D265S, D265A, P329G/D265A/N297G, or V234A/G237A/P238S/H268A/V309L/A330S/P331S or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In particular embodiments of the combination therapy, the effector-silent anti-CTLA-4 antibody comprises an $IgG_4$ Fc domain having an S228P amino acid substitution and further comprising (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N267A, P329G, and D265A/N297A or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of N267A, P329G, and D265A/N297A or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In a further embodiment of the combination therapy, the effector-silent anti-CTLA-4 antibody fragment, which lacks an Fc domain, is or comprises a single-chain variable fragment (scFv), an antigen binding fragment (Fab), or an antigen binding fragment dimer $F(ab')_2$.

In particular embodiments of the combination therapy, the effector-silent anti-CTLA-4 antibody or effector-silent anti-CTLA-4 antibody fragment comprises the three heavy chain (HC) complementarity determining regions (CDRs) and three light chain (LC) CDRs of an anti-CTLA-4 antibody selected from the group consisting of ipilimumab, tremelimumab, REGN4659, AGEN1884w, 8D2/8D2 (RE), 8D2/8D2 (RE)-Variant 1, 8D2H1L1, 8D2H1L1-Variant 1, 8D2H2L2, 8D2H2L2-Variant 1, 8D3H3L3, 8D2H2L15, 8D2H2L15-Variant 1, 8D2H2L17, and 8D2H2L17-Variant 1.

In particular embodiments of the combination therapy, the effector-silent anti-CTLA-4 antibody or effector-silent anti-CTLA-4 antibody fragment comprises the $V_H$ and $V_L$ of ipilimumab, the $V_H$ and $V_L$ of tremelimumab, the $V_H$ and $V_L$ of REGN4659, the $V_H$ and $V_L$ of AGEN1884w, the $V_H$ and $V_L$ of 8D2/8D2 (RE), the $V_H$ and $V_L$ of 8D2/8D2 (RE)-Variant 1, the $V_H$ and $V_L$ of 8D2H1L1, the $V_H$ and $V_L$ of 8D2H1L1-Variant 1, the $V_H$ and $V_L$ of 8D2H2L2, the $V_H$ and $V_L$ of 8D2H2L2-Variant 1, the $V_H$ and $V_L$ of 8D3H3L3, the $V_H$ and $V_L$ of 8D2H2L15, the $V_H$ and $V_L$ of 8D2H2L15-Variant 1, the $V_H$ and $V_L$ of 8D2H2L17, or the $V_H$ and $V_L$ of 8D2H2L17-Variant 1.

In particular embodiments, the effector-silent anti-CTLA-4 antibody or effector-silent anti-CTLA-4 antibody fragment comprises (i) a $V_H$ comprising the amino acid sequence set forth in SEQ ID NO:7 and a $V_L$ comprising the amino acid sequence set forth in SEQ ID NO: 8; (ii) a $V_H$ comprising the amino acid sequence set forth in SEQ ID NO:15 and a $V_L$ comprising the amino acid sequence set forth in SEQ ID NO:16; (iii) a $V_H$ comprising the amino acid sequence set forth in SEQ ID NO:95 and a $V_L$ comprising the amino acid sequence set forth in SEQ ID NO:96; or, (iv) a $V_H$ having the amino acid sequence set forth in SEQ ID NO:97 and a $V_L$ having the amino acid sequence set forth in SEQ ID NO:98.

In particular embodiments, the effector-silent anti-CTLA4 antibody or effector-silent anti-CTLA-4 antibody fragment comprises (i) a $V_H$ domain comprising the amino acid sequence set forth in SEQ ID NO:73 and a $V_L$ domain comprising the amino acid sequence set forth in SEQ ID NO:74; (ii) a $V_H$ domain comprising the amino acid sequence set forth in SEQ ID NO: 75 and a $V_L$ domain comprising the amino acid sequence set forth in SEQ ID NO:76; (iii) a $V_H$ domain comprising the amino acid sequence set forth in SEQ ID NO:77 and a $V_L$ domain comprising the amino acid sequence set forth in SEQ ID NO:78; (iv) a $V_H$ domain comprising the amino acid sequence set forth in SEQ ID NO:79 and a $V_L$ domain comprising the amino acid sequence set forth in SEQ ID NO:80; (v) a $V_H$ domain comprising the amino acid sequence set forth in SEQ ID NO:81 and a $V_L$ domain comprising the amino acid sequence set forth in SEQ ID NO:82; (vi) a $V_H$ domain comprising the amino acid sequence set forth in SEQ ID NO:83 and a $V_L$ domain comprising the amino acid sequence set forth in SEQ ID NO: 84; (vii) a $V_H$ domain comprising the amino acid sequence set forth in SEQ ID NO:85 and a $V_L$ domain comprising the amino acid sequence set forth in SEQ ID NO:86; (viii) a $V_H$ domain comprising the amino acid sequence set forth in SEQ ID NO:87 and a $V_L$ domain comprising the amino acid sequence set forth in SEQ ID NO:88; (ix) a $V_H$ domain comprising the amino acid sequence set forth in SEQ ID NO:89 and a $V_L$ domain comprising the amino acid sequence set forth in SEQ ID NO:90; (x) a $V_H$ domain comprising the amino acid sequence set forth in SEQ ID NO:91 and a $V_L$ domain comprising the amino acid sequence set forth in SEQ ID NO: 92; or (xi) a $V_H$ domain comprising the amino acid sequence set forth in SEQ ID NO:93 and a $V_L$ domain comprising the amino acid sequence set forth in SEQ ID NO:94.

In further embodiments of the combination therapy, the effector-silent CTLA-4 blocking agent is an effector-silent anti-CTLA-4 antibody selected from the effector-silent anti-CTLA-4 antibodies disclosed in Tables 4-18.

In a further embodiment of the combination therapy, the effector-silent CTLA-4 binding agent is an effector-silent anti-CTLA-4 antibody fragment that comprises one or more immunoglobulin single variable domains (ISVDs), each ISVD comprising the variable domain ($V_{HH}$) of a camelid heavy chain only antibody; with the proviso that none of the ISVDs comprises a $V_{HH}$ having a CDR1 comprising the amino sequence FYGMG (SEQ ID NO:69, a CDR2 comprising the amino acid sequence DIRTSAGRTTYADSVKG (SEQ ID NO:70), and a CDR3 comprising amino acid EMSGISGWDY (SEQ ID NO:71) or EPSGISGWDY (SEQ ID NO: 72) as those ISVDs are disclosed in International Patent Application WO2008071447, WO2017087587, and WO2017087588, or a $V_{HH}$ that comprises 1, 2, or 3 mutations in CDR3 as disclosed in WO2008071447, with the exception that ISVDs comprising said CDRs in embodiments wherein the one or more ISVDs are fused or linked to an effector-silent heterologous HC domain or Fc domain, including, for example, any one of the effector-silent antibody HC domains or Fc domains disclosed herein are not excluded by this proviso.

In particular embodiments of the combination therapy, the anti-PD-1 antibody or anti-PD-1 antibody fragment comprises the three heavy chain complementarity determining regions (CDRs) and three light chain CDRs of pembrolizumab, nivolumab, or cemiplimab-rwlc. In particular embodiments of the combination therapy, the anti-PD-1 antibody comprises (i) the $V_H$ and $V_L$ of pembrolizumab; (ii) the $V_H$ and $V_L$ of nivolumab; or, (iii) the $V_H$ and $V_L$ of cemiplimab-rwlc.

In further embodiments, the anti-PD-1 antibody or anti-PD-1 antibody fragment comprises (i) a $V_H$ having the amino acid sequence set forth in SEQ ID NO:29 and a $V_L$ having the amino acid sequence set forth in SEQ ID NO:30; (ii) a $V_H$ having the amino acid sequence set forth in SEQ ID NO:23 and a $V_L$ having the amino acid sequence set forth in SEQ ID NO: 24; or, (iii) a $V_H$ having the amino acid sequence set forth in SEQ ID NO:99 and a $V_L$ having the amino acid sequence set forth in SEQ ID NO: 100. In a further embodiment, the anti-PD1 antibody comprises (i) a HC having the amino acid sequence set forth in SEQ ID NO:27 and a LC having the amino acid sequence set forth in SEQ ID NO:28; (ii) an HC having the amino acid sequence set forth in SEQ ID NO:25 and a LC having the amino acid sequence set forth in SEQ ID NO:26; or (iii) an HC having the amino acid sequence set forth in SEQ ID NO: 101 and a LC having the amino acid sequence set forth in SEQ ID NO:102.

In particular embodiments of the combination therapy, the anti-PD-L1 antibody or anti-PD-L1 antibody fragment comprises (i) the $V_H$ and $V_L$ domains of atezolizumab; (ii) the $V_H$ and $V_L$ domains of avelumab; or, (iii) the $V_H$ and $V_L$ domains of durvalumab.

In further embodiments; the anti-PD-L1 antibody or anti-PD-L1 antibody fragment comprise (i) a $V_H$ domain comprising the amino acid sequence set forth in SEQ ID NO: 103 and a $V_L$ domain comprising the amino acid sequence set forth in SEQ ID NO:104; (ii) a $V_H$ domain comprising the amino acid sequence set forth in SEQ ID NO:105 and a $V_L$ domain comprising the amino acid sequence set forth in SEQ ID NO: 106; or, (iii) a $V_H$ domain comprising the amino acid sequence set forth in SEQ ID NO:107 and a $V_L$ domain comprising the amino acid sequence set forth in SEQ ID NO: 108.

In particular embodiments of the combination therapy, the anti-PD-1 or anti-PD-L1 antibody may comprise an $IgG_1$, $IgG_2$, or $IgG_4$ Fc domain as disclosed herein, which may comprise a C-terminal lysine or lack either a C-terminal lysine or a C-terminal glycine-lysine dipeptide.

In particular embodiments of the combination therapy, the anti-PD-1 or anti-PD-L1 antibody comprises (i) an $IgG_2$ or $IgG_4$ Fc domain; (ii) an $IgG_1$, $IgG_2$, or $IgG_4$ Fc domain comprising a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (iii) an $IgG_1$ Fc domain comprising N297A, L234A/L235A/D265A, L234A/L235A/P329G, L235E, D265A, E233A/L235A, L235G/G236R, S267E/L328F, S2339D/A330L/I332E, or D265A/N297G amino acid substitutions or the mutated Fc domain further comprising 1, 2, 3, 4, 5, 6, 7, 8, 9, or 10 additional amino acid substitutions, insertions, and/or deletions; (iv) an $IgG_2$ Fc domain comprising N297A/D265S, D265A, P329G/D265A/N297G, or V234A/G237A/P238S/H268A/V309L/A330S/P331S amino acid substitutions or the mutated Fc domain further comprising 1, 2, 3, 4, 5, 6, 7, 8, 9, or 10 additional amino acid substitutions, insertions, and/or deletions; or (v) an $IgG_4$ Fc domain comprising an S228P amino acid substitution and an N267A, P329G, or D265A/N297A amino acid substitution or the mutated Fc domain further comprising 1, 2, 3, 4, 5, 6, 7, 8, 9, or 10 additional amino acid substitutions, insertions, and/or deletions, wherein the amino acid positions are identified according to Eu numbering.

In particular embodiments of the combination therapy, the PD-1 blocking agent is an anti-PD-1 antibody selected from the anti-PD-1 antibodies disclosed in Tables 19-27 or an anti-PD-L1 antibody selected from the anti-PD-L1 antibodies disclosed in Tables 28-36.

In a further embodiment of the combination therapy, the anti-PD-1 antibody fragment or anti-PD-L1 antibody fragment, each of which lacks an Fc domain, is a single-chain variable fragment (scFv), an antigen binding fragment (Fab), or an antigen binding fragment dimer $F(ab')_2$.

In a further embodiment of the combination therapy, the anti-PD-1 or anti-PD-L1 antibody fragment comprises one or more ISVDs, each ISVD comprising the $V_{HH}$ of a camelid heavy chain only antibody.

In particular embodiments of the combination therapy, the CTLA-4 blocking agent is administered at a dose comprising about 1 mg/kg to about 3 mg/kg of the CTLA-4 blocking agent or a fixed dose of the CTLA-4 blocking agent that does not depend on the individual's weight and is greater than about 100 mg.

In particular embodiments of the combination therapy, the CTLA-4 blocking agent is administered at a dose comprising between 1 mg/kg and 3 mg/kg of the CTLA-4 blocking agent.

In particular embodiments of the combination therapy, the CTLA-4 blocking agent is administered at a dose comprising between 3 mg/kg to 10 mg/kg of the CTLA-4 blocking agent.

In particular embodiments of the combination therapy, the CTLA-4 blocking agent is administered at a dose comprising more than about 10 mg/kg of the CTLA-4 blocking agent.

In particular embodiments of the combination therapy, the PD-1 blocking agent is administered at a dose comprising about 2 or 3 mg/kg or more, or a fixed dose that does not depend on the individual's weight and is about 200 mg or more.

In particular embodiments of the combination therapy, the PD-1 blocking agent is administered at a dose that does not depend on the individual's weight that is between 200 mg and 400 mg.

In particular embodiments of the combination therapy, the PD-1 blocking agent is administered at a dose that does not depend on the individual's weight and is 400 mg.

In particular embodiments of the combination therapy, the PD-1 blocking agent is administered to the individual first and the CTLA-4 blocking agent is administered to the individual second or the CTLA-4 blocking agent is administered to the individual first and the PD-1 blocking agent is administered to the individual second. In a particular embodiment, the Pd-1 blocking agent and the CTLA-4 blocking agent are administered concurrently.

In particular embodiments of the combination therapy, the individual is administered a chemotherapy agent prior to, concurrent with, or subsequent to the combination therapy. In particular embodiments, the chemotherapy agent is selected from the group consisting of actinomycin, all-trans retinoic acid, alitretinoin, azacitidine, azathioprine, bexarotene, bleomycin, bortezomib, carmofur, carboplatin, capecitabine, cisplatin, chlorambucil, cyclophosphamide, cytarabine, dacarbazine, daunorubicin, docetaxel, doxifluridine, doxorubicin, epirubicin, epothilone, etoposide, fluorouracil, gemcitabin, hydroxyurea, idarubicin, imatinib, ixabepilone, irinotecan, mechlorethamine, melphalan, mercaptopurine, methotrexate, mitoxantrone, nitrosoureas, oxaliplatin, paclitaxel, pemetrexed, romidepsin, tegafur, temozolomide (oral dacarbazine), teniposide, tioguanine, topotecan, utidelone, valrubicin, vemurafenib, vinblastine, vincristine, vindesine, vinorelbine, and vorinostat.

In particular embodiments of the combination therapy, the cancer is melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In particular embodiments of the combination therapy, the cancer is pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

In particular embodiments of the combination therapy, the individual is a human, the CTLA-4 blocking agent binds a human CTLA-4, the PD-1 blocking agent binds a human PD-1, and the PD-L1 blocking agent binds a human PD-L1.

Antibodies and Compositions

The present invention further provides an effector-silent anti-CTLA-4 antibody or effector-silent anti-CTLA-4 antibody fragment, each comprising a $V_H$ and a $V_L$, wherein the $V_H$ comprises three heavy chain CDRs and the $V_L$ comprises three light chain CDRs, which together bind CTLA-4. In particular embodiments, the CTLA-4 is a human CTLA-4.

In more specific embodiments, the effector-silent anti-CTLA-4 antibody comprises an $IgG_1$ Fc domain having (i)

a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions with the proviso that the effector-silent anti-CTLA-4 antibody does not include ipilimumab consisting of solely an N297A substitution; (ii) an amino acid substitution mutation selected from the group consisting of N297A, L234A/L235A/D265A, L234A/L235A/P329G, L235E, D265A, E233A/L235A,S267E/L328F, S2339D/A330L/I332E, L235G/G236R, N297A/D356E/L358M, L234F/L235E/P331S/D365E/L358M, and D265A/N297G or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of L234A/L235A/D265A, L234A/L235A/P329G, L235E, D265A, E233A/L235A,S267E/L328F, S2339D/A330L/I332E, L235G/G236R, D356E/L358M, L234F/L235E/P331S/D365E/L358M, and D265A or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In particular embodiments, the effector-silent anti-CTLA-4 antibody comprises an IgG$_2$ Fc domain having (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N297A/D265S, D265A, P329G/D265A/N297G, or V234A/G237A/P238S/H268A/V309L/A330S/P331S or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of N297A/D265S, D265A, P329G/D265A/N297G, or V234A/G237A/P238S/H268A/V309L/A330S/P331S or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In particular embodiments, the effector-silent anti-CTLA-4 antibody comprises an IgG$_4$ Fc domain having an S228P amino acid substitution and further comprising (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N267A, P329G, and D265A/N297A or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of N267A, P329G, and D265A/N297A or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In particular embodiments, the effector-silent anti-CTLA-4 antibody or effector-silent anti-CTLA-4 antibody fragment comprises the three heavy chain (HC) complementarity determining regions (CDRs) and three light chain (LC) CDRs of an anti-CTLA-4 antibody selected from the group consisting of ipilimumab, tremelimumab, REGN4659, AGEN1884w, 8D2/8D2 (RE), 8D2H1L1, 8D2H2L2, 8D3H3L3, 8D2H2L15, and 8D2H2L17.

In particular embodiments, the effector-silent anti-CTLA-4 antibody or effector-silent anti-CTLA-4 antibody fragment comprises the $V_H$ and $V_L$ of ipilimumab, the $V_H$ and $V_L$ of tremelimumab, the $V_H$ and $V_L$ of REGN4659, the $V_H$ and $V_L$ of AGEN1884w, the $V_H$ and $V_L$ of 8D2/8D2 (RE), the $V_H$ and $V_L$ of 8D2H1L1, the $V_H$ and $V_L$ of 8D2H2L2, the $V_H$ and $V_L$ of 8D3H3L3, the $V_H$ and $V_L$ of 8D2H2L15, or the $V_H$ and $V_L$ of 8D2H2L17.

In particular embodiments, the effector-silent anti-CTLA-4 antibody or effector-silent anti-CTLA-4 antibody fragment comprises the $V_H$ and $V_L$ of 8D2/8D2 (RE)-Variant 1, the $V_H$ and $V_L$ of 8D2H1L1-Variant 1, the $V_H$ and $V_L$ of 8D2H2L2-Variant 1, the $V_H$ and $V_L$ of 8D2H2L15-Variant 1, or the $V_H$ and $V_L$ of 8D2H2L17-Variant 1. These variants comprise a substitution of isoleucine for the methionine at position 18 in the $V_H$ amino acid sequence.

In particular embodiments, the effector-silent anti-CTLA-4 antibody or anti-effector-silent CTLA-4 antibody fragment comprises either (i) a $V_H$ having the amino acid sequence set forth in SEQ ID NO:7 and a $V_L$ having the amino acid sequence set forth in SEQ ID NO: 8; (ii) a $V_H$ having the amino acid sequence set forth in SEQ ID NO: 15 and a $V_L$ having the amino acid sequence set forth in SEQ ID NO: 16; (iii) a $V_H$ having the amino acid sequence set forth in SEQ ID NO:95 and a $V_L$ having the amino acid sequence set forth in SEQ ID NO: 96; or, (iv) a $V_H$ having the amino acid sequence set forth in SEQ ID NO:97 and a $V_L$ having the amino acid sequence set forth in SEQ ID NO:98.

In particular embodiments, the effector-silent anti-CTLA4 antibody or effector-silent anti-CTLA-4 antibody fragment comprises either (i) a $V_H$ domain comprising the amino acid sequence set forth in SEQ ID NO:73 and a $V_L$ domain comprising the amino acid sequence set forth in SEQ ID NO:74; (ii) a $V_H$ domain comprising the amino acid sequence set forth in SEQ ID NO:75 and a $V_L$ domain comprising the amino acid sequence set forth in SEQ ID NO: 76; (iii) a $V_H$ domain comprising the amino acid sequence set forth in SEQ ID NO:77 and a $V_L$ domain comprising the amino acid sequence set forth in SEQ ID NO:78; (iv) a $V_H$ domain comprising the amino acid sequence set forth in SEQ ID NO:79 and a $V_L$ domain comprising the amino acid sequence set forth in SEQ ID NO:80; (v) a $V_H$ domain comprising the amino acid sequence set forth in SEQ ID NO:81 and a $V_L$ domain comprising the amino acid sequence set forth in SEQ ID NO:82; (vi) a $V_H$ domain comprising the amino acid sequence set forth in SEQ ID NO:83 and a $V_L$ domain comprising the amino acid sequence set forth in SEQ ID NO: 84; (vii) a $V_H$ domain comprising the amino acid sequence set forth in SEQ ID NO:85 and a $V_L$ domain comprising the amino acid sequence set forth in SEQ ID NO:86; (viii) a $V_H$ domain comprising the amino acid sequence set forth in SEQ ID NO:87 and a $V_L$ domain comprising the amino acid sequence set forth in SEQ ID NO:88; (ix) a $V_H$ domain comprising the amino acid sequence set forth in SEQ ID NO:89 and a $V_L$ domain comprising the amino acid sequence set forth in SEQ ID NO:90; (x) a $V_H$ domain comprising the amino acid sequence set forth in SEQ ID NO:91 and a $V_L$ domain comprising the amino acid sequence set forth in SEQ ID NO: 92; or (xi) a $V_H$ domain comprising the amino acid sequence set forth in SEQ ID NO:93 and a $V_L$ domain comprising the amino acid sequence set forth in SEQ ID NO:94.

In particular embodiments, the effector-silent anti-CTLA-4 antibody fragment is selected from the group consisting of F(ab), F(ab')2, Fv, and scFv.

In a further embodiment, the effector-silent anti-CTLA-4 antibody fragment comprises one or more immunoglobulin single variable domains (ISVDs), each ISVD comprising the variable domain ($V_{HH}$) of a camelid heavy chain only antibody; with the proviso that none of the ISVDs comprise a $V_{HH}$ that comprises a CDR1 comprising the amino sequence FYGMG (SEQ ID NO:69, a CDR2 comprising the amino acid sequence DIRTSAGRTTYADSVKG (SEQ ID NO:70), and a CDR3 comprising amino acid EMSGISGWDY (SEQ ID NO:71) or EPSGISGWDY (SEQ ID NO:72) as those ISVDs are disclosed in International Patent Application WO2008071447, WO2017087587, and WO2017087588, or a $V_{HH}$ that comprises 1, 2, or 3 mutations in CDR3 as disclosed in WO2008071447, with the exception that ISVDs comprising said CDRs in embodiments wherein the one or more ISVDs are fused or linked to an effector-silent heterologous HC domain or Fc domain, including, for example, any one of the effector-silent antibody HC domains or Fc domains disclosed herein are not excluded by this proviso.

The present invention further provides each of the effector-silent anti-CTLA-4 antibodies disclosed in Tables 4-18 with the proviso that the effector-silent anti-CTLA-4 antibody does not include ipilimumab consisting of solely an N297A substitution.

The present invention further provides a composition comprising an effector-silent anti-CTLA-4 antibody or effector-silent anti-CTLA-4 antibody fragment as disclosed herein and a pharmaceutically acceptable carrier.

The present invention further provides an anti-PD-1 antibody comprising
(a) a heavy chain (HC) having a HC variable domain ($V_H$) and a light chain (LC) having a LC variable domain ($V_L$), wherein (i) the $V_H$ comprises at least the three HC-complementarity determining regions (CDRs) of pembrolizumab and the $V_L$ comprises at least the three LC-CDRs of pembrolizumab, (ii) the $V_H$ comprises at least the three HC-CDRs of nivolumab and the $V_L$ comprises at least the three LC-CDRs of nivolumab, or (iii) the $V_H$ comprises at least the three HC-CDRs of cemiplimab-rwlc and the $V_L$ comprises at least the three LC-CDRs of cemiplimab-rwlc, and
(b) an $IgG_1$, $IgG_2$, or $IgG_4$ Fc domain comprising (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an $IgG_1$ Fc domain comprising N297A, L234A/L235A/D265A, L234A/L235A/P329G, L235E, D265A, E233A/L235A, N297A/D356E/L358M, L234F/L235E/P331S/D356E/L358M, or D265A/N297G amino acid substitutions or the mutated Fc domain further comprising 1, 2, 3, 4, 5, 6, 7, 8, 9, or additional amino acid substitutions, insertions, and/or deletions; (iii) an $IgG_2$ Fc domain comprising N297A/D265S, D265A, P329G/D265A/N297G, or V234A/G237A/P238S/H268A/V309L/A330S/P331S amino acid substitutions or the mutated Fc domain further comprising 1, 2, 3, 4, 5, 6, 7, 8, 9, or 10 additional amino acid substitutions, insertions, and/or deletions; or (iv) an $IgG_4$ Fc domain comprising an S228P amino acid substitution and an N267A, P329G, D265A/N297A amino acid substitution or the mutated Fc domain further comprising 1, 2, 3, 4, 5, 6, 7, 8, 9, or 10 additional amino acid substitutions, insertions, and/or deletions, wherein the amino acid positions are identified according to Eu numbering.

In further still embodiments of the anti-PD-1 antibody above, the anti-PD-1 antibody comprises either (i) a $V_H$ having the amino acid sequence set forth in SEQ ID NO:29 and a $V_L$ having the amino acid sequence set forth in SEQ ID NO:30, (ii) a $V_H$ having the amino acid sequence set forth in SEQ ID NO:23 and a $V_L$ having the amino acid sequence set forth in SEQ ID NO:24, or (iii) a $V_H$ having the amino acid sequence set forth in SEQ ID NO:99 and a $V_L$ having the amino acid sequence set forth in SEQ ID NO:100.

In particular embodiments of the anti-PD-1 antibody, the $IgG_1$, $IgG_2$, or $IgG_4$ Fc domain as disclosed herein may further comprise a C-terminal lysine or lack either a C-terminal lysine or a C-terminal glycine-lysine dipeptide.

The present invention further provides an anti-PD-1 antibody fragment comprising a heavy chain (HC) having a HC variable domain ($V_H$) and a light chain (LC) having a LC variable domain ($V_L$), wherein (i) the $V_H$ comprises at least the three HC-complementarity determining regions (CDRs) of pembrolizumab and the $V_L$ comprises at least the three LC-CDRs of pembrolizumab, (ii) the $V_H$ comprises at least the three HC-CDRs of nivolumab and the $V_L$ comprises at least the three LC-CDRs of nivolumab, or (iii) the $V_H$ comprises at least the three HC-CDRs of cemiplimab-rwlc and the $V_L$ comprises at least the three LC-CDRs of cemiplimab-rwlc.

In further still embodiments of the anti-PD-1 antibody fragment, the anti-PD-1 antibody fragment comprises either (i) a $V_H$ having the amino acid sequence set forth in SEQ ID NO: 29 and a $V_L$ having the amino acid sequence set forth in SEQ ID NO:30, (ii) a $V_H$ having the amino acid sequence set forth in SEQ ID NO:23 and a $V_L$ having the amino acid sequence set forth in SEQ ID NO:24, or (iii) a $V_H$ having the amino acid sequence set forth in SEQ ID NO: 99 and a $V_L$ having the amino acid sequence set forth in SEQ ID NO:100.

In particular embodiments of the above anti-PD-1 antibody fragments, the anti-PD-1 antibody fragment is selected from the group consisting of F(ab), F(ab')$_2$, Fv, and scFv.

The present invention further provides each of the anti-PD-1 antibodies disclosed in Tables 19-27.

The present invention further provides a composition comprising an anti-PD-1 antibody or anti-PD-1 antibody fragment as disclosed herein and a pharmaceutically acceptable carrier.

The present invention further provides an anti-PD-L1 antibody comprising (a) a heavy chain (HC) having a HC variable domain ($V_H$) and a light chain (LC) having a LC variable domain ($V_L$), wherein (i) the $V_H$ comprises at least the three HC-complementarity determining regions (CDRs) of durvalumab and the $V_L$ comprises at least the three LC-CDRs of durvalumab, (ii) the $V_H$ comprises at least the three HC-CDRs of avelumab and the $V_L$ comprises at least the three LC-CDRs of avelumab, or (iii) the $V_H$ comprises at least the three HC-CDRs of atezolizumab and the $V_L$ comprises at least the three LC-CDRs of atezolizumab, and (b) an IgG$_1$, IgG$_2$, or IgG$_4$ Fc domain comprising (i) a mutation in the N-glycosylation site Asn-Xaa-Ser/Thr beginning at amino acid position 297 that abolishes N-glycosylation at said N-glycosylation site or the mutated Fc domain comprising 1, 2, 3, 4, 5, 6, 7, 8, 9, or 10 additional amino acid substitutions, insertions, and/or deletions; (ii) an IgG$_1$ Fc domain comprising N297A, L234A/L235A/D265A, L234A/L235A/P329G, L235E, D265A, E233A/L235A, N297A/D356E/L358M, L234F/L235E/P331S/D356E/L358M, or D265A/N297G amino acid substitutions or the mutated Fc domain comprising 1, 2, 3, 4, 5, 6, 7, 8, 9, or 10 additional amino acid substitutions, insertions, and/or deletions; (iii) an IgG$_2$ Fc domain comprising N297A/D265S, D265A, P329G/D265A/N297G, or V234A/G237A/P238S/H268A/V309L/A330S/P331S amino acid substitutions or the mutated Fc domain comprising 1, 2, 3, 4, 5, 6, 7, 8, 9, or 10 additional amino acid substitutions, insertions, and/or deletions; or (iv) an IgG$_4$ Fc domain comprising an S228P amino acid substitution and an N267A, P329G, D265A/N297A amino acid substitution or the mutated Fc domain comprising 1, 2, 3, 4, 5, 6, 7, 8, 9, or 10 additional amino acid substitutions, insertions, and/or deletions, wherein the amino acid positions are identified according to Eu numbering, with the proviso that when the $V_H$ and $V_L$ have the amino acid sequences of SEQ ID NO: 107 and SEQ ID NO:108, respectively, then the heavy chain (HC) constant domain is not an IgG$_1$ isotype with N297A/D356E/L358M combination of substitutions or when the $V_H$ and $V_L$ have the amino acid sequences of SEQ ID NO:103 and SEQ ID NO: 104, respectively, then the HC constant domain is not an IgG$_1$ isotype with L234F/L235E/P331S/D356E/L358M combination of substitutions.

In further still embodiments of the anti-PD-L1 antibody above, the anti-PD-L1 antibody comprises either (i) a $V_H$ having the amino acid sequence set forth in SEQ ID NO:103 and a $V_L$ having the amino acid sequence set forth in SEQ ID NO:104, (ii) a $V_H$ having the amino acid sequence set forth in SEQ ID NO:105 and a $V_L$ having the amino acid sequence set forth in SEQ ID NO:106, or (iii) a $V_H$ having the amino acid sequence set forth in SEQ ID NO: 107 and a $V_L$ having the amino acid sequence set forth in SEQ ID NO:108.

In particular embodiments of the anti-PD-L1 antibody, the IgG$_1$, IgG$_2$, or IgG$_4$ Fc domain as disclosed herein may further comprise a C-terminal lysine or lack either a C-terminal lysine or C-terminal glycine-lysine dipeptide.

The present invention further provides an anti-PD-L1 antibody fragment comprising a heavy chain (HC) having a HC variable domain ($V_H$) and a light chain (LC) having a LC variable domain ($V_L$), wherein (i) the $V_H$ comprises at least the three HC-complementarity determining regions (CDRs) of durvalumab and the $V_L$ comprises at least the three LC-CDRs of durvalumab, (ii) the $V_H$ comprises at least the three HC-CDRs of avelumab and the $V_L$ comprises at least the three LC-CDRs of avelumab, or (iii) the $V_H$ comprises at least the three HC-CDRs of atezolizumab and the $V_L$ comprises at least the three LC-CDRs of atezolizumab.

In further still embodiments, the anti-PD-L1 antibody fragment comprises either (i) a $V_H$ having the amino acid sequence set forth in SEQ ID NO:103 and a $V_L$ having the amino acid sequence set forth in SEQ ID NO:104, (ii) a $V_H$ having the amino acid sequence set forth in SEQ ID NO:105 and a $V_L$ having the amino acid sequence set forth in SEQ ID NO:106, or (iii) a $V_H$ having the amino acid sequence set forth in SEQ ID NO: 107 and a $V_L$ having the amino acid sequence set forth in SEQ ID NO:108.

In particular embodiments of the above anti-PD-L1 antibody fragments, the anti-PD-1 antibody fragment is selected from the group consisting of F(ab), F(ab')$_2$, Fv, and scFv.

The present invention further provides each of the anti-PD-L1 antibodies disclosed in Tables 28-36 with the proviso that when the $V_H$ and $V_L$ have the amino acid sequences of SEQ ID NO: 107 and SEQ ID NO: 108, respectively, then the heavy chain (HC) constant domain is not an IgG$_1$ isotype with N297A/D356E/L358M combination of substitutions or when the $V_H$ and $V_L$ have the amino acid sequences of SEQ ID NO:103 and SEQ ID NO: 104, respectively, then the HC constant domain is not an IgG$_1$ isotype with L234F/L235E/P331S/D356E/L358M combination of substitutions.

The present invention further provides a composition comprising an anti-PD-L1 antibody or anti-PD-L1 antibody fragment disclosed herein and a pharmaceutically acceptable carrier.

The present invention further provides a composition comprising (i) an anti-CTLA-4 antibody disclosed herein and an anti-PD-1 antibody disclosed herein and a pharmaceutically acceptable carrier; or (ii) an anti-CTLA-4 antibody disclosed herein and an anti-PD-L1 antibody disclosed herein and a pharmaceutically acceptable carrier.

The present invention further provides a composition comprising (i) an anti-CTLA-4 antibody fragment disclosed herein and an anti-PD-1 antibody disclosed herein and a pharmaceutically acceptable carrier or (ii) an anti-CTLA-4 antibody fragment disclosed herein and an anti-PD-L1 antibody disclosed herein and a pharmaceutically acceptable carrier.

The present invention further provides a composition comprising (i) an anti-CTLA-4 antibody fragment disclosed herein and an anti-PD-1 antibody fragment disclosed herein and a pharmaceutically acceptable carrier or (ii) an anti-CTLA-4 antibody fragment disclosed herein and an anti-PD-L1 antibody fragment disclosed herein and a pharmaceutically acceptable carrier.

The present invention further provides a composition comprising (i) an anti-CTLA-4 antibody disclosed herein and an anti-PD-1 antibody fragment disclosed herein and a pharmaceutically acceptable carrier or (ii) an anti-CTLA-4 antibody disclosed herein and an anti-PD-L1 antibody fragment disclosed herein and a pharmaceutically acceptable carrier.

The present invention further provides any one of the anti-CTLA-4, anti-PD-1, or anti-PD-L1 antibodies or compositions as disclosed herein for the treatment of cancer in an individual or for the preparation of a medicament for the treatment of cancer in an individual.

The present invention further provides any one of the anti-CTLA-4, anti-PD-1, or anti-PD-L1 antibody fragments or compositions as disclosed herein for the treatment of cancer in an individual or for the preparation of a medicament for the treatment of cancer in an individual.

In particular embodiments, the cancer is melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In particular embodiments, the cancer is pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

BRIEF DESCRIPTION OF THE DRAWINGS

FIG. 1A: Gut inflammatory gene expression profiling following administration of an Fc-competent anti-CTLA-4 antibody (α-CTLA4) or effector-silent anti-CTLA-4 antibody have a D265A substitution (α-CTLA4 (D265S)). After seven weeks of twice weekly treatment, the proximal small intestine was collected for evaluation of gut inflammatory markers by reverse transcription-quantitative polymerase chain reaction (PCR). A heat map of the fold change in expression of gut inflammatory genes for the two antibodies compared to isotype control treatment is shown. Expression was analyzed in multiple panels and cycle threshold data was normalized to ubiquitin within each panel. Normalized data from genes analyzed as part of multiple panels were averaged prior to determining the fold change over isotype control. FIG. 1B: weight loss over the time of the experiment. FIG. 1C: Intestinal permeability was assessed by measuring FITC-dextran fluorescence in the serum at day 49 and 50. FIG. 1D: histologic findings for relative gut inflammation and severity of colitis were examined and scored by a certified pathologist. FIG. 1E: representative photomicrographs of hematoxylin and eosin (H & E) stained histological sections of the colon from day 55.

FIG. 2A: comparison of the effector-silent CTLA4 ISVD (CTLA4 nAb) to effector-competent α-CTLA4; FIG. 2B: splenic activated T cells were cultured three days in the presence of CLTA4 nAb or α-CTLA4 as indicated. Proliferation (FIG. 2C), production of IFNγ (FIG. 2D), and IL-2 (FIG. 22E) were measured and plotted as fold change over the isotype control (mouse IgG$_{2a}$). Data are representative of two-three independent experiment.

FIG. 3A: CT26 tumor-bearing mice received a dose of the indicated antibody (α-CTLA4, a-PD1, α-CTLA4 (D265A)) at 20 mpk and/or CTLA4 nAb at 30 mpk every four days for five doses when tumors reached an average size of 100 mm$^3$ (ranges 78-125 mm$^3$). Data shows the mean tumor volume over a 32 day period. Results are representative of two independent experiments (n=10 mice per group); FIG. 3B: CD8 T cells/Foxp3+ Treg ratio in the tumor at day one post treatment as indicated. Results are representative of two independent experiments (n=7 mice per group); FIG. 3C and FIG. 3D: Gene expression profile from whole tumor at day eight post treatment. Results are representative of one or two independent experiments (n=5 mice per group). * p<0.05, p<0.01, *p<0.001 (Unpaired-t test). Error bar±SEM.

FIG. 4A: weight loss over the time of the experiment; FIG. 4B: histological assessment of enteritis in proximal jujenum at day 55; FIG. 4C: photomicrographs of H&E stained histological section of the colon; FIG. 4D: shows a heat map of the fold change in expression of gut inflammatory genes for indicated samples compared to isotype control treatment is shown. Expression was analyzed in multiple panels and cycle threshold data was normalized to ubiquitin within each panel. Normalized data from genes analyzed as part of multiple panels was averaged prior to determined fold change over isotype control.

FIG. 5A: Photomicrographs of H&E stained histological section of the ear skin. FIG. 5B: Absolute number of ear skin IL-17-producing T cells, Foxp3+ Treg cells and neutrophils were measured by flow cytometry. FIG. 5C: photomicrographs of H & E stained histological section of the kidney (top panel), liver (middle panel) and lung (bottom panel). Results are representative of one out two independent experiments (n=4-8 mice per group). Scale bars represent 100 µm. Error bar±SEM.

FIG. 6A: intracellular CTLA-4 staining in CT26-tumor bearing mice in indicated organs. FIG. 6B: mean Fluorescence Intensity (MFI) of CTLA-4 on Foxp3+ Treg cells. p<0.01, p<0.001 (Paired-t test). FIG. 6C and FIG. 6D: Representative dot plot and statistics of colon lamina propria and CT26 tumor infiltrating Foxp3+ Treg 24 hours after treatment as indicated. Data are representative of two to four independent experiments (n=4-12 mice per group) p<0.01, ***p<0.001 (Unpaired-t test). Error bar±SEM.

FIG. 7A: weight loss over the time of the experiment. FIG. 7B: photomicrographs of H&E stained histological section of the colon and FIG. 7C: pathology score at day 47 (n=14-18 mice per group). FIG. 7D: gene expression profile of the whole colon at day 47 post naïve T cell transfer (n=6 mice per group). Data are representative of 1 out 2 independent experiments. Ns=Not Significant ****p<0.0001 (Unpaired-t test). Error bar±SEM.

FIGS. 8A-8E: FcγR engagement and CTLA-4 blockade activate colon macrophages. FIG. 8A and FIG. 8B: CD16/CD32 surface expression on macrophages isolated from spleen, colon lamina propria and tumor from CT26-bearing mice, was assessed by flow cytometry. FIG. 8C: proportion of macrophages (CD45+CD11b+F4/80+) in the spleen, colon lamina propria and tumor from CT26-bearing mice, was assessed by flow cytometry. FIG. 8D: Il1b, Tnfα, Ifnγ and Stat1 mRNA expression was assessed from the colon of mice treated with α-CTLA4, α-CTLA4 (D265A), or CTLA4 nAb at day 0, 10, and 18 post-treatment. Data are representative of two independent experiments (n=8-10 mice per group). ns=not significant, p<0.01, *p<0.001 (Paired-t test). Error bar±SEM. FIG. 8E: Proportion of colon lamina propria IL-17-producing CD4+ T cells (CD45+ TCRb+CD4+CD8a-IL-17A+), absolute number of IFNγ-producing CD8a+ T cells (CD45+ TCRb+CD4-CD8a+

IFNγ+) and Neutrophils (CD45+CD11b+Ly6G$^{high}$) were measured by flow cytometry. Results are representative of 1 out 2 independent experiments (n=4-8 mice per group). **p<0.01 (Unpaired-t test). Scale bars represent 100 μm Error bar±SEM.

Figure 9A:
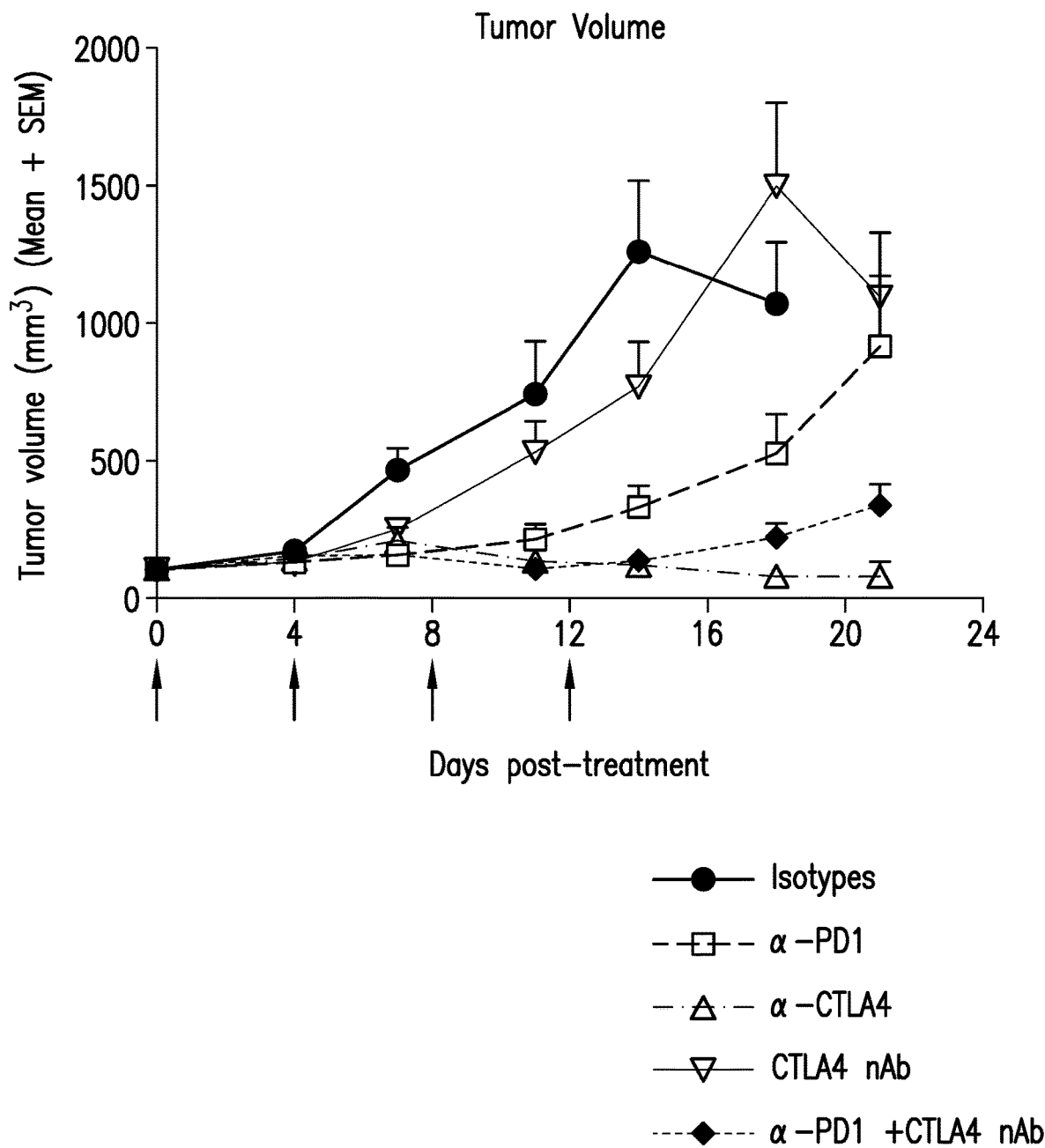
Figure 9B:
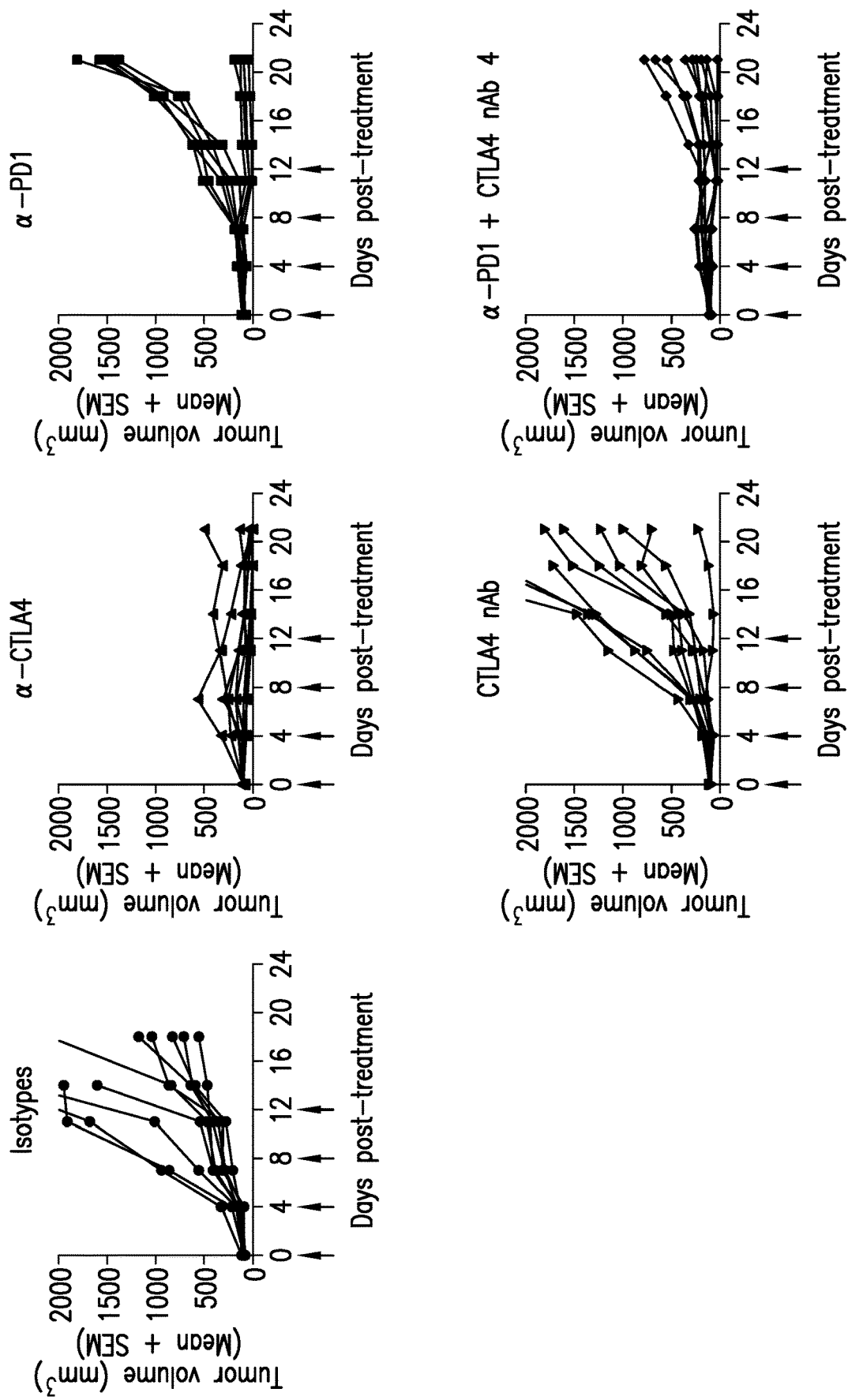

FIGS. 9A-9B: Anti-tumor Efficacy in the Mouse Syngeneic MB49 Bladder Tumor Model Study. FIG. 9A: MB49 tumor-bearing mice received a dose of the indicated antibody (30 mg/kg CTLA-4 nAb, 10 mg/kg α-CTLA-4, 5 mg/kg a-PD1, or combination of CTLA4 nAb and a-PD-1) every four days for four doses when tumors reached an average size of 102 mm$^3$ (ranges 87-117 mm$^3$). Data shows the mean tumor volume over a 21 day period. Results are representative of two independent experiments (n=10 mice per group). FIG. 9B: shows the individual animal tumor volumes for each treatment group. Complete responses (CR) through day 21 are presented for responsive treatment groups. Data show results from an experiment with n=10 mice per group.

Figure 10A:
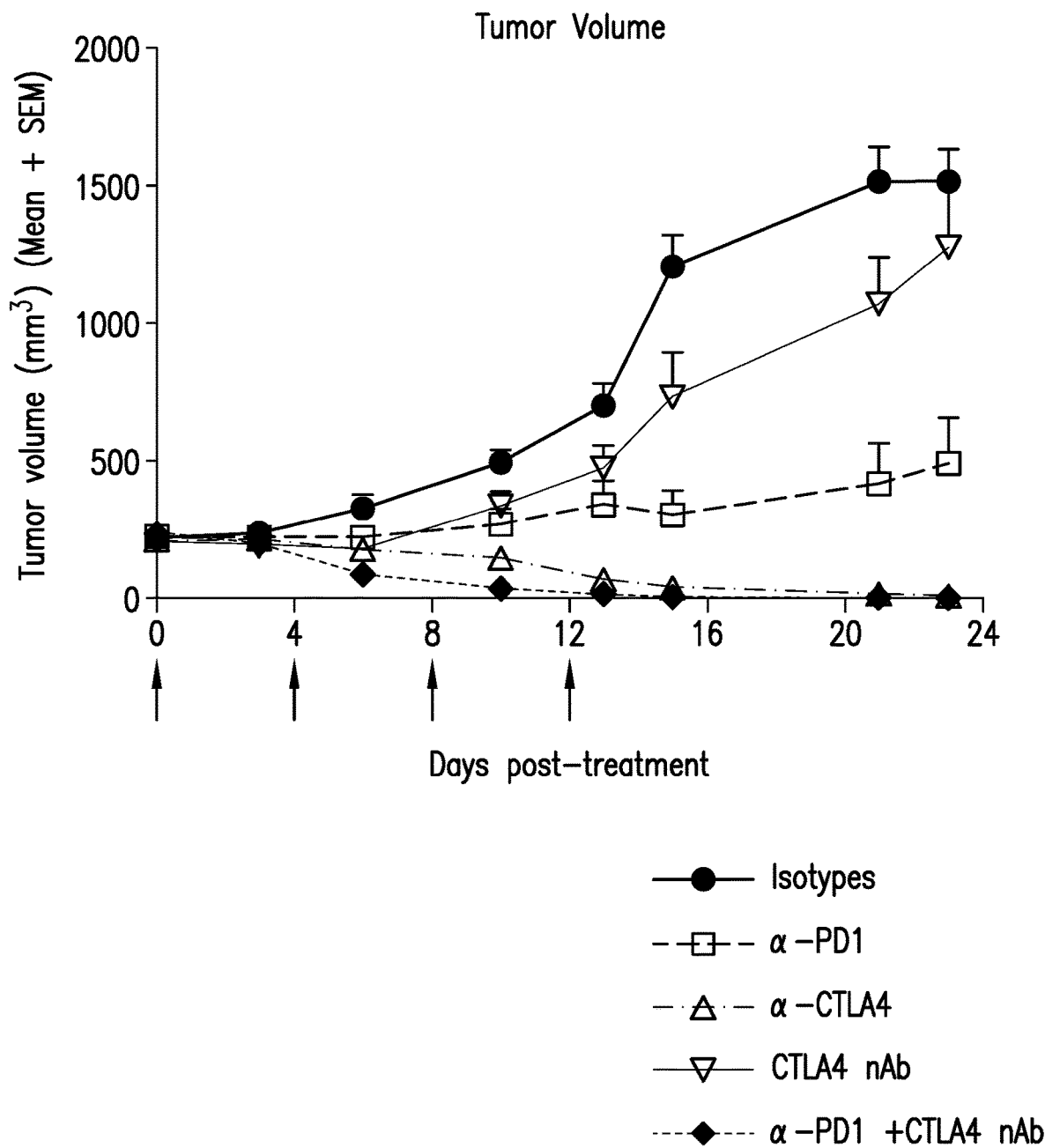
Figure 10B:
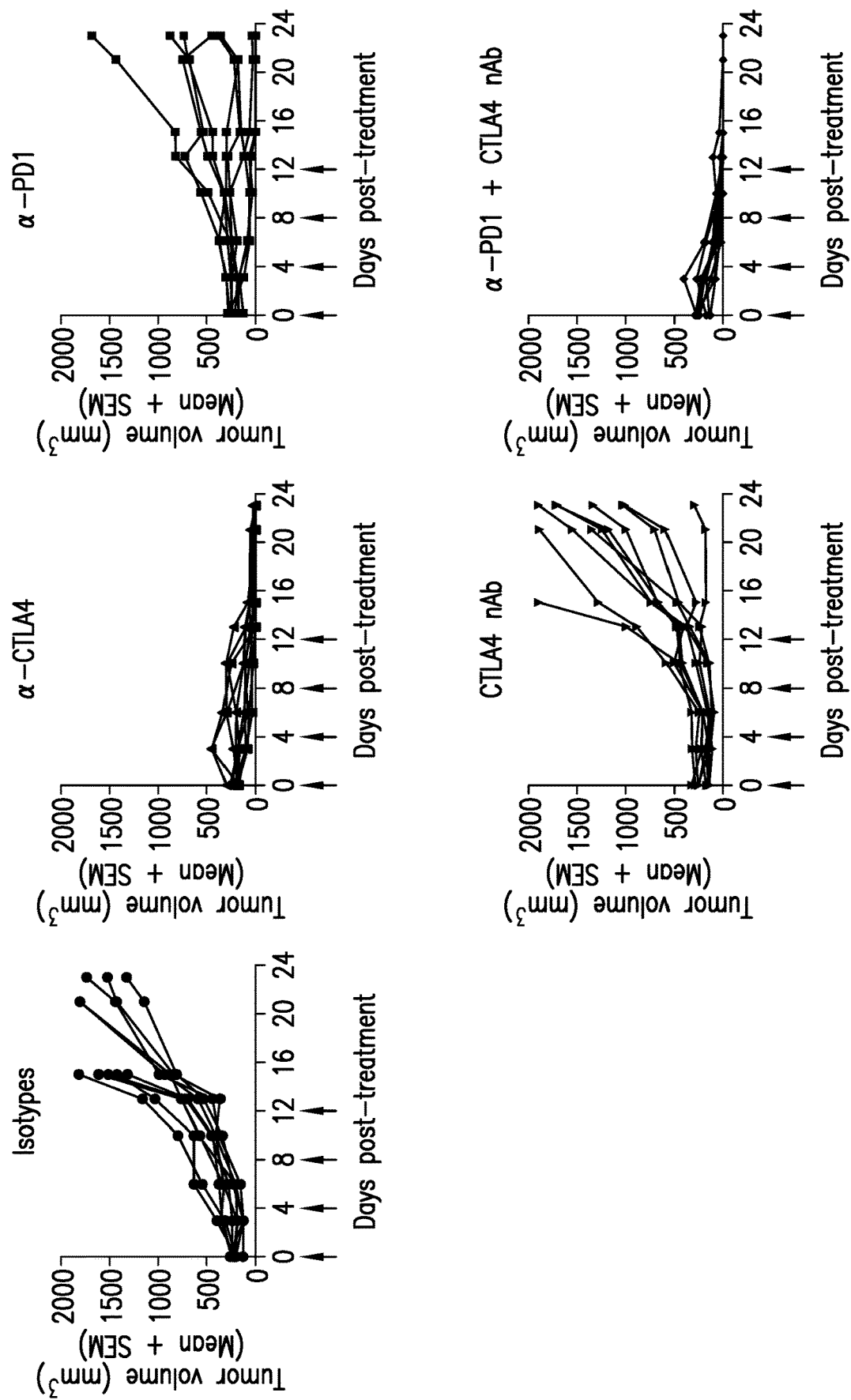

FIGS. 10A-10B: Anti-tumor Efficacy in the Mouse Syngeneic MC38 Colon Tumor Model Study. FIG. 10A: MC38 tumor-bearing mice received a dose of the indicated antibody (30 mg/kg CTLA-4 nAb, 10 mg/kg α-CTLA4, 5 mg/kg a-PD1, or combination of CTLA4 nAb and a-PD-1) every four days for four doses when tumors reached an average size of 220 mm$^3$ (ranges 179-261 mm$^3$). Data shows the mean tumor volume over a 23 day period. Results are representative of two independent experiments (n=10 mice per group). FIG. 10B: shows the individual animal tumor volumes for each treatment group. Complete responses (CR) through day 23 23 are presented for responsive treatment groups. Data show results from an experiment with n=10 mice per group.

Figure 11:
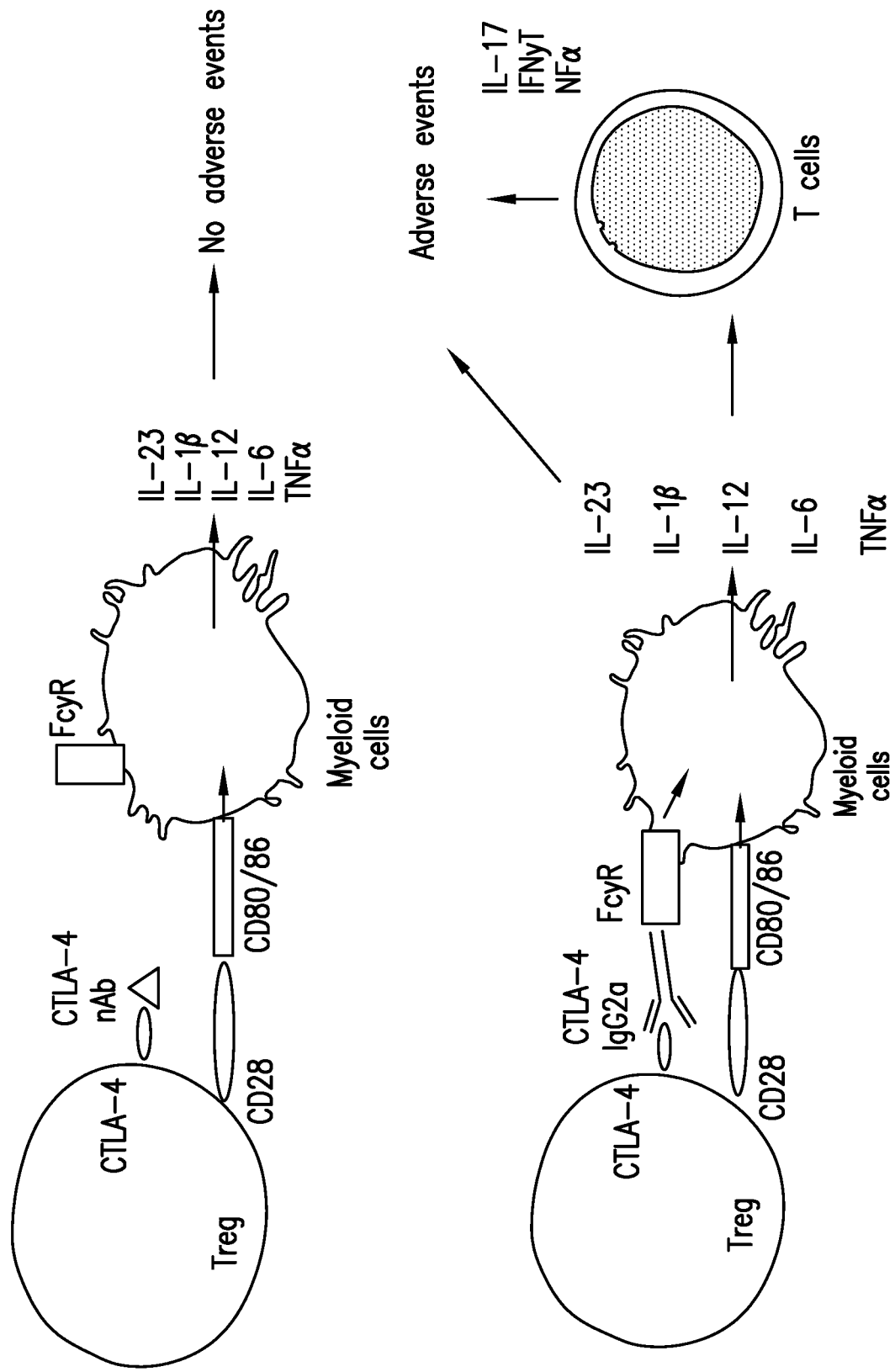

FIG. 11: Induction of gut inflammation by effector cells. A cartoon illustrating Fc-mediated induction of gut inflammation can be induced by Effector T cells, independent of Treg depletion.

DETAILED DESCRIPTION OF THE INVENTION

Definitions

"Adverse event" or "AE" as used herein is set forth in Common Terminology Criteria for Adverse events (CTCAE) Version 5.0, published Nov. 27, 2017, by the U.S. Department of health and Human Services as any unfavorable and unintended sign (including an abnormal laboratory finding), symptom, or disease temporally associated with the use of a medical treatment with the use of a medical treatment or procedure in a human individual that may or may not be considered related to the medical treatment or procedure. An AE is a term that is a unique representation of a specific event used for medical documentation and scientific analyses. A medical treatment may have one or more associated AEs and each AE may have the same or different level of severity. The severity of an AE is assigned a Grade. The CTCAE displays Grades 1 through 5 with unique clinical descriptions of severity for each AE based on this general guideline: Grade 1, mild, or asymptomatic or mild symptoms, clinical or diagnostic observations only, or intervention not indicated; Grade 2, moderate, or minimal, local or noninvasive intervention indicated, or limiting age-appropriate instrumental activities of daily living (ADL); Grade 3, severe or medically significant but not immediately life-threatening, or hospitalization or prolongation of hospitalization indicated, or disabling, or limiting self-care (ADL); Grade 4, life-threatening consequences or urgent intervention indicated; and Grade 5, death related to AE.

"Antibody" as used herein refers to a glycoprotein comprising either (a) at least two heavy chains (HCs) and two light chains (LCs) inter-connected by disulfide bonds, or (b) in the case of a species of camelid antibody, at least two heavy chains (HCs) inter-connected by disulfide bonds. Each HC is comprised of a heavy chain variable region or domain (V$_H$) and a heavy chain constant region or domain. In certain naturally occurring IgG, IgD and IgA antibodies, the heavy chain constant region is comprised of three domains, C$_H$1, C$_H$2 and C$_H$3. In general, the basic antibody structural unit for antibodies is a tetramer comprising two HC/LC pairs, except for the species of camelid antibodies comprising only two HCs, in which case the structural unit is a homodimer. Each tetramer includes two identical pairs of polypeptide chains, each pair having one LC (about 25 kDa) and HC chain (about 50-70 kDa).

In certain naturally occurring antibodies, each light chain is comprised of an LC variable region or domain (V$_L$) and a LC constant domain. The LC constant domain is comprised of one domain, CL. The human V$_H$ includes six family members: V$_H$1, V$_H$2, V$_H$3, V$_H$4, V$_H$5, and V$_H$6; and the human V$_L$ includes 16 family members: V$_κ$1, V$_κ$2, V$_κ$3, V$_κ$4, V$_κ$5, V$_κ$6, V$_λ$1, V$_λ$2, V$_λ$3, V$_λ$4, V$_λ$5, V$_λ$6, V$_λ$7, V18, V19, and V210. Each of these family members can be further divided into particular subtypes. The V$_H$ and V$_L$ domains can be further subdivided into regions of hypervariability, termed complementarity determining regions (CDRs), interspersed with regions that are more conserved, termed framework regions (FR). Each V$_H$ and V$_L$ is composed of three CDR regions and four FR regions, arranged from amino-terminus to carboxy-terminus in the following order: FR1, CDR1, FR2, CDR2, FR3, CDR3, FR4.

The variable regions of the heavy and light chains contain a binding domain comprising the CDRs that interacts with an antigen. The constant regions of the antibodies may mediate the binding of the immunoglobulin to host tissues or factors, including various cells of the immune system (e.g., effector cells) and the first component (C1q) of the classical complement system. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

Typically, the numbering of the amino acids in the heavy chain constant domain begins with number 118, which is in accordance with the Eu numbering scheme. The Eu numbering scheme is based upon the amino acid sequence of human IgG1 (Eu), which has a constant domain that begins at amino acid position 118 of the amino acid sequence of the IgG1 described in Edelman et al., Proc. Natl. Acad. Sci. USA. 63:78-85 (1969), and is shown for the IgG1, IgG2, IgG3, and IgG4 constant domains in Béranger, et al., Ed. Ginetoux, Correspondence between the IMGT unique numbering for C-DOMAIN, the IMGT exon numbering, the Eu and Kabat numberings: Human IGHG, Created: 17/05/2001, Version: Aug. 6, 2016, which is accessible at www.imgt.org/IMGTScientificChart.

In general, while a VH/VL pair of an antibody comprises six CDRs, three CDRs on the VH and three CDRs on the VL, the state of the art recognizes that in most cases, the CDR3 region of the heavy chain is the primary determinant of antibody specificity, and examples of specific antibody generation based on CDR3 of the heavy chain alone are known in the art (e.g., Beiboer et al., J. Mol. Biol. 296:833-849 (2000); Klimka et al., British J. Cancer 83:252-260 (2000); Rader et al., Proc. Natl. Acad. Sci. USA 95:8910-8915 (1998); Xu et al., Immunity 13:37-45 (2000). See Kabat et al. Sequences of Proteins of Immunological Interest, 5th Ed. Public Health Service, National Institutes of Health, Bethesda, Md. (1991) (defining the CDR regions of an antibody by sequence); see also Chothia & Lesk J. Mol. Biol. 196:901-917 (1987) (defining the CDR regions of an antibody by structure).

The following general rules disclosed in www.bioinf.org.uk: Prof. Andrew C. R. Martin's Group and reproduced in the table below may be used to identify the CDRs in an antibody sequence that comprise those amino acids that specifically interact with the amino acids comprising the epitope in the antigen to which the antibody binds. There are rare examples where these generally constant features do not occur; however, the Cys residues are the most conserved feature.

TABLE 1

| | |
|---|---|
| Light chain CDR1 | |
| Start | About amino acid residue 24 |
| Residue before | Usually a Cys |
| Residue after | Usually a Trp. Typically Trp-Tyr-Gln, but also, Trp-Leu-Gln, Trp-Phe-Gln, or Trp-Tyr-Leu |
| Length | 10 to 17 amino acid residues |
| Light chain CDR2 | |
| Start | Usually 16 amino acid residues after the end of CDR1 |
| Residues before | Generally Ile-Tyr, but also, Val-Tyr, Ile-Lys, or Ile-Phe |
| Length | Usually seven amino acid residues |
| Light chain CDR3 | |
| Start | Usually 33 amino acid residues after end of CDR2 |
| Residue before | Usually Cys |
| Residues after | Usually Phe-Gly-Xaa-Gly (SEQ ID NO: 65) |
| Length | Seven to 11 amino acid residues |
| Heavy chain CDR1 | |
| Start | About amino acid residue 26 (usually four amino acid residues after a Cys) [Chothia/AbM definition]; Kabat definition starts five amino acid residues later |
| Residues before | Usually Cys-Xaa-Xaa-Xaa (SEQ ID NO: 66) |
| Residues after | Usually a Trp. Typically Trp-Val, but also, Trp-Ile or Trp-Ala |
| Length | 10 to 12 amino acid residues [AbM definition]; Chothia definition excludes the last four amino acid residues |
| Heavy chain CDR2 | |
| Start | Usually 15 amino acid residues after the end of Kabat/AbM definition) of heavy chain CDR1 |
| Residues before | Typically Leu-Glu-Trp-Ile-Gly (SEQ ID NO: 67), but a number of variations |
| Residues after | Lys/Arg-Leu/Ile/Val/Phe/Thr/Ala-Thr/Ser/Ile/Ala |
| Length | Kabat definition 16 to 19 amino acid residues; AbM (and recent Chothia) definition ends seven amino acid residues earlier |
| Heavy chain CDR3 | |
| Start | Usually 33 amino acid residues after end of heavy chain CDR2 (usually two amino acid residues after a Cys) |
| Residues before | Usually Cys-Xaa-Xaa (typically Cys-Ala-Arg) |
| Residues after | Usually Trp-Gly-Xaa-Gly (SEQ ID NO: 68) |
| Length | Three to 25 amino acid residues |

In general, the basic antibody structural unit comprises a tetramer. Each tetramer includes two identical pairs of polypeptide chains, each pair having one LC (about 25 kDa) and HC chain (about 50-70 kDa). The amino-terminal portion of each chain includes a variable region of about 100 to 110 or more amino acids primarily responsible for antigen recognition. The carboxy-terminal portion of the HC may define a constant region primarily responsible for effector function of the antibody. Typically, human LCs are classified as kappa and lambda LCs. Furthermore, human HCs are typically classified as mu, delta, gamma, alpha, or epsilon, and define the antibody's isotype as IgM, IgD, IgG, IgA, and IgE, respectively. Within LCs and HCs, the variable and constant regions are joined by a "J" region of about 12 or more amino acids, with the HC also including a "D" region of about 10 more amino acids. See generally, *Fundamental Immunology*, Ch. 7 (Paul, W., ed., 2nd ed. Raven Press, N.Y. (1989).

The heavy chain of an antibody may or may not have a terminal lysine (K) residue, or the terminal glycine and lysine (GK) residues. Thus, in particular embodiments of the antibodies herein comprises a heavy chain constant region amino acid sequence shown herein further lacking a terminal lysine and terminating with a glycine residue or further embodiments in which the terminal glycine residue is also lacking. This is because the terminal lysine and sometimes glycine and lysine together may be cleaved during expression of the antibody or cleaved off when introduced into the human body with no apparent adverse effect on antibody efficacy, stability, or immunogenicity. In some cases, the nucleic acid molecule encoding the heavy chain may purposely omit the codons encoding the terminal lysine or the codons for the terminal lysine and glycine.

"Antibody fragment" or "Antigen binding fragment" as used herein refers to fragments of full-length antibodies, i.e. antibody fragments that retain the ability to bind specifically to the antigen bound by the full-length antibody but are less than full-length and which either lack an Fc domain in its entirety or lack those portions of the Fc domain that confer binding of the antibody to the FcγRs. Examples of antibody binding fragments include, but are not limited to, Fab, Fab', F(ab')₂, and Fv fragments; diabodies; scFv molecules; NANOBODIES, and multispecific antibodies formed from antibody fragments.

"Chimeric antibody" as used herein is an antibody having the variable domain from a first antibody and the constant domain from a second antibody wherein (i) the first and second antibodies are from different species (U.S. Pat. No. 4,816,567; and Morrison et al., Proc. Natl. Acad. Sci. USA 81:6851-6855 (1984)) or (ii) the first and second antibodies are from different isotypes, e.g., variable domain from an IgG$_1$ antibody and the constant domains from an IgG$_4$ antibody). In one aspect, the variable domains are obtained from a non-human antibody such as a mouse antibody (the "parental antibody"), and the constant domain sequences are obtained from a human antibody. In a further aspect, the variable domains are humanized variable domains from a mouse antibody and the constant domains of a human antibody.

"Combination therapy" as used herein refers to treatment of a human or animal individual comprising administering a first therapeutic agent and a second therapeutic agent consecutively or concurrently to the individual. In general, the first and second therapeutic agents are administered to the individual separately and not as a mixture; however, there may be embodiments where the first and second therapeutic agents are mixed prior to administration.

"Conservative substitution" as used herein refers to substitutions of amino acids with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. *Molecular Biology of the Gene*, The Benjamin/Cummings Pub. Co., p. 224 (4th Ed.) (1987)). In addition, substitutions of structurally or functionally similar amino acids are less likely to disrupt biological activity. Exemplary conservative substitutions are set forth in Table 2.

TABLE 2

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Cytotoxic T lymphocyte-associated antigen-4," "CTLA-4," "CTLA4," "CTLA-4 antigen" and "CD152" (see, e.g., Murata, Am. J. Pathol. 155:453-460 (1999)) are used interchangeably, and include variants, isoforms, species homologs of human CTLA-4, and analogs having at least one common epitope with CTLA-4 (see, e.g., Balzano, Int. J. Cancer Suppl. 7:28-32 (1992)). The complete CTLA-4 nucleic acid sequence can be found under GenBank Accession No. L15006.

"Effector function" as used herein refers to those biological activities attributable to the Fc region of an antibody and which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. Antibodies act by a number of mechanisms, most of which engage other arms of the immune system. Antibodies can simply block interactions of molecules or they can activate the classical complement pathway (known as complement dependent cytotoxicity or CDC) by interaction of C1q on the C1 complex with clustered antibodies. Critically antibodies also act as a link between the antibody-mediated and cell-mediated immune responses through engagement of Fc receptors.

"Effector-silent" as used herein refers to an antibody or antibody fragment that displays (i) no measurable binding to one or more Fc receptors (FcRs) as may be measured in a Biacore assay wherein an association constant in the micromolar range indicates no measurable binding or (ii) measurable binding to one or more FcRs as may be measured in a Biacore assay that is reduced compared to the binding that is typical for an antibody of the same isotype. In particular embodiments, the antibody may comprise one or more mutations in the HC constant domain and the Fc domain in particular such that the mutated antibody has reduced or no measurable binding to FcγRIIIa, FcγRIIa, and FcγRI compared to a wild-type antibody of the same isotype as the mutated antibody. In particular embodiments, the affinity or association constant of an effector-silent antibody to one or more of FcγRIIIa, FcγRIIa, and FcγRI is reduced by at least 1000-fold compared to the affinity of the wild-type isotype; reduced by at least 100-fold to 1000-fold compared to the affinity of the wild-type isotype reduced by at least 50-fold to 100-fold compared to the affinity of the wild-type isotype; or at least 10-fold to 50-fold compared to the affinity of the wild-type isotype. In particular embodiments, the effector-silent antibody has no detectable or measurable binding to one or more of the FcγRIIIa, FcγRIIa, and FcγRI as compared to binding by the wild-type isotype. In general, effector-silent antibodies will lack measurable antibody-dependent cell-mediated cytotoxicity (ADCC) activity. An effector-silent antibody fragment lacks an Fc domain or those portions of an Fc domain that confer binding to FcRs and as such would display no detectable or measurable binding to one or more of FcγRIIIa, FcγRIIa, or FcγRI. For effector-silent antibody or antibody fragments, the binding is measured against human FcRs.

"Fab fragment" as used herein comprises of one LC and the $V_H$ and $C_H1$ of one HC and excludes the remainder of the HC constant domain. The $C_H1$ of the Fab molecule cannot form a disulfide bond with another Fab fragment or HC containing molecule. A "Fab fragment" can be the product of papain cleavage of an antibody.

"Fab' fragment" as used herein comprises one LC and a fragment of one HC that contains the $V_H$ domain and the HC constant domain up to a region between the $C_H1$ and $C_H2$ domains and excludes the remainder of the HC constant domain, such that an inter-chain disulfide bond can be formed between the two HCs of two Fab' fragments to form a $F(ab')_2$ molecule.

"$F(ab')_2$ fragment" as used herein comprises two LCs and two HC fragments, each HC fragment containing the $V_H$ domain and the HC constant domain up to a region between the $C_H1$ and $C_H2$ domains and excludes the remainder of the HC constant domain, such that an inter-chain disulfide bond is formed between the two HCs. A $F(ab')_2$ fragment thus is composed of two Fab' fragments that are held together by a disulfide bond between the two heavy chains. An $F(ab')_2$ fragment may be obtained by digesting an antibody with pepsin, which cleaves the antibody at a site between the $C_H1$ and $C_H2$ domains.

"Fc domain", or "Fc" as used herein is the crystallizable fragment domain or region obtained from an antibody that comprises the $C_H2$ and $C_H3$ domains of an antibody. In an antibody, the two Fc domains are held together by two or more disulfide bonds and by hydrophobic interactions of the $C_H3$ domains. The Fc domain may be obtained by digesting an antibody with the protease papain.

"Fc receptors" or "FcRs" as used herein are key immune regulatory receptors connecting the antibody mediated (humoral) immune response to cellular effector functions. Receptors for all classes of immunoglobulins have been identified, including FcγR (IgG), FcεRI (IgE), FcαRI (IgA), FcμR (IgM) and FcδR (IgD). There are three classes of receptors for human IgG found on leukocytes: CD64 (FcγRI), CD32 (FcγRIIa, FcγRIIb and FcγRIIc) and CD16

(FcγRIIIa and FcγRIIIb). FcγRI is classed as a high affinity receptor (nanomolar range KD) while FcγRII and FcγRIII are low to intermediate affinity (micromolar range KD). In antibody dependent cellular cytotoxicity (ADCC), FcRs on the surface of effector cells (natural killer cells, macrophages, monocytes and eosinophils) bind to the Fc region of an IgG which itself is bound to a target cell. Upon binding a signaling pathway is triggered which results in the secretion of various substances, such as lytic enzymes, perforin, granzymes and tumor necrosis factor, which mediate in the destruction of the target cell. The level of ADCC effector function various for human IgG subtypes. Although this is dependent on the allotype and specific FcR in simple terms ADCC effector function is high for human $IgG_1$ and $IgG_3$, and low for $IgG_2$ and $IgG_4$.

"Fv region" as used herein comprises a single $V_H$ and $V_L$ pair wherein the $V_H$ polypeptide and the $V_L$ polypeptide are held together by disulfide bonds.

"Humanization" (also called Reshaping or CDR-grafting) as used herein is a well-established technique for reducing the immunogenicity of monoclonal antibodies (mAbs) from xenogeneic sources (commonly rodent) and for improving the effector functions (ADCC, complement activation, C1q binding). The engineered mAb is engineered using the techniques of molecular biology, however simple CDR-grafting of the rodent complementarity-determining regions (CDRs) into human frameworks often results in loss of binding affinity and/or specificity of the original mAb. In order to humanize an antibody, the design of the humanized antibody includes variations such as conservative amino acid substitutions in residues of the CDRs, and back substitution of residues from the rodent mAb into the human framework regions (back mutations). The positions can be discerned or identified by sequence comparison for structural analysis or by analysis of a homology model of the variable regions' three-dimensional structure. The process of affinity maturation has most recently used phage libraries to vary the amino acids at chosen positions. Similarly, many approaches have been used to choose the most appropriate human frameworks in which to graft the rodent CDRs. As the datasets of known parameters for antibody structures increases, so does the sophistication and refinement of these techniques. Consensus or germline sequences from a single antibody or fragments of the framework sequences within each light or heavy chain variable region from several different human mAbs can be used. Another approach to humanization is to modify only surface residues of the rodent sequence with the most common residues found in human mAbs and has been termed "resurfacing" or "veneering." Often, the human or humanized antibody is substantially non-immunogenic in humans.

"Humanized antibody" as used herein refers to forms of antibodies or antibody fragments that contain sequences from both human and non-human (e.g., murine, rat) antibodies. In general, the humanized antibody will comprise all of at least one, and typically two, variable domains, in which the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (e.g., Fc domain).

"Hyperproliferative disease" as used herein refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, benign prostatic hypertrophy).

"Immune-related adverse events" or irAE" as used herein refers to AEs that are autoimmune manifestations due to unbalancing the immune system as may be attributed to use of one or more immune checkpoint inhibitors such as anti-PD-1, anti-PD-L1, and anti-CTLA-4 antibodies.

"Immune response" as used herein refers to the action of, for example, lymphocytes, antigen presenting cells, phagocytic cells, granulocytes, and soluble macromolecules produced by the above cells or the liver (including antibodies, cytokines, and complement) that result in selective damage to, destruction of, or elimination from the human body of invading pathogens, cells or tissues infected with pathogens, cancerous cells, or, in cases of autoimmunity or pathological inflammation, normal human cells or tissues.

"Immunoglobulin single variable domain" (also referred to as "ISV" or ISVD") as used herein is generally used to refer to immunoglobulin variable domains (which may be heavy chain or light chain domains, including $V_H$, $V_{HH}$ or $V_L$ domains) that can form a functional antigen binding site without interaction with another variable domain (e.g. without a $V_H/V_L$ interaction as is required between the $V_H$ and $V_L$ domains of conventional 4-chain monoclonal antibody). Examples of ISVDs include NANOBODIES (including a $V_{HH}$, a humanized $V_{HH}$ and/or a camelized VHS such as camelized human VHS), IgNAR, domains, (single domain) antibodies (such as dAbs™) that are $V_H$ domains or that are derived from a $V_H$ domain and (single domain) antibodies (such as dAbs™) that are $V_L$ domains or that are derived from a $V_L$ domain. ISVDs that are based on and/or derived from heavy chain variable domains (such as $V_H$ or $V_{HH}$ domains) are generally preferred.

"Monoclonal antibody" as used herein refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example. See also Presta J. Allergy Clin. Immunol. 116:731 (2005).

"NANOBODY" and "NANOBODIES" as used herein are registered trademarks of Ablynx N.V.

"Non-human amino acid sequences" as used herein with respect to antibodies or immunoglobulins refers to an amino acid sequence that is characteristic of the amino acid sequence of a non-human mammal. The term does not include amino acid sequences of antibodies or immunoglobulins obtained from a fully human antibody library where diversity in the library is generated in silico (See for example, U.S. Pat. No. 8,877,688 or 8,691,730).

"PD-1" refers to the programmed Death 1 (PD-1) protein, an inhibitory member of the extended CD28/CTLA-4 family of T cell regulators (Okazaki et al., Curr. Opin. Immunol. 14:391779-82 (2002); Bennett et al., J. Immunol. 170:711-8 (2003)). Other members of the CD28 family include CD28, CTLA-4, ICOS and BTLA. The PD-1 gene encodes a 55 kDa type I transmembrane protein (Agata et al., Intl. Immunol. 8:765-72 (1996)). Two ligands for PD-1 have been identified, PD-L1 (B7-H1) and PD-L2 (B7-DC), that have been shown to downregulate T cell activation upon binding to PD-1 (Freeman et al. (2000) J. Exp. Med. 192:1027-34; Carter et al. (2002) Eur. J. Immunol. 32:634-43). PD-1 is known as an immunoinhibitory protein that negatively regulates TCR signals (Ishida, Y. et al., EMBO J. 11:3887-3895 (1992); Blank, C. et al., Immunol. Immunother. 56(5):739-745 (Epub 2006 December 29)). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al., J. Mol. Med. 81:281-7 (2003); Blank et al., Cancer Immunol. Immunother. 54:307-314 (2005); Konishi et al., Clin. Cancer Res. 10:5094-100 (2004)). Immune suppression can be reversed by inhibiting the local interaction of PD-1 with PD-L1 or PD-L2; the effect is additive when the interaction of PD-1 with PD-L2 is blocked as well (Iwai et al., Proc. Nat'l. Acad. Sci. USA 99:12293-12297 (2002); Brown et al., J. Immunol. 170:1257-66 (2003)).

"Programmed Death 1," "Programmed Cell Death 1," "Protein PD-1," "PD-1" "PD1," "PDCD1," "hPD-1" and "hPD-1" are used interchangeably, and include variants, isoforms, species homologs of human PD-1, and analogs having at least one common epitope with PD-1. The complete PD-1 sequence can be found under GenBank Accession No. U64863.

"ScFv" or "single-chain variable fragment" as used herein is a fusion protein comprising a $V_H$ and $V_L$ fused or linked together by a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker.

"Subtherapeutic dose" as used herein means a dose of a therapeutic compound (e.g., an antibody) that is lower than the usual or typical dose of the therapeutic compound when administered alone for the treatment of a hyperproliferative disease (e.g., cancer). The dose of a therapeutic compound may vary depending on the disease being targeted. For example, a subtherapeutic dose of CTLA-4 antibody is a single dose of the antibody at less than about 3 mg/kg, i.e., the known monotherapy dose of anti-CTLA-4 antibody YERVOY for treatment of unresectable or metastatic melanoma, or a single dose of YERVOY at less than about 10 mg/kg, the known monotherapy dose for adjuvant melanoma.

"Treat" or "treating" as used herein means to administer a therapeutic agent, such as a composition containing any of the antibodies or antigen binding fragments thereof of the present invention, internally or externally to a subject or patient having one or more disease symptoms, or being suspected of having a disease, for which the agent has therapeutic activity or prophylactic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a human or animal subject with a disorder, disease or symptom, or with the potential to develop such a disorder, disease or symptom.

"Therapeutically effective amount" as used herein refers to a quantity of a specific substance sufficient to achieve a desired effect in a subject being treated. For instance, this may be the amount of CTLA-4 blocking agent necessary to inhibit activation of CTLA-4 and induce an anti-tumor response or the amount necessary for enhanced anti-PD-1 or PD-L1 responsiveness when co-administered with anti-PD-1 or anti-PD-L1 blocking agent, respectively.

"Therapeutic index", also known as "therapeutic window", "safety window" or "therapeutic ratio" as used herein is a comparison of the amount of a therapeutic agent that causes a therapeutic effect to the amount of the therapeutic agent that causes toxicity.

"Treatment" as it applies to a human or veterinary individual, as used herein refers to therapeutic treatment, which encompasses contact of antibodies or antigen binding fragments to a human or animal individual who is in need of treatment with the antibodies or antibody fragments.

"$V_{HH}$" as used herein indicates that the $V_H$ domain is obtained from or originated or derived from a HC antibody. Heavy chain antibodies are functional antibodies that have two HCs and no LCs. Heavy chain antibodies exist in and are obtainable from Camelids, members of the biological family Camelidae.

Introduction

PD-1 antagonists such as the commercially marketed anti-PD-1 antibodies KEYTRUDA and OPDIVO comprise a human $IgG_4$ backbone, which has reduced FcγR function, because pre-clinical studies with anti-PD-1 antibodies with FcγR binding function showed poor anti-tumor efficacy due to depletion of CD8+ cytotoxic T cells (CTL), which are essential for tumor immunotherapy (See e.g., International Patent Application WO2014/089113). In contrast, monotherapies using anti-CTLA-4 antibodies were shown in pre-clinical experiments that compared mouse $IgG_{2a}$-anti-CTLA-4 antibodies, which have high FcγR-binding affinity, with mutant mouse $IgG_1$-anti-CTLA-4 antibodies, which lack measurable FcγR-binding affinity, to require FcγR function in order to effect strong anti-tumor y responses (See e.g., Selby et al., Cancer Immunol Res. 1:32-42 (2013). The requirement for FcγR function in the anti-CTLA-4 antagonist monotherapy correlated with depletion of T regulatory cells (Treg) in murine tumor models due to higher CTLA-4 expression on TILs (Simpson et al., J. Exp. Med. 210:1695-710 (2013)) compared to Treg populations in spleen or lymph nodes.

Figure 3A:
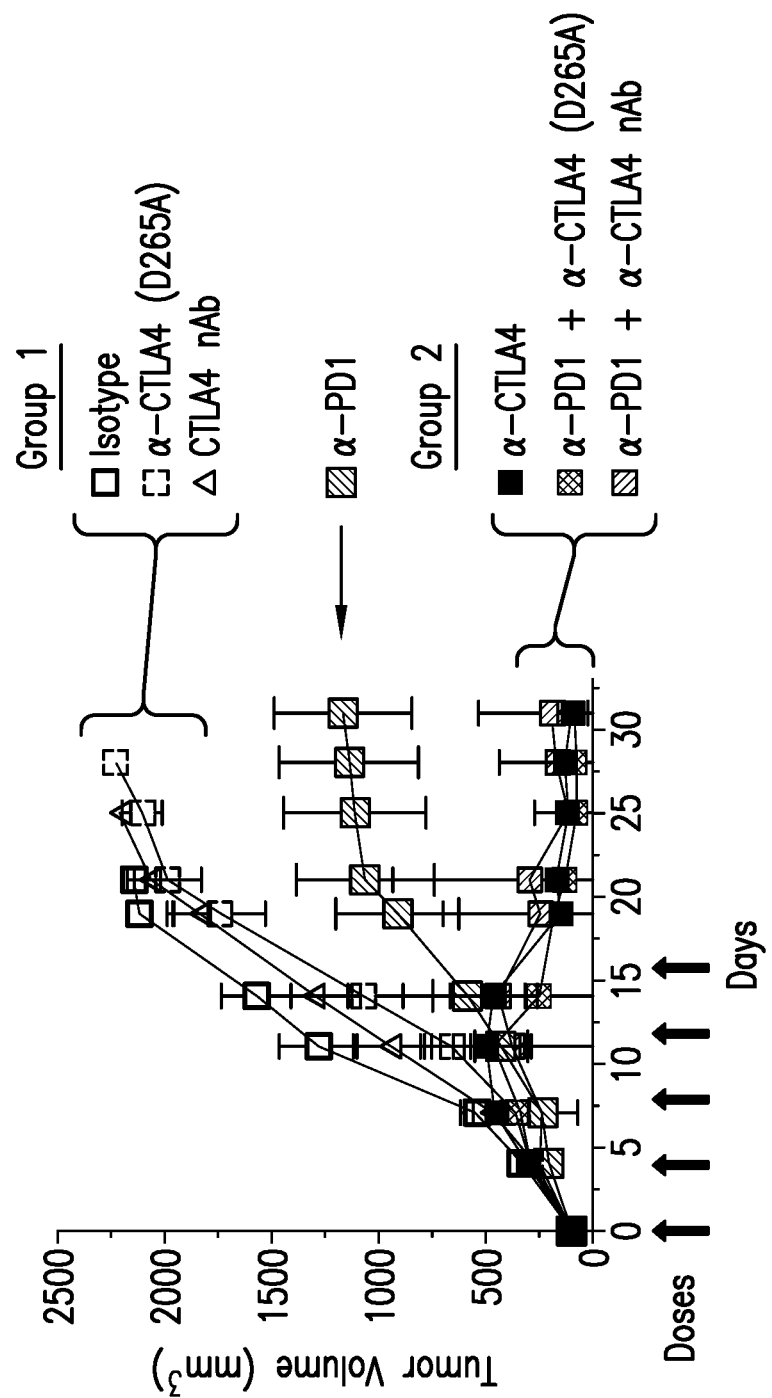
FIGS. 3A-3D: CTLA4 nAb in combination with an anti-PD-1 antibody (a-PD1) has potent anti-tumoral efficacy.

The inventors of the instant invention hypothesized that the requirement for FcγR function for anti-CTLA-4 antibody efficacy may be circumvented by combining the anti-CTLA-4 antibody with an anti-PD-1 antibody. This hypothesis is supported by emerging data illustrating a critical role for CD28-mediated co-stimulation in anti-PD-1-mediated activation of exhausted $CD8^+$ cytotoxic T cells. Anti-CTLA-4 and anti-PD-1 antibodies exert their anti-tumor activities via different mechanisms. Importantly, the combination effects of the anti-CTLA-4 and anti-PD-1 antibodies are not merely additive, as the combined blockade exerted by the two antibodies results in activation of a large number of genes, including proliferation-associated and chemokine genes, that are not activated by either antibody alone (see for Example FIGS. 3C and 4D). These data suggest that the mechanism of action for the CTLA-4 blockade in a monotherapy differs from its mechanism of action when performed in combination with the PD-1 blockade.

Emerging data indicates the importance of CD28-mediated co-stimulation in activating effector T (Teff) cells following the PD-1 blockade. PD-1 signaling dephosphorylates CD28, rather than TCR as previously assumed, and CD28 signaling is required for the enhanced anti-tumor response observed following the PD-1 blockade. Therefore, while a monotherapy CTLA-4 blockade may primarily target T cell priming events, combining the CTLA-4 blockade with a PD-1 blockade can be expected to facilitate activation of exhausted T cells beyond what would be expected from a PD-1 blockade alone. The inventors postulated that this mechanism is enhanced by CTLA-4 antagonists, which enables increased CD28-mediated activation, independent of the function of Fc-receptors, and the depletion of $T_{reg}$ cells, which may play an important factor for irAE mediated toxicity.

A potential caveat then for anti-CTLA-4 antibodies that bind FcRs (Fc-functional antibodies) is that $T_{reg}$ depletion or cell bridging of myeloid cells with T cells may induce undesired immune-related inflammation. The inventors hypothesized that it is Fc function that may be contributing to the observed irAEs associated with CTLA-4 blockade cancer immunotherapy. One critique that has been used to argue against the potential role of Fc function for the induction of irAEs has been that both ipilimumab (on a human $IgG_1$ backbone) and tremelimumab (on a human $IgG_2$ backbone) treatment are associated with gut inflammation. While the human $IgG_2$ Fc domain has significantly lower affinity for human FcγRs compared to human $IgG_1$, direct comparison of antibodies with human $IgG_2$ and IgG backbones have shown that both elicit similar levels of Fc function using in vitro ADCC and ADCP bioassays (e.g., Vargas et al., Cancer Cell. 33:649-663 (2018)). Moreover, in vivo $T_{reg}$ depletion and anti-tumor activity of chimeric anti-mouse CTLA-4 antibodies with either a human $IgG_1$ isotype backbone or a human $IgG_2$ isotype backbone were equivalent in human FcγR knock-in mice (Vargas et al., ibid.).

A key impediment for assessing the potential role of Fc function for inducing gut inflammation in syngeneic tumor models has been the lack of measurable inflammation and colitis using mouse anti-CTLA-4 surrogate antibodies. To circumvent this impediment, the inventors have employed a PCR-based panel that was previously developed by Cayatte et al., Clin. Transl. Gastroenterol. 3: e10 (2012) to measure upregulation of gut inflammatory genes associated with inflammatory bowel disease (IBD) in a mouse IBD model. As shown in the examples herein, this PCR-based panel enabled the inventors to detect increased expression of biomarker genes indicative of gut inflammation in mice treated with an Fc functional anti-mouse CTLA-4 antibody (α-CTLA4), even in the absence of overt colitis or histological evidence of tissue damage (See FIGS. 1A, 3C, and 4D. This observation of subclinical stimulation of gut inflammation gene expression pathways inspired the inventors to extend the treatment schedule to determine if the underlying inflammation would progress to development of clinical colitis. This irAE colitis mouse model enabled the inventors to run empirical experiments to assess the requirement of Fc function for induction of gut inflammation in the context or absence of concomitant anti-tumor responses in syngeneic tumor models utilized in immuno-oncology preclinical development.

Figure 4A:
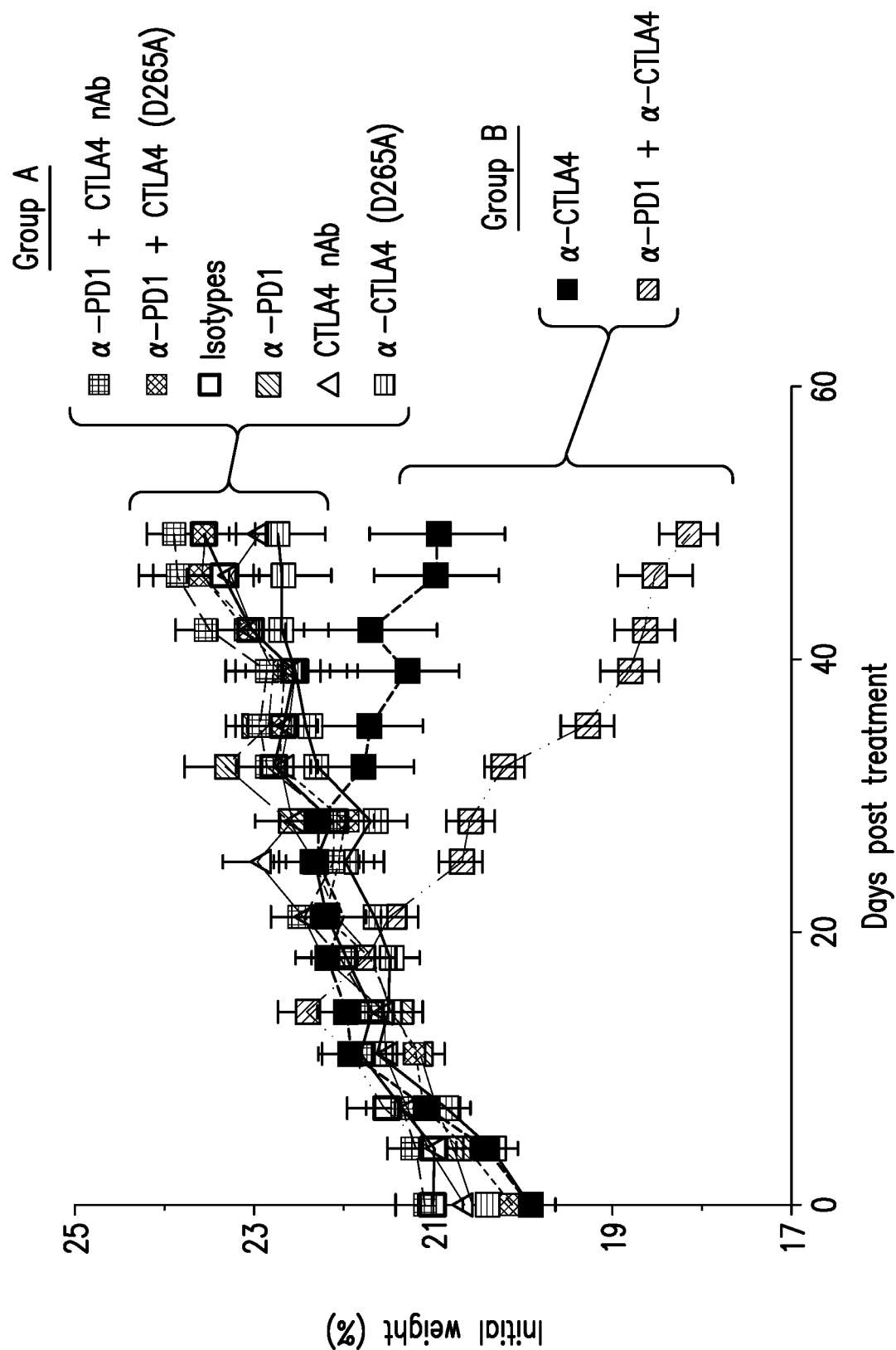
FIGS. 4A-4D: Anti-CTLA-4 antibody mediated colitis is Fc-dependent. Balb/c mice were treated twice a week with antibodies (α-CTLA4, a-PD1, α-CTLA4 (D265A)) alone or in combination with CTLA4 nAb as indicated for 55 days.

The results described in the examples clearly show that in a monotherapy setting, neither an effector-silent anti-CTLA-4 antibody nor an effector-silent anti-CTLA-4 antibody fragment elicits measurable anti-tumor activity. However, administering the effector-silent antibody or effector-silent antibody fragment in combination with an anti-PD1 antibody results in antitumor activity that is comparable to the anti-tumor activity elicited by an effector-functional anti-CTLA-4 antibody either alone or in combination with an anti-PD-1 antibody (See FIG. 3A) and without the gut or skin irAEs observed for the effector-functional anti-CTLA-4 antibody alone or in combination with an anti-PD-1 antibody (FIGS. 4B and 5A) or loss of weight (FIG. 4A). In light of these results and the inventors' discovery of a potential $T_{reg}$-independent mechanism associated with Fc-mediated anti-tumor activity and gut-inflammation, the present invention makes possible CTLA-4/PD-1 blockade combination anti-cancer immunotherapies with improved therapeutic index and broader utility.

Combination Therapies

The present invention provides anti-cancer combination therapies, which comprise, administering to an individual in need of a cancer therapy (i) a PD-1 blocking agent selected from the group consisting of an anti-PD-1 antibody, an anti-PD-L1 antibody, an effector-silent anti-PD-1 antibody, an effector-silent anti-PD-L1 antibody, an effector-silent anti-PD-1 antibody fragment, and an effector-silent anti-PD-L1 antibody fragment; and, (ii) an effector-silent CTLA-4 blocking agent selected from the group consisting of an effector-silent anti-CTLA-4 antibody and an effector-silent anti-CTLA-4 antibody fragment.

The effector-silent CTLA-4 blocking agent may be administered in a combination therapy with a PD-1 blocking agent at doses that are greater than the subtherapeutic 1 mg/kg dose of ipilimumab approved by the U.S. FDA for ipilimumab/nivolumab combination therapies targeting advance renal cell carcinoma or microsatellite instability-high or mismatch repair deficient metastatic colorectal cancer and with a lower risk of inducing skin or gut irAEs greater than Grade 1-2 according to the criteria set forth in *Common Terminology Criteria for Adverse events* (*CTCAE*) *Version* 5.0, for the duration of the combination therapy or for at least a portion of the time period the individual is undergoing the combination therapy than is observed for the ipilimumab/nivolumab combination therapies. In particular embodiments, the doses do not induce irAEs greater than Grade 1 for the duration of the combination therapy or for at least a portion of the time period the individual is undergoing the combination therapy.

Thus, in particular embodiments, the effector-silent CTLA-4 blocking agent may be administered to an individual at a dose greater than 1 mg/kg. In particular embodiments, the effector-silent CTLA-4 blocking agent may be administered to an individual at a dose of at least 3 mg/kg. In particular embodiments, the effector-silent CTLA-4 blocking agent may be administered to an individual at a dose of at least 10 mg/kg. In particular embodiments, the effector-silent CTLA-4 blocking agent may be administered to an individual at a dose of at least 15 mg/kg. In particular embodiments, the effector-silent CTLA-4 blocking agent may be administered to an individual at a dose of at least 20 mg/kg. In particular embodiments, the effector-silent CTLA-4 blocking agent may be administered to an individual at a dose between 3 mg/kg and 20 mg/kg. In particular embodiments, the effector-silent CTLA-4 blocking agent may be administered to an individual at a fixed dose that does not depend on the individual's weight, for example, a dose that is greater than 100 mg.

In particular embodiments of the combination therapy, the effector-silent CTLA-4 blocking agent is an effector-silent anti-CTLA-4 antibody or (b) effector-silent anti-CTLA-4 antibody fragment. Because effector function activity is not wanted for the anti-CTLA-4 antibody, the anti-CTLA-4 antibody either has an HC domain that has been engineered to be "effector-silent", that is, modifying its Fc domain to have reduced or no measurable FcR binding compared to the Fc domain of a wild-type antibody of the same isotype as the effector-silent antibody (e.g., Fc domain of non-mutated $IgG_1$, $IgG_2$, $IgG_3$, or $IgG_4$ Fc domain) as determined by a Biacore assay. An effector-silent anti-CTLA-4 antibody fragment either lacks an Fc domain or those regions of the Fc domain that bind one or more FcRs.

In particular embodiments, the combination therapy of the present invention is administered to an individual prior to or subsequent to surgery to remove a tumor and may be used before, during, or after radiation therapy.

In particular embodiments, the combination therapy of the present invention is administered to an individual who has not been previously treated with a biotherapeutic or chemotherapeutic agent, i.e., the individual is treatment-naïve. In other embodiments, the combination therapy is administered to an individual who has failed to achieve a sustained response after a prior therapy with a biotherapeutic or chemotherapeutic agent, i.e., the individual is treatment-experienced.

In particular embodiments, the combination therapy of the present invention is used to treat a tumor that is large enough to be found by palpation or by imaging techniques well known in the art, such as MRI, ultrasound, or CAT scan. In some embodiments, a combination therapy of the invention is used to treat an advanced stage tumor having dimensions of at least about 200 mm$^3$, 300 mm$^3$, 400 mm$^3$, 500 mm$^3$, 750 mm$^3$, or up to 1000 mm$^3$.

In particular embodiments, the combination therapy of the present invention is administered to an individual who has a cancer that tests positive for PD-L1 expression. In some embodiments, PD-L1 expression is detected using a diagnostic anti-human PD-L1 antibody, or antigen binding fragment thereof, in an immunohistochemical (IHC) assay on fixed formalin paraffin embedded (FFPE) or frozen tissue section of a tumor sample removed from the individual. An individual's physician may order a diagnostic test to determine PD-L1 expression in a tumor tissue sample removed from the individual prior to initiation of treatment with combination therapy of the present invention but it is envisioned that the physician could order the first or subsequent diagnostic tests at any time after initiation of treatment, such as for example, after completion of a treatment cycle.

The combination therapy may comprise any one of the exemplary effector-silent anti-CTLA-4 antibodies or effector-silent anti-CTLA-4 antibody fragments disclosed herein in combination with any one of the exemplary anti-PD-1 antibodies or anti-PD-1 antibody fragments disclosed herein or any one of the exemplary anti-PD-L1 antibodies or anti-PD-L1 antibody fragments disclosed herein.

(a) Effector-Silent Antibodies

An effector-silent antibody of the present invention comprises an HC constant domain or Fc domain thereof that has been modified such that the antibody displays no measurable binding to one or more FcRs or displays reduced binding to one or more FcRs compared to that of an unmodified antibody of the same IgG isotype. The effector-silent antibodies may in further embodiments display no measurable binding to each of FcγRIIIa, FcγRIIa, and FcγRI or display reduced binding to each of FcγRIIIa, FcγRIIa, and FcγRI compared to that of an unmodified antibody of the same IgG isotype. In particular embodiments, the HC constant domain or Fc domain is a human HC constant domain or Fc domain.

In particular embodiments, the effector-silent antibody comprises an Fc domain of an $IgG_1$ or $IgG_2$, $IgG_3$, or $IgG_4$ isotype that has been modified to lack N-glycosylation of the asparagine (Asn) residue at position 297 (Eu numbering system) of the HC constant domain. The consensus sequence for N-glycosylation is Asn-Xaa-Ser/Thr (wherein Xaa at position 298 is any amino acid except Pro); in all four isotypes the N-glycosylation consensus sequence is Asn-Ser-Thr. The modification may be achieved by replacing the codon encoding the Asn at position 297 in the nucleic acid molecule encoding the HC constant domain with a codon encoding another amino acid, for example Ala, Asp, Gln, Gly, or Glu, e.g. N297A, N297Q, N297G, N297E, or N297D. Alternatively, the codon for Ser at position 298 may be replaced with the codon for Pro or the codon for Thr at position 299 may be replaced with any codon except the codon for Ser. In a further alternative each of the amino acids comprising the N-glycosylation consensus sequence is replaced with another amino acid. Such modified IgG molecules have no measurable effector function. In particular embodiments, these mutated HC molecules may further comprise 1, 2, 3, 4, 5, 6, 7, 8, 9, or 10 additional amino acid substitutions, insertions, and/or deletions, wherein said substitutions may be conservative mutations or non-conservative mutations. In further embodiments, such IgGs modified to lack N-glycosylation at position 297 may further include one or more additional mutations disclosed herein for eliminating measurable effector function.

An exemplary $IgG_1$ HC constant domain mutated at position 297, which abolishes the N-glycosylation of the HC constant domain, is set forth in SEQ ID NO:44, an exemplary $IgG_2$ HC constant domain mutated at position 297, which abolishes the N-glycosylation of the HC constant, is set forth in SEQ ID NO:50, and an exemplary $IgG_4$ HC constant domain mutated at position 297 to abolish N-glycosylation of the HC constant domain is set forth in SEQ ID NO:56. In particular embodiments, these mutated HC molecules may further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the Fc domain of the $IgG_1$ $IgG_2$, $IgG_3$, or $IgG_4$ HC constant domain comprising the effector-silent antibody is modified to include one or more amino acid substitutions selected from E233P, L234A, L235A, L235E, N297A, N297D, D265S, and P331S (wherein the positions are identified according to Eu numbering) and wherein said HC constant domain is effector-silent. In particular embodiments, the modified $IgG_1$ further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the HC constant domain comprises L234A, L235A, and D265S substitutions (wherein the positions are identified according to Eu numbering). In particular embodiments, the HC constant domain comprises an amino acid substitution at position Pro329 and at least one further amino acid substitution selected from E233P, L234A, L235A, L235E, N297A, N297D, D265S, and P331S (wherein the positions are identified according to Eu numbering). These and other substitutions are disclosed in WO9428027; WO2004099249; WO20121300831, U.S. Pat. Nos. 9,708,406; 8,969,526; 9,296,815; Sondermann et al. Nature 406, 267-273 (20 Jul. 2000)).

In particular embodiments of the above, the HC constant domain comprises an L234A/L235A/D265A; L234A/L235A/P329G; L235E; D265A; D265A/N297G; or V234A/G237A/P238S/H268A/V309L/A330S/P331S substitutions, wherein the positions are identified according to Eu numbering. In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the effector-silent antibody comprises an $IgG_1$ isotype, in which the Fc domain of the HC constant domain has been modified to be effector-silent by substituting the amino acids from position 233 to position 236 of the $IgG_1$ with the corresponding amino acids of the human $IgG_2$ HC and substituting the amino acids at positions 327, 330, and 331 with the corresponding amino acids of the human $IgG_4$ HC, wherein the positions are identified according to Eu numbering (Armour et al., Eur. J. Immunol. 29(8):2613-24 (1999); Shields et al., J. Biol. Chem. 276(9): 6591-604(2001)). In particular embodiments, the modified $IgG_1$ further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the effector-silent antibody comprises a $V_H$ domain fused or linked to a hybrid human immunoglobulin HC constant domain, which includes a hinge region, a $CH_2$ domain and a $CH_3$ domain in an N-terminal to C-terminal direction, wherein the hinge region comprises an at least partial amino acid sequence of a human IgD hinge region or a human $IgG_1$ hinge region; and the $CH_2$ domain is of a human $IgG_4$ $CH_2$ domain, a portion of which, at its N-terminal region, is replaced by 4-37 amino acid residues of an N-terminal region of a human $IgG_2$ $CH_2$ or human IgD $CH_2$ domain. Such hybrid human HC constant domain is disclosed in U.S. Pat. No. 7,867,491, which is incorporated herein by reference in its entirety.

In particular embodiments, the effector-silent antibody comprises an $IgG_4$ HC constant domain in which the serine at position 228 according to the Eu system is substituted with proline, see for example SEQ ID NO: 52. This modification prevents formation of a potential inter-chain disulfide bond between the cysteines at positions Cys226 and Cys229 in the EU system and which may interfere with proper intra-chain disulfide bond formation. See Angal et al. Mol. Imunol. 30:105 (1993); see also (Schuurman et al., Mol. Immunol. 38:1-8, (2001); SEQ ID NOs: 14 and 41). In further embodiments, the $IgG_4$ constant domain includes in addition to the S228P substitution, a P239G, D265A, or D265A/N297G amino acid substitution, wherein the positions are identified according to Eu numbering. In particular embodiments of the above, the $IgG_4$ HC constant domain is a human HC constant domain. In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

Exemplary $IgG_1$ HC constant domains include HC constant domains comprising an amino acid sequence selected from the group consisting of amino acid sequences set forth in SEQ ID NO:38, SEQ ID NO:39, SEQ ID NO:40, SEQ ID NO:41, SEQ ID NO:42, SEQ ID NO: 43, and SEQ ID NO:44. Exemplary $IgG_2$ HC constant domains have an amino acid sequence selected from the group consisting of amino acid sequences set forth in SEQ ID NO: 46, SEQ ID NO:47, SEQ ID NO:48, and SEQ ID NO:49. Exemplary $IgG_4$ HC constant domains have an amino acid sequence selected from the group consisting of amino acid sequences set forth in SEQ ID NO:53, SEQ ID NO:54, SEQ ID NO:55, and SEQ ID NO:56.

More specific examples of effector-silent antibodies are described below in combination with particular exemplary effector-silent anti-CTLA-4 antibodies, anti-PD-1 antibodies, and anti-PD-1 antibodies.

(b) Exemplary Effector-Silent Anti-CTLA-4 Antibodies

Exemplary effector-silent anti-CTLA-4 antibodies that may be used in the combination therapy of the present invention and compositions comprising these antibodies include any effector-silent anti-CTLA-4 antibody that binds CTLA-4 and inhibits CTLA-4 from binding B7. Specific effector-silent anti-CTLA-4 antibodies include the following effector silent anti-CTLA-4 antibodies and compositions comprising any one of these antibodies and a pharmaceutically acceptable carrier.

In particular embodiments, the effector-silent anti-CTLA-4 antibody comprises (i) a $V_H$ comprising the three HC-CDRs of ipilimumab fused or linked to an HC constant domain that displays no measurable binding to the FcγRIIIA, FcγRIIA, and FcγRI or reduced binding compared to a polypeptide comprising the wild-type IgG constant domain region as determined by a Biacore assay and (ii) a $V_L$ comprising the three LC-CDRs of ipilimumab fused or linked to an LC kappa or lambda constant domain. The three HC-CDRs comprise SEQ ID NO:4, SEQ ID NO: 5, and SEQ ID NO:6, respectively, and the three LC-CDRs comprise SEQ ID NO:1, SEQ ID NO: 2, and SEQ ID NO:3, respectively.

In further embodiments, the effector-silent anti-CTLA-4 antibody comprises (i) a $V_H$ comprising the three HC-CDRs of tremelimumab fused or linked to an HC constant domain that displays no measurable binding to the FcγRIIIA, FcγRIIA, and FcγRI or reduced binding compared to a polypeptide comprising the wild-type IgG constant domain region as determined by a Biacore assay and (ii) a $V_L$ comprising the three LC-CDRs of tremelimumab fused or linked to an LC kappa or lambda constant domain. The three HC-CDRs comprise SEQ ID NO: 12, SEQ ID NO: 13, and SEQ ID NO: 14, respectively, and the three LC-CDRs comprise SEQ ID NO:9, SEQ ID NO: 10, and SEQ ID NO: 11, respectively.

In further embodiments, the effector-silent anti-CTLA-4 antibody comprises either (i) the $V_H$ and $V_L$ domains of ipilimumab, (ii) the $V_H$ and $V_L$ domains of tremelimumab, (iii) the $V_H$ and $V_L$ domains of REGN4659, (iv) the $V_H$ and $V_L$ domains of AGEN1884w, or (v) the $V_H$ and $V_L$ domains of anti-CTLA-4 antibody clone 2C8 disclosed in International Patent Application WO2017194265. The ipilimumab $V_H$ domain comprises the amino acid sequence set forth in SEQ ID NO:7 and V$_L$ domain comprises the amino acid sequence set forth in SEQ ID NO:8. The tremelimumab V$_H$ domain comprises the amino acid sequence set forth in SEQ ID NO:15 and V$_L$ domain comprises the amino acid sequence set forth in SEQ ID NO: 16. The REGN4659 V$_H$ domain comprises the amino acid sequence set forth in SEQ ID NO:95 and V$_L$ domain comprises the amino acid sequence set forth in SEQ ID NO:96. The AGEN1884w V$_H$ domain comprises the amino acid sequence set forth in SEQ ID NO:97 and V$_L$ domain comprises the amino acid sequence set forth in SEQ ID NO:98. In particular embodiments, the V$_H$ and V$_L$ domains further comprise 1, 2, 3, 4, 5, 6, 7, 8, 9, or 10 additional amino acid substitutions, insertions, and/or deletions, wherein said substitutions may be conservative mutations or non-conservative mutations.

In further embodiments, the effector-silent anti-CTLA-4 antibody comprises the V$_H$ and V$_L$ domains of 8D2/8D2 (RE) (See U.S. Published Patent Application No. 20170216433 and International Application WO2018183408), 8D2H1L1, 8D2H2L2, 8D3H3L3, 8D2H2L15, or 8D2H2L17, wherein the V$_H$ domain is fused or linked to an HC constant domain that displays no measurable binding to the FcγRIIIA, FcγRIIA, and FcγRI or reduced binding compared to a polypeptide comprising the wild-type IgG constant domain region as determined by a Biacore assay and the V$_L$ domain is fused or linked to a LC kappa or lambda constant domain.

In particular embodiments, the effector-silent anti-CTLA-4 antibody comprises a variant of 8D2/8D2 (RE), 8D2H1L1, 8D2H2L2, 8D2H2L15, or 8D2H2L17, wherein the methionine at position 18 in the V$_H$ amino acid sequence of the variant is substituted with isoleucine. Thus, the effector-silent anti-CTLA-4 antibody may comprise the V$_H$ and V$_L$ of 8D2/8D2 (RE)-Variant 1, the V$_H$ and V$_L$ of 8D2H1L1-Variant 1, the V$_H$ and V$_L$ of 8D2H2L2-Variant 1, the V$_H$ and V$_L$ of 8D2H2L15-Variant 1, or the V$_H$ and V$_L$ of 8D2H2L17-Variant 1.

In further embodiments, the effector silent anti-CTLA4 antibody has a (i) a V$_H$ domain comprising the amino acid sequence set forth in SEQ ID NO:73 and a V$_L$ domain comprising the amino acid sequence set forth in SEQ ID NO:74; (ii) a V$_H$ domain comprising the amino acid sequence set forth in SEQ ID NO:75 and a V$_L$ domain comprising the amino acid sequence set forth in SEQ ID NO:76; (iii) a V$_H$ domain comprising the amino acid sequence set forth in SEQ ID NO:77 and a V$_L$ domain comprising the amino acid sequence set forth in SEQ ID NO: 78; (iv) a V$_H$ domain comprising the amino acid sequence set forth in SEQ ID NO:79 and a V$_L$ domain comprising the amino acid sequence set forth in SEQ ID NO:80; (v) a V$_H$ domain comprising the amino acid sequence set forth in SEQ ID NO:81 and a V$_L$ domain comprising the amino acid sequence set forth in SEQ ID NO:82; (vi) a V$_H$ domain comprising the amino acid sequence set forth in SEQ ID NO:83 and a V$_L$ domain comprising the amino acid sequence set forth in SEQ ID NO:84; (vii) a V$_H$ domain comprising the amino acid sequence set forth in SEQ ID NO:85 and a V$_L$ domain comprising the amino acid sequence set forth in SEQ ID NO: 86; (viii) a V$_H$ domain comprising the amino acid sequence set forth in SEQ ID NO:87 and a V$_L$ domain comprising the amino acid sequence set forth in SEQ ID NO:88; (ix) a V$_H$ domain comprising the amino acid sequence set forth in SEQ ID NO:89 and a V$_L$ domain comprising the amino acid sequence set forth in SEQ ID NO:90; (x) a V$_H$ domain comprising the amino acid sequence set forth in SEQ ID NO:91 and a V$_L$ domain comprising the amino acid sequence set forth in SEQ ID NO:92; or (xi) a V$_H$ domain comprising the amino acid sequence set forth in SEQ ID NO:93 and a V$_L$ domain comprising the amino acid sequence set forth in SEQ ID NO:94. In particular embodiments, the V$_H$ and V$_L$ domains further comprise 1, 2, 3, 4, 5, 6, 7, 8, 9, or 10 additional amino acid substitutions, insertions, and/or deletions, wherein said substitutions may be conservative mutations or non-conservative mutations.

In further embodiments of the effector-silent anti-CTLA-4 antibody, the V$_H$ domain is fused or linked to an IgG$_4$ HC constant domain or an IgG$_1$, IgG$_2$, or IgG$_4$ HC constant domain that has been modified to include one or more mutations to render the resulting anti-CTLA4 antibody effecter-silent.

In one embodiment, the effector-silent anti-CTLA-4 antibody comprises an IgG$_1$ Fc domain having (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N297A, L234A/L235A/D265A, L234A/L235A/P329G, L235E, D265A, E233A/L235A,S267E/L328F, S2339D/A330L/I332E, L235G/G236R, N297A/D356E/L358M, L234F/L235E/P331S/D365E/L358M, and D265A/N297G or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of L234A/L235A/D265A, L234A/L235A/P329G, L235E, D265A, E233A/L235A,S267E/L328F, S2339D/A330L/I332E, L235G/G236R, D356E/L358M, L234F/L235E/P331S/D365E/L358M, and D265A or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In another embodiment, the effector-silent anti-CTLA-4 antibody comprises an IgG$_2$ Fc domain having (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N297A/D265S, D265A, P329G/D265A/N297G, or V234A/G237A/P238S/H268A/V309L/A330S/P331S or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of N297A/D265S, D265A, P329G/D265A/N297G, or V234A/G237A/P238S/H268A/V309L/A330S/P331S or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

In a further embodiment, the effector-silent anti-CTLA-4 antibody comprises an IgG$_4$ Fc domain having an S228P amino acid substitution and further comprising (i) a mutation in the N-glycosylation site Asn-Xaa-Ser/Thr beginning at amino acid position 297 that abolishes N-glycosylation at said N-glycosylation site or the mutated Fc domain further comprising 1, 2, 3, 4, 5, 6, 7, 8, 9, or 10 additional amino acid substitutions, insertions, and/or deletions; (ii) an amino acid substitution mutation selected from the group consisting of N267A, P329G, and D265A/N297A or the mutated Fc domain further comprising 1, 2, 3, 4, 5, 6, 7, 8, 9, or 10 additional amino acid substitutions, insertions, and/or deletions; or (iii) a mutation in the N-glycosylation site Asn-Xaa-Ser/Thr beginning at amino acid position 297 that abolishes N-glycosylation at said N-glycosylation site and an amino acid substitution mutation selected from the group consisting of N267A, P329G, and D265A/N297A or the mutated Fc domain further comprising 1, 2, 3, 4, 5, 6, 7, 8, 9, or 10 additional amino acid substitutions, insertions, and/or deletions, wherein the amino acid positions in (i), (ii), and (iii) are identified according to Eu numbering.

Tables 4-18 provide specific exemplary anti-CTLA-4 antibodies that may be used in combination with an anti-PD-1 or anti-PD-L1 antibody in a therapy to treat an individual who has cancer. The present invention also provides the antibodies shown in the tables except for ipilimumab consisting solely of an N297A substitution and compositions, each composition comprising an antibody shown in the tables and a pharmaceutically acceptable carrier except for a composition comprising ipilimumab consisting solely of an N297A substitution. All HC amino acid substitution positions in Tables 4-18 are according to the Eu numbering scheme.

TABLE 4

| Ab No. | Ipilimumab IgG$_1$ derivatives Isotype and HC Substitutions | HC constant domain | $V_H$ | $V_L$ | LC constant domain |
|---|---|---|---|---|---|
| 1-1 | IgG$_1$ (L234A/L235A/D265S) | 38 | 7 | 8 | 57 or 117 |
| 1-2 | IgG$_1$ (L234A/L235A/P329G) | 39 | 7 | 8 | 57 or 117 |
| 1-3 | IgG$_1$ (L235E) | 40 | 7 | 8 | 57 or 117 |
| 1-4 | IgG$_1$ (D265A) | 41 | 7 | 8 | 57 or 117 |
| 1-5 | IgG$_1$ (D265A/N297G) | 42 | 7 | 8 | 57 or 117 |
| 1-6 | IgG$_1$ (E233A/L235A) | 43 | 7 | 8 | 57 or 117 |
| 1-7 | IgG$_1$ (N297X) | 44 | 7 | 8 | 57 or 117 |
| 1-8 | IgG$_1$ (N297A/D356E/L358M) | 116 | 7 | 8 | 57 or 117 |
| 1-9 | IgG$_1$ (L234F/L235E/P331S/D356E/L358M) | 117 | 7 | 8 | 57 or 117 |

TABLE 5

| Ab No. | Ipilimumab IgG$_2$ derivatives Isotype and HC Substitutions | HC constant domain | $V_H$ | $V_L$ | LC constant domain |
|---|---|---|---|---|---|
| 2-1 | IgG$_2$ (D265S) | 46 | 7 | 8 | 57 or 117 |
| 2-2 | IgG$_2$ (P329G) | 47 | 7 | 8 | 57 or 117 |
| 2-3 | IgG$_2$ (D265A) | 48 | 7 | 8 | 57 or 117 |

TABLE 5-continued

| Ab No. | Ipilimumab IgG$_2$ derivatives Isotype and HC Substitutions | HC constant domain | $V_H$ | $V_L$ | LC constant domain |
|---|---|---|---|---|---|
| 2-4 | IgG$_2$ (D265A/N297G) | 49 | 7 | 8 | 57 or 117 |
| 2-5 | IgG$_2$ (N297X) | 50 | 7 | 8 | 57 or 117 |
| 2-6 | 1gG$_2$ (V234A/G237A/P238S/H268A/V309L/A330S/P331S) | 51 | 7 | 8 | 57 or 117 |

TABLE 6

| Ab No. | Ipilimumab IgG$_4$ derivatives Isotype and HC Substitutions | HC constant domain | $V_H$ | $V_L$ | LC constant domain |
|---|---|---|---|---|---|
| 3-1 | IgG$_4$ (S228P) | 52 | 7 | 8 | 57 or 117 |
| 3-2 | IgG$_4$ (S228P/P329G) | 53 | 7 | 8 | 57 or 117 |
| 3-3 | IgG$_4$ (S228P/D265A) | 54 | 7 | 8 | 57 or 117 |
| 3-4 | IgG$_4$ (S228P/D265A/N297G) | 55 | 7 | 8 | 57 or 117 |
| 3-5 | IgG$_4$ (S228P/N297X) | 56 | 7 | 8 | 57 or 117 |

TABLE 7

Tremelimumab IgG$_1$ derivatives

| Ab No. | Isotype and HC Substitutions | HC constant domain | $V_H$ | $V_L$ | LC constant domain |
|---|---|---|---|---|---|
| 4-1 | IgG$_1$ (L234A/L235A/D265S) | 38 | 15 | 16 | 57 or 117 |
| 4-2 | IgG$_1$ (L234A/L235A/P329G) | 39 | 15 | 16 | 57 or 117 |
| 4-3 | IgG$_1$ (L235E) | 40 | 15 | 16 | 57 or 117 |
| 4-4 | IgG$_1$ (D265A) | 41 | 15 | 16 | 57 or 117 |
| 4-5 | IgG$_1$ (D265A/N297G) | 42 | 15 | 16 | 57 or 117 |
| 4-6 | IgG$_1$ (E233A/L235A) | 43 | 15 | 16 | 57 or 117 |
| 4-7 | IgG$_1$ (N297X) | 44 | 15 | 16 | 57 or 117 |
| 4-8 | IgG$_1$ (N297A/D356E/L358M) | 116 | 15 | 16 | 57 or 117 |
| 4-9 | IgG$_1$ (L234F/L235E/P331S/D356E/L358M) | 117 | 15 | 16 | 57 or 117 |

TABLE 8

Tremelimumab IgG$_2$ derivatives

| Ab No. | Isotype and HC Substitutions | HC constant domain | $V_H$ | $V_L$ | LC constant domain |
|---|---|---|---|---|---|
| 5-1 | IgG$_2$ (D265S) | 46 | 15 | 16 | 57 or 117 |

TABLE 8-continued

Tremelimumab IgG$_2$ derivatives

| Ab No. | Isotype and HC Substitutions | HC constant domain | V$_H$ | V$_L$ | LC constant domain |
|---|---|---|---|---|---|
| 5-2 | IgG$_2$ (P329G) | 47 | 15 | 16 | 57 or 117 |
| 5-3 | IgG$_2$ (D265A) | 48 | 15 | 16 | 57 or 117 |
| 5-4 | IgG$_2$ (D265A/N297G) | 49 | 15 | 16 | 57 or 117 |
| 5-5 | IgG$_2$ (N297X) | 50 | 15 | 16 | 57 or 117 |
| 5-6 | IgG$_2$ (V234A/G237A/P238S/H268A/V309L/A330S/P331S) | 51 | 15 | 16 | 57 or 117 |

TABLE 9

Tremelimumab IgG$_4$ derivatives

| Ab No. | Isotype and HC Substitutions | HC constant domain | V$_H$ | V$_L$ | LC constant domain |
|---|---|---|---|---|---|
| 6-1 | IgG$_4$ (S228P) | 52 | 15 | 16 | 57 or 117 |
| 6-2 | IgG$_4$ (S228P/P329G) | 53 | 15 | 16 | 57 or 117 |
| 6-3 | IgG$_4$ (S228P/D265A) | 54 | 15 | 16 | 57 or 117 |
| 6-4 | IgG$_4$ (S228P/D265A/N297G) | 55 | 15 | 16 | 57 or 117 |
| 6-5 | IgG$_4$ (S228P/N297X) | 56 | 15 | 16 | 57 or 117 |

TABLE 10

REGN4659 IgG$_1$ derivatives

| Ab No. | Isotype and HC Substitutions | HC constant domain | V$_H$ | V$_L$ | LC constant domain |
|---|---|---|---|---|---|
| 7-1 | IgG$_1$ (L234A/L235A/D265S) | 38 | 95 | 96 | 57 or 117 |
| 7-2 | IgG$_1$ (L234A/L235A/P329G) | 39 | 95 | 96 | 57 or 117 |
| 7-3 | IgG$_1$ (L235E) | 40 | 95 | 96 | 57 or 117 |
| 7-4 | IgG$_1$ (D265A) | 41 | 95 | 96 | 57 or 117 |
| 7-5 | IgG$_1$ (D265A/N297G) | 42 | 95 | 96 | 57 or 117 |
| 7-6 | IgG$_1$ (E233A/L235A) | 43 | 95 | 96 | 57 or 117 |
| 7-7 | IgG$_1$ (N297X) | 44 | 95 | 96 | 57 or 117 |
| 7-8 | IgG$_1$ (N297A/D356E/L358M) | 116 | 95 | 96 | 57 or 117 |
| 7-9 | IgG$_1$ (L234F/L235E/P331S/D356E/L358M) | 117 | 95 | 96 | 57 or 117 |

TABLE 11

REGN4659 IgG$_2$ derivatives

| Ab No. | Isotype and HC Substitutions | HC constant domain | V$_H$ | V$_L$ | LC constant domain |
|---|---|---|---|---|---|
| 8-1 | IgG$_2$ (D265S) | 46 | 95 | 96 | 57 or 117 |
| 8-2 | IgG$_2$ (P329G) | 47 | 95 | 96 | 57 or 117 |
| 8-3 | IgG$_2$ (D265A) | 48 | 95 | 96 | 57 or 117 |
| 8-4 | IgG$_2$ (D265A/N297G) | 49 | 95 | 96 | 57 or 117 |
| 8-5 | IgG$_2$ (N297X) | 50 | 95 | 96 | 57 or 117 |
| 8-6 | IgG$_2$ (V234A/G237A/P238S/H268A/V309L/A330S/P331S) | 51 | 95 | 96 | 57 or 117 |

TABLE 12

REGN4659 IgG$_4$ derivatives

| Ab No. | Isotype and HC Substitutions | HC constant domain | V$_H$ | V$_L$ | LC constant domain |
|---|---|---|---|---|---|
| 9-1 | IgG$_4$ (S228P) | 52 | 95 | 96 | 57 or 117 |
| 9-2 | IgG$_4$ (S228P/P329G) | 53 | 95 | 96 | 57 or 117 |
| 9-3 | IgG$_4$ (S228P/D265A) | 54 | 95 | 96 | 57 or 117 |
| 9-4 | IgG$_4$ (S228P/D265A/N297G) | 55 | 95 | 96 | 57 or 117 |
| 9-5 | IgG$_4$ (S228P/N297X) | 56 | 95 | 96 | 57 or 117 |

TABLE 13

AGEN1884w IgG$_1$ derivatives

| Ab No. | Isotype and HC Substitutions | HC constant domain | V$_H$ | V$_L$ | LC constant domain |
|---|---|---|---|---|---|
| 10-1 | IgG$_1$ (L234A/L235A/D265S) | 38 | 97 | 98 | 57 or 117 |
| 10-2 | IgG$_1$ (L234A/L235A/P329G) | 39 | 97 | 98 | 57 or 117 |
| 10-3 | IgG$_1$ (L235E) | 40 | 97 | 98 | 57 or 117 |
| 10-4 | IgG$_1$ (D265A) | 41 | 97 | 98 | 57 or 117 |
| 10-5 | IgG$_1$ (D265A/N297G) | 42 | 97 | 98 | 57 or 117 |
| 10-6 | IgG$_1$ (E233A/L235A) | 43 | 97 | 98 | 57 or 117 |
| 10-7 | IgG$_1$ (N297X) | 44 | 97 | 98 | 57 or 117 |
| 10-8 | IgG$_1$ (N297A/D356E/L358M) | 116 | 97 | 98 | 57 or 117 |
| 10-9 | IgG$_1$ (L234F/L235E/P331S/D356E/L358M) | 117 | 97 | 98 | 57 or 117 |

TABLE 14

AGEN1884w IgG$_2$ derivatives

| Ab No. | Isotype and HC Substitutions | HC constant domain | $V_H$ | $V_L$ | LC constant domain |
|---|---|---|---|---|---|
| 11-1 | IgG$_2$ (D265S) | 46 | 97 | 98 | 57 or 117 |
| 11-2 | IgG$_2$ (P329G) | 47 | 97 | 98 | 57 or 117 |
| 11-3 | IgG$_2$ (D265A) | 48 | 97 | 98 | 57 or 117 |
| 11-4 | IgG$_2$ (D265A/N297G) | 49 | 97 | 98 | 57 or 117 |
| 11-5 | IgG$_2$ (N297X) | 50 | 97 | 98 | 57 or 117 |
| 11-6 | IgG$_2$ (V234A/G237A/P238S/H268A/V309L/A330S/P331S) | 51 | 97 | 98 | 57 or 117 |

TABLE 15

AGEN1884w IgG$_4$ derivatives

| Ab No. | Isotype and HC Substitutions | HC constant domain | $V_H$ | $V_L$ | LC constant domain |
|---|---|---|---|---|---|
| 12-1 | IgG$_4$ (S228P) | 52 | 97 | 98 | 57 or 117 |
| 12-2 | IgG$_4$ (S228P/P329G) | 53 | 97 | 98 | 57 or 117 |
| 12-3 | IgG$_4$ (S228P/D265A) | 54 | 97 | 98 | 57 or 117 |
| 12-4 | IgG$_4$ (S228P/D265A/N297G) | 55 | 97 | 98 | 57 or 117 |
| 12-5 | IgG$_4$ (S228P/N297X) | 56 | 97 | 98 | 57 or 117 |

TABLE 16

8D2/8D2 (RE), 8D2/8D2 (RE)—Variant 1, 8D2H1L1, 8D2H1L1—Variant 1, 8D2H2L2, 8D2H2L2—Variant 1, 8D3H3L3, 8D2H2L15, 8D2H2L15—Variant 1, 8D2H2L17, and 8D2H2L17—Variant 1 IgG$_1$ derivatives

| Ab No* | Isotype and HC Substitutions | HC constant domain | $V_H$ + $V_L$ pair | LC constant domain |
|---|---|---|---|---|
| 13-1n | IgG$_1$ (L234A/L235A/D265S) | 38 | a = 73 + 74, b = 75 + 76, | 57 or 117 |
| 13-2n | IgG$_1$ (L234A/L235A/P329G) | 39 | c = 77 + 78, d = 79 + 80, | 57 or 117 |
| 13-3n | IgG$_1$ (L235E) | 40 | e = 81 + 82, f = 83 + 84, | 57 or 117 |
| 13-4n | IgG$_1$ (D265A) | 41 | g = 85 + 86, h = 87 + 88, | 57 or 117 |
| 13-5n | IgG$_1$ (D265A/N297G) | 42 | i = 89 + 90, j = 91 + 92, or k = 93 + 94 | 57 or 117 |
| 13-6n | IgG$_1$ (E233A/L235A) | 43 | | 57 or 117 |
| 13-7n | IgG$_1$ (N297X) | 44 | | 57 or 117 |
| 13-8n | IgG$_1$ (N297A/D356E/L358M) | 116 | | 57 or 117 |
| 13-9n | IgG$_1$ (L234F/L235E/P331S/D356E/L358M) | 117 | | 57 or 117 |

*n = a, b, c, d, e, f, g, h, i, j, or k

TABLE 17

8D2/8D2 (RE), 8D2/8D2 (RE)—Variant 1, 8D2H1L1, 8D2H1L1—Variant 1, 8D2H2L2, 8D2H2L2—Variant 1, 8D3H3L3, 8D2H2L15, 8D2H2L15—Variant 1, 8D2H2L17, and 8D2H2L17—Variant 1 IgG$_2$ derivatives

| Ab No.* | Isotype and HC Substitutions | HC constant domain | $V_H$ + $V_L$ Pair | LC constant domain |
|---|---|---|---|---|
| 14-1n | IgG$_2$ (D265S) | 46 | a = 73 + 74, b = 75 + 76, | 57 or 117 |
| 14-2n | IgG$_2$ (P329G) | 47 | c = 77 + 78, d = 79 + 80, | 57 or 117 |
| 14-3n | IgG$_2$ (D265A) | 48 | e = 81 + 82, f = 83 + 84, | 57 or 117 |
| 14-4n | IgG$_2$ (D265A/N297G) | 49 | g = 85 + 86, h = 87 + 88, | 57 or 117 |
| 14-5n | IgG$_2$ (N297X) | 50 | i = 89 + 90, j = 91 + 92, or k = 93 + 94 | 57 or 117 |
| 14-6n | IgG$_2$ (V234A/G237A/P238S/H268A/V309L/A330S/P331S) | 51 | | 57 or 117 |

*n = a, b, c, d, e, f, g, h, i, j, or k

TABLE 18

8D2/8D2 (RE), 8D2/8D2 (RE)—Variant 1, 8D2H1L1, 8D2H1L1—Variant 1, 8D2H2L2, 8D2H2L2—Variant 1, 8D3H3L3, 8D2H2L15, 8D2H2L15—Variant 1, 8D2H2L17, and 8D2H2L17—Variant 1 IgG$_4$ derivatives

| Ab No.* | Isotype and HC Substitutions | HC constant domain | $V_H$ + $V_L$ pair | LC constant domain |
|---|---|---|---|---|
| 15-1n | IgG$_4$ (S228P) | 52 | a = 73 + 74, b = 75 + 76, | 57 or 117 |
| 15-2n | IgG$_4$ (S228P/P329G) | 53 | c = 77 + 78, d = 79 + 80, | 57 or 117 |
| 15-3n | IgG$_4$ (S228P/D265A) | 54 | e = 81 + 82, f = 83 + 84, | 57 or 117 |
| 15-4n | IgG$_4$ (S228P/D265A/N297G) | 55 | g = 85 + 86, h = 87 + 88, | 57 or 117 |
| 15-5n | IgG$_4$ (S228P/N297X) | 56 | i = 89 + 90, j = 91 + 92, or k = 93 + 94 | 57 or 117 |

*n = a, b, c, d, e, f, g, h, i, j, or k (c) Exemplary Effector-Silent Anti-CTLA-4 Antibody Fragments Exemplary effector-silent anti-CTLA-4 antibody fragments that may be used in the combination therapy of the present invention and compositions comprising the same include any antibody fragment that binds CTLA-4 and inhibits CTLA-4 from binding B7. Specific examples of these anti-CTLA-4 antibody fragments include the following anti-CTLA-4 antibody fragments and compositions, each composition comprising an effector-silent anti-CTLA-4 antibody fragment and a pharmaceutically acceptable carrier.

In particular embodiments, the effector-silent anti-CTLA-4 antibody fragment is an Fv, scFv, F(ab), or F(ab')$_2$ that comprises (i) a $V_H$ comprising the three HC-CDRs of ipilimumab and (ii) a $V_L$ comprising the three LC-CDRs of ipilimumab. The three HC-CDRs comprise SEQ ID NO: 1, SEQ ID NO:2, and SEQ ID NO:3, respectively, and the three LC-CDRs comprise SEQ ID NO:4, SEQ ID NO:5, and SEQ ID NO:7, respectively.

In particular embodiments, the effector-silent anti-CTLA-4 antibody fragment comprises (i) a $V_H$ comprising the three HC-CDRs of tremelimumab and (ii) a $V_L$ comprising the three LC-CDRs of tremelimumab. The three HC-CDRs comprise SEQ ID NO:9, SEQ ID NO: 10, and SEQ ID NO:11, respectively, and the three LC-CDRs comprise SEQ ID NO:12, SEQ ID NO: 13, and SEQ ID NO:14, respectively.

In particular embodiments, the effector-silent anti-CTLA-4 antibody fragment comprises either (i) the $V_H$ and $V_L$ domains of ipilimumab, (ii) the $V_H$ and $V_L$ domains of tremelimumab, (iii) the $V_H$ and $V_L$ domains of REGN4659, (iv) the $V_H$ and $V_L$ domains of AGEN1884w, or (v) the $V_H$ and $V_L$ domains of anti-CTLA-4 antibody clone 2C8 disclosed in International Patent Application WO2017194265. The ipilimumab $V_H$ domain comprises the amino acid sequence set forth in SEQ ID NO:7 and $V_L$ domain comprising the amino acid sequence set forth in SEQ ID NO:8. The tremelimumab $V_H$ domain comprises the amino acid sequence set forth in SEQ ID NO:15 and $V_L$ domain comprising the amino acid sequence set forth in SEQ ID NO:16. The REGN4659 $V_H$ domain comprises the amino acid sequence set forth in SEQ ID NO:95 and $V_L$ domain comprising the amino acid sequence set forth in SEQ ID NO: 96. The AGEN1884w $V_H$ domain comprises the amino acid sequence set forth in SEQ ID NO: 97 and $V_L$ domain comprising the amino acid sequence set forth in SEQ ID NO:98.

In particular embodiments, the effector-silent anti-CTLA-4 antibody fragment comprises the $V_H$ and $V_L$ of ipilimumab, the $V_H$ and $V_L$ of tremelimumab, the $V_H$ and $V_L$ of REGN4659, the $V_H$ and $V_L$ of AGEN1884w, the $V_H$ and $V_L$ of 8D2/8D2 (RE), the $V_H$ and $V_L$ of 8D2H1L1, the $V_H$ and $V_L$ of 8D2H2L2, the $V_H$ and $V_L$ of 8D3H3L3, the $V_H$ and $V_L$ of 8D2H2L15, or the $V_H$ and $V_L$ of 8D2H2L17.

In particular embodiments, the anti-CTLA-4 antibody or anti-CTLA-4 antibody fragment comprises the $V_H$ and $V_L$ of 8D2/8D2 (RE)-Variant 1, the $V_H$ and $V_L$ of 8D2H1L1-Variant 1, the $V_H$ and $V_L$ of 8D2H2L2-Variant 1, the $V_H$ and $V_L$ of 8D2H2L15-Variant 1, or the $V_H$ and $V_L$ of 8D2H2L17-Variant 1.

In particular embodiments, the effector-silent anti-CTLA-4 antibody fragment comprises either (i) a $V_H$ domain comprising the amino acid sequence set forth in SEQ ID NO: 73 and a $V_L$ domain comprising the amino acid sequence set forth in SEQ ID NO:74; (ii) a $V_H$ domain comprising the amino acid sequence set forth in SEQ ID NO:75 and a $V_L$ domain comprising the amino acid sequence set forth in SEQ ID NO:76; (iii) a $V_H$ domain comprising the amino acid sequence set forth in SEQ ID NO:77 and a $V_L$ domain comprising the amino acid sequence set forth in SEQ ID NO:78; (iv) a $V_H$ domain comprising the amino acid sequence set forth in SEQ ID NO:79 and a $V_L$ domain comprising the amino acid sequence set forth in SEQ ID NO: 80; (v) a $V_H$ domain comprising the amino acid sequence set forth in SEQ ID NO:81 and a $V_L$ domain comprising the amino acid sequence set forth in SEQ ID NO:82; (vi) a $V_H$ domain comprising the amino acid sequence set forth in SEQ ID NO:83 and a $V_L$ domain comprising the amino acid sequence set forth in SEQ ID NO:84; (vii) a $V_H$ domain comprising the amino acid sequence set forth in SEQ ID NO:85 and a $V_L$ domain comprising the amino acid sequence set forth in SEQ ID NO:86; (viii) a $V_H$ domain comprising the amino acid sequence set forth in SEQ ID NO:87 and a $V_L$ domain comprising the amino acid sequence set forth in SEQ ID NO: 88; (ix) a $V_H$ domain comprising the amino acid sequence set forth in SEQ ID NO:89 and a $V_L$ domain comprising the amino acid sequence set forth in SEQ ID NO:90; (x) a $V_H$ domain comprising the amino acid sequence set forth in SEQ ID NO:91 and a $V_L$ domain comprising the amino acid sequence set forth in SEQ ID NO:92; or (xi) a $V_H$ domain comprising the amino acid sequence set forth in SEQ ID NO:93 and a $V_L$ domain comprising the amino acid sequence set forth in SEQ ID NO:94.

In particular embodiments, the effector-silent anti-CTLA-4 antibody fragment comprises one or more immunoglobulin single variable domains (ISVDs), each ISVD comprising the variable domain ($V_{HH}$) of a camelid heavy chain only antibody with the proviso that the ISVD does not comprise a CDR1 comprising the amino sequence FYGMG (SEQ ID NO: 69, a CDR2 comprising the amino acid sequence DIRTSAGRTTYADSVKG (SEQ ID NO: 70), and a CDR3 comprising amino acid EMSGISGWDY (SEQ ID NO:71) or EPSGISGWDY (SEQ ID NO:72) as those ISVDs disclosed in International Patent Application WO2008071447, WO2017087587, and WO2017087588 and ISVD variants comprising 1, 2, or 3 mutations in CDR3 as disclosed in WO2008071447, with the exception that not excluded by the proviso are ISVDs comprising said CDRs in embodiments wherein the one or more ISVDs are fused or linked to an effector-silent antibody constant domain or Fc domain, for example, any one of the effector-silent antibody constants or Fc domains disclosed herein.

(d) Exemplary Anti-PD-1 Antibodies

Exemplary anti-PD-1 antibodies that may be used in the combination therapy of the present invention include any antibody that binds PD-1 and inhibits PD-1 from binding PD-L1. In a further embodiment, the exemplary anti-PD-1 antibody is selected from the group consisting of nivolumab, pembrolizumab, and cemiplimab-rwlc. Exemplary antibodies include the following anti-PD-1 antibodies and compositions comprising an anti-PD1 antibody and a pharmaceutically acceptable salt.

Pembrolizumab, also known as KEYTRUDA, lambrolizumab, MK-3475 or SCH-900475, is a humanized anti-PD-1 antibody described in U.S. Pat. No. 8,354,509 and WO2009/114335 and disclosed, e.g., in Hamid, et al., New England J. Med. 369 (2): 134-144 (2013). The heavy and light chains for pembrolizumab are shown by the amino acid sequences set forth in SEQ ID NOs: 27 and 28, respectively.

Nivolumab, also known as OPDIVO, MDX-1106-04, ONO-4538, or BMS-936558, is a fully human IgG4 anti-PD-1 antibody described in WO2006/121168 and U.S. Pat. No. 8,008,449. The heavy and light chains for nivolumab are shown by the amino acid sequences set forth in SEQ ID NOs: 25 and 26, respectively.

Cemiplimab-rwlc, also known as cemiplimab, LIBTAYO or REGN2810, is a recombinant human $IgG_4$ monoclonal antibody that is described in WO2015112800 and U.S. Pat. No. 9,987,500. The heavy and light chains for cemiplimab-rwlc are shown by the amino acid sequences set forth in SEQ ID NOs: 101 and 102, respectively.

In particular embodiments, the anti-PD-1 antibody comprises (i) a $V_H$ comprising the three HC-CDRs of pembrolizumab fused or linked to an effector-silent HC constant domain and (ii) a $V_L$ comprising the three LC-CDRs of pembrolizumab fused or linked to a LC kappa or lambda constant domain. The three HC-CDRs comprise SEQ ID NO:31, SEQ ID NO:32, and SEQ ID NO:33, respectively, and the three LC-CDRs comprise SEQ ID NO:34, SEQ ID NO:35, and SEQ ID NO:36, respectively.

In particular embodiments, the anti-PD-1 antibody comprises (i) a $V_H$ comprising the three HC-CDRs of nivolumab fused or linked to an effector-silent HC constant domain and (ii) a $V_L$ comprising the three LC-CDRs of nivolumab fused or linked to a LC kappa or lambda constant domain. The three HC-CDRs comprise SEQ ID NO: 17, SEQ ID NO: 18, and SEQ ID NO: 19, respectively, and the three LC-CDRs comprise SEQ ID NO:20, SEQ ID NO:21, and SEQ ID NO:2, respectively.

In particular embodiments, the anti-PD-1 antibody comprises (i) a $V_H$ comprising the three HC-CDRs of cemiplimab-rwlc fused or linked to an effector-silent HC constant domain and (ii) a $V_L$ comprising the three LC-CDRs of nivolumab fused or linked to a LC kappa or lambda constant domain.

In particular embodiments, the anti-PD-1 antibody comprises (i) the $V_H$ and $V_L$ domains of pembrolizumab, wherein the $V_H$ domain is fused or linked to an effector-silent HC constant domain and the $V_L$ domain is fused or linked to a LC kappa or lambda constant domain; (ii) the $V_H$ and $V_L$ domains of nivolumab, wherein the $V_H$ domain is fused or linked to an effector-silent HC constant domain and the $V_L$ domain is fused or linked to an LC kappa or lambda constant domain; or (iii) the $V_H$ and $V_L$ domains of cemiplimab-rwlc, wherein the $V_H$ domain is fused or linked to an effector-silent HC constant domain and the $V_L$ domain is fused or linked to an LC kappa or lambda constant domain. The pembrolizumab $V_H$ domain comprises the amino acid sequence set forth in SEQ ID NO:29 and the $V_L$ domain comprises the amino acid sequence set forth in SEQ ID NO:30. The nivolumab $V_H$ domain comprises the amino acid sequence set forth in SEQ ID NO:23 and the $V_L$ domain comprises the amino acid sequence set forth in SEQ ID NO:24. The cemiplimab-rwlc $V_H$ domain comprises the amino acid sequence set forth in SEQ ID NO:99 and $V_L$ domain comprises the amino acid sequence set forth in SEQ ID NO: 100. In particular embodiments, the $V_H$ and $V_L$ domains may further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the anti-PD-1 antibody $V_H$ domain may be fused or linked to an $IgG_1$, $IgG_2$, $IgG_3$, or $IgG_4$ HC constant domain that is not currently linked to the particular $V_H$ or is linked to an $IgG_1$, $IgG_2$, $IgG_3$, or $IgG_4$ HC constant domain has been modified to include one or more mutations in the Fc domain that render the resulting anti-PD-1 antibody effecter-silent.

In certain embodiments, the HC constant domain is of an $IgG_1$, $IgG_2$, $IgG_3$, or $IgG_4$ isotype, which is modified to lack N-glycosylation of the asparagine (Asn) residue at position 297 of the HC constant domain by replacing the codon for the Asn at position 297 in the nucleic acid molecule encoding the HC constant domain with a codon for another amino acid, for example Gln. In further embodiments, such IgGs modified to lack N-glycosylation at position 297 further includes one or more additional mutations disclosed herein for eliminating detectable effector function. In particular embodiments, the HC constant domain is a human HC constant domain. In particular embodiments, the molecules further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the present invention provides an anti-PD-1 antibody that comprises an $IgG_4$ HC constant domain that has been modified to have an S228P substitution and further include in addition to the S228P substitution, a P239G, D265A, or D265A/N297G amino acid substitutions, wherein the positions are identified according to Eu numbering. In particular embodiments of the above, the $IgG_4$ HC constant domain is a human HC constant domain. In particular embodiments, the molecules further comprise 1, 2, 3, 4, 5, 6, 7, 8, 9, or 10 additional amino acid substitutions, insertions, and/or deletions, wherein said substitutions may be conservative mutations or non-conservative mutations.

In another embodiment, the anti-PD-1 antibody may comprise a human $IgG_1$ isotype, in which the Fc domain of the HC constant domain has been modified to be effector-silent by substituting the amino acids from position 233 to position 236 of the $IgG_1$ with the corresponding amino acids of the human $IgG_2$ HC and substituting the amino acids at positions 327, 330, and 331 with the corresponding amino acids of the human $IgG_4$ HC, wherein the positions are identified according to Eu numbering. In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

In another embodiment, the Fc domain of the $IgG_1$ $IgG_2$, $IgG_3$, or $IgG_4$ HC constant domain is modified to include one or more amino acid substitutions selected from E233P, L234A, L235A, L235E, N297A, N297D, D265S, and P331S and wherein said polypeptide exhibits no measurable binding to the FcγRIIIA, FcγRIIA, and FcγRI or reduced binding compared to a polypeptide comprising the wild-type IgG constant domain region as determined by a Biacore assay. These and other substitutions are disclosed in WO9428027; WO2004099249; WO20121300831, U.S. Pat. Nos. 9,708,406; 8,969,526; 9,296,815; Sondermann et al. Nature 406, 267-273 (20 Jul. 2000)). In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

Tables 19-27 provide specific exemplary anti-PD-1 antibodies that may be used in combination with an anti-CTLA-4 antibody as disclosed herein in a therapy to treat an individual who has cancer. The present invention also provides the antibodies shown in the tables and compositions, each composition comprising an antibody shown the tables and a pharmaceutically acceptable carrier. All HC amino acid substitution positions in Tables 19-27 are according to the Eu numbering scheme.

TABLE 19 pembrolizumab $IgG_1$ derivatives

| | | SEQ ID NO. | | | |
|---|---|---|---|---|---|
| Ab No. | Isotype and HC Substitutions | HC constant domain | $V_H$ | $V_L$ | LC constant domain |
| 16-1 | $IgG_1$ (L234A/L235A/D265S) | 38 | 29 | 30 | 57 or 117 |
| 16-2 | $IgG_1$ (L234A/L235A/P329G) | 39 | 29 | 30 | 57 or 117 |
| 16-3 | $IgG_1$ (L235E) | 40 | 29 | 30 | 57 or 117 |
| 16-4 | $IgG_1$ (D265A) | 41 | 29 | 30 | 57 or 117 |
| 16-5 | $IgG_1$ (D265A/N297G) | 42 | 29 | 30 | 57 or 117 |
| 16-6 | $IgG_1$ (E233A/L235A) | 43 | 29 | 30 | 57 or 117 |
| 16-7 | $IgG_1$ (N297X) | 44 | 29 | 30 | 57 or 117 |
| 16-8 | $IgG_1$ (N297A/D356E/L358M) | 116 | 29 | 30 | 57 or 117 |

TABLE 19-continued pembrolizumab IgG₁ derivatives

| Ab No. | Isotype and HC Substitutions | HC constant domain | V_H | V_L | LC constant domain |
|---|---|---|---|---|---|
| 16-9 | IgG₁ (L234F/L235E/P331S/D356E/L358M) | 117 | 29 | 30 | 57 or 117 |

TABLE 20

Pembrolizumab IgG₂ derivatives

| Ab No. | Isotype and HC Substitutions | HC constant domain | V_H | V_L | LC constant domain |
|---|---|---|---|---|---|
| 17-1 | IgG₂ (D265S) | 46 | 29 | 30 | 57 or 117 |
| 17-2 | IgG₂ (P329G) | 47 | 29 | 30 | 57 or 117 |
| 17-3 | IgG₂ (D265A) | 48 | 29 | 30 | 57 or 117 |
| 17-4 | IgG₂ (D265A/N297G) | 49 | 29 | 30 | 57 or 117 |
| 17-5 | IgG₂ (N297X) | 50 | 29 | 30 | 57 or 117 |
| 17-6 | IgG₂ (V234A/G237A/P238S/H268A/V309L/A330S/P331S) | 51 | 29 | 30 | 57 or 117 |

TABLE 21

Pembrolizumab IgG₄ derivatives

| Ab No. | Isotype and HC Substitutions | HC constant domain | V_H | V_L | LC constant domain |
|---|---|---|---|---|---|
| 18-1 | IgG₄ (S228P) | 52 | 29 | 30 | 57 or 117 |
| 18-2 | IgG₄ (S228P/P329G) | 53 | 29 | 30 | 57 or 117 |
| 18-3 | IgG₄ (S228P/D265A) | 54 | 29 | 30 | 57 or 117 |
| 18-4 | IgG₄ (S228P/D265A/N297G) | 55 | 29 | 30 | 57 or 117 |
| 18-5 | IgG₄ (S228P/N297X) | 56 | 29 | 30 | 57 or 117 |

TABLE 22

| Ab No. | Nivolumab IgG₁ derivatives Isotype and HC Substitutions | HC constant domain | V_H | V_L | LC constant domain |
|---|---|---|---|---|---|
| 19-1 | IgG₁ (L234A/L235A/D265S) | 38 | 23 | 24 | 57 or 117 |
| 19-2 | IgG₁ (L234A/L235A/P329G) | 39 | 23 | 24 | 57 or 117 |
| 19-3 | IgG₁ (L235E) | 40 | 23 | 24 | 57 or 117 |
| 19-4 | IgG₁ (D265A) | 41 | 23 | 24 | 57 or 117 |
| 19-5 | IgG₁ (D265A/N297G) | 42 | 23 | 24 | 57 or 117 |
| 19-6 | IgG₁ (E233A/L235A) | 43 | 23 | 24 | 57 or 117 |
| 19-7 | IgG₁ (N297X) | 44 | 23 | 24 | 57 or 117 |
| 19-8 | IgG₁ (N297A/D356E/L358M) | 116 | 23 | 24 | 57 or 117 |
| 19-9 | IgG₁ (L234F/L235E/P331S/D356E/L358M) | 117 | 23 | 24 | 57 or 117 |

TABLE 23

| Ab No. | Nivolumab IgG₂ derivatives Isotype and HC Substitutions | HC constant domain | V_H | V_L | LC constant domain |
|---|---|---|---|---|---|
| 20-1 | IgG₂ (D265S) | 46 | 23 | 24 | 57 or 117 |
| 20-2 | IgG₂ (P329G) | 47 | 23 | 24 | 57 or 117 |
| 20-3 | IgG₂ (D265A) | 48 | 23 | 24 | 57 or 117 |
| 20-4 | IgG₂ (D265A/N297G) | 49 | 23 | 24 | 57 or 117 |
| 20-5 | IgG₂ (N297X) | 50 | 23 | 24 | 57 or 117 |
| 20-6 | IgG₂ (V234A/G237A/P238S/H268A/V309L/A330S/P331S) | 51 | 23 | 24 | 57 or 117 |

TABLE 24

| Ab No. | Nivolumab IgG₄ derivatives Isotype and HC Substitutions | HC constant domain | V_H | V_L | LC constant domain |
|---|---|---|---|---|---|
| 21-1 | IgG₄ (S228P) | 52 | 23 | 24 | 57 or 117 |
| 21-2 | IgG₄ (S228P/P329G) | 53 | 23 | 24 | 57 or 117 |
| 21-3 | IgG₄ (S228P/D265A) | 54 | 23 | 24 | 57 or 117 |
| 21-4 | IgG₄ (S228P/D265A/N297G) | 55 | 23 | 24 | 57 or 117 |
| 21-5 | IgG₄ (S228P/N297X) | 56 | 23 | 24 | 57 or 117 |

TABLE 25

| Ab No. | Cemiplimab-rwlc IgG₁ derivatives isotype and HC Substitutions | HC constant domain | V_H | V_L | LC constant domain |
|---|---|---|---|---|---|
| 22-1 | IgG₁ (L234A/L235A/D265S) | 38 | 99 | 100 | 57 or 117 |
| 22-2 | IgG₁ (L234A/L235A/P329G) | 39 | 99 | 100 | 57 or 117 |
| 22-3 | IgG₁ (L235E) | 40 | 99 | 100 | 57 or 117 |
| 22-4 | IgG₁ (D265A) | 41 | 99 | 100 | 57 or 117 |

TABLE 25-continued

| Ab No. | Cemiplimab-rwlc IgG$_1$ derivatives isotype and HC Substitutions | HC constant domain | V$_H$ | V$_L$ | LC constant domain |
|---|---|---|---|---|---|
| 22-5 | IgG$_1$ (D265A/N297G) | 42 | 99 | 100 | 57 or 117 |
| 22-6 | IgG$_1$ (E233A/L235A) | 43 | 99 | 100 | 57 or 117 |
| 22-7 | IgG$_1$ (N297X) | 44 | 99 | 100 | 57 or 117 |
| 22-8 | IgG$_1$ (N297A/D356E/L358M) | 116 | 99 | 100 | 57 or 117 |
| 22-9 | IgG$_1$ (L234F/L235E/P331S/D356E/L358M) | 117 | 99 | 100 | 57 or 117 |

TABLE 26

| Ab No. | Cemiplimab-rwlc IgG$_2$ derivatives isotype and HC Substitutions | HC constant domain | V$_H$ | V$_L$ | LC constant domain |
|---|---|---|---|---|---|
| 23-1 | IgG$_2$ (D265S) | 46 | 99 | 100 | 57 or 117 |
| 23-2 | IgG$_2$ (P329G) | 47 | 99 | 100 | 57 or 117 |
| 23-3 | IgG$_2$ (D265A) | 48 | 99 | 100 | 57 or 117 |
| 23-4 | IgG$_2$ (D265A/N297G) | 49 | 99 | 100 | 57 or 117 |
| 23-5 | IgG$_2$ (N297X) | 50 | 99 | 100 | 57 or 117 |
| 23-6 | IgG$_2$ (V234A/G237A/P238S/H268A/V309L/A330S/P331S) | 51 | 99 | 100 | 57 or 117 |

TABLE 27

| Ab No. | Cemiplimab-rwlc IgG$_4$ derivatives isotype and HC Substitutions | HC constant domain | V$_H$ | V$_L$ | LC constant domain |
|---|---|---|---|---|---|
| 24-1 | IgG$_4$ (S228P) | 52 | 99 | 100 | 57 or 117 |
| 24-2 | IgG$_4$ (S228P/P329G) | 53 | 99 | 100 | 57 or 117 |
| 24-3 | IgG$_4$ (S228P/D265A) | 54 | 99 | 100 | 57 or 117 |
| 24-4 | IgG$_4$ (S228P/D265A/N297G) | 55 | 99 | 100 | 57 or 117 |
| 24-5 | IgG$_4$ (S228P/N297X) | 56 | 99 | 100 | 57 or 117 |

(e) Exemplary Anti-PD-1 Antibody Fragments

Exemplary anti-PD-1 antibody fragments that may be used in the combination therapy of the present invention include any anti-PD-1 antibody fragment that binds PD-1 and inhibits PD-1 from binding PD-L1 and further include the following anti-PD-1 antibody fragments that bind PD-1 and compositions comprising the following anti-PD-1 antibody fragments and a pharmaceutically acceptable carrier.

In particular embodiments, the antibody fragment is an Fv or scFv comprising the pembrolizumab V$_H$ having the amino acid sequence set forth in SEQ ID NO:29 and the pembrolizumab V$_L$ having the amino acid sequence set forth in SEQ ID NO:30.

In particular embodiments, the anti-PD-1 antibody fragment is a F(ab) comprising the pembrolizumab V$_H$ having the amino acid sequence set forth in SEQ ID NO:29 and the pembrolizumab V$_H$ having the amino acid sequence set forth in SEQ ID NO:30.

In particular embodiments, the anti-PD-1 antibody fragment is a F(ab')$_2$ comprising the pembrolizumab V$_H$ having the amino acid sequence set forth in SEQ ID NO:29 and the pembrolizumab V$_H$ having the amino acid sequence set forth in SEQ ID NO:30.

In particular embodiments, the anti-PD-1 antibody fragment is an Fv or scFv comprising the nivolumab V$_H$ having the amino acid sequence set forth in SEQ ID NO:23 and the nivolumab V$_H$ having the amino acid sequence set forth in SEQ ID NO:24.

In particular embodiments, the anti-PD-1 antibody fragment is a F(ab) comprising the nivolumab V$_H$ having the amino acid sequence set forth in SEQ ID NO:23 and the nivolumab V$_H$ having the amino acid sequence set forth in SEQ ID NO:24.

In particular embodiments, the anti-PD-1 antibody fragment is a F(ab')$_2$ comprising the nivolumab V$_H$ having the amino acid sequence set forth in SEQ ID NO:23 and the nivolumab V$_H$ having the amino acid sequence set forth in SEQ ID NO:24.

In particular embodiments, the anti-PD-1 antibody fragment comprises one or more immunoglobulin single variable domains (ISVDs), each ISVD comprising the variable domain (V$_{HH}$) of a camelid heavy chain only antibody with the proviso that ISVD does not comprise a CDR1 comprising the amino sequence THAMG (SEQ ID NO:73, a CDR2 comprising the amino acid sequence VITWSGGITTYADSVKG (SEQ ID NO:74) or VITVSGGITYYADSVKG (SEQ ID NO:75), and a CDR3 comprising amino acid DKHQSSWYDY (SEQ ID NO:76) or DKHQSSFYDY (SEQ ID NO:77) as those ISVDs disclosed in International Patent Application WO2008071447, WO2017087587, and WO2017087589 and variants comprising 1, 2, or 3 mutations in CDR3 as set forth in WO2008071447, with the exception that not excluded by the proviso are ISVDs comprising said CDRs in embodiments wherein the one or more ISVDs are fused or linked to an effector-silent antibody constant domain or Fc domain, for example, any one of the effector-silent antibody constant domains or Fc domains disclosed herein.

(f) Exemplary anti-PD-L1 antibodies

Exemplary anti-PD-L1 antibodies that may be used in the combination therapy of the present invention include any anti-PD-L1 antibody that inhibits PD-1 from binding PD-L1 and further includes the following anti-PD-L1 antibodies and compositions comprising the following anti-PD-L1 antibodies and a pharmaceutically acceptable carrier. In particular embodiments, the anti-PD-L1 antibody is selected from the group consisting atezolizumab, avelumab, and durvalumab.

In particular embodiments, the anti-PD-L1 antibody comprises (i) the V$_H$ and V$_L$ domains of atezolizumab, wherein the V$_H$ domain is fused or linked to an HC constant domain or effector-silent HC constant domain and the V$_L$ domain is fused or linked to an LC kappa or lambda constant domain, (ii) the V$_H$ and V$_L$ domains of avelumab, wherein the V$_H$ domain is fused or linked to an HC constant domain or effector-silent HC constant domain and the V$_L$ domain is fused or linked to an LC kappa or lambda constant domain, or (iii) the V$_H$ and V$_L$ domains of durvalumab, wherein the V$_H$ domain is fused or linked to an HC constant domain or effector-silent HC constant domain and the V$_L$ domain is fused or linked to an LC kappa or lambda constant domain. The durvalumab V$_H$ domain comprises the amino acid sequence set forth in SEQ ID NO: 103 and $V_L$ domain comprises the amino acid sequence set forth in SEQ ID NO: 104. The avelumab $V_H$ domain comprises the amino acid sequence set forth in SEQ ID NO: 105 and $V_L$ domain comprises the amino acid sequence set forth in SEQ ID NO:106. The atezolizumab $V_H$ domain comprises the amino acid sequence set forth in SEQ ID NO:107 and $V_L$ domain comprises the amino acid sequence set forth in SEQ ID NO:108. In particular embodiments, the $V_H$ and $V_L$ domains further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the anti-PD-L1 antibody $V_H$ domain may be fused or linked to an $IgG_1$, $IgG_2$, $IgG_3$, or $IgG_4$ HC constant domain that is not currently linked to the particular $V_H$ or is linked to an $IgG_1$, $IgG_2$, $IgG_3$, or $IgG_4$ HC constant domain has been modified to include one or more mutations in the Fc domain that render the resulting anti-PD-L1 antibody effecter-silent.

In certain embodiments, the HC constant domain is of the $IgG_1$, $IgG_2$, $IgG_3$, or $IgG_4$ isotype, which is modified to lack N-glycosylation of the asparagine (Asn) residue at position 297 of the HC constant domain by replacing the codon for the Asn at position 297 in the nucleic acid molecule encoding the HC constant domain with a codon for another amino acid, for example Gln. Alternatively, the codon for Ser may be replaced with the codon for Pro or the codon for Thr may be replaced with any codon except the codon for Ser, e.g. N297A, N297G, or N297D. Alternatively, all three codons are modified. In further embodiments, such IgGs modified to lack N-glycosylation at position 297 further includes one or more additional mutations disclosed herein for eliminating detectable effector function. In particular embodiments, the HC constant domain is a human HC constant domain. In particular embodiments, the molecules further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the present invention provides an anti-PD-L1 antibody that comprises an $IgG_4$ HC constant domain that has been modified to have an S228P substitution and further include in addition to the S228P substitution, a P239G, D265A, or D265A/N297G amino acid substitutions, wherein the positions are identified according to Eu numbering. In particular embodiments of the above, the $IgG_4$ HC constant domain is a human HC constant domain. In particular embodiments, the molecules further comprise 1, 2, 3, 4, 5, 6, 7, 8, 9, or 10 additional amino acid substitutions, insertions, and/or deletions, wherein said substitutions may be conservative mutations or non-conservative mutations.

In another embodiment, the anti-PD-L1 antibody may comprise a human $IgG_1$ isotype, in which the Fc domain of the HC constant domain has been modified to be effector-silent by substituting the amino acids from position 233 to position 236 of the $IgG_1$ with the corresponding amino acids of the human $IgG_2$ HC and substituting the amino acids at positions 327, 330, and 331 with the corresponding amino acids of the human $IgG_4$ HC, wherein the positions are identified according to Eu numbering. In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

In another embodiment, the Fc domain of the $IgG_1$, $IgG_2$, $IgG_3$, or $IgG_4$ HC constant domain is modified to include one or more amino acid substitutions selected from E233P, L234A, L235A, L235E, N297A, N297D, D265S, and P331S and wherein said polypeptide exhibits no measurable binding to the FcγRIIIA, FcγRIIA, and FcγRI or reduced binding compared to a polypeptide comprising the wild-type IgG constant domain region as determined by a Biacore assay. These and other substitutions are disclosed in WO9428027; WO2004099249; WO20121300831, U.S. Pat. Nos. 9,708,406; 8,969,526; 9,296,815; Sondermann et al. Nature 406, 267-273 (20 Jul. 2000)). In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

Tables 28-36 provide exemplary anti-PD-L1 antibodies, which may be used in combination with an anti-CTLA-4 antibody as disclosed herein in a therapy to treat an individual who has cancer. The present invention also provides the antibodies shown the tables, except for antibodies 25-9 and 31-8, and compositions, each composition comprising an antibody shown in the table, except for antibodies 25-9 and 31-8, and a pharmaceutically acceptable carrier. All HC amino acid substitution positions in Tables 28-36 are according to the Eu numbering scheme.

TABLE 28

| Ab No. | Durvalumab $IgG_1$ derivatives Isotype and HC Substitutions | HC constant domain | $V_H$ | $V_L$ | LC constant domain |
|---|---|---|---|---|---|
| 25-1 | $IgG_1$ (L234A/L235A/D265S) | 38 | 103 | 104 | 57 or 117 |
| 25-2 | $IgG_1$ (L234A/L235A/P329G) | 39 | 103 | 104 | 57 or 117 |
| 25-3 | $IgG_1$ (L235E) | 40 | 103 | 104 | 57 or 117 |
| 25-4 | $IgG_1$ (D265A) | 41 | 103 | 104 | 57 or 117 |
| 25-5 | $IgG_1$ (D265A/N297G) | 42 | 103 | 104 | 57 or 117 |
| 25-6 | $IgG_1$ (E233A/L235A) | 43 | 103 | 104 | 57 or 117 |
| 25-7 | $IgG_1$ (N297X) | 44 | 103 | 104 | 57 or 117 |
| 22-8 | $IgG_1$ (N297A/D356E/L358M) | 116 | 103 | 104 | 57 or 117 |
| 25-9 | $IgG_1$ (L234F/L235E/P331S/D356E/L358M) | 117 | 103 | 104 | 57 or 117 |

TABLE 29

| Ab No. | Durvalumab $IgG_2$ derivatives Isotype and HC Substitutions | HC constant domain | $V_H$ | $V_L$ | LC constant domain |
|---|---|---|---|---|---|
| 26-1 | $IgG_2$ (D265S) | 46 | 103 | 104 | 57 or 117 |
| 26-2 | $IgG_2$ (P329G) | 47 | 103 | 104 | 57 or 117 |
| 26-3 | $IgG_2$ (D265A) | 48 | 103 | 104 | 57 or 117 |
| 26-4 | $IgG_2$ (D265A/N297G) | 49 | 103 | 104 | 57 or 117 |
| 26-5 | $IgG_2$ (N297X) | 50 | 103 | 104 | 57 or 117 |
| 26-6 | IgG2 (V234A/G237A/P238S/H268A/V309L/A330S/P331S) | 51 | 103 | 104 | 57 or 117 |

TABLE 30

| Ab No. | Durvalumab IgG$_4$ derivatives Isotype and HC Substitutions | SEQ ID NO. | | | |
|---|---|---|---|---|---|
| | | HC constant domain | V$_H$ | V$_L$ | LC constant domain |
| 27-1 | IgG$_4$ (S228P) | 52 | 103 | 104 | 57 or 117 |
| 27-2 | IgG$_4$ (S228P/P329G) | 53 | 103 | 104 | 57 or 117 |
| 27-3 | IgG$_4$ (S228P/D265A) | 54 | 103 | 104 | 57 or 117 |
| 27-4 | IgG$_4$ (S228P/D265A/N297G) | 55 | 103 | 104 | 57 or 117 |
| 27-5 | IgG$_4$ (S228P/N297X) | 56 | 103 | 104 | 57 or 117 |

TABLE 31

| Ab No. | Avelumab IgG$_1$ derivatives Isotype and HC Substitutions | SEQ ID NO. | | | |
|---|---|---|---|---|---|
| | | HC constant domain | V$_H$ | V$_L$ | LC constant domain |
| 28-1 | IgG$_1$ (L234A/L235A/D265S) | 38 | 105 | 106 | 57 or 117 |
| 28-2 | IgG$_1$ (L234A/L235A/P329G) | 39 | 105 | 106 | 57 or 117 |
| 28-3 | IgG$_1$ (L235E) | 40 | 105 | 106 | 57 or 117 |
| 28-4 | IgG$_1$ (D265A) | 41 | 105 | 106 | 57 or 117 |
| 28-5 | IgG$_1$ (D265A/N297G) | 42 | 105 | 106 | 57 or 117 |
| 28-6 | IgG$_1$ (E233A/L235A) | 43 | 105 | 106 | 57 or 117 |
| 28-7 | IgG$_1$ (N297X) | 44 | 105 | 106 | 57 or 117 |
| 28-8 | IgG$_1$ (N297A/D356E/L358M) | 116 | 105 | 106 | 57 or 117 |
| 28-9 | IgG$_1$ (L234F/L235E/P331S/D356E/L358M) | 117 | 105 | 106 | 57 or 117 |

TABLE 32

| Ab No. | Avelumab IgG$_2$ derivatives Isotype and HC Substitutions | SEQ ID NO. | | | |
|---|---|---|---|---|---|
| | | HC constant domain | V$_H$ | V$_L$ | LC constant domain |
| 29-1 | IgG$_2$ (D265S) | 46 | 105 | 106 | 57 or 117 |
| 29-2 | IgG$_2$ (P329G) | 47 | 105 | 106 | 57 or 117 |
| 29-3 | IgG$_2$ (D265A) | 48 | 105 | 106 | 57 or 117 |
| 29-4 | IgG$_2$ (D265A/N297G) | 49 | 105 | 106 | 57 or 117 |
| 29-5 | IgG$_2$ (N297X) | 50 | 105 | 106 | 57 or 117 |
| 29-6 | IgG$_2$ (V234A/G237A/P238S/H268A/V309L/A330S/P331S) | 51 | 105 | 106 | 57 or 117 |

TABLE 33

| Ab No. | Avelumab IgG$_4$ derivatives Isotype and HC Substitutions | SEQ ID NO. | | | |
|---|---|---|---|---|---|
| | | HC constant domain | V$_H$ | V$_L$ | LC constant domain |
| 30-1 | IgG$_4$ (S228P) | 52 | 105 | 106 | 57 or 117 |
| 30-2 | IgG$_4$ (S228P/P329G) | 53 | 105 | 106 | 57 or 117 |
| 30-3 | IgG$_4$ (S228P/D265A) | 54 | 105 | 106 | 57 or 117 |
| 30-4 | IgG$_4$ (S228P/D265A/N297G) | 55 | 105 | 106 | 57 or 117 |
| 30-5 | IgG$_4$ (S228P/N297X) | 56 | 105 | 106 | 57 or 117 |

TABLE 34

| Ab No. | Atezolizumab IgG$_1$ derivatives Isotype and HC Substitutions | SEQ ID NO. | | | |
|---|---|---|---|---|---|
| | | HC constant domain | V$_H$ | V$_L$ | LC constant domain |
| 31-1 | IgG$_1$ (L234A/L235A/D265S) | 38 | 107 | 108 | 57 or 117 |
| 31-2 | IgG$_1$ (L234A/L235A/P329G) | 39 | 107 | 108 | 57 or 117 |
| 31-3 | IgG$_1$ (L235E) | 40 | 107 | 108 | 57 or 117 |
| 31-4 | IgG$_1$ (D265A) | 41 | 107 | 108 | 57 or 117 |
| 31-5 | IgG$_1$ (D265A/N297G) | 42 | 107 | 108 | 57 or 117 |
| 31-6 | IgG$_1$ (E233A/L235A) | 43 | 107 | 108 | 57 or 117 |
| 31-7 | IgG$_1$ (N297X) | 44 | 107 | 108 | 57 or 117 |
| 31-8 | IgG$_1$ (N297A/D356E/L358M) | 116 | 107 | 108 | 57 or 117 |
| 31-9 | IgG$_1$ (L234F/L235E/P331S/D356E/L358M) | 117 | 107 | 108 | 57 or 117 |

TABLE 35

| Ab No. | Atezolizumab IgG$_2$ derivatives Isotype and HC Substitutions | SEQ ID NO. | | | |
|---|---|---|---|---|---|
| | | HC constant domain | V$_H$ | V$_L$ | LC constant domain |
| 32-1 | IgG$_2$ (D265S) | 46 | 107 | 108 | 57 or 117 |
| 32-2 | IgG$_2$ (P329G) | 47 | 107 | 108 | 57 or 117 |
| 32-3 | IgG$_2$ (D265A) | 48 | 107 | 108 | 57 or 117 |
| 32-4 | IgG$_2$ (D265A/N297G) | 49 | 107 | 108 | 57 or 117 |
| 32-5 | IgG$_2$ (N297X) | 50 | 107 | 108 | 57 or 117 |
| 32-6 | IgG$_2$ (V234A/G237A/P238S/H268A/V309L/A330S/P331S) | 51 | 107 | 108 | 57 or 117 |

TABLE 36

| Ab No. | Atezolizumab IgG$_4$ derivatives Isotype and HC Substitutions | SEQ ID NO. | | | |
|---|---|---|---|---|---|
| | | HC constant domain | V$_H$ | V$_L$ | LC constant domain |
| 33-1 | IgG$_4$ (S228P) | 52 | 107 | 108 | 57 or 117 |
| 33-2 | IgG$_4$ (S228P/P329G) | 53 | 107 | 108 | 57 or 117 |
| 33-3 | IgG$_4$ (S228P/D265A) | 54 | 107 | 108 | 57 or 117 |
| 33-4 | IgG$_4$ (S228P/D265A/N297G) | 55 | 107 | 108 | 57 or 117 |
| 33-5 | IgG$_4$ (S228P/N297X) | 56 | 107 | 108 | 57 or 117 |

(g) Exemplary Anti-PD-L1 Antibody Fragments

Exemplary anti-PD-L1 antibody fragments that may be used in the combination 5 therapy of the present invention includes any anti-PD-L1 antibody fragment that binds PD-L1 and inhibits PD-L1 from binding PD-1 and further includes the following anti-PD-L1 antibody fragments and compositions, each composition comprising a following anti-PD-L1 antibody fragment and a pharmaceutically acceptable carrier.

In particular embodiments, the anti-PD-L1 antibody fragment is an Fv or scFv comprising the durvalumab V$_H$ having the amino acid sequence set forth in SEQ ID NO:103 and the durvalumab V$_L$ having the amino acid sequence set forth in SEQ ID NO:104.

In particular embodiments, the anti-PD-L1 antibody fragment is a F(ab) comprising the durvalumab V$_H$ having the amino acid sequence set forth in SEQ ID NO: 103 and the durvalumab V$_H$ having the amino acid sequence set forth in SEQ ID NO:104.

In particular embodiments, the anti-PD-L1 antibody fragment is a F(ab')$_2$ comprising the durvalumab V$_H$ having the amino acid sequence set forth in SEQ ID NO:103 and the durvalumab V$_H$ having the amino acid sequence set forth in SEQ ID NO: 104.

In particular embodiments, the anti-PD-L1 antibody fragment is an Fv or scFv comprising the avelumab V$_H$ having the amino acid sequence set forth in SEQ ID NO:105 and the avelumab V$_H$ having the amino acid sequence set forth in SEQ ID NO: 106.

In particular embodiments, the anti-PD-L1 antibody fragment is a F(ab) comprising the avelumab V$_H$ having the amino acid sequence set forth in SEQ ID NO:105 and the avelumab V$_H$ having the amino acid sequence set forth in SEQ ID NO: 106.

In particular embodiments, the anti-PD-L1 antibody fragment is a F(ab')$_2$ comprising the avelumab V$_H$ having the amino acid sequence set forth in SEQ ID NO: 105 and the avelumab V$_H$ having the amino acid sequence set forth in SEQ ID NO: 106.

In particular embodiments, the anti-PD-L1 antibody fragment is an Fv or scFv comprising the atezolizumab V$_H$ having the amino acid sequence set forth in SEQ ID NO:107 and the atezolizumab V$_H$ having the amino acid sequence set forth in SEQ ID NO:108.

In particular embodiments, the anti-PD-L1 antibody fragment is a F(ab) comprising the atezolizumab V$_H$ having the amino acid sequence set forth in SEQ ID NO:107 and the atezolizumab V$_H$ having the amino acid sequence set forth in SEQ ID NO:108.

In particular embodiments, the anti-PD-L1 antibody fragment is a F(ab')$_2$ comprising the atezolizumab V$_H$ having the amino acid sequence set forth in SEQ ID NO:107 and the atezolizumab V$_H$ having the amino acid sequence set forth in SEQ ID NO:108.

In particular embodiments, the anti-PD-L1 antibody fragment comprises one or more immunoglobulin single variable domains (ISVDs), each ISVD comprising the variable domain (V$_{HH}$) of a camelid heavy chain only antibody with the proviso that ISVD does not comprise an anti-PD-L1 ISVD disclosed in International Application WO2008071447 having SEQ ID NO: 394-399 therein or disclosed in WO2009030285, both of which are incorporated herein by reference, with the exception that not excluded by the proviso are ISVDs wherein the one or more ISVDs are fused or linked to an effector-silent antibody constant domain or Fc domain, for example, any one of the effector-silent antibody constant domains or Fc domains disclosed herein.

(h) Exemplary Combination Therapy Dosing Regimens

The present invention provides anti-cancer therapies that combine the immune-stimulating effects of a PD-1 blocking agent with the anti-tumor effects of a CTLA-4 blocking agent but without the dermatologic or gut irAEs typically observed for CTLA-4 blocking agents administered in combination with PD-1 blocking agents. A feature of the present invention is that the CTLA-4 blocking agent lacks measurable binding to one or more FcRs as determined in a Biacore assay or reduced binding to one or more FcRs compared to that of a wild-type antibody of the same isotype as measured in a Biacore assay. Thus, the CTLA-4 blocking agents display no measurable or display reduced effector function, which enables the effector-silent CTLA-4 blocking agents to be used in combination therapies with PD-1 blocking agents at doses and dosing durations not available with CTLA-4 blocking agents that display effector function. This feature distinguishes the CTLA-4 blocking agents of the present invention from the currently available CTLA-4 blocking agents.

In a typical dosing regimen of the present invention, the CTLA-4 blocking agent and the PD-1 blocking agent may be administered to the individual concurrently in separate doses and in different formats. In general, the CTLA-4 blocking agent of the present invention may be administered in a combination therapy with a PD-1 blocking agent at least at the same dose, dosing frequency, and treatment duration currently approved by the U.S. FDA for the ipilimumab/nivolumab combination therapy for particular indications. However, the combination therapy is not limited to the particular indications approved by the U.S. FDA but may include any indication that may benefit from the combination therapy of the present invention. The currently approved dose is 1 mg/kg of ipilimumab following the administration of nivolumab provided at a dose of 3 mg/kg. This dose combination may then be repeated every three weeks for four doses with the doses of nivolumab continuing every two weeks thereafter as needed. However, in further embodiments, the CTLA-4 blocking agent of the present invention may be administered in the combination therapy at a dose that is more than 1 mg/kg, for example a dose of at least 3 mg/kg. In a further still embodiment, the dose may be at least 10 mg/kg and in further still embodiments, the dose may be between about 1 mg/kg and 10 mg/kg. In particular embodiments, the CTLA-4 blocking agent of the present invention may be administered for at the same dosing frequency and treatment duration as that in the approved ipilimumab/nivolumab combination therapy. In particular embodiments, the CTLA-4 blocking agents of the present invention may be administered at the same dosing frequency and treatment duration as that for nivolumab in the approved ipilimumab/nivolumab combination therapy.

In particular embodiments of the combination therapy, the CTLA-4 blocking agent is administered in a dose that is not based on the weight of the individual. Thus, in particular embodiments, the CTLA-4 binding agent may be administered at a dose between about 10 mg and 300 mg. In a further embodiment, the dose is selected from the group consisting of 10 mg, 25 mg, 50 mg, 75 mg, 100 mg, 150 mg, 200 mg, 250 mg, and 300 mg.

In the combination therapy of the present invention, the PD-1 blocking agent may be administered at the same dose, dosing frequency, and treatment duration as that approved for the PD-1 blocking agent in a monotherapy for particular indications. The dose of the CTLA-4 blocking agent may be as cited above and the CTLA-4 blocking agent may be administered at the same dosing frequency and treatment duration as cited above or at a dosing frequency and treatment duration as for the particular PD-1 blocking agent that is paired with the CTLA-4 blocking agent.

The particular dose of the currently marketed PD-1 blocking agents vary between the PD-1 blocking agents, thus in particular embodiments of the combination therapy of the present invention, the dose, dosing frequency, and/or treatment duration may be at least the same as that approved by the U.S. FDA for the particular PD-1 blocking agent for particular indications. For example, pembrolizumab is approved for a dose of 200 mg every three weeks as needed (pediatric individuals (two years up to 18 years) at 2 mg/kg up to 200 mg every three weeks as needed); nivolumab is approved at a dose of 3 mg/kg every 2 weeks; cemiplimab-rwlc is approved for a dose of 350 mg every three weeks as needed; atezolizumab is approved for a dose of 1200 mg every three weeks as needed; avelumab is approved for a dose of 10 mg/kg or 800 mg every two weeks as needed; and durvalumab is approved for a dose of 10 mg/kg every two weeks as needed.

In particular embodiments of the combination therapy, the PD-1 blocking agent is an anti-PD-1 antibody or anti-PD-1 antibody fragment, which may be administered at a dose from about 150 mg to about 250 mg, from about 175 mg to about 250 mg, from about 200 mg to about 250 mg, from about 150 mg to about 240 mg, from about 175 mg to about 240 mg, or from about 200 mg to about 240 mg. In some embodiments, the dose of the anti-PD-1 antibody or antigen binding fragment thereof is 150 mg, 175 mg, 200 mg, 225 mg, 240 mg, or 250 mg. In further embodiments, the anti-PD-1 antibody or anti-PD-1 antibody fragment may be administered at a frequency of every three weeks as needed. In another embodiment of the combination therapy of the present invention, the anti-PD-1 antibody or anti-PD-1 antibody fragment may be administered at dose greater than 250 mg, for example, a dose of about 400 mg at a frequency of every six weeks as needed.

In particular embodiments of the combination therapy, the PD-1 blocking agent is an anti-PD-1 antibody or anti-PD-1 antibody fragment, which may be administered at a dose from about 10 mg/kg to about 1200 mg. In further embodiments, the anti-PD-1 antibody or anti-PD-1 antibody fragment may be administered at a frequency of every two to three weeks as needed.

While the PD-1 blocking agent may be administered at least at the doses, dosing frequencies, and treatment durations approved for the currently marketed PD-1 blocking agents in a monotherapy, the actual doses, dosing frequencies, and treatment durations for any particular combination of the present invention may differ from those that are approved for the PD-1 blocking agent monotherapies. Thus, in particular embodiments of the combination therapy of the present invention, the dose, dosing frequency, and treatment duration of any particular PD-1 blocking agent in the combination therapy will be determined from clinical trials conducted for the combination therapy.

In a particular embodiment of the combination therapy, the PD-1 blocking agent is nivolumab or an effector-silent variant of nivolumab, which is administered to an individual intravenously at a dose of 3 mg/kg over 30 to 60 minutes every two-three weeks as needed and wherein each dose of the CTLA-4 blocking agent is administered intravenously following the administration of the PD-1 blocking agent for the same treatment duration as the PD-1 blocking agent or for duration less than or more than the PD-1 blocking agent duration. In a particular embodiment, the nivolumab or effector-silent variant of nivolumab is administered intravenously to an individual at an initial dose of 3 mg/kg intravenously over 30 minutes followed by administration of the CTLA-4 blocking agent intravenously over 30 minutes on the same day, every three weeks for four doses, then nivolumab is administered intravenously at a fixed dose of 240 mg every two weeks over 30 minutes or 480 mg every four weeks over 30 minutes.

In a particular embodiments, the PD-1 blocking agent is pembrolizumab or effector-silent variant of pembrolizumab, which is administered to an adult individual intravenously at a dose of 200 mg over 30 minutes every three weeks as needed or to a pediatric individual intravenously at a dose of 2 mg/kg up to a maximum of about 200 mg over 30 minutes every three weeks wherein each treatment is followed by a dose of the CTLA-4 blocking agent wherein each dose of the CTLA-4 blocking agent is administered intravenously following administration of the PD-1 blocking agent for the same treatment duration as the PD-1 blocking agent or for duration less than or more than the PD-1 blocking agent duration.

In a particular embodiments, the PD-1 blocking agent is pembrolizumab or effector-silent variant of pembrolizumab, which is administered to an adult individual intravenously at a dose of 400 mg over 30 minutes every six weeks as needed wherein each treatment is followed by a dose of the CTLA-4 blocking agent wherein each dose of the CTLA-4 blocking agent is administered intravenously following the administration of the PD-1 blocking agent for the same treatment duration as the PD-1 blocking agent or for duration less than or more than the PD-1 blocking agent duration.

In a particular embodiment of the combination therapy, the PD-1 blocking agent is cemiplimab-rwlc or an effector-silent variant of cemiplimab-rwlc, which is administered to an individual intravenously at a dose of 350 mg over 30 minutes every three weeks as needed and wherein each dose of the CTLA-4 blocking agent is administered intravenously following the administration of the PD-1 blocking agent for the same treatment duration as the PD-1 blocking agent or for duration less than or more than the PD-1 blocking agent duration. In a particular embodiment, the cemiplimab-rwlc or effector-silent variant of cemiplimab-rwlc is administered intravenously to an individual at an initial dose of 350 mg over 30 minutes followed by administration of the CTLA-4 blocking agent over 30 minutes on the same day every three weeks as needed.

In a particular embodiment of the combination therapy, the PD-1 blocking agent is atezolizumab or an effector-silent variant of atezolizumab, which is administered to an individual intravenously at a dose of 1200 mg over 60 minutes every three weeks as needed and wherein each dose of the CTLA-4 blocking agent is administered intravenously following the administration of the PD-1 blocking agent for the same treatment duration as the PD-1 blocking agent or for duration less than or more than the PD-1 blocking agent duration. In a particular embodiment, the atezolizumab or effector-silent variant of atezolizumab is administered intravenously to an individual at an initial dose of 1200 mg over 60 minutes followed by administration of the CTLA-4 blocking agent over 30 minutes on the same day every three weeks as needed.

In a particular embodiment of the combination therapy, the PD-1 blocking agent is avelumab or an effector-silent variant of avelumab, which is administered to an individual intravenously at a dose of 10 mg/kg or 800 mg over 60 minutes every two weeks as needed and wherein each dose of the CTLA-4 blocking agent is administered intravenously following the administration of the PD-1 blocking agent for the same treatment duration as the PD-1 blocking agent or for duration less than or more than the PD-1 blocking agent duration. In a particular embodiment, the avelumab or effector-silent variant of avelumab is administered intravenously to an individual at an initial dose of 10 mg/kg or 800 mg over 60 minutes followed by administration of the CTLA-4 blocking agent over 30 minutes on the same day every two weeks as needed.

In a particular embodiment of the combination therapy, the PD-1 blocking agent is durvalumab or an effector-silent variant of durvalumab, which is administered to an individual intravenously at a dose of 10 mg/kg over 60 minutes every two weeks as needed and wherein each dose of the CTLA-4 blocking agent is administered intravenously following the administration of the PD-1 blocking agent for the same treatment duration as the PD-1 blocking agent or for duration less than or more than the PD-1 blocking agent duration. In a particular embodiment, the durvalumab or effector-silent variant of durvalumab is administered intravenously to an individual at an initial dose of 10 mg/kg over 60 minutes followed by administration of the CTLA-4 blocking agent over 30 minutes on the same day every two weeks as needed.

While the currently approved CTLA-4 blocking agents and PD-1 blocking agents are provided in formulations at a concentration that permits intravenous administration to an individual over a 30 to 60 minute time frame, the combination therapies of the present invention contemplate embodiments in which the CTLA-4 blocking agent and/or the PD-1 blocking agent are each provided in a formulation at a concentration that permits each to be separately administered to an individual in a single injection. Being able to provide at least one of the two blocking agents in a single injection would significantly reduce the time for administering both blocking agent to the individual.

In a further embodiment, the present invention provides a combination therapy in which the CTL-4 blocking agent and the PD-1 blocking agent are co-administered at the same time. Co-administration may be accomplished by providing the CTLA-4 and PD-1 blocking agents in separate formulations and simultaneously providing each formulation to the individual, either by separate IVs or mixing prior to administering the mixture by IV to the individual by IV, or by separate injection of each formulation into the individual. Co-administration may also be accomplished by providing the CTLA-4 and PD-1 blocking agents in a single formulation that is then administered to the individual in a single IV or in a single injection.

(i) Combination Therapy Treatments

The combination therapy of the present invention may be used for the treatment any proliferative disease, in particular, treatment of cancer. In particular embodiments, the combination therapy of the present invention may be used to treat melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In another embodiment, the combination therapy of the present invention may be used to treat pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

The currently marketed PD-1 blocking agents are approved by the U.S. FDA to treat at least one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma. Thus, the combination therapy of the present invention may be used to treat at least one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma.

(j) Combination Therapy in Combination with Chemotherapy

The combination therapy of the present invention may be administered to an individual having a cancer in combination with chemotherapy. The individual may undergo the chemotherapy at the same time the individual is undergoing the combination therapy of the present invention. The individual may undergo the combination therapy of the present invention after the individual has completed chemotherapy. The individual may be administered the chemotherapy after completion of the combination therapy. The combination therapy of the present invention may also be administered to an individual having recurrent or metastatic cancer with disease progression or relapse cancer and who is undergoing chemotherapy or who has completed chemotherapy.

The chemotherapy may include a chemotherapy agent selected from the group consisting of
  (i) alkylating agents, including but not limited to, bifunctional alkylators, cyclophosphamide, mechlorethamine, chlorambucil, and melphalan;
  (ii) monofunctional alkylators, including but not limited to, dacarbazine, nitrosoureas, and temozolomide (oral dacarbazine);
  (iii) anthracyclines, including but not limited to, daunorubicin, doxorubicin, epirubicin, idarubicin, mitoxantrone, and valrubicin;
  (iv) cytoskeletal disruptors (taxanes), including but not limited to, paclitaxel, docetaxel, abraxane, and taxotere;

(v) epothilones, including but not limited to, ixabepilone, and utidelone;
(vi) histone deacetylase inhibitors, including but not limited to, vorinostat, and romidepsin;
(vii) inhibitors of topoisomerase i, including but not limited to, irinotecan, and topotecan;
(viii) inhibitors of topoisomerase ii, including but not limited to, etoposide, teniposide, and tafluposide;
(ix) kinase inhibitors, including but not limited to, bortezomib, erlotinib, gefitinib, imatinib, vemurafenib, and vismodegib;
(x) nucleotide analogs and precursor analogs, including but not limited to, azacitidine, azathioprine, fluoropyrimidines (e.g., such as capecitabine, carmofur, doxifluridine, fluorouracil, and tegafur) cytarabine, gemcitabine, hydroxyurea, mercaptopurine, methotrexate, and tioguanine (formerly thioguanine);
(xi) peptide antibiotics, including but not limited to, bleomycin and actinomycin; a platinum-based agent, including but not limited to, carboplatin, cisplatin, and oxaliplatin;
(xii) retinoids, including but not limited to, tretinoin, alitretinoin, and bexarotene; and (xiii) vinca alkaloids and derivatives, including but not limited to, vinblastine, vincristine, vindesine, and vinorelbine.

Selecting a dose of the chemotherapy agent for chemotherapy depends on several factors, including the serum or tissue turnover rate of the entity, the level of symptoms, the immunogenicity of the entity, and the accessibility of the target cells, tissue or organ in the individual being treated. The dose of the additional therapeutic agent should be an amount that provides an acceptable level of side effects. Accordingly, the dose amount and dosing frequency of each additional therapeutic agent will depend in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dose regimen may be made by the clinician, e.g., using parameters or factors known or suspected in the art to affect treatment or predicted to affect treatment, and will depend, for example, the individual's clinical history (e.g., previous therapy), the type and stage of the cancer to be treated and biomarkers of response to one or more of the therapeutic agents in the combination therapy.

For example, pembrolizumab is currently approved by the U.S. FDA for a combination therapy for (i) treating non-small cell lung cancer (NSCLC) comprising pembrolizumab with pemetrexed and platinum chemotherapy or carboplatin and either paclitaxel or nab-paclitaxel; and (ii) treating head and neck squamous cell cancer (HNSCC) comprising pembrolizumab and platinum-containing chemotherapy, and atezolizumab is currently approved for a combination therapy for treating NSCLC comprising bevacizumab (anti-VEGF-A antibody marketed under the tradename AVASTIN), paclitaxel, and carboplatin.

Thus, the present invention contemplates embodiments of the combination therapy of the present invention that further includes a chemotherapy step comprising platinum-containing chemotherapy, pemetrexed and platinum chemotherapy or carboplatin and either paclitaxel or nab-paclitaxel. In particular embodiments, the combination therapy with a chemotherapy step may be used for treating at least NSCLC and HNSCC.

The combination therapy further in combination with a chemotherapy step may be used for the treatment any proliferative disease, in particular, treatment of cancer. In particular embodiments, the combination therapy of the present invention may be used to treat melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In another embodiment, the combination therapy further in combination with a chemotherapy step may be used to treat pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

In particular embodiments, the combination therapy with a chemotherapy step may be used to treat one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma.

The following examples are intended to promote a further understanding of the present invention.

Example 1

Fc-Function is Required for Induction of Gut Inflammation irAEs

Gut inflammatory irAEs have been observed in cancer patients during immunotherapy with either anti-CTLA-4 antibody monotherapy or in combination with an anti-PD-1 antibody. Preclinical studies of CTLA-4 deficient mice in constitutive and conditional knock out models have demonstrated development of profound immune mediated inflammatory disease in multiple organs. However, treatment of syngeneic tumor models with surrogate anti-CTLA-4 antibodies has not been reported to induce overt irAEs predictive of the toxicities observed in cancer patients. Similarly, histopathological assessment for gut inflammation was assessed in the CT26 syngeneic or xenograph model (mice inoculated with the CT26 colon carcinoma cell line). CT26 tumor bearing mice treated with Fc-competent anti-mouse CTLA-4 mAb 9D9-mIgG$_{2a}$ (α-CTLA-4 or α-CTLA4) (q4×4), resulted in a minimal granulocytic infiltrate (grade 1 of 5) observed in the lamina propria gut tissues. No granulocytic infiltrates were observed in cohorts treated with Fc-mutant anti-mCTLA-4 mAb 9D9-mIgG$_1$-D265A (α-CTLA-4 (D265A)), Fc-less anti-mCTLA-4

ISVD F894 (CTLA-4 Nab), or isotypes. However, no accompanying ulceration or other tissue damage was observed.

The α-CTLA-4 (D265A) Fc-mutant lacks measurable affinity for Fcγ receptors (Nimmerjahn et al., Immunity, 23:41-51 (2005)) and therefor lacks Fc-effector function. In mice, the anti-tumor efficacy of anti-mouse CTLA4 mAb monotherapy is dependent on the ability of the antibody to mediate intra-tumoral regulatory T cell depletion via Fc-effector function (Selby et al., op. cit). As such, both CTLA-4 Nab and α-CTLA-4 (D265A) were not expected to have monotherapy anti-tumor benefit.

The minimal histopathological findings prompted us to evaluate gene expression profiles as potentially more sensitive means to detect markers of inflammatory cell activation in the gut. We utilized a PCR gene-expression panel that we had previously developed for proteomic and expression profiling of genes associated with gut inflammation in fecal samples and biopsies of inflammatory bowel disease (IBD) preclinical models and patients (Cayatte, C, et. al., *Clinical and Translational Gastroenterology*, 3: e10 (2012)).

Figure 1A:
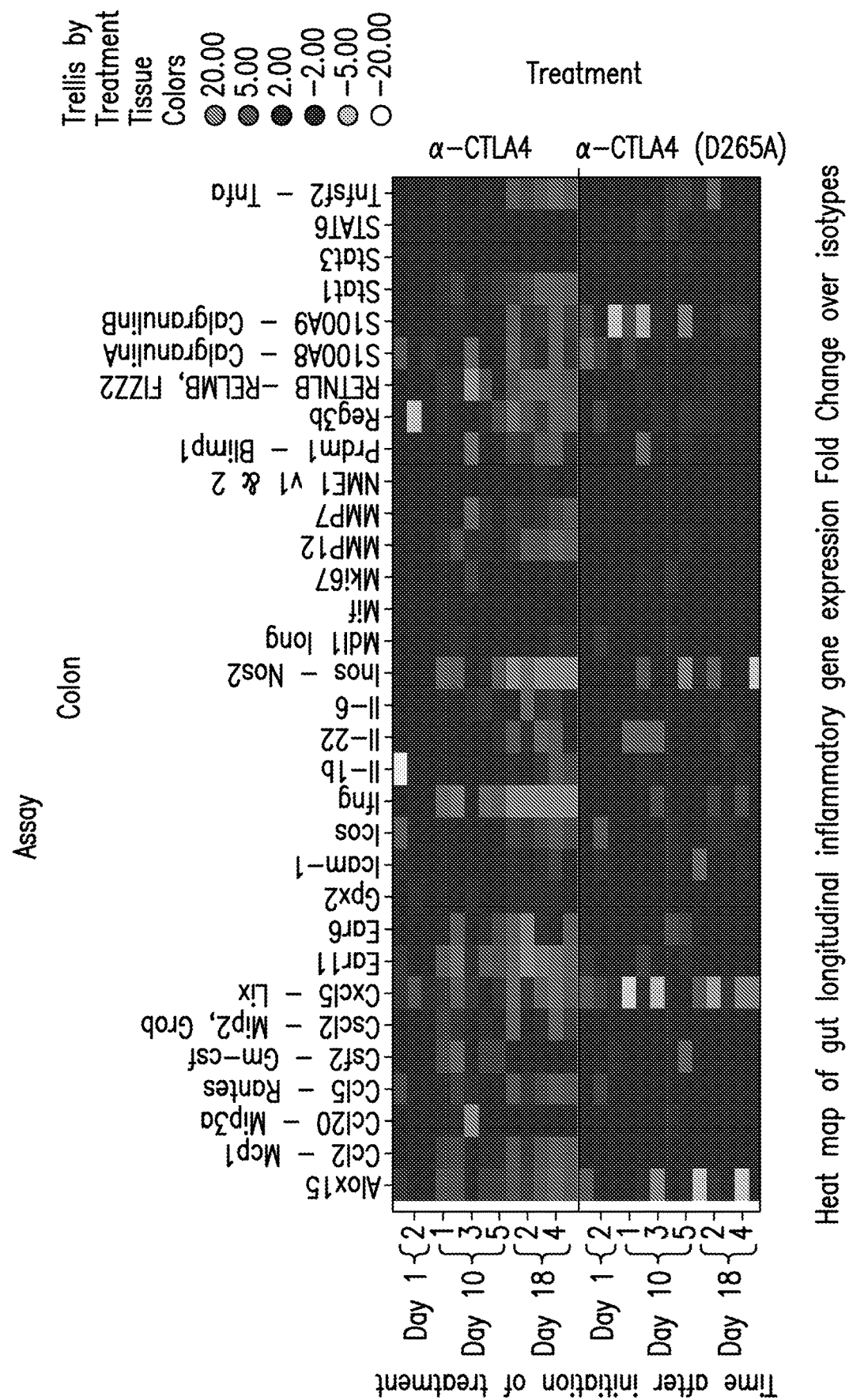
FIGS. 1A-1E: CTLA-4 blockade mediated colitis is Fc-dependent. Balb/c mice were treated twice a week with antibodies as indicated for 55 days.

Gene expression profiles were measured in small intestine and colon tissue samples at various times following initiation of treatment with α-CTLA-4 and compared with α-CTLA-4 (D265A) to specifically assess the role of Fc-function for induction gut inflammation. As illustrated in FIG. 1A, expression of numerous gut inflammatory genes was upregulated in the proximal small intestine samples from mice treated with α-CTLA-4 but not from mice treated with α-CTLA-4 (D265A). The results showed that the manifestation of gut inflammatory pathways may be detected by gene expression in small intestine and colon tissue in a subclinical setting.

Upregulation of genes associated with gut inflammation allowed us to assess the effect of sustained treatment on progression to clinical enterocolitis, as observed in ipilimumab treated patients following six to seven weeks or more of treatment (Samaan et al., Nat. Rev. Gastroenterol. Hepatol. 15:222-234 (2018)). To assess the relative effects of CTLA-4 blockade and Fc-function on gut inflammation and progression to enterocolitis, BALB/c mice were dosed twice weekly with α-CTLA-4, α-CTLA-4 (D265A). Two groups of mice were treated with Fc-competent α-CTLA-4, one group of mice with CT26 tumors and one group of naïve BALB/c mice with no tumors, to assess potential contributions from tumor growth and induction of tumor immunity on induction of gut inflammation. Body weights and body condition scores were evaluated twice weekly throughout the sustained treatment to monitor for progression to enterocolitis.

Figure 1B:
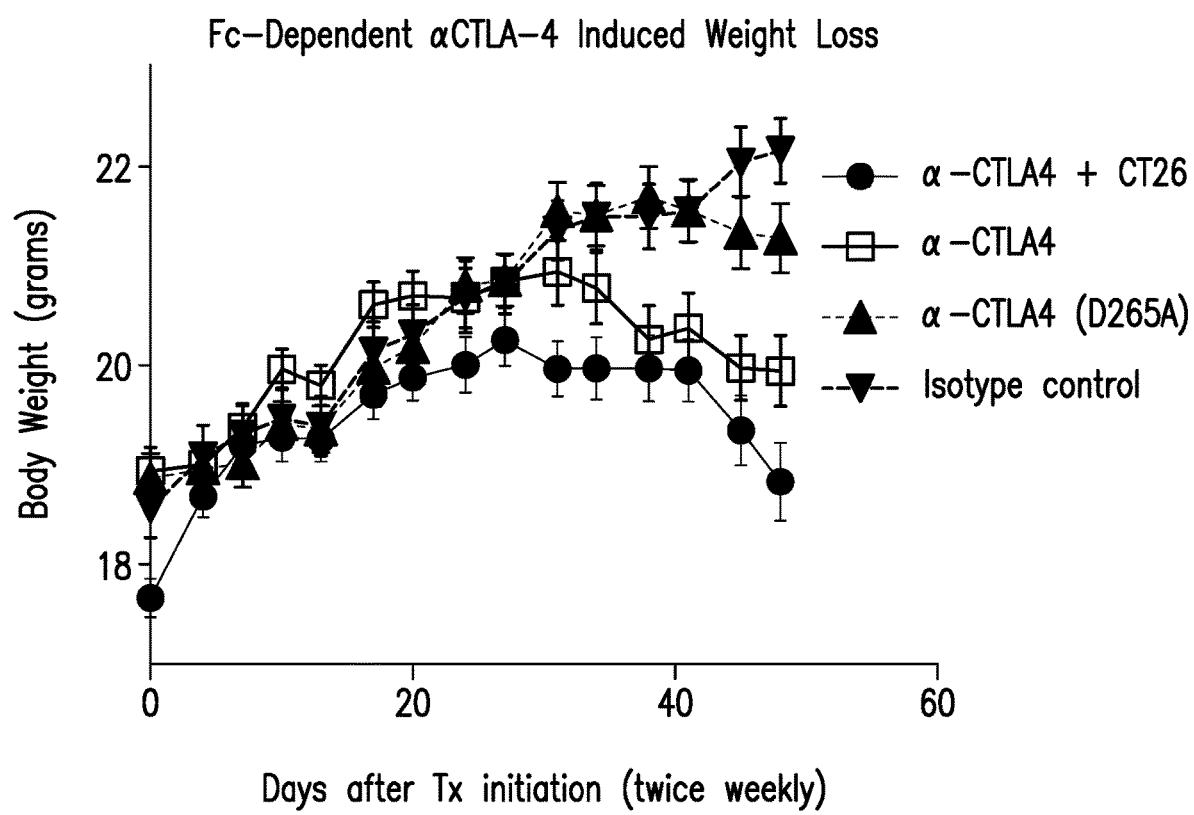
Figure 1C:
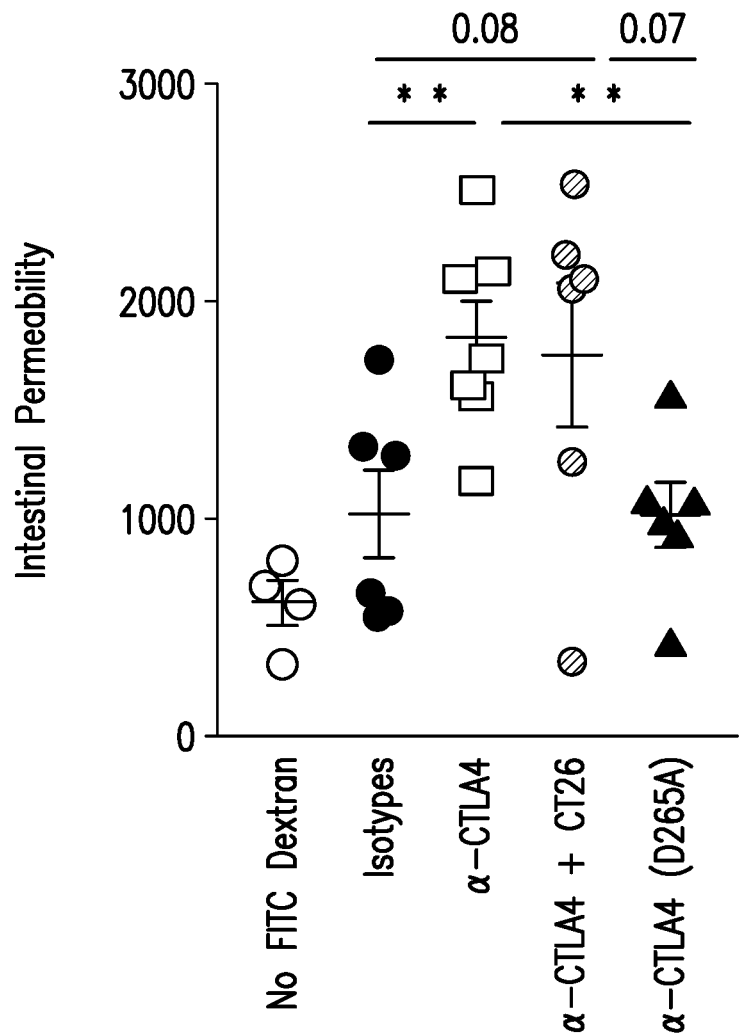
Figure 1D:
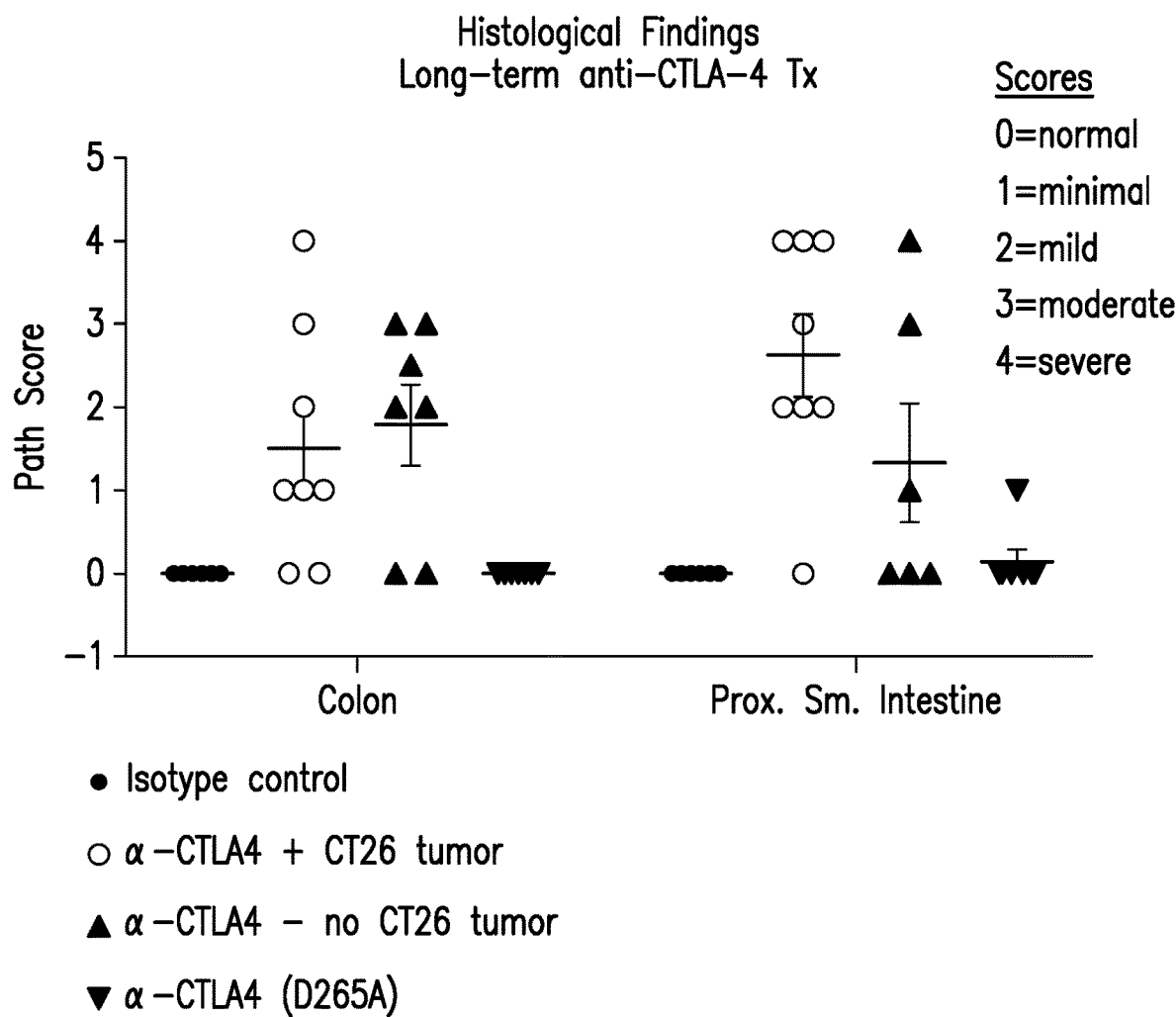
Figure 1E:
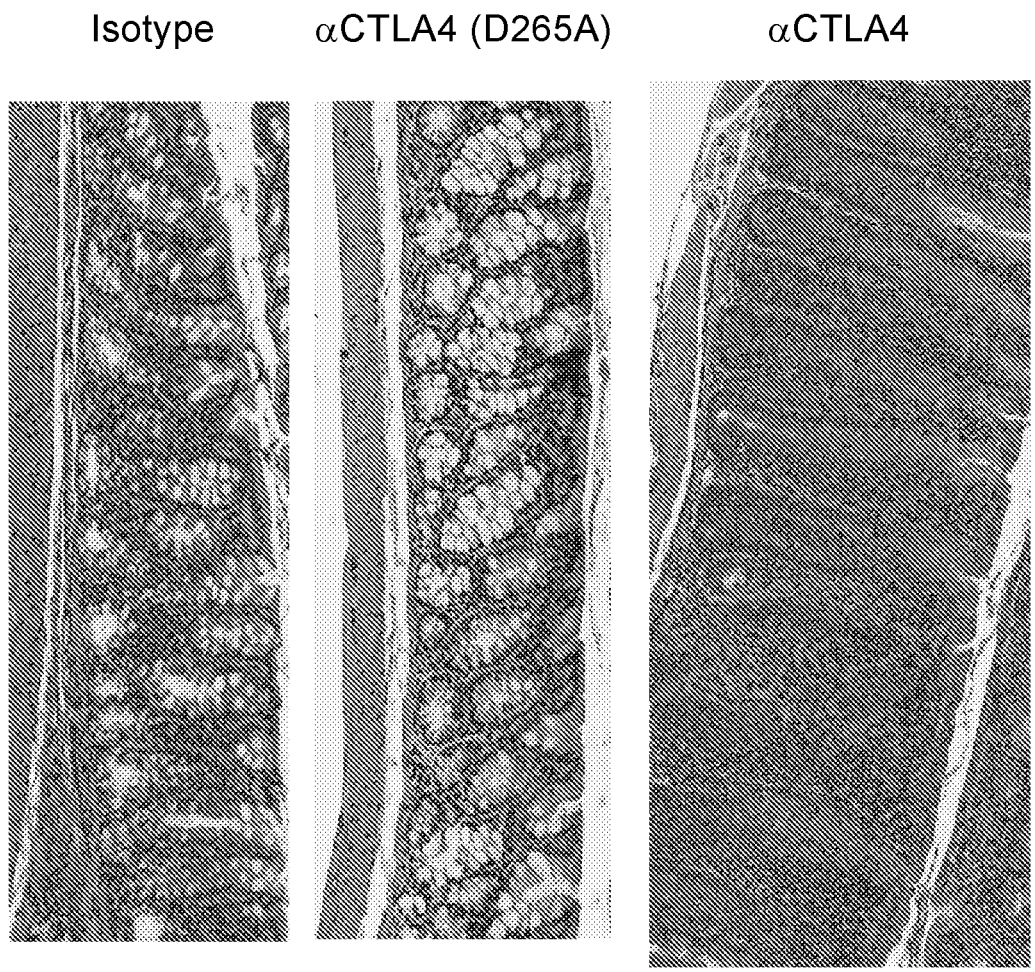

Body weights continued to increase through day 50 in mice dosed with isotype antibodies and α-CTLA-4 (D265A). In contrast, mice dosed with α-CTLA-4 showed a decrease in mean body weight after about 35 to 40 days (FIG. 1B). Intestinal permeability was increased in both with α-CTLA-4 treated groups but not in mice treated with α-CTLA-4 (D265A) treated mice, as assessed in FITC-dextran gavaged mice at day 49 and 50 (FIG. 1C). Histologic evidence of inflammation in proximal small intestine and colon as assessed by a pathologist (L.A) revealed progression to moderate and severe enterocolitis in α-CTLA-4 treated groups (FIG. 1 D and FIG. 1E), with extensive immune infiltration, thickening of mucosa and loss of goblet cells. In contrast, no enterocolitis was observed in α-CTLA-4 (D265A) treated mice providing evidence that Fc-function is required for CTLA-4 blockade induced enterocolitis. Notably, tumor growth and anti-tumor responses were not required for α-CTLA-4 induced gut inflammation.

It has previously been reported that anti-CTLA-4 antibodies with strong FcγR function are required for strong monotherapy anti-tumor responses in experiments comparing mouse $IgG_{2a}$-chimeric antibodies with high FcγR-affinity with mutant-$IgG_1$ chimeras with no detectable FcγR-binding (Selby et al., Cancer Immunol. Res. 1:32-42 (2013)). The specific depletion of $T_{regs}$ in the tumor ostensibly plays a key role in the strong monotherapy observed with anti-CTLA-4 antibodies on the mouse $IgG_{2a}$ ($mIgG_{2a}$) backbone (Simpson et al., J. Exp. Med. 210:1695-710 (2013). Recent reports demonstrating the importance of CD28 for anti-PD-1 efficacy (See references) suggested to us that augmentation of CD28 function by blocking the stronger interaction of CTLA-4 for ligands CD80 and CD86 with a CTLA-4 antagonist may provide strong combination anti-tumor efficacy without the requirement for $T_{reg}$ TIL depletion. ISVDs, specific for mouse CTLA-4 (mCTLA-4), capable of inhibiting binding to CD80 and CD86 were developed using a single-domain $V_{HH}$ antibody fragment derived from heavy chain only camelid antibodies. These small, 15 kDa proteins lack Fc regions and thus do not bind FcγRs. For comparison with a fully Fc-functional antibody, we utilized α-CTLA-4, previously shown to have strong monotherapy anti-tumor efficacy (See references). To control for the potential effects of binding a different CTLA-4 epitope, we utilized α-CTLA-4 (D265A), which lacks detectable affinity for FcγRs to control for the requirement of strong FcγR-function for anti-tumor efficacy and tolerability.

Figure 2A:
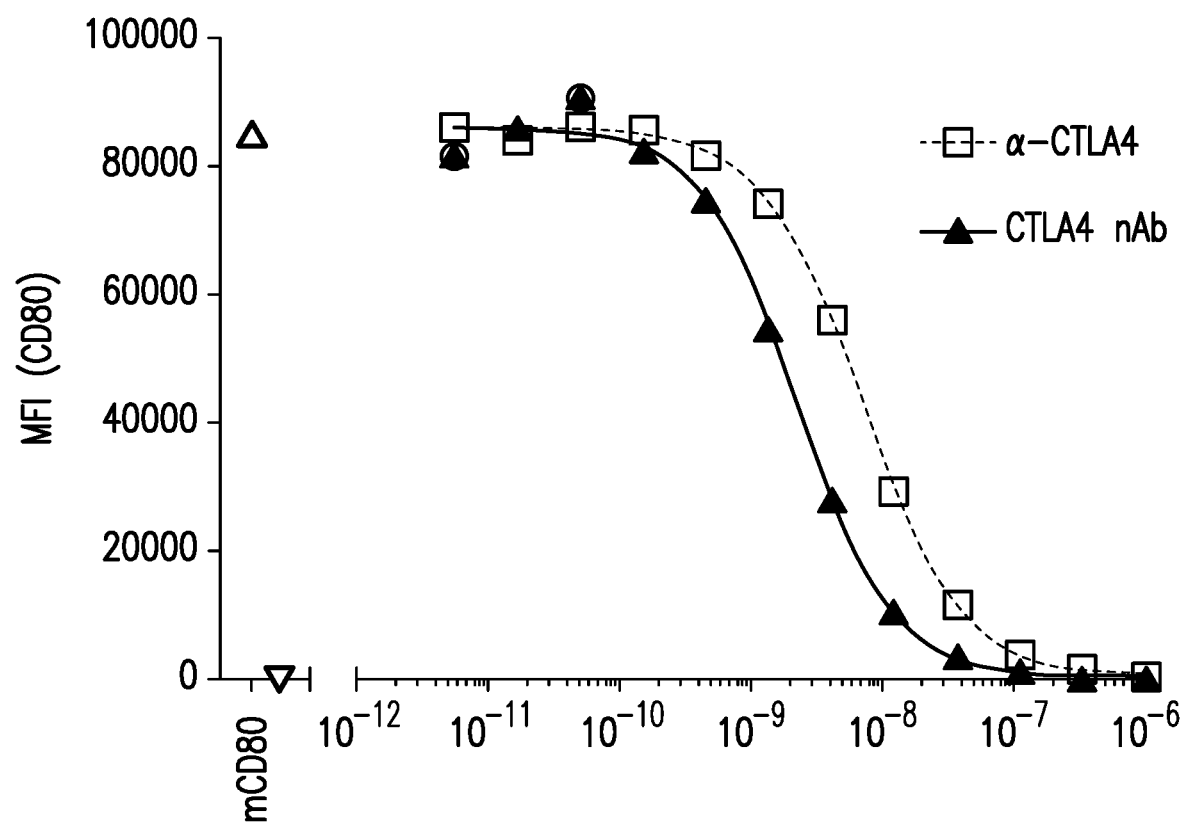
FIGS. 2A-2E: Characterization of CTLA-4 ISVD (nAb).
Figure 2B:
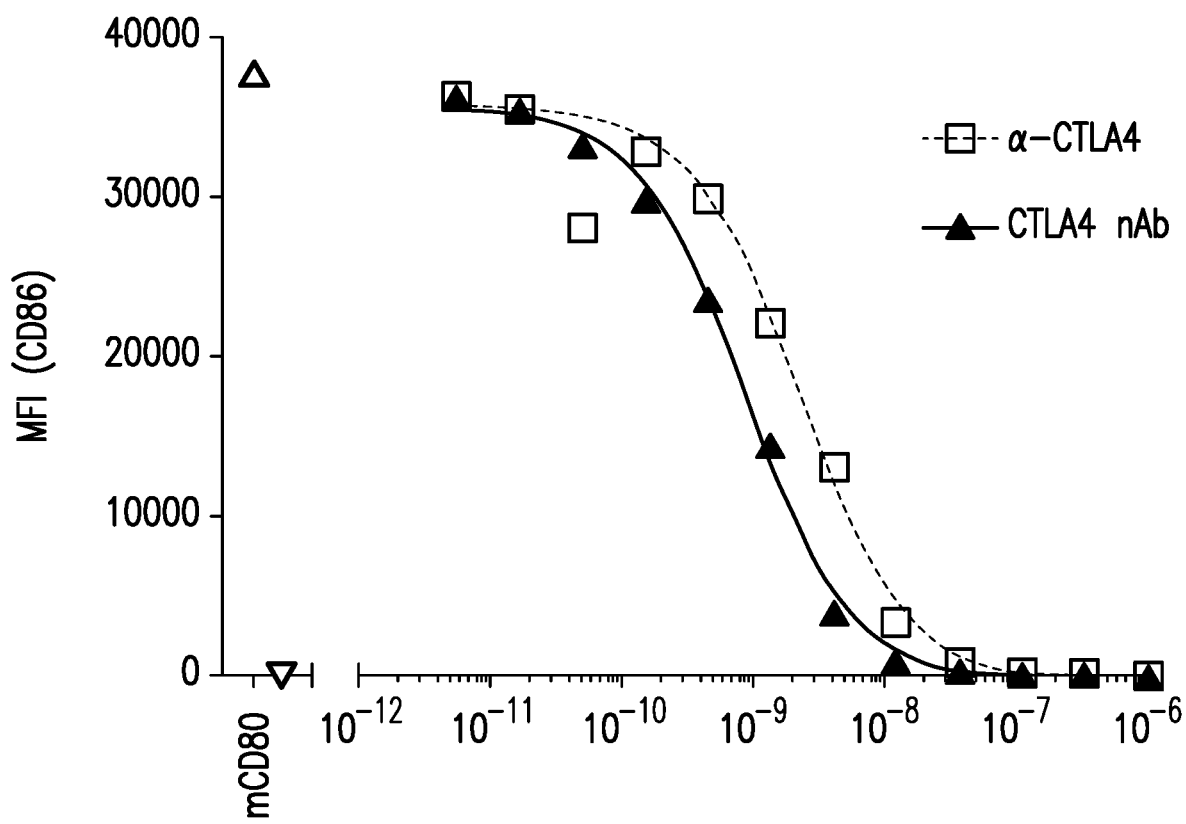
Figure 2C:
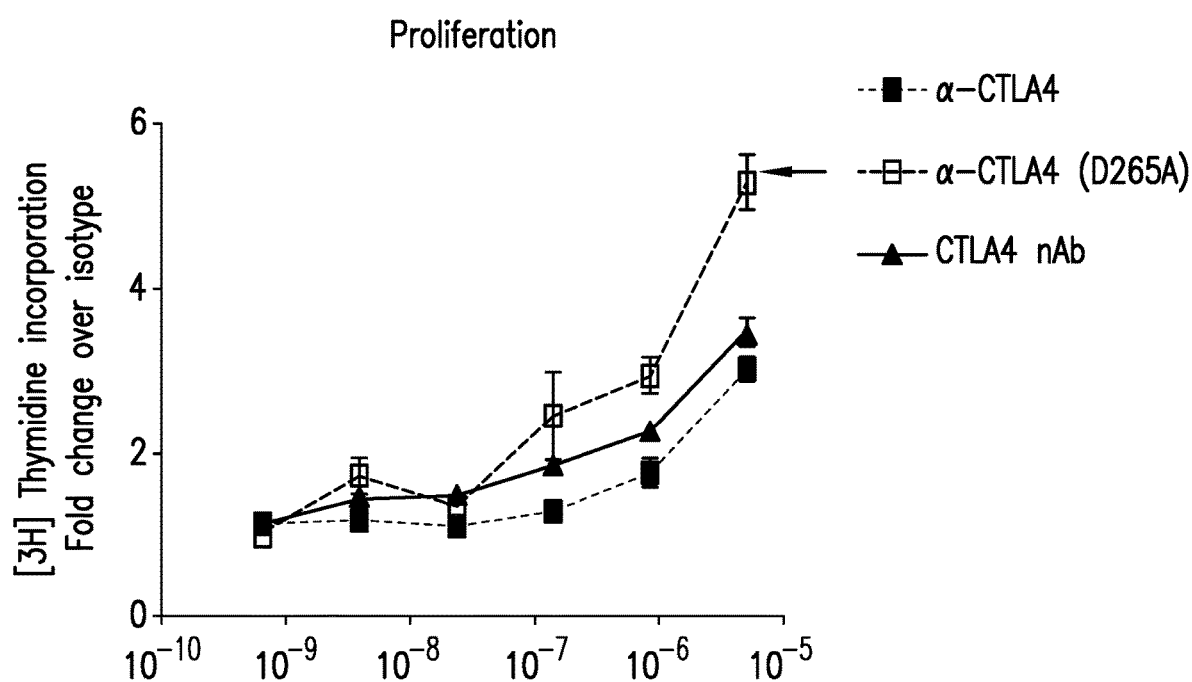
Figure 2D:
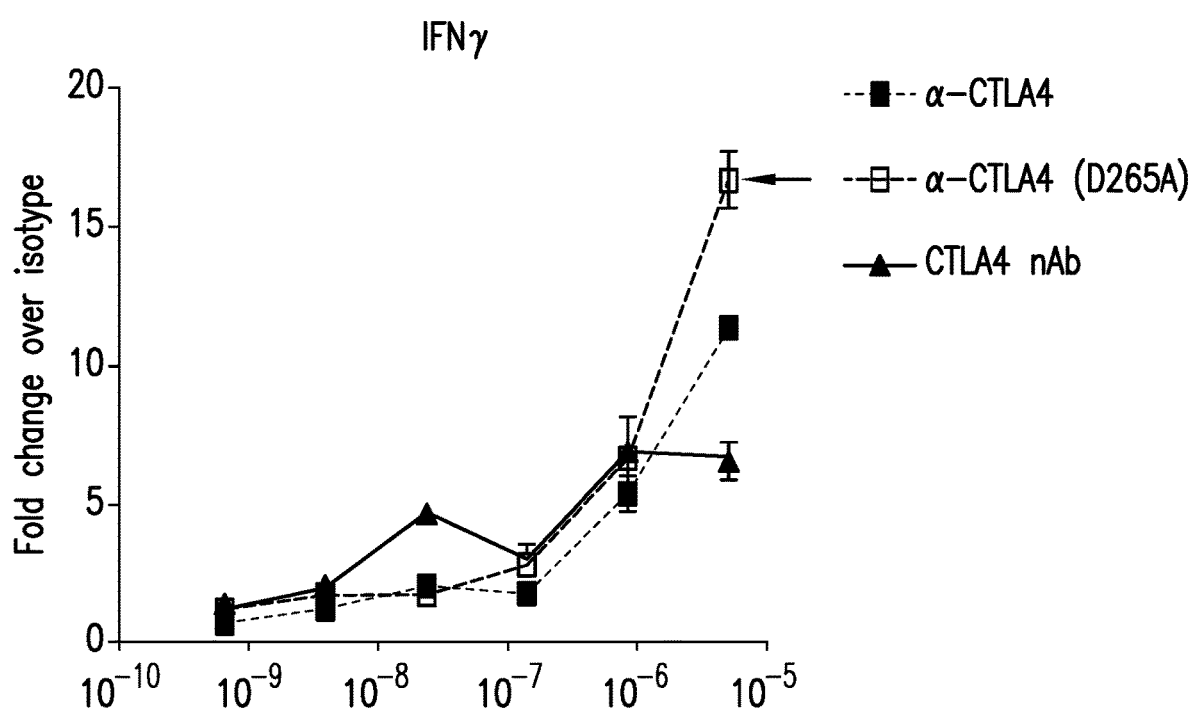
Figure 2E:
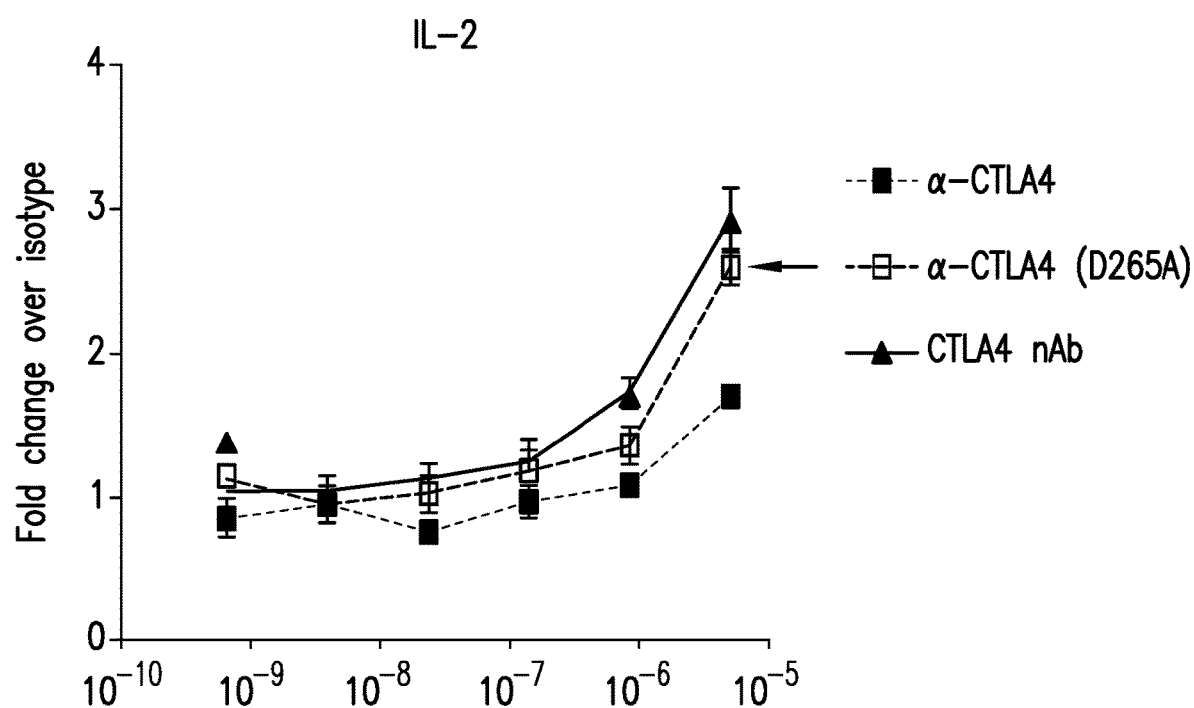

The CTLA-4 nAb composed of two anti-CTLA-4 $V_{HH}$ domains linked by a 35GS-linker and an anti-human albumin $V_{HH}$ domain as a half-life extension (HLE) subunit See SEQ ID NO:61). The anti-CTLA-4 $V_{HH}$ scored a 96% inhibition for both CD80 and CD86 compared with α-CTLA-4, which was used as a reference antagonist (100%) (FIG. 2A and FIG. 2B). The CTLA-4 nAb was further compared to α-CTLA-4 and effector-silent α-CTLA-4 (D265A) in an in vitro MLR-based bioassay for the capacity to increase proliferation (FIG. 2C), IFNγ (FIG. 2D), and IL-2 responses (FIG. 2E).

Figure 3B:
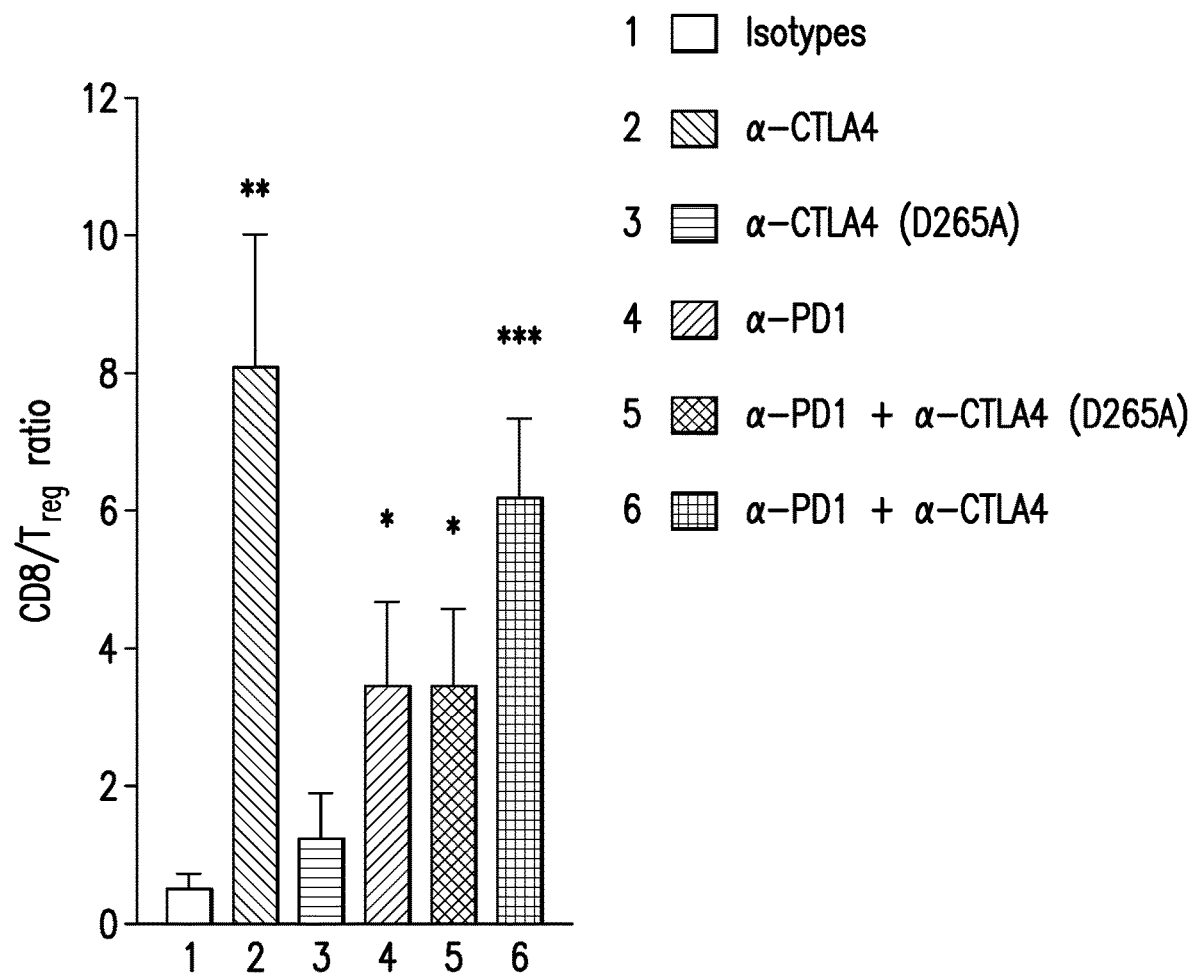
Figure 3C:
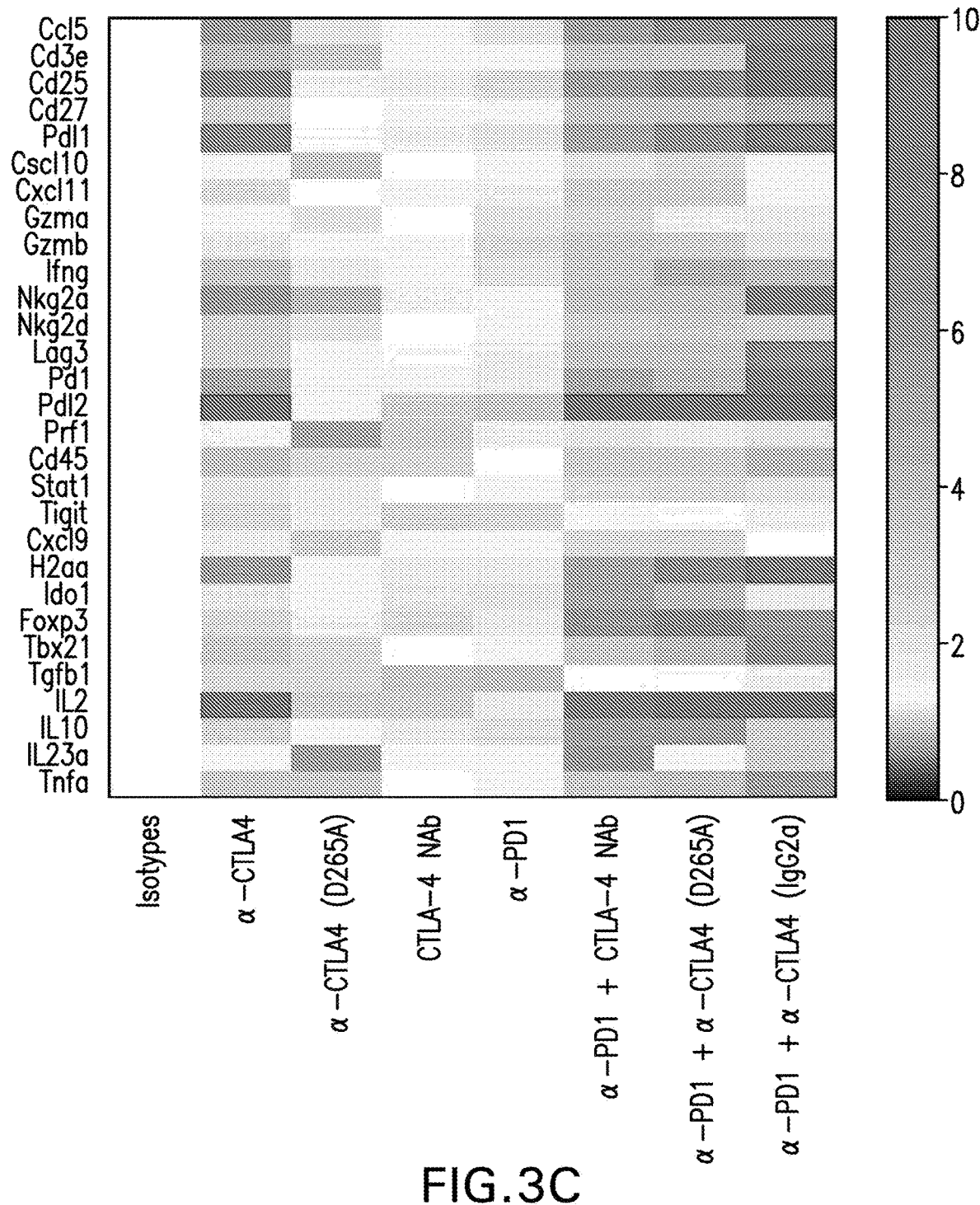
Figure 3D:
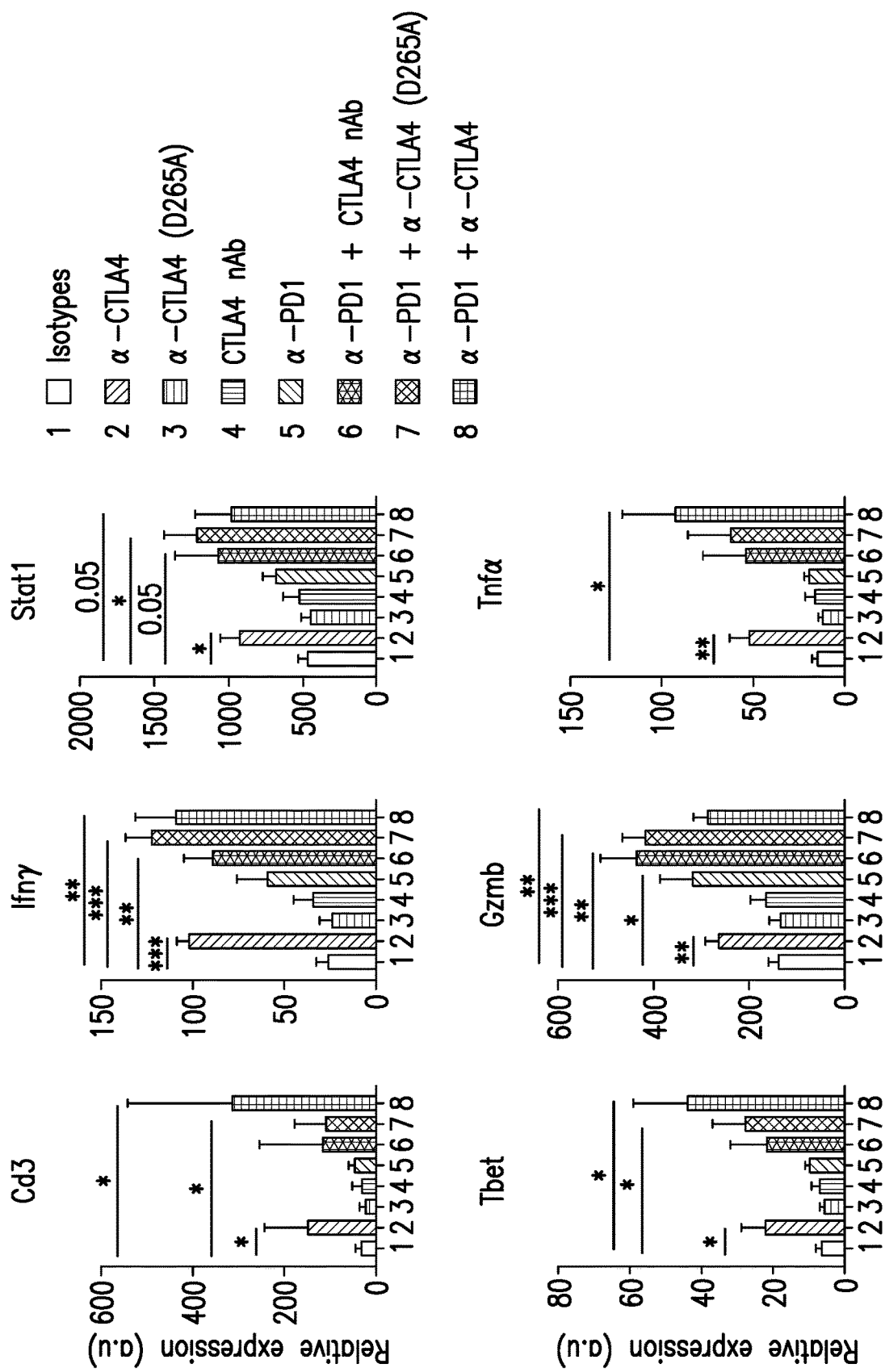
Figure 3E:
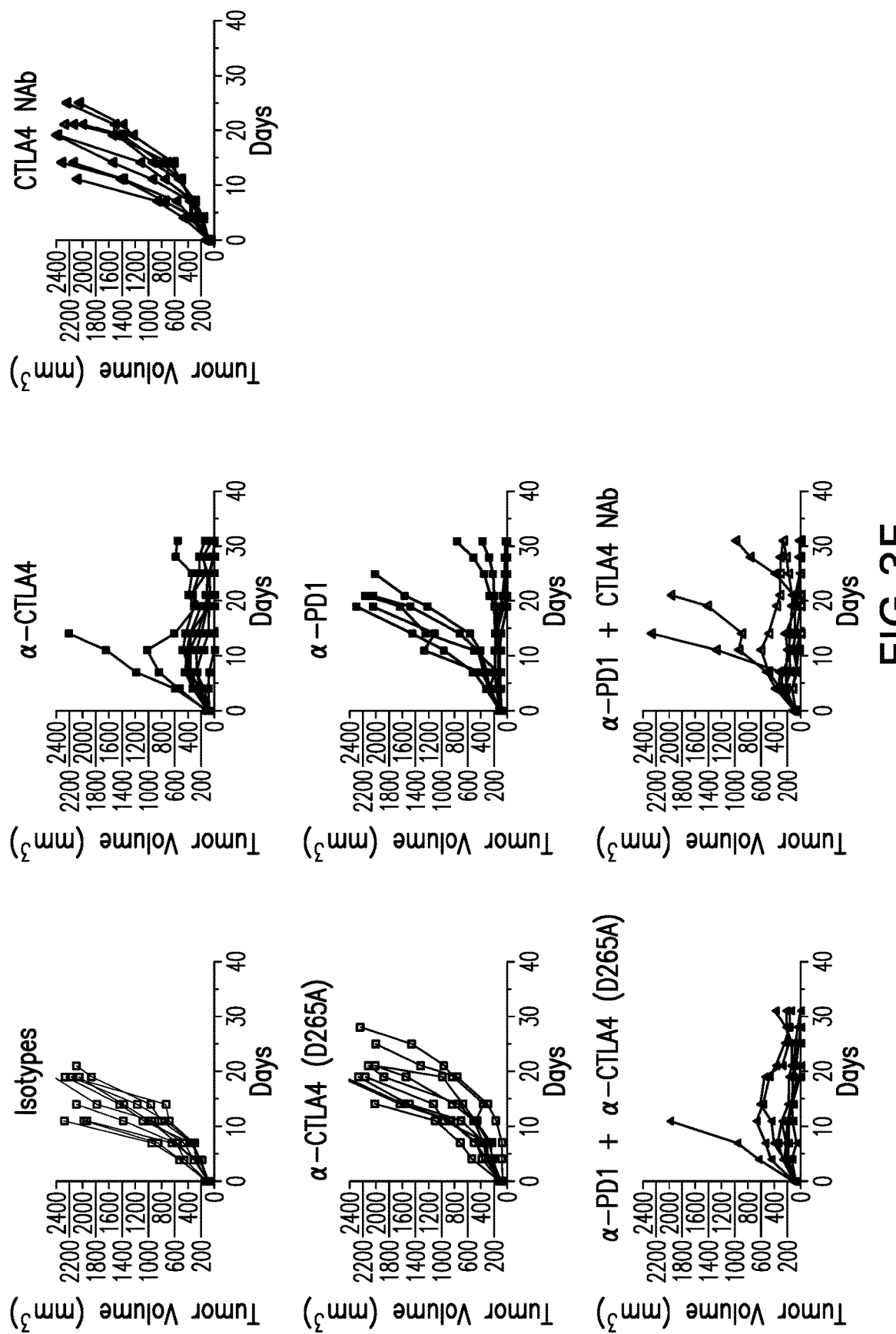
FIG. 3E: shows the individual animal tumor volumes for each treatment group compared to isotype controls. Complete responses (CR) through day 39 are presented for responsive treatment groups. Data are representative of two independent experiments with n=10 mice per group.

Fc-Function for CTLA-4 Blockade is not Required in PD-1 Combination Immunotherapy The relative anti-tumor efficacy induced by monotherapy with the three CTLA-4 antagonists and in combination therapy with anti-mouse PD-1 antibody mDX400 (α-PD-1) was assessed by measure the change in tumor volume over time in the syngeneic CT26 colon carcinoma tumor model (FIG. 3A-3E), which is only moderately responsive to anti-PD-1 monotherapy. No anti-tumor activity was observed in monotherapy cohorts treated with either CTLA-4 nAb or α-CTLA-4 (D265A) and was comparable to the isotype controls (Group 1 in FIG. 3A). Strong anti-tumor monotherapy activity was observed in mice treated with α-CTLA-4 consistent with prior reports demonstrating the requirement for Fc-function in anti-CTLA-4 antibodies for anti-tumor monotherapy efficacy in mouse syngeneic tumor models (Simpson et al., J. Exp. Med. 210:1695-710 (2013)) (Group 2 in FIG. 3A) and treatment with α-PD-1 alone provided low to modest anti-tumor growth inhibition compared to α-CTLA-4. However, combination therapy with CTLA-4 nAb or α-CTLA-4 (D265A) with α-PD-1 provided strong anti-tumor benefit comparable to that observed with α-CTLA-4 alone or α-CTLA-4 in combination with α-PD-1 (Group 2 of FIG. 3A). The CTLA-4 nAb and α-CTLA-4 (D265A) bind separate epitopes on CTLA-4, thus the effect is not specific to the epitope. Further evidence for robust combination benefit, independent of Fc-function was evident as similar anti-tumor responses were observed in α-PD-1 combination treatments between CTLA-4 nAb, α-CTLA-4 (D265A), and α-CTLA-4. FIG. 3D shows the individual results for each of the 10 mice treatments summarized in FIG. 3A. Expansion of CD8 T cells and increased CD8/Treg ratios were observed in α-CTLA-4 treated mice and in mice receiving a combination of α-CTLA-4 (D265S) plus α-PD-1 treated mice compared to mice that received α-CTLA-4 (D265S) alone (FIG. 3B). These results indicate that anti-CTLA-4 antagonists, lacking in Fc-function, combined with an anti-PD-1 antagonist provided superior anti-tumor efficacy than that achievable with anti-PD-1 antagonist monotherapy and provided anti-tumor efficacy in the combination similar in effect as the anti-tumor efficacy of anti-CTLA-4 antibodies with Fc-function in a monotherapy.

We investigated regulation of immune response genes associated with effective cancer immunotherapy in tumors on nine-days after initiation of treatment to elucidate potential complimentary mechanisms associated with the strong combination activity. PCR-expression profiling of tumors from mice treated with α-CTLA-4 showed strong upregulation of numerous genes associated with effective immunotherapy (FIG. 3C), including IFNγ, IFN-response genes, chemokines, pro-inflammatory cytokines, and MHC. Only modest upregulation was observed in tumors from α-CTLA-4 (D265A) treated mice indicating that the strong upregulation observed in α-CTLA-4 treated tumors was at least partially dependent on Fc-function. Modest responses were also observed in tumors from CTLA-4 nAb and α-PD-1 treated mice. In contrast, robust upregulation of tumor immune response genes was observed in combination therapy cohorts treated with CTLA-4 nAb or α-CTLA-4 (D265A) plus α-PD-1. FIG. 3D shows neither CTLA-4 nAb or α-CTLA-4 (D265A) has anti-tumor activity in the absence of the PD-1 blockade. These data support the hypothesis that complimentary mechanisms for pure CTLA-4 blockade and PD-1 blockade can provide strong combination benefit in an Fc-independent manner.

Figure 4B:
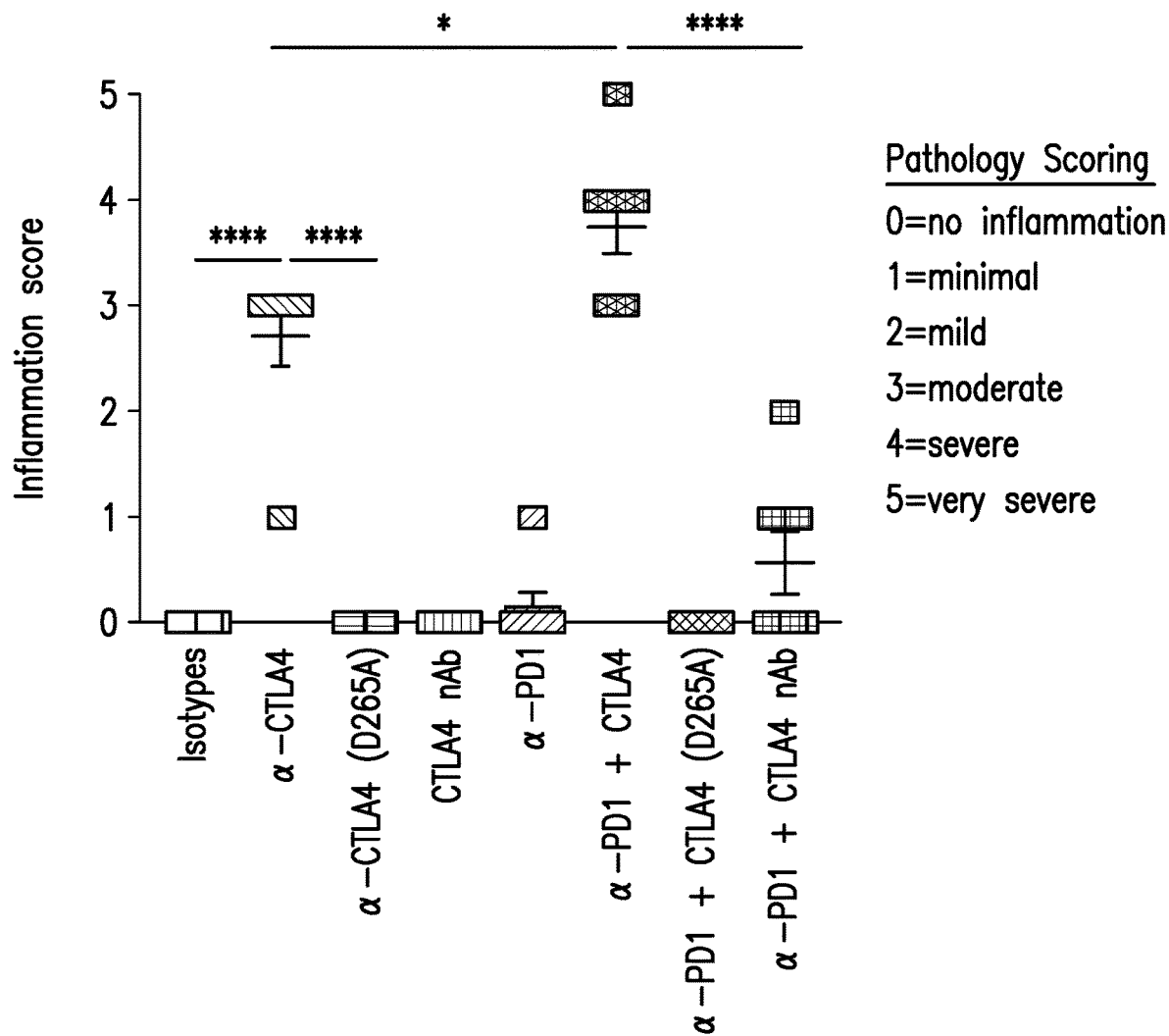
Figure 4C:
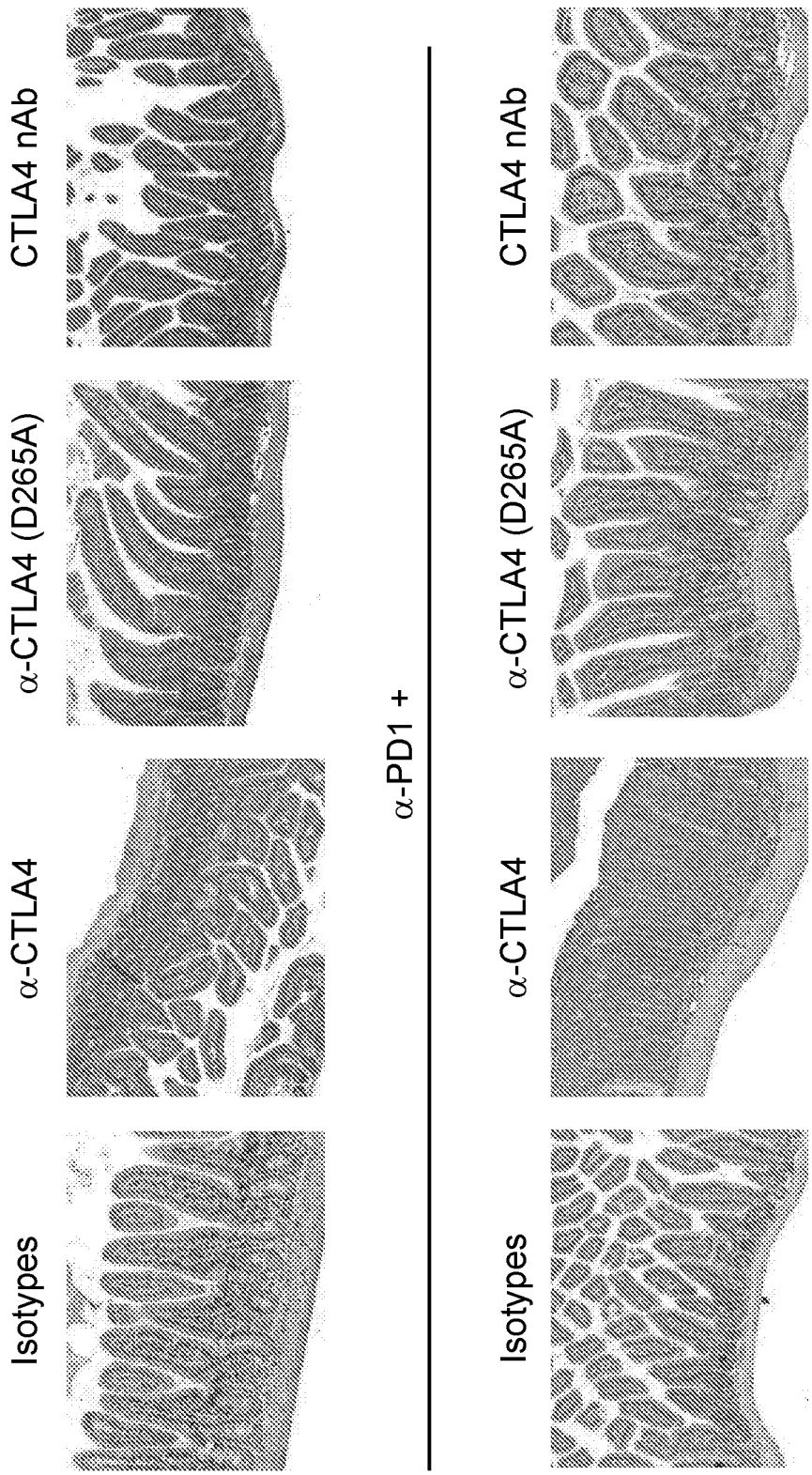
Figure 4D:
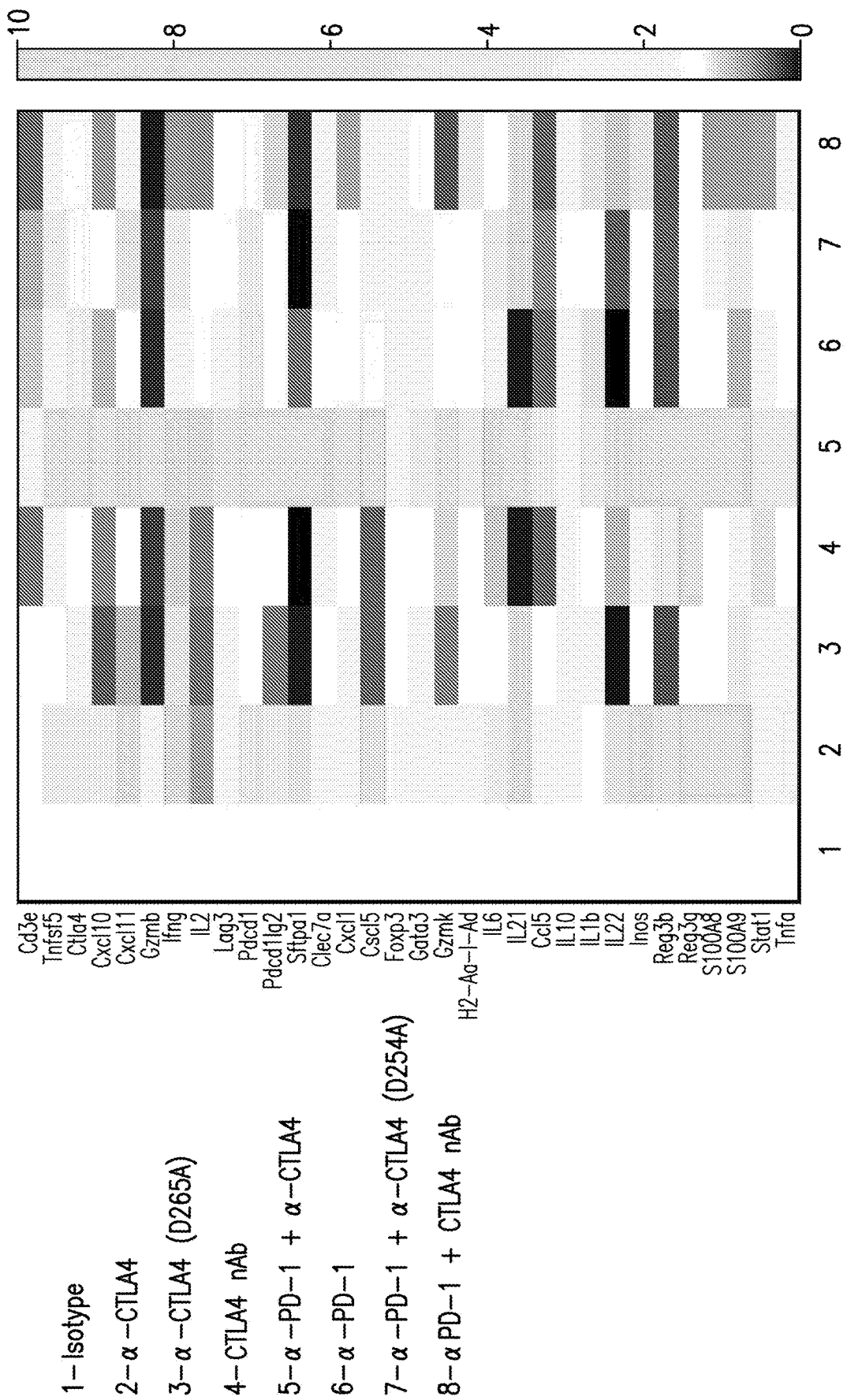

CTLA-4 Blockade without Fc-Function Combined with Anti-PD-1 Provides Superior Therapeutic Index A prominent feature of immune checkpoint blockade is clinically validated combination benefit of anti-PD-1 and anti-CTLA-4 antibodies resulting in superior clinical efficacy when compared to targeting either checkpoint pathway alone. However, immune-related toxicities (irAEs) associated with CTLA-4 blockade combination therapy with anti-PD-1 have been associated with increased induction of gut inflammation in patients (Ribas & Wolchok, Science 359: 1350-1355 (2018). In addition, both α-CTLA (D265A) and Fc-less CTLA-4 nAb required combination with α-PD-1 in order to induce strong anti-tumor immunity. To control for potential effects of strong tumor immunity on induction of gut inflammation, we examined gut inflammation expression profiles in mice receiving combination therapy with a-PD-1 plus either α-CTLA, α-CTLA (D265A), or CTLA-4 nAb after five-treatments, on day 18 after initiation of treatment (FIG. 4D).

To assess the relative effects of CTLA-4 blockade and Fc-function on gut inflammation, naïve BALB/c mice were dosed twice weekly with α-CTLA, α-CTLA (D265A), Fc-less CTLA4 nAb, α-PD-1, or with combinations of α-PD-1 with the various anti-mCTLA4 antagonists. Body weights and body condition scores were evaluated twice weekly throughout the study. Mouse body weights in all groups increased through approximately Day 20 (FIG. 4A). Body weights continued to increase through day 50 in mice dosed with isotype, α-CTLA (D265A), CTLA4 nAb, or α-PD-1 or combinations thereof. Mice dosed with α-CTLA showed a decrease in mean body weight after about day 30 to near pre-treatment levels by day 50. Administration of α-CTLA in combination with α-PD-1 led to a more rapid decrease in mean body weight below pre-treatment levels from day 20 through the day 50. Notably, mice dosed with α-CTLA, the body condition score for 2 of 8 mice dropped to 2 (under-conditioned) beginning on day 42 and beginning on day 28 in mice treated with α-CTLA in combination with α-PD-1. These cohorts presented glossy, scruffy fur, and swollen abdomen were observed in these cohorts.

Analysis of inflammation was scheduled after seven weeks of dosing, when mice dosed with α-CTLA showed loss of body weight over the time period, which was exacerbated when administered in combination with α-PD-1 (Group B in FIG. 4A). In contrast, none of the effector-silent CTLA-4 blocking agents or α-PD-1 showed any significant weight loss compared to the isotype controls during the time period (Group A in FIG. 4B).

All mice from the combination treatment groups and four mice from the isotype control and α-PD-1 treatment groups were euthanized on day 50 for tissue collection. The four remaining mice from the isotype control and α-PD-1 treatment groups and all mice from the single agent treatment groups were euthanized on day 54 for tissue collection. At the time of necropsy, the proximal small intestine and colon were resected for RT-qPCR to determine the expression of the inflammatory genes and for assessment of inflammation by histopathology.

A heat map of gene expression in the proximal small intestine from each treatment group relative to isotype control is shown in (FIG. 4D). Administration of α-CTLA was sufficient to induce upregulation of inflammatory genes in the jejunum (FIG. 4D) and colon (FIG. 4E). The combination of α-CTLA with α-PD-1 induced an even stronger upregulation of inflammatory genes than the α-CTLA monotherapy. In contrast, administration of CTLA-4 nAb induced little or no gut inflammatory gene expression and only modest upregulation when combined with α-PD-1. Similarly, administration of α-CTLA (D265A) alone or in combination with α-PD-1 resulted in minimal to low induction of inflammatory genes. Gut permeability, assessed in serum after FITC-dextran gavage, was significantly increased in mice treated with α-CTLA and mice receiving combination treatment with α-CTLA and α-PD-1.

Severity of inflammation in the proximal small intestine was scored by histological assessment of enteritis in proximal jejunum on day 50. By histopathological assessment, administration of α-CTLA resulted in mild to severe inflammation in most mice. In cohorts treated with a combination of α-CTLA and α-PD-1, sustained treatment induced moderate to very severe inflammation in all mice (FIG. 4B). Mice with very severe enteritis, presented with jejunitis, diffuse neutrophilic lesions with moderate numbers of mast cells and degeneration of neurons of Meissner plexus. In contrast, administration of either CTLA-4 nAb or α-CTLA (D265A) did not induce inflammation in the histopathology assessment. Administration of CTLA-4 nAb in combination with α-PD-1 led to no inflammation or minimal to mild inflammation in several mice. Administration of α-CTLA (D265A) in combination with α-PD-1, led to mild inflammation in only one of the eight mice. Representative photomicrographs demonstrate the relative level of inflammation in each treatment group (FIG. 4C).

Figure 5A:
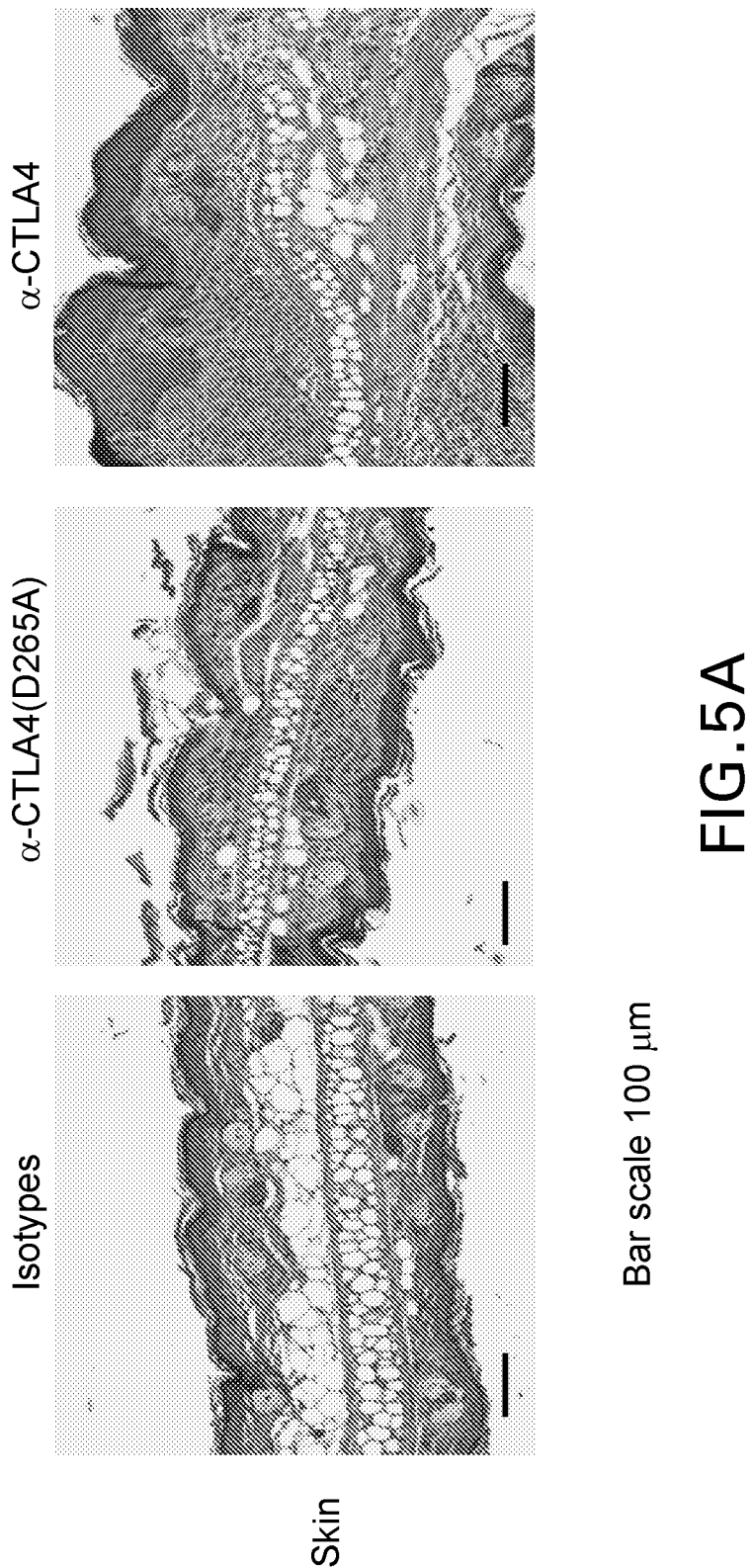
FIGS. 5A-5C: Fc effector function Anti-CTLA-4 drives skin but not system inflammation. Balb/c mice were treated twice a week with α-CTLA4 or α-CTLA4 (D265A) as indicated for 55 days.
Figure 5B:
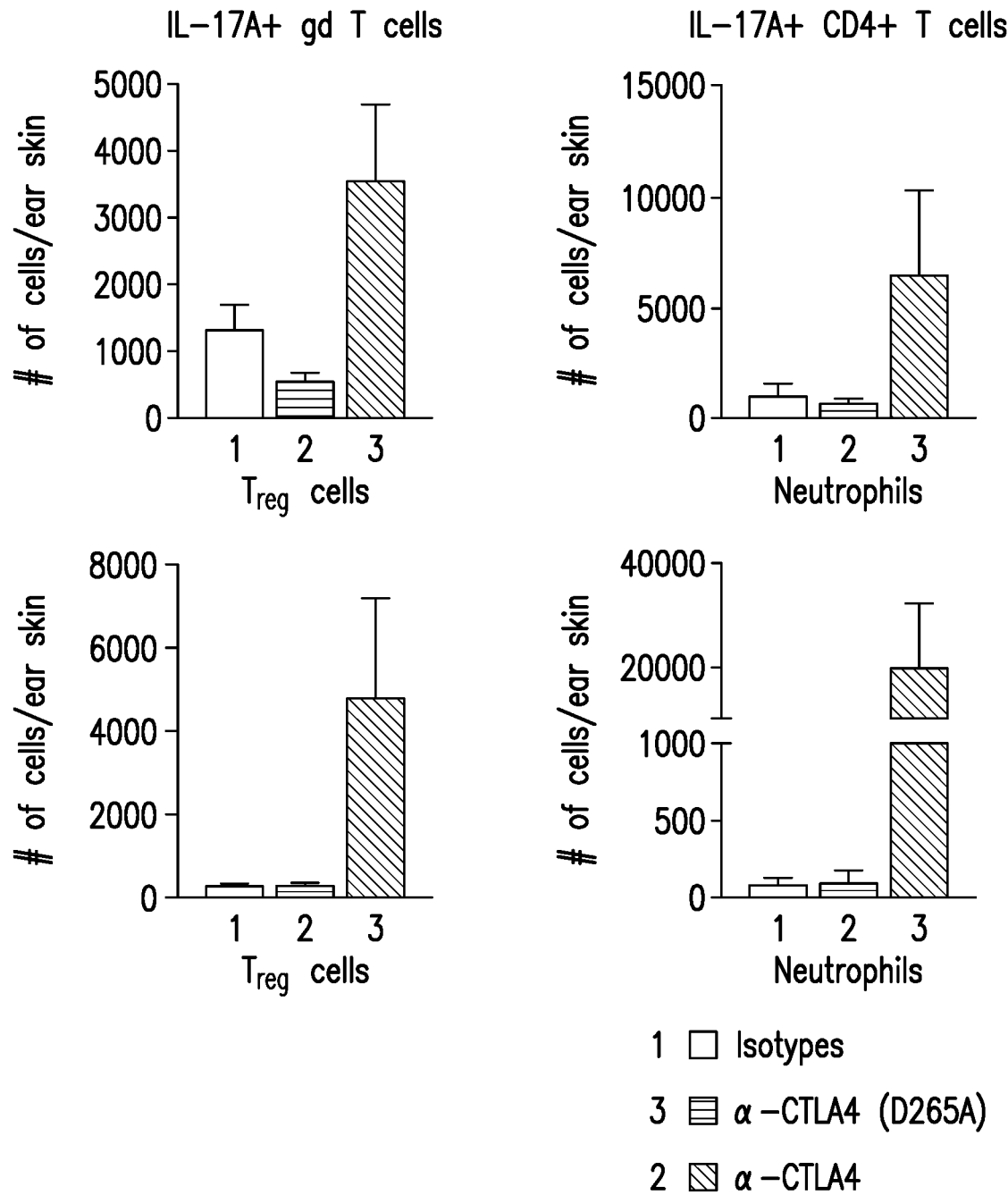
Figure 5C:
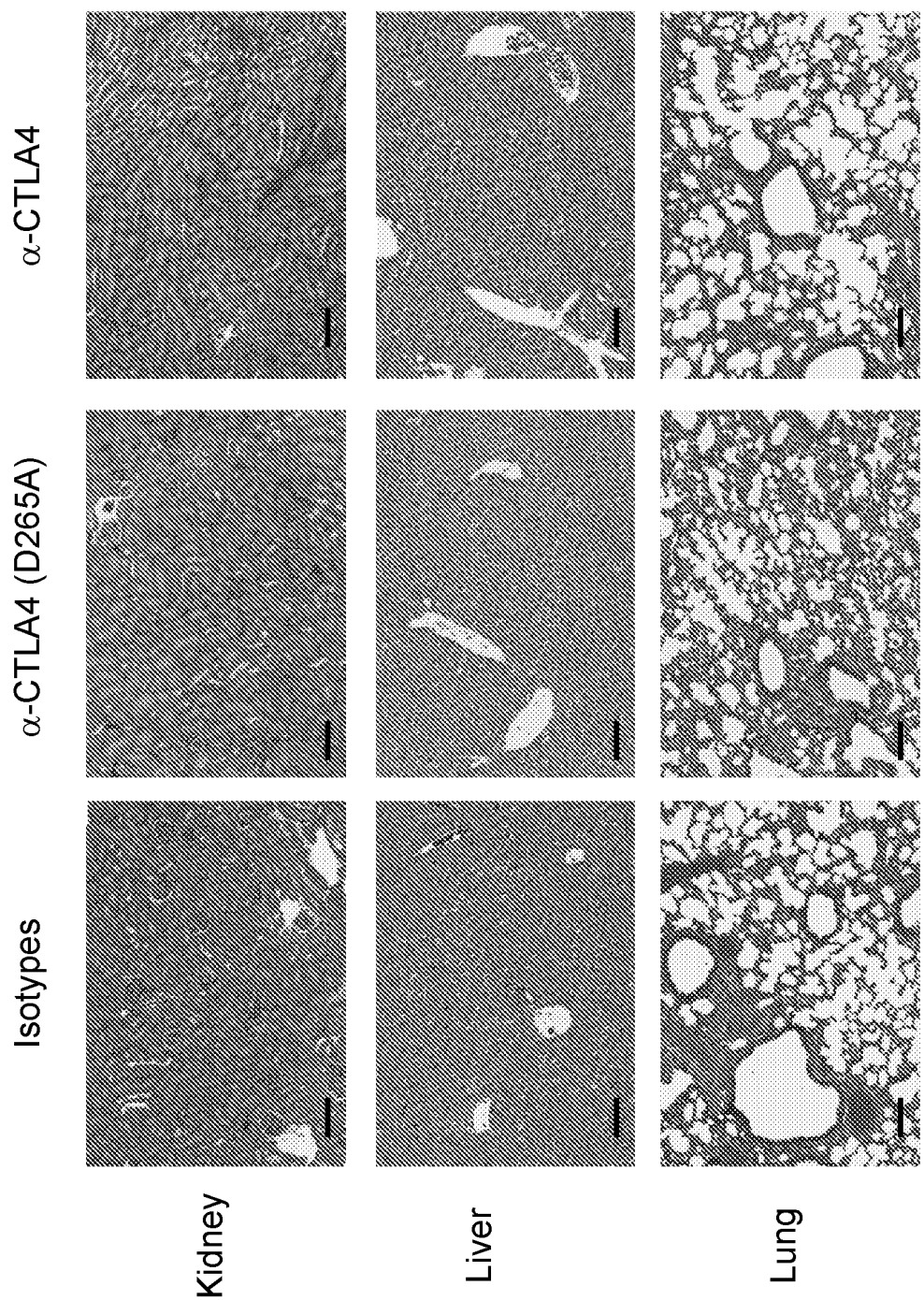

As shown in FIGS. 5A-5C, α-CTLA-4 Fc effector function drives skin inflammation (FIG. 5A) but not systemic inflammation, where there was no detectable inflammation in kidney, liver, or lung (FIG. 5C). Absolute number of ear skin IL-17-producing T cells, Foxp3+ Treg cells and neutrophils were measured by flow cytometry. As shown in FIG. 5B, elevated levels of IL-17-producing T cells, Foxp3+ Treg cells and neutrophils were present in ear skin from mice treated with α-CTLA-4 but not with α-CTLA-4 (D265A). Together, these data support a key role of the Fc-effector function in the induction of gut inflammation by anti-mouse CTLA-4 antibodies having effector function. Fc-effector function contributed to anti-mouse α-CTLA induced gut inflammation in the BALB/c mouse model of enterocolitis, whereas gut inflammation is mild or absent in mice treated with CTLA-4 nAb or in mice treated with α-CTLA (D265A).

In summary, two attributes were associated with induction of gut inflammation in the CT26 tumor model by α-CTLA-4. First, CTLA-4 specificity was required as Fc-functional isotype controls did not elicit gene expression associated with inflammation. However, blocking of CTLA-4 binding to CD80/CD86 ligands was insufficient to induce upregulation of inflammatory genes in the bowels of the CTLA-4 nAb and the α-CTLA-4 (D265A) treated mice. Hence, the strong Fc-function capacity present in the $IgG_{2a}$ isoform in the α-CTLA-4 was required for induction of gut inflammation.

Activation of Gut Inflammation is Initiated by Activation of Teff Cells Independent of Depletion of $T_{regs}$ The mechanism of action (MOA) for anti-CTLA-4 mediated anti-tumor immunity is theoretically mediated by pharmacodynamics (PD) effects on T regulatory ($T_{reg}$) cells as well as on T effector ($T_{eff}$) cell populations (CTL, TH1 cells, etc.). Depletion of $T_{reg}$ cells within the tumor microenvironment (TILs) is a prominent MOA for anti-CTLA-4 antibodies in murine syngeneic tumor models (Simpson et al., op. cit.). Additionally, Fc-FcγR co-engagement by anti-CTLA-4 mAbs modulates T cell receptor (TCR) and CD28 signaling resulting in enhanced T cell activation independent of $T_{reg}$ depletion (Waight et al., Cancer Cell, 33:1033-1047 (2018)).

Figure 6A:
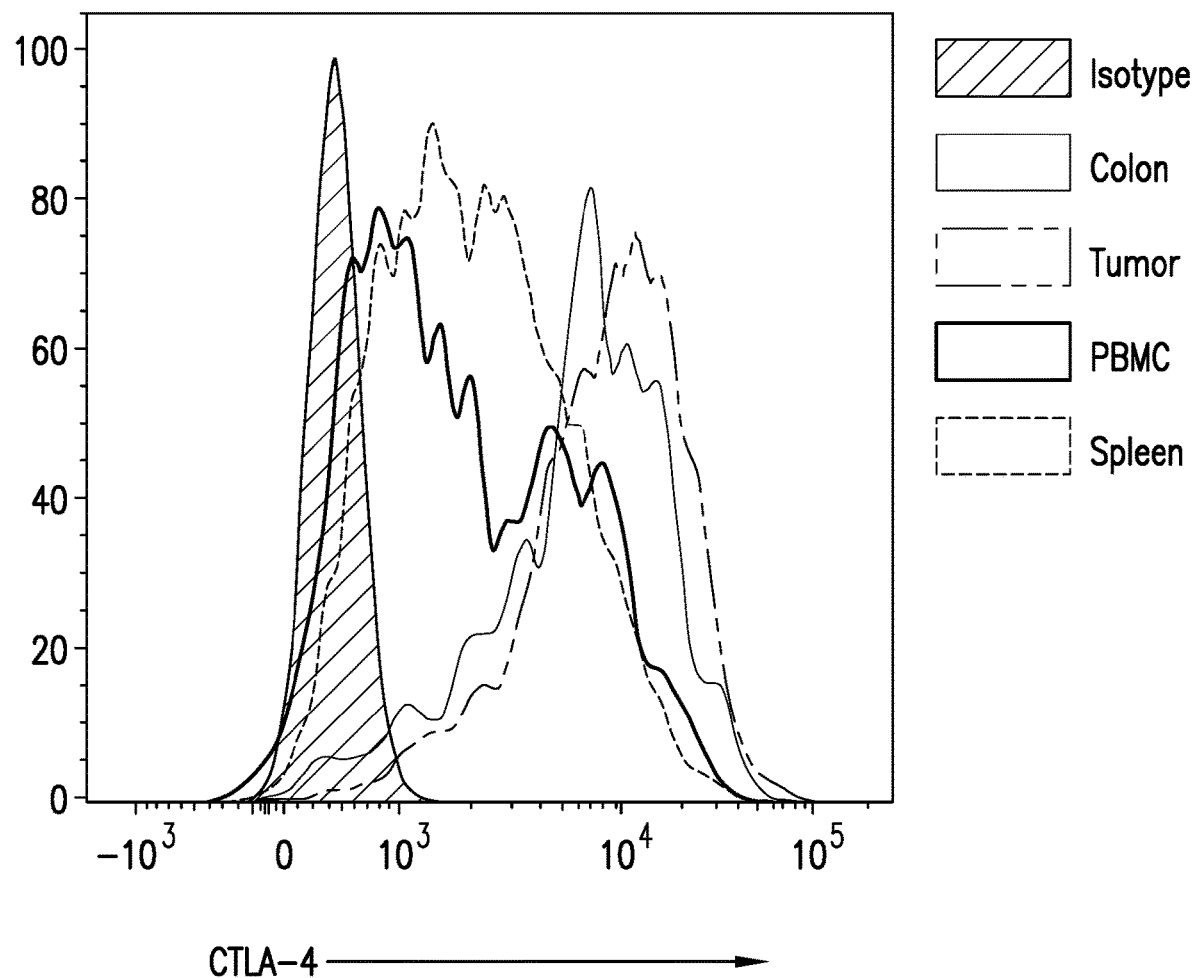
FIGS. 6A-6D: Fc-sufficient anti-CTLA-4 antibody does not deplete colon Foxp3+ $T_{regs}$.
Figure 6B:
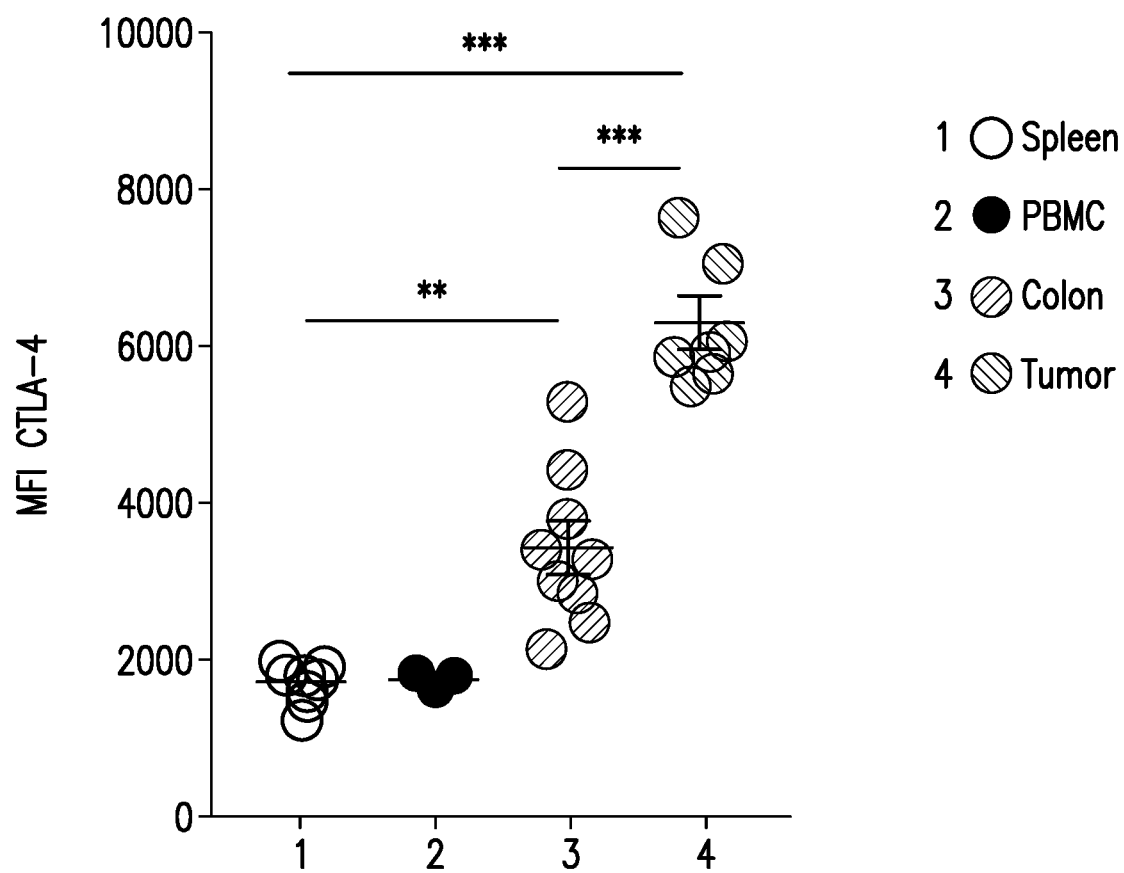
Figure 6C:
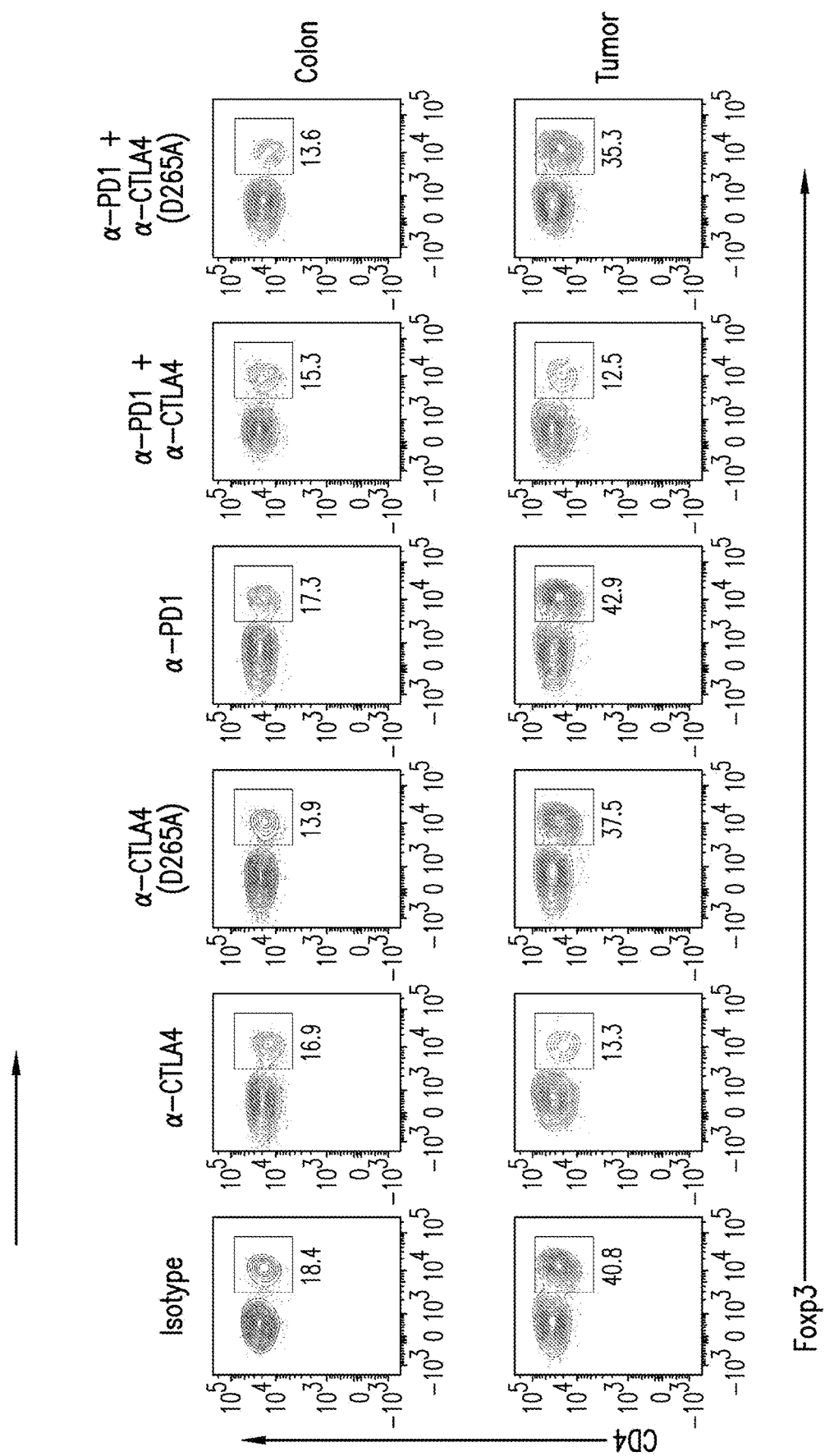
Figure 6D:
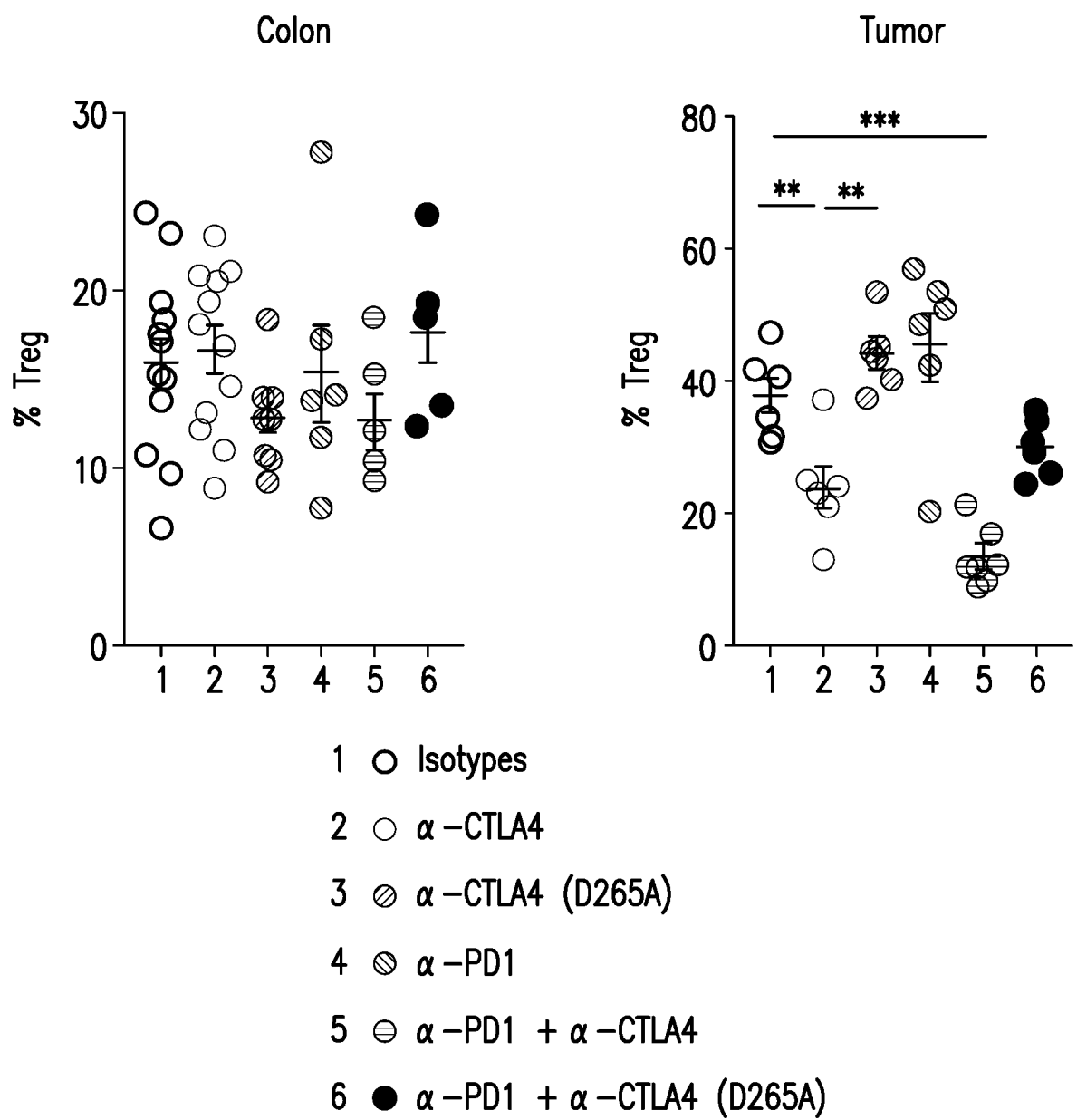

To characterize differential effects of effects of α-CTLA-4 from CTLA-4 nAb on $T_{regs}$ and T effector cells, flow cytometry was conducted on T cell populations from tumor (TILs), lamina propria of the colon, blood and spleen 20-hours following subcutaneous administration. We were able to measure CTLA-4 expression levels in $T_{regs}$ from mice treated with α-CTLA-4 or α-CTLA-4 (D265A) using anti-CTLA-4 mAb clone UC10-4B9 (ThermoFisher) as they do not cross-block, enabling staining of drug-bound CTLA-4. As reported previously in the literature (Selby et al. op. cit., Simpson et al. op. cit.), we observed differential expression of CTLA-4 in $T_{regs}$ within spleen (CTLA-4lo) and tumor microenvironments ($T_{reg}^{hi}$) of CT26 tumor bearing mice. $T_{regs}$ within PBMC expressed bi-modal levels of CTLA-4lo-mid. Interestingly, $T_{regs}$ from the lamina propria of the colon expressed bi-modal levels of CTLA-4$^{mid-hi}$. The CTLA-4$^{hi}$ $T_{regs}$ in the colon expressed similar levels to Treg TIL populations. The differential expression levels of CTLA-4 on the various T cell populations impacts the capacity for ADCC mediated depletion due to receptor density dependent killing mechanisms. While $T_{reg}$ populations normally express higher levels of CTLA-4, $T_{regs}$ in the tumor environment express much higher levels (3.3-fold higher, MFI=8,100 in isotype controls of Treg TILs) than those found in spleen (MFI=2,400). Lamina propria $T_{regs}$ from the colon which expressed higher CTLA-4 levels (CTLA-4$^{hi}$ mode MFI=10,000) resembled $T_{reg}$ TILs for relative expression levels using flow cytometry (FIG. 6A). As illustrated in FIGS. 6B-6D, significant depletion of $T_{regs}$ was limited to TILs from the tumor microenvironment of mice treated with α-CTLA-4, which have the highest density of CTLA-4 expression. Treatment with Fc-mutant α-CTLA-4 (D265A), which lacks Fc-function, did not result in $T_{reg}$ depletion.

Based merely on the assumption that cells expressing higher CTLA-4 levels would be predisposed for depletion by α-CTLA, we predicted that CTLA-4hi $T_{regs}$ in the Lamina propria would be depleted, similar to $T_{reg}$ TIL populations. Surprisingly, only $T_{regs}$ TILs isolated from tumors of α-CTLA-4 treated mice appeared to be depleted. Lamina propria derived $T_{regs}$ from colons of α-CTLA-4 treated mice did not appear to be depleted. No detectable depletion of lamina propria derived $T_{regs}$ from colons of α-CTLA-4 treated mice was observed, suggesting that that the induction of gut inflammation was not initiated by a loss of $T_{regs}$ in the gut mucosa.

Figure 7A:
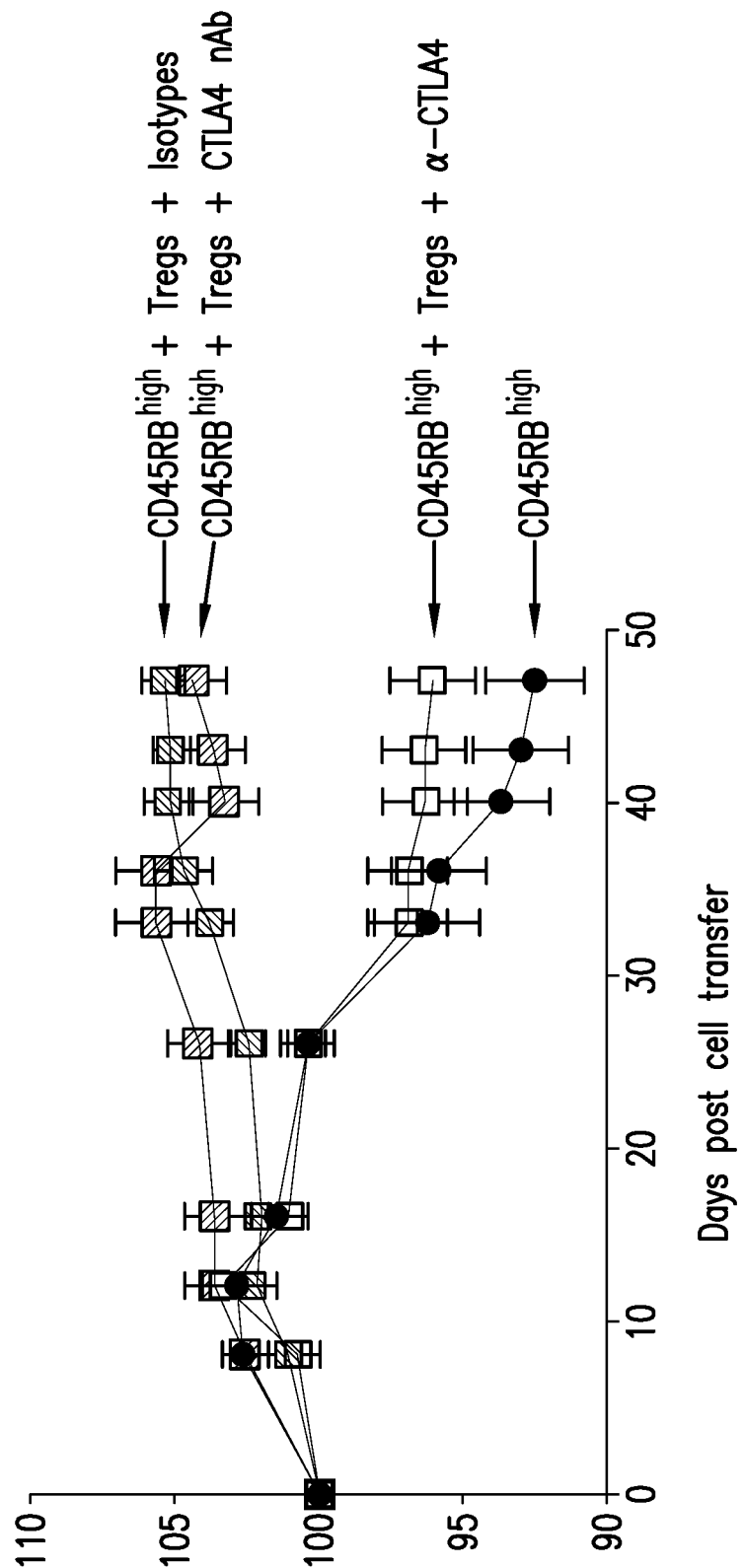
FIGS. 7A-7D: Fc-function mediated gut in anti-CTLA-4 impaired Treg-mediated suppression of colitis. Splenic CD45Rbhigh Naïve T cells were transferred into CB17-SCID recipient mice and treated with α-CTLA-4 or CTLA4 nAb as indicated.
Figure 7B:
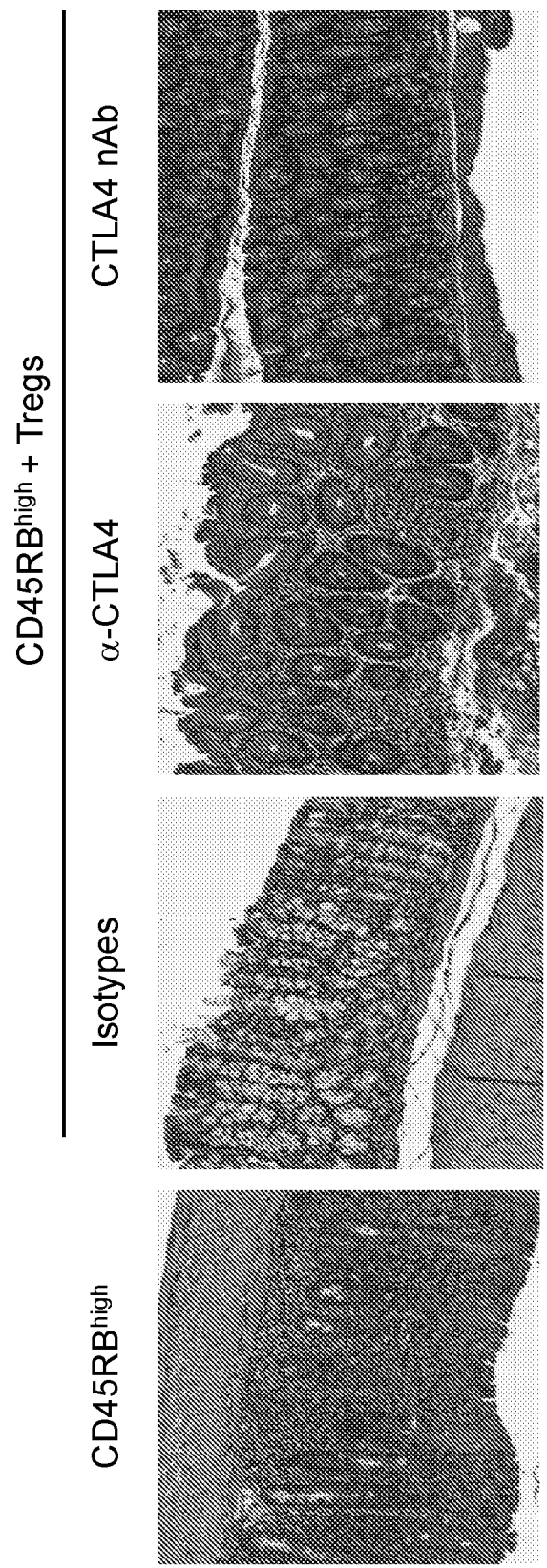
Figure 7C:
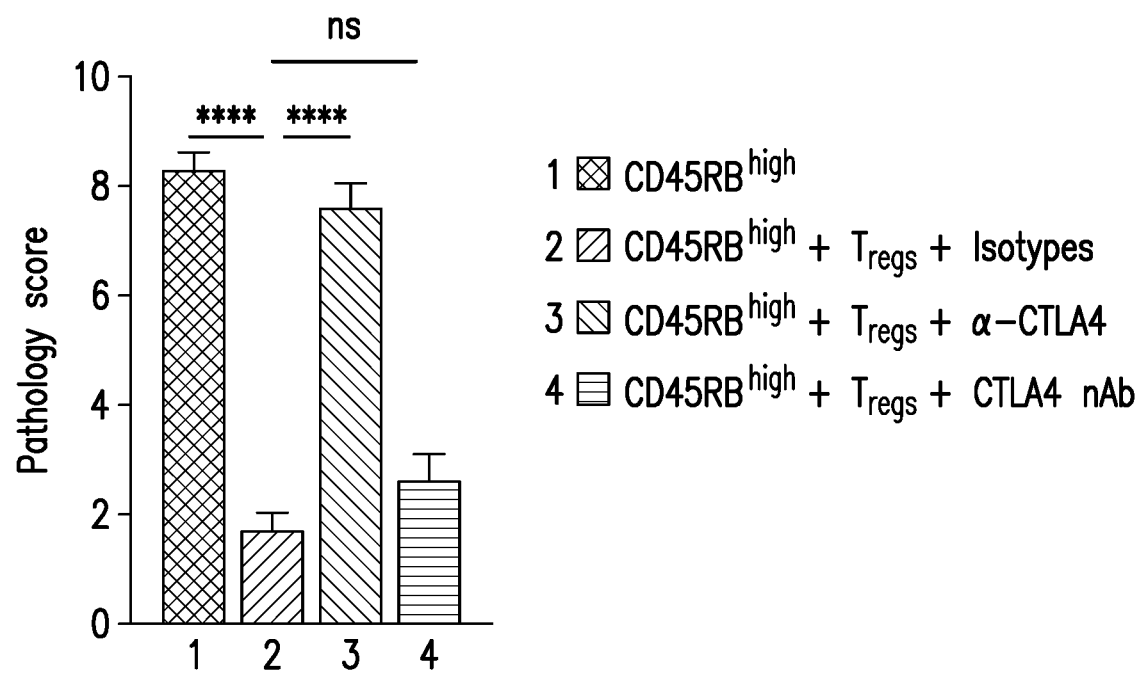
Figure 7D:
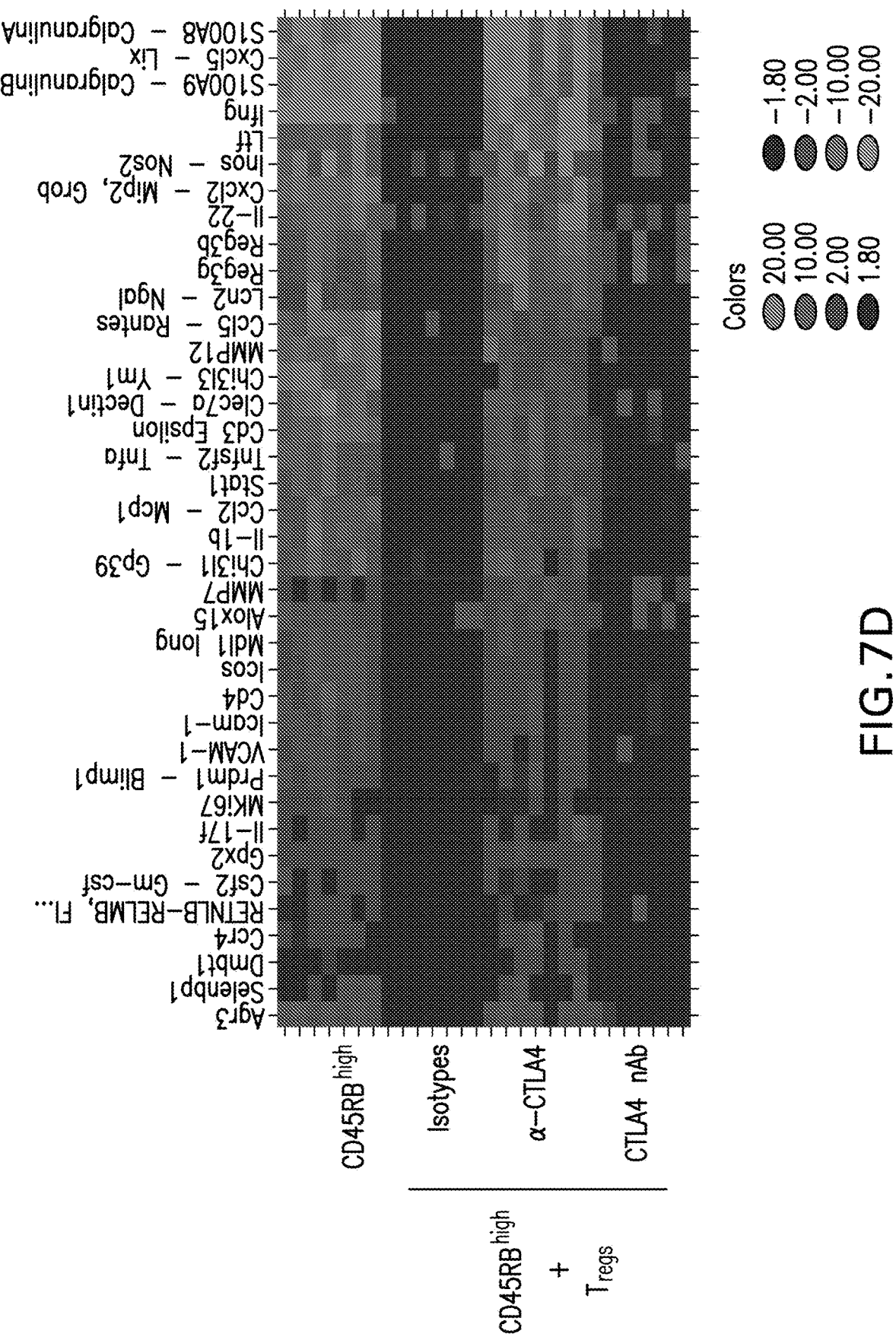

We investigated possible phenotypic changes in $T_{regs}$ effecting suppressor function that may have contributed to α-CTLA-4 induced gut inflammation. Colonic lamina propria (LP) $T_{regs}$ from MC38 tumor implanted FoxP3 GLD reporter mice were sorted for PCR expression profiling of genes associated with $T_{reg}$ function (FIG. 7A). However, no significant gene expression differences were observed in LP $T_{reg}$ cells from α-CTLA compared to α-CTLA-4 (D265A) treated mice. The potential effect of Fc-function on $T_{regs}$ was further investigated using the CD45RB$^{hi}$ T cell transfer model of colitis. Passive transfer of $T_{reg}$ cells with CD45RB$^{hi}$ T cells protected mice from development of Colitis (FIG. 7B-7C). Treatment of mice co-administered $T_{reg}$ cells with CD45RBhi T cells with α-CTLA-4 resulted in a loss of $T_{reg}$ protection and development of colitis. In contrast, loss of protection was not observed in CTLA-4 nAb treated mice (FIG. 7B-7C). Gene expression profile from flow cytometry sorted colon Foxp3+ $T_{reg}$ cells from mice 24 hours post treatment showed significant upregulation of gene expression from mice treated with α-CTLA-4, which is similar to that observed with CD45RB$^{high}$, compared to the gene expression observed with cells obtained from mice treated with CTLA-4 nAb or isotype controls. Collectively, these results suggest Fc-mediated $T_{reg}$ depletion is not essential for induction of gut inflammation by α-CTLA-4 but the regulatory function of $T_{regs}$ in response to gut inflammation may be modulated.

Figure 8A:
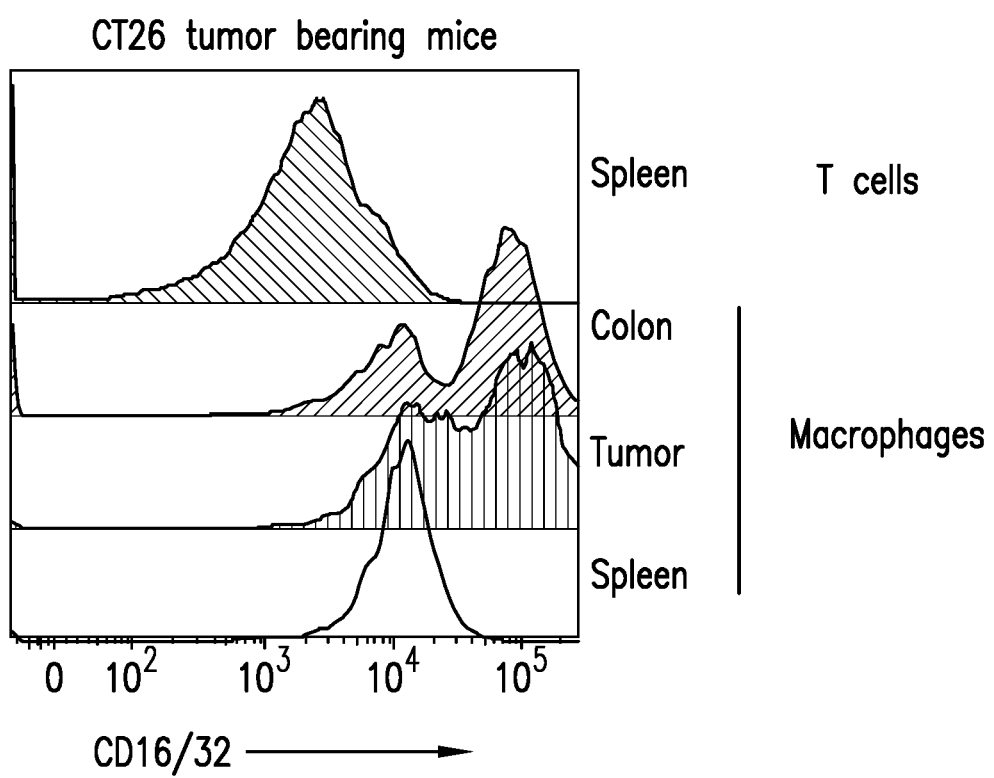
Figure 8D:
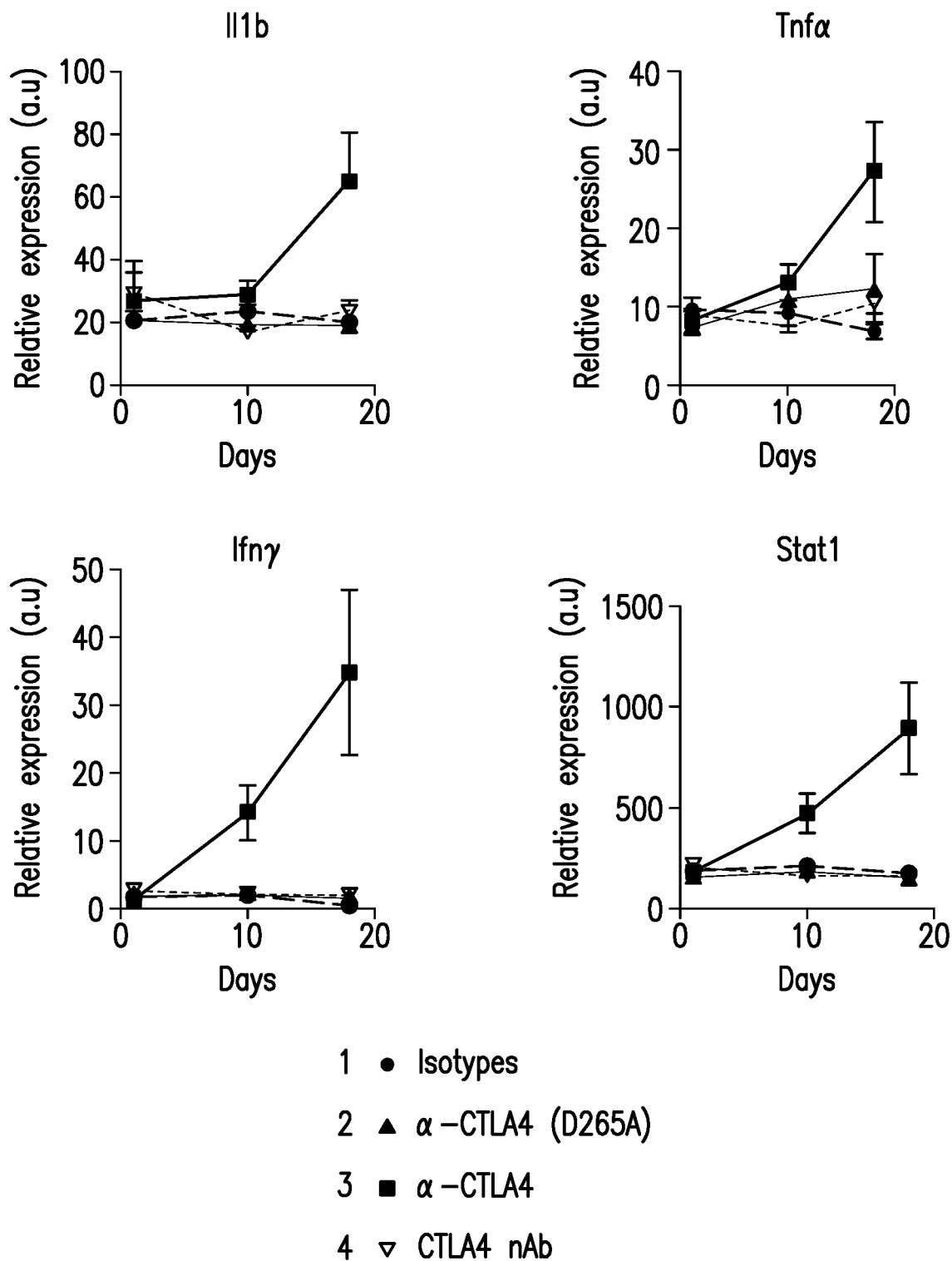

The restricted expression of CTLA-4 and CD28 on T cells and CD80, CD86 and FcγR on antigen presenting cells may play a key role for Fc-functional α-CTLA-4 nAb activation of T cells independent of $T_{reg}$ depletion (Waight et. al., Cancer Cell, 33:1033-1047, 2018). Fc-enhanced activation in tumors is advantageous but could contribute to inadvertent irAEs in gut tissues. We investigated potential contribution of Fc-function in immune effector cell activation in gut tissues. Flow cytometric analysis of CD16/32 expression on macrophages from both tumor and colon showed significantly higher level of FcR on antigen presenting cells compared to splenic macrophages (FIGS. 8A & 8B). Additionally, the proportion of CD45$^+$CD11b$^+$F4/80$^+$ macrophages in tumor and colon lamina propria was substantially higher than in spleen (FIG. 8C). Fc-function was required for activation of IL1β, TNFα and IFNγ cytokine responses in gut tissues and were evident as early as 10-days after initiation of treatment, well before overt evidence of gut inflammation suggesting a key role in irAE induction (FIG. 8C).

Figure 8E:
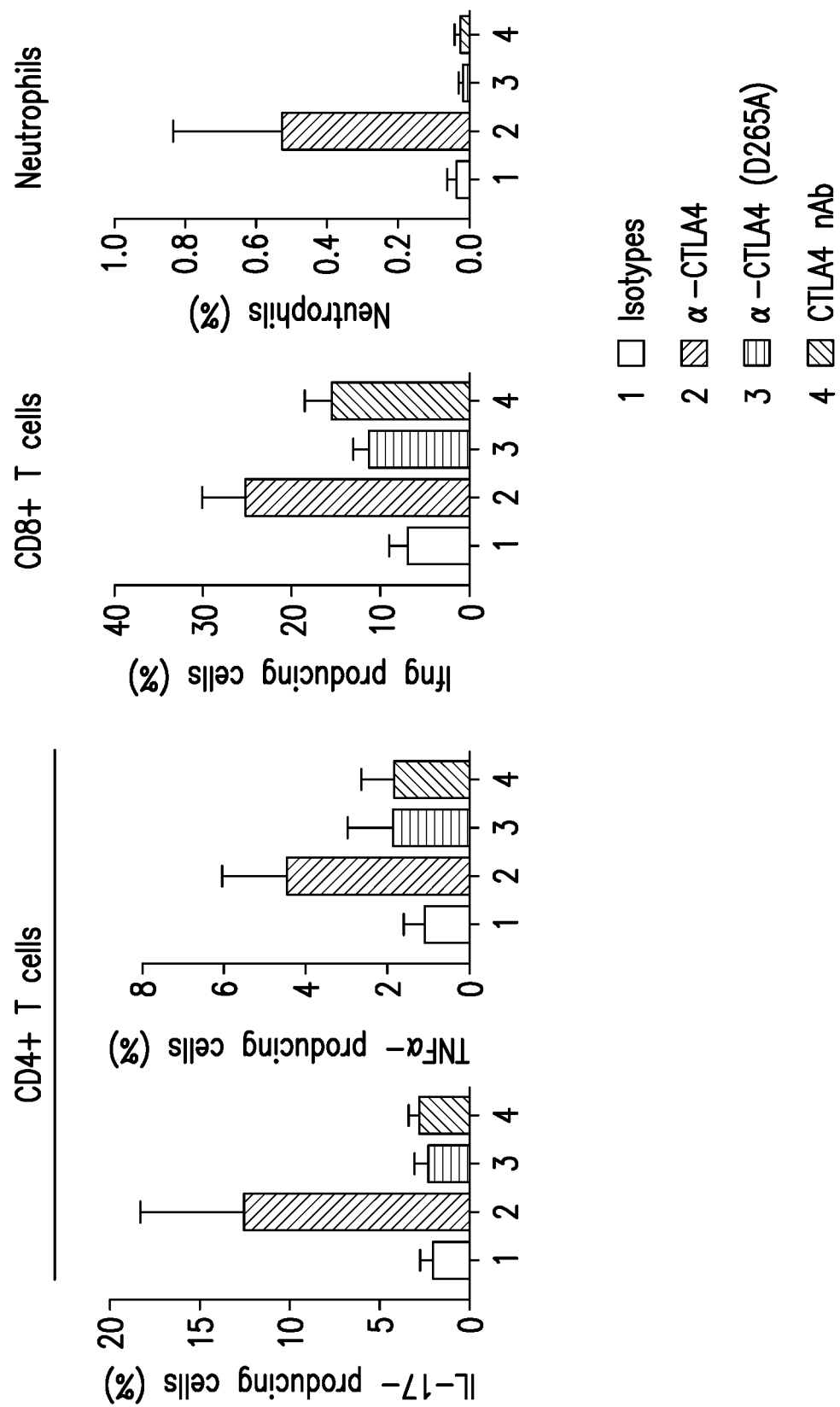

Cytokine responses in CD4 T cells isolated from colon lamina propria of α-CTLA-4 treated mice after one month of treatment showed a higher proportion of IL-17, TNFα and IFNγ producing cells associated with Fc-mediated gut inflammation (FIG. 8E). Additionally, an Fc-dependent increase in neutrophils was also induced in α-CTLA-4 treated mice (FIG. 8E). Collectively, the results indicate CTLA-4 blockade associated gut inflammation in induced by Fc-mediated activation of effector cells, augmented by FcγR-antibody enhancement of cellular bridging of APC with T cells resulting in stimulation of inflammatory cytokine responses as illustrated in FIG. 11. Fc-mediated induction of gut inflammation can be induced by Effector T cells, independent of Treg depletion.

Discussion

Several recent reports have supported a key role for Fc-function for CTLA-4 blockade monotherapy in syngeneic mouse cancer immunotherapy tumor models (International patent Application WO 2014/089113; Selby et al., Cancer Immunol. Res. 32-42 (2013); Vargas et al., Cancer Cell, 33:649-663 (2018)). Ingram et al. reported in Proc. Natl. Acad. Sci. USA 115:3912-3917, (2018) that to provide an anti-CTLA-4 ISVD with anti-tumor efficacy required fusing an Fc domain to the ISVD. Indeed, we observed similar lack of efficacy when treating tumors with CTLA-4 nAb or α-CTLA-4 (D265A) as a monotherapy. Specific depletion of tumor infiltrating $T_{regs}$, which express higher cell surface CTLA-4 levels, has been demonstrated to contribute to tumor efficacy in tumor models (Simpson et al., J. Exp. Med., 210:1695-1710 (2013); Selby et al., Cancer Immunol. Res 1:32-42 (2013).

The induction of enterocolitis by α-CTLA-4 was not associated with detectable depletion of $T_{reg}$ in residing in the lamina propria. Our work expands on the potential for CTLA-4 blockade in anti-cancer treatments by demonstrating strong anti-tumor activity when combined with anti-PD-1 antibodies and without the induction strong gut inflammation. Fc-function was not required to achieve combination benefit for the CTLA-4 and PD-1 blockades. Combination treatments comprising a CTLA-4 nAb or α-CTLA-4 (D265A) with α-PD-1 induced similar activation of IFNγ-associated immune response genes in tumors as those induced by α-CTLA-4 bearing strong Fc-function. In contrast, strong gut inflammation progressing to enterocolitis was primarily observed in mice treated with α-CTLA-4 and was increased when combined with anti-PD-1 antibody mDX400. These results indicate that simple blockade of CTLA-4, facilitating activation of CD28, is sufficient to increase anti-tumor responses of exhausted T cells when combined with PD-1 blockade.

A previous report by Kamphorst et al. in Science 355: 1423-1427 (2017) demonstrated that PD-1 blockade rescue of exhausted CD8 T cells requires CD28 co-stimulation of TCR activation. Moreover, a companion report by Hui et. al. in Science 355:1428-1433 (2017) demonstrated that the co-receptor, CD28, is strongly preferred over the TCR as a target for dephosphorylation by PD-1-recruited Shp2 phosphatase and that CD28 is preferentially dephosphorylated. Our results show that the complimentary activation of the TCR co-receptor CD28 mediated by simple blocking of CTLA-4 by anti-CTLA-4 antibodies without Fc-function and blockade of PD-1 mediated dephosphorylation of CD28 may be sufficient to achieve a combination benefit for cancer immunotherapy. The advantage of a simple combination blockade, without Fc-mediated enhanced activation through Fc-FcγR bridging, may be it permits a larger therapeutic index that enables a higher dose range and longer treatment times. This advantage may also facilitate further combinations with chemotherapeutic standards of care due to a lower gut inflammation irAE risk profile.

EXPERIMENTAL PROCEDURES

Mice

Wild-type C57BL/6J mice were obtained from Jackson laboratories. Wild-type Balb/c and CB17-SCID mice were obtained from Taconic. B6.Foxp3GDL (GFP-DTR-luciferase) mice generated and maintained under specific pathogen-free conditions and kept in microisolators with filtered air at the Merck Research Laboratories (MRL) animal facility at Palo Alto, California. All animal procedures were approved by the Institutional Animal Care and Use Committee of MRL in accordance with guidelines of the Association for Assessment and Accreditation of Laboratory Animal Care.

Tumor Challenge and Treatment

For syngeneic tumor experiments, the CT26, MC38, and MB49 tumor models were used. 8- to 12-week-old Balb/c or C57BL/6J mice were subcutaneously (s.c.) injected with 3 x105 CT26 cells on the flank. Tumor diameter was measured by electronic calipers and tumor volume was calculated by length×width×width×½. Treatments were started when tumors reached approximately 100 mm³. Mice were treated twice a week subcutaneously (s.c.) with α-CTLA-4, α-CTLA-4 (D265A), mouse anti-IgG$_1$-D265A antibody isotype control, mouse anti-IgG$_{2a}$ antibody isotype control, α-PD-1 antibodies at 10 mg/kg. Mice were treated twice a week s.c. with CTLA-4 nAb or ISVD control at 30 mg/kg.

α-CTLA-4 comprises a HC having the amino acid sequence set forth in SEQ ID NO: 58 and a LC having the amino acid sequence of SEQ ID NO:59.

α-CTLA-4 (D265A) comprises a HC having the amino acid sequence set forth in SEQ ID NO:60 and a LC having the amino acid sequence of SEQ ID NO:60.

α-PD-1 comprises a HC having the amino acid sequence set forth in SEQ ID NO: 63 and a LC having the amino acid sequence of SEQ ID NO:64.

CTLA-4 nAb comprises the amino acid sequence set forth in SEQ ID NO:61.

Anti-PD-1 ISVD F037 (PD-1 nAb) comprises the amino acid sequence set forth in SEQ ID NO:62.

Induction of Colitis and Skin Inflammation

Naïve 8- to 12-week-old Balb/c mice were treated twice a week s.c. for eight weeks with α-CTLA-4, α-CTLA-4 (D265A), mouse anti-IgG$_1$-D265A isotype control, mouse anti-IgG$_{2a}$ isotype control, antibodies at 20 mg/kg. Mice were treated twice a week s.c. with CTLA-4 nAb or ISVD control at 30 mg/kg. at day 55, Plasma was collected for ELISA and Luminex assays. Organs were collected and treated as follows: 1) fixed in 10% neutral buffered formalin and stained paraffin-embedded tissue sections with H&E to evaluate tissue pathology; 2) snap-frozen in liquid nitrogen for further RNA extraction; or 3) placed in HBSS for cell isolation.

T Cell-Driven Colitis

Spleen cells from Balb/c mice were processed and purified for CD4 using magnetic bead separation (STEM CELL Technologies). TCRb+ CD4+ CD25− CD45RB$^{high}$ T cells (CD45RB$^{high}$ T cells) and TCRb+ CD4+ CD25+ CD45RBlow (T$_{reg}$ cells) were sorted with FACS Aria (BD). 3×10⁵ CD45RB$^{high}$ T cells and 1×10⁵ T$_{reg}$ cells were injected intravenously. Mice were dosed i.p. twice a week with 350 μg of α-CTLA-4 or isotype control or 600 μg of CTLA-4 nAb or ISVD control. Mice were monitored and weighed for seven weeks post injection.

Intestinal Permeability

Mice were gavaged with FITC-Dextran (4 kDa, Sigma-Aldrich) four hours prior to fluorescence measurement of FITC in the serum.

Colon Lamina Propria, Skin and Tumor Cell Isolation

Colon lamina propria cells were isolated by first removing epithelial cells through the incubation of 0.5-cm gut tissue pieces in Hank's buffered salt solution containing 5 mM EDTA and 10 mM HEPES for 20 minutes at 37° C. and then repeating this incubation one additional time. The remaining tissue was cut into small fragments and then digested with HBSS 1× medium containing 0.250 mg/mL LIBERASE (Roche), 30 U/mL DNase I (Sigma-Aldrich) and DISPASE (Corning) at the same conditions. The resulting cell suspension was layered on to a 40%/80% PERCOLL gradient and centrifuged for 10 minutes at 600 g; LP cells were recovered at the interface.

Ear skins were chopped and digested HBSS 1× medium containing 0.250 mg/mL LIBERASE (Roche), 30 U/mL DNase I (Sigma-Aldrich) and DISPASE (Corning) for 90 minutes at 37° C. Cell suspension was filtered and washed twice with HBSS 1× buffer. Tumors were chopped and digested HBSS 1× medium containing 0.250 mg/mL LIBERASE (Roche), 30 U/mL DNase I (Sigma-Aldrich) and DISPASE (Corning) for 30 minutes at 37° C. Cell suspension was filtered and washed twice with HBSS 1× buffer.

Histology from colon, ear skin, liver, lung, kidney strips were fixed in 10% neutral buffered formalin overnight, transferred to 70% ethanol, processed routinely, embedded in paraffin, sectioned at 4-5 μm, then stained with hematoxylin and eosin (H & E). Colons were scored for severity of disease by a pathologist in a blinded fashion according to three criteria: Inflammation: when present was characterized by infiltration with large numbers (60-70%) of mononuclear cells (macrophages and lymphocytes) and 30-40% of neutrophils and band cells. The scoring of inflammation includes severity of infiltration, loss of glands, erosion, dilatation of glandular lumina, presence of crypt abscess and degeneration of epithelial cells. Inflammation was scored on a scale of 0-4, 0=negative; 1=minimum, 2=mild; 3=moderate; 4 severe. Apoptosis: The prevalence of apoptotic bodies were scored on a scale of 0-3, 0=negative; 1=low, 2=moderate; 3=high. Regeneration: Regenerative changes assessed include scoring of the prevalence of mitotic figures in the upper ⅓ of the mucosa, nuclear density (nuclear crowding) within individual glandular structures, regularity of the surface epithelium. Apoptosis was scored on a scale of 0-3, 0=negative; 1=low, 2=moderate; 3=high.

Flow Cytometry and Antibodies

Cells were resuspended in PBS and stained on ice for 30 minutes in the dark with a fixable viability stain (BD Bioscience). Then, cells were resuspended into the stain buffer (FBS, BD bioscience) and stained on ice for 30 minutes with various combinations of directly fluorochrome-conjugated. For intracellular antigens, surface stained cells were permeabilized, fixed with Foxp3 staining buffer set (eBiosciences) for 30 minutes on ice and then stained with specific antibodies. Mouse antibodies: CD45 (30-F11), CD8a (53-6.7), CTLA-4 (UC10-4B9), CD11c (HL3), CD11b (M1/70), TCRβ (H57-597), TCRγδ (GL3), CD4 (RM4-5 or GK1.5), CD25 (PC61), CD45RB (16A), Ly6G (1A8), F4/80 (T45-2342), CD16/32 (2.4G2), IFNγ (XMG1.2), IL-17A (TC11-18H10), TNFα (MP6-XT22), Foxp3 (FJK-16s). All of the antibodies were purchased from BD biosciences, Biolegend or eBioscience. For all samples, acquisition was performed on LSR II flow cytometer (BD). Data were analyzed using FLOWJO software (Tree Star).

When cytokine production was measured by flow cytometry, cells were stimulated with 500 ng/mL Ionomycin, 50 ng/mL PMA (Sigma-Aldrich). After one hour, Brefeldin A (BD Bioscience) was added for another two hours prior to staining.

Mouse Allogeneic Mixed Leukocyte Reaction (MLR) Assay 2.105 Mouse C57B6/J (8-12 weeks old, female) splenic T cells were isolated using the EASYSEP Mouse T Cell Isolation Kit (STEMCELL) and co-culture with $1 \times 10^5$ irradiated (at 2000 rad) Balb/c mouse splenocytes in the presence of indicated concentration of α-CTLA-4, α-CTLA-4 (D265A), CTLA-4 nAb or isotypes controls. At day three, supernatant was collected and IL-2 and IFN-gamma production were measured by ELISA according to manufacturer's protocol (Meso Scale Discovery). Cells were then pulsed with [3H]-thymidine (1 μCi per well) for six hours or 16-18 hours. Cells were harvested onto glass fiber filters using a cell harvester. Filters were counted in a MicroBeta plate counter (PerkinElmer Microbeta 2450) according to manufacturer's instruction.

Total RNA Isolation from Tissues and Cells and Subsequent Gene Expression Analysis Using the Fluidigm BIOMARK Platform.

For real-time PCR analysis, total RNA was isolated by either of two methods. Organs were homogenized in RNA STAT-60 (Tel-Test Inc., Friendswood, TX) with a polytron homogenizer and then RNA extraction was performed with the MagMAX-96 for Microarrays Kit (ThermoFisher Scientific, Waltham, MA) per manufacturer's instructions. For cellular samples, RNA was isolated using the ARCTURUS PICOPURE RNA Isolation Kit per manufacturer's instructions (ThermoFisher Scientific, Waltham, MA).

DNase-treated total RNA was reverse-transcribed using QUANTITECT Reverse Transcription (Qiagen, Valencia, CA) per manufacturer's instructions. Primers were obtained commercially from ThermoFisher Scientific (Foster City, CA). Gene specific pre-amplification was done on at least 2 ng cDNA per Fluidigm BIOMARK manufacturer's instructions (Fluidigm, Foster City). Real-time quantitative PCR was then done on the Fluidigm BIOMARK using two unlabeled primers at 900 nM each and 250 nM of FAM-labeled probe (ThermoFisher Scientific, Foster City, CA) with TAQMAN Universal PCR Master Mix containing UNG. Samples and primers were run on either a 48×48 array or 96×96 array per manufacturer's instructions (Fluidigm, Foster City). Ubiquitin levels were measured in a separate reaction and used to normalize the data by the ΔCt method. (Using the mean cycle threshold value for ubiquitin and the gene of interest for each sample, the equation $1.8^{\wedge}(Ct$ ubiquitin minus Ct gene of interest$) \times 10^4$ was used to obtain the normalized values.). Primer references sequences are available on demand.

Statistics

Two-tailed paired and unpaired t test were used to calculate statistical significance in the rest of this study. * $P<0.05$,  $P<0.01$, * $P<0.001$. Statistics were performed using GraphPad PRISM 7 software.

Example 2

The anti-tumor efficacy of CTLA-4 nAb was assessed in the mouse syngeneic MB49 tumor model. MB49 cells are a urothelial carcinoma line derived from an adult C57BL/6 mouse by exposure of primary bladder epithelial cell explants to 7,12-dimethylbenz [a] anthracene (DMBA) for 24 hours followed by long-term culture. The syngeneic murine model of bladder cancer has been widely used for more than 35 years.

MB49 mouse bladder cancer cells were implanted subcutaneously (s.c.) into 80 mice and animals were assigned to five treatment groups with 10 mice each. When the median starting tumor volume reached 103 mm$^3$, mice were injected s.c. once every four days for a total of four doses. An irrelevant control ISVD (30 mg/kg, lot number 01AQL) and 5 mg/kg mIgG$_1$ isotype control mAb (lot number 64AIS) were administered as a treatment control. Treatments included 30 mg/kg CTLA-4 nAb, 10 mg/kg Fc-competent α-CTLA-4 (D265A), 5 mg/kg α-PD-1, or combinations of CTLA4 targeting agents and α-PD-1. Tumor growth was monitored for 21 days post treatment initiation.

FIG. 9A shows the individual animal tumor volumes for each treatment group. Complete responses (CR) through Day 21 are presented for responsive treatment groups. FIG. 9B shows the mean tumor volume and standard error of the mean for each treatment group (starting number n=10/ group). Tumor volumes form animals that were removed from the study due to large tumor volumes were carried forward in the mean until the last measurement was taken for that treatment group. FIGS. 9A-9B show that like in the CT26 colon tumor model (see FIG. 3A), the MB49 bladder tumor model and in the MC38 colon tumor models, combination therapy with Fc-less CTLA-4 nAb with α-PD-1 provided strong anti-tumor benefit, independent of Fc-function.

Example 3

The anti-tumor efficacy of CTLA-4 nAb was assessed in the mouse syngeneic MC38 tumor model. MC38 mouse colon cancer cells were implanted SC into 80 mice and animals were assigned to five treatment groups with 10 mice each. When the median starting tumor volume reached 246 mm$^3$, mice were injected SC once every four days for a total of four doses. An irrelevant control ISVD (30 mg/kg) and 5 mg/kg mIgG$_1$ isotype control mAb were administered as a treatment control. Treatments included 30 mg/kg CTLA-4 nAb, 10 mg/kg Fc-competent α-CTLA-4 (D265A), 5 mg/kg α-PD-1, or combinations of CTLA4 targeting agents and α-PD-1. Tumor growth was monitored for 23 days post treatment initiation.

FIG. 10A shows the individual animal tumor volumes for each treatment group. Complete responses (CR) through Day 23 are presented for responsive treatment groups. FIG. 10B shows the mean tumor volume and standard error of the mean for each treatment group (starting number n=10/ group). Tumor volumes form animals that were removed from the study due to large tumor volumes were carried forward in the mean until the last measurement was taken for that treatment group. FIGS. 10A-10B show that like in the CT26 colon tumor model (see FIG. 3A), the MB49 bladder tumor model and in the MC38 colon tumor models, combination therapy with Fc-less CTLA-4 nAb with α-PD-1 provided strong anti-tumor benefit, independent of Fc-function.

Sequences

TABLE of Sequences
(All amino acid positions are identified using Eu numbering)

| SEQ ID NO: | Description | Sequence |
|---|---|---|
| 1 | Ipilimumab LC-CDR1 | RASQSVGSSYLA |
| 2 | Ipilimumab LC-CDR2 | GAFSRAT |
| 3 | Ipilimumab LC-CDR3 | QQYGSSPWT |
| 4 | Ipilimumab HC-CDR1 | SYTMH |
| 5 | Ipilimumab HC-CDR2 | FISYDGNNKYYADSVKG |
| 6 | Ipilimumab HC-CDR3 | TGWLGPFDY |
| 7 | Ipilimumab V$_H$ | QVQLVESGGGVVQPGRSLRLSCAASGFTFSSYTM HWVRQAPGKGLEWVTFISYDGNNKYYADSVKGR FTISRDNSKNTLYLQMNSLRAEDTAIYYCARTGWL GPFDYWGQGTLVTVSS |
| 8 | Ipilimumab V$_L$ | EIVLTQSPGTLSLSPGERATLSCRASQSVGSSYLAW YQQKPGQAPRLLIYGAFSRATGIPDRFSGSGSGTDF TLTISRLEPEDFAVYYCQQYGSSPWTFGQGTKVEI K |
| 9 | Tremelimumab LC-CDR1 | RASQSVGSSYLA |
| 10 | Tremelimumab LC-CDR2 | GAFSRAT |
| 11 | Tremelimumab LC-CDR3 | QQYGSSPWT |
| 12 | Tremelimumab HC-CDR1 | SYGMH |

TABLE of-continued

Sequences
(All amino acid positions are identified using Eu numbering)

| SEQ ID NO: | Description | Sequence |
|---|---|---|
| 13 | Tremelimumab HC-CDR2 | ISYDGNNKYYADSVKG |
| 14 | Tremelimumab HC-CDR3 | YGSSP |
| 15 | Tremelimumab $V_H$ | GVVQPGRSLRLSCAASGFTFSSYGMHWVRQAPGK GLEWVAVIWYDGSNKYYADSVKGRFTISRDNSKN TLLQMNSLRAETAVYYCARDPRGATLYYYYYGM DVWGQGTTVTVSS |
| 16 | Tremelimumab $V_L$ | PSSLSASVGDRVTITCRASQSINSYLDWYQQKPGK APKLLIYAASSLQSGVPSRFSGSGSGTDFTLTISSLQ PEDFATYYCQQYYSTPFTFGPGTKVEIK |
| 17 | Nivolumab HC-CDR1 | NSGMH |
| 18 | Nivolumab HC-CDR2 | VIWYDGSKRYYADSVKG |
| 19 | Nivolumab HC-CDR3 | NDDY |
| 20 | Nivolumab LC-CDR1 | RASQSVSSYLA |
| 21 | Nivolumab LC-CDR2 | DASNRAT |
| 22 | Nivolumab LC-CDR3 | QQSSNWPRT |
| 23 | Nivolumab VH | QVQLVESGGGVVQPGRSLRLDCKASGITFSNSGM HWRQAPGKGLEWVAVIWYDGSKRYYADSVKG RFTISRDNSKNTLFLQMNSLRAEDTAVYYCATND DYWGQGTLVTVSS |
| 24 | Nivolumab VL | EIVLTQSPATLSLSPGERATLSCRASQSVSSYLAWY QQKPGQAPRLLIYDASNRATGIPARFSGSGSGTDFT LTISSLEPEDFAVYYCQQSSNWPRTFGQGTKVEIK |
| 25 | Nivolumab HC (IgG4 S228P) | QVQLVESGGGVVQPGRSLRLDCKASGITFSNSGM HWRQAPGKGLEWVAVIWYDGSKRYYADSVKG RFTISRDNSKNTLFLQMNSLRAEDTAVYYCATND DYWGQGTLVTVSS*ASTKGPSVFPLAPCSRSTSESTAA LGCLVKDYFPEPVTVSWNSGALTSGVHTFPAVLQSSG LYSLSSVVTVPSSSLGTKTYTCNVDHKPSNTKVDKRVE SKYGPPCPPCPAPEFLGGPSVFLFPPKPKDTLMISRT PEVTCVVVDVSQEDPEVQFNWYVDGVEVHNAKTKPR EEQFNSTYRVVSVLTVLHQDWLNGKEYKCKVSNKGL PSSIEKTISKAKGQPREPQVYTLPPSQEEMTKNQVSLT CLVKGFYPSDIAVEWESNGQPENNYKTTPPVLDSDGS FFLYSRLTVDKSRWQEGNVFSCSVMHEALHNHYTQK SLSLSLGK* |
| 26 | Nivolumab LC | EIVLTQSPATLSLSPGERATLSCRASQSVSSYLAWY QQKPGQAPRLLIYDASNRATGIPARFSGSGSGTDFT LTISSLEPEDFAVYYCQQSSNWPRTFGQGTKVEIKR TVAAPSVFIFPPSDEQLKSGTASVVCLLNNFYPREA KVQWKVDNALQSGNSQESVTEQDSKDSTYSLSST LTLSKADYEKHKVYACEVTHQGLSSPVTKSFNRG EC |
| 27 | Pembrolizumab HC (IgG4 S228P) | QVQLVQSGVEVKKPGASVKVSCKASGYTFTNYY MYWVRQAPGQGLEWMGGINPSNGGTNFNEKFKN RVTLTTDSSTTTAYMELKSLQFDDTAVYYCARRD YRFDMGFDYWGQGTTVTVSS*ASTKGPSVFPLAPCS RSTSESTAALGCLVKDYFPEPVTVSWNSGALTSGVHTF PAVLQSSGLYSLSSVVTVPSSSLGTKTYTCNVDHKPSNT KVDKRVESKYGPPCPPCPAPEFLGGPSVFLFPPKPK DTLMISRTPEVTCVVVDVSQEDPEVQFNWYVDGVEV HNAKTKPREEQFNSTYRVVSVLTVLHQDWLNGKEYK CKVSNKGLPSSIEKTISKAKGQPREPQVYTLPPSQEEM TKNQVSLTCLVKGFYPSDIAVEWESNGQPENNYKTTP PVLDSDGSFFLYSRLTVDKSRWQEGNVFSCSVMHEAL HNHYTQKSLSLSLGK* |
| 28 | Pembrolizumab LC | EIVLTQSPATLSLSPGERATLSCRASKGVSTSGYSY LHWYQQKPGQAPRLLIYLASYLESGVPARFSGSGS |

TABLE of-continued

Sequences
(All amino acid positions are identified using Eu numbering)

| SEQ ID NO: | Description | Sequence |
|---|---|---|
| | | GTDFTLTISSLEPEDFAVYYCQHSRDLPLTFGGGTK VEIKRTVAAPSVFIFPPSDEQLKSGTASVVCLLNNF YPREAKVQWKVDNALQSGNSQESVTEQDSKDSTY SLSSTLTLSKADYEKHKVYACEVTHQGLSSPVTKS FNRGEC |
| 29 | Pembrolizumab VH | QVQLVQSGVEVKKPGASVKVSCKASGYTFTNYY MYWVRQAPGQGLEWMGGINPSNGGTNFNEKFKN RVTLTTDSSTTTAYMELKSLQFDDTAVYYCARRD YRFDMGFDYWGQGTTVTVSS |
| 30 | Pembrolizumab VL | EIVLTQSPATLSLSPGERATLSCRASKGVSTSGYSY LHWYQQKPGQAPRLLIYLASYLESGVPARFSGSGS GTDFTLTISSLEPEDFAVYYCQHSRDLPLTFGGGTK VEIK |
| 31 | Pembrolizumab HC-CDR1 | GYTFTNYYMY |
| 32 | Pembrolizumab HC-CDR2 | NPSNGGTNFNEKFKN |
| 33 | Pembrolizumab HC-CDR3 | RDYRFDMGFDY |
| 34 | Pembrolizumab LC-CDR1 | RASKGVSTSGYSYLH |
| 35 | Pembrolizumab LC-CDR2 | LASYLES |
| 36 | Pembrolizumab LC-CDR3 | CQHSRDLPLT |
| 37 | Human IgG1 HC constant domain | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSRDELTKNQ VSLTCLVKGFYPSDIAVEWESNGQPENNYKTTPPV LDSDGSFFLYSKLTVDKSRWQQGNVFSCSVMHEA LHNHYTQKSLSLSPGK |
| 38 | Human IgG1 HC Constant domain (L234A L235A D265S) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPEAAGGPSVFLFPPKPKDTLMISRTPEV TCVVVSVSHEDPEVKFNWYVDGVEVHNAKTKPR EEQYNSTYRVVSVLTVLHQDWLNGKEYKCKVSN KALPAPIEKTISKAKGQPREPQVYTLPPSRDELTKN QVSLTCLVKGFYPSDIAVEWESNGQPENNYKTTPP VLDSDGSFFLYSKLTVDKSRWQQGNVFSCSVMHE ALHNHYTQKSLSLSPGK |
| 39 | Human IgG1 HC Constant domain (L234A L235A P329G) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPEAAGGPSVFLFPPKPKDTLMISRTPEV TCVVVSVSHEDPEVKFNWYVDGVEVHNAKTKPR EEQYNSTYRVVSVLTVLHQDWLNGKEYKCKVSN KALGAPIEKTISKAKGQPREPQVYTLPPSRDELTKN QVSLTCLVKGFYPSDIAVEWESNGQPENNYKTTPP VLDSDGSFFLYSKLTVDKSRWQQGNVFSCSVMHE ALHNHYTQKSLSLSPGK |
| 40 | Human IgG1 HC Constant domain (L235E) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELEGGPSVFLFPPKPKDTLMISRTPEV TCVVVDVSHEDPEVKFNWYVDGVEVHNAKTKPR EEQYNSTYRVVSVLTVLHQDWLNGKEYKCKVSN KALPAPIEKTISKAKGQPREPQVYTLPPSRDELTKN |

TABLE of-continued

Sequences
(All amino acid positions are identified using Eu numbering)

| SEQ ID NO: | Description | Sequence |
|---|---|---|
| | | QVSLTCLVKGFYPSDIAVEWESNGQPENNYKTTPP VLDSDGSFFLYSKLTVDKSRWQQGNVFSCSVMHE ALHNHYTQKSLSLSPGK |
| 41 | Human IgG1 HC Constant domain (D265A) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVAVSHEDPEVKFNWYVDGVEVHNAKTKPRE EQYNSTYRVVSVLTVLHQDWLNGKEYKCKVSNK ALPAPIEKTISKAKGQPREPQVYTLPPSRDELTKNQ VSLTCLVKGFYPSDIAVEWESNGQPENNYKTTPPV LDSDGSFFLYSKLTVDKSRWQQGNVFSCSVMHEA LHNHYTQKSLSLSPGK |
| 42 | Human IgG1 HC Constant domain (D265A N297G) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVAVSHEDPEVKFNWYVDGVEVHNAKTKPRE EQYGSTYRVVSVLTVLHQDWLNGKEYKCKVSNK ALPAPIEKTISKAKGQPREPQVYTLPPSRDELTKNQ VSLTCLVKGFYPSDIAVEWESNGQPENNYKTTPPV LDSDGSFFLYSKLTVDKSRWQQGNVFSCSVMHEA LHNHYTQKSLSLSPGK |
| 43 | Human IgG1 HC Constant domain (E233A/L235A) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPALAAGGPSVFLFPPKPKDTLMISRTPEV TCVVVDVSHEDPEVKFNWYVDGVEVHNAKTKPR EEQYNSTYRVVSVLTVLHQDWLNGKEYKCKVSN KALPAPIEKTISKAKGQPREPQVYTLPPSRDELTKN QVSLTCLVKGFYPSDIAVEWESNGQPENNYKTTPP VLDSDGSFFLYSKLTVDKSRWQQGNVFSCSVMHE ALHNHYTQKSLSLSPGK |
| 44 | Human IgG1 HC Constant domain (N297X, wherein X is any amino acid other than N) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVDVSHEDPEVKFNWYVDGVEVHNAKTKPRE EQYXSTYRVVSVLTVLHQDWLNGKEYKCKVSNK ALPAPIEKTISKAKGQPREPQVYTLPPSRDELTKNQ VSLTCLVKGFYPSDIAVEWESNGQPENNYKTTPPV LDSDGSFFLYSKLTVDKSRWQQGNVFSCSVMHEA LHNHYTQKSLSLSPGK |
| 45 | Human IgG2 HC Constant domain | ASTKGPSVFPLAPCSRSTSESTAALGCLVKDYFPEP VTVSWNSGALTSGVHTFPAVLQSSGLYSLSSVVTV PSSNFGTQTYTCNVDHKPSNTKVDKTVERKCCVE CPPCPAPPVAGPSVFLFPPKPKDTLMISRTPEVTCV VVDVSHEDPEVQFNWYVDGVEVHNAKTKPREEQ FNSTFRVVSVLTVVHQDWLNGKEYKCKVSNKGLP APIEKTISKTKGQPREPQVYTLPPSREEMTKNQVSL TCLVKGFYPSDISVEWESNGQPENNYKTTPPMLDS DGSFFLYSKLTVDKSRWQQGNVFSCSVMHEALHN HYTQKSLSLSPGK |
| 46 | Human IgG2 HC Constant domain (D265S) | ASTKGPSVFPLAPCSRSTSESTAALGCLVKDYFPEP VTVSWNSGALTSGVHTFPAVLQSSGLYSLSSVVTV PSSNFGTQTYTCNVDHKPSNTKVDKTVERKCCVE CPPCPAPPVAGPSVFLFPPKPKDTLMISRTPEVTCV VVSVSHEDPEVQFNWYVDGVEVHNAKTKPREEQF NSTFRVVSVLTVVHQDWLNGKEYKCKVSNKGLP APIEKTISKTKGQPREPQVYTLPPSREEMTKNQVSL TCLVKGFYPSDISVEWESNGQPENNYKTTPPMLDS DGSFFLYSKLTVDKSRWQQGNVFSCSVMHEALHN HYTQKSLSLSPGK |
| 47 | Human IgG2 HC Constant domain (P329G) | ASTKGPSVFPLAPCSRSTSESTAALGCLVKDYFPEP VTVSWNSGALTSGVHTFPAVLQSSGLYSLSSVVTV PSSNFGTQTYTCNVDHKPSNTKVDKTVERKCCVE CPPCPAPPVAGPSVFLFPPKPKDTLMISRTPEVTCV |

TABLE of-continued

Sequences
(All amino acid positions are identified using Eu numbering)

| SEQ ID NO: | Description | Sequence |
|---|---|---|
| | | VVDVSHEDPEVQFNWYVDGVEVHNAKTKPREEQ<br>FNSTFRVVSVLTVVHQDWLNGKEYKCKVSNKGL<br>GAPIEKTISKTKGQREPQVYTLPPSREEMTKNQVS<br>LTCLVKGFYPSDISVEWESNGQPENNYKTTPPMLD<br>SDGSFFLYSKLTVDKSRWQQGNVFSCSVMHEALH<br>NHYTQKSLSLSPGK |
| 48 | Human IgG2 HC Constant domain (D265A) | ASTKGPSVFPLAPCSRSTSESTAALGCLVKDYFPEP<br>VTVSWNSGALTSGVHTFPAVLQSSGLYSLSSVVTV<br>PSSNFGTQTYTCNVDHKPSNTKVDKTVERKCCVE<br>CPPCPAPPVAGPSVFLFPPKPKDTLMISRTPEVTCV<br>VVAVSHEDPEVQFNWYVDGVEVHNAKTKPREEQ<br>FNSTFRVVSVLTVVHQDWLNGKEYKCKVSNKGLP<br>APIEKTISKTKGQPREPQVYTLPPSREEMTKNQVSL<br>TCLVKGFYPSDISVEWESNGQPENNYKTTPPMLDS<br>DGSFFLYSKLTVDKSRWQQGNVFSCSVMHEALHN<br>HYTQKSLSLSPGK |
| 49 | Human IgG2 HC Constant domain (D265A N297G) | ASTKGPSVFPLAPCSRSTSESTAALGCLVKDYFPEP<br>VTVSWNSGALTSGVHTFPAVLQSSGLYSLSSVVTV<br>PSSNFGTQTYTCNVDHKPSNTKVDKTVERKCCVE<br>CPPCPAPPVAGPSVFLFPPKPKDTLMISRTPEVTCV<br>VVAVSHEDPEVQFNWYVDGVEVHNAKTKPREEQ<br>FGSTFRVVSVLTVVHQDWLNGKEYKCKVSNKGLP<br>APIEKTISKTKGQPREPQVYTLPPSREEMTKNQVSL<br>TCLVKGFYPSDISVEWESNGQPENNYKTTPPMLDS<br>DGSFFLYSKLTVDKSRWQQGNVFSCSVMHEALHN<br>HYTQKSLSLSPGK |
| 50 | Human IgG2 HC Constant domain (N297X, wherein X is any amino acid other than N) | ASTKGPSVFPLAPCSRSTSESTAALGCLVKDYFPEP<br>VTVSWNSGALTSGVHTFPAVLQSSGLYSLSSVVTV<br>PSSNFGTQTYTCNVDHKPSNTKVDKTVERKCCVE<br>CPPCPAPPVAGPSVFLFPPKPKDTLMISRTPEVTCV<br>VVDVSHEDPEVQFNWYVDGVEVHNAKTKPREEQ<br>FXSTFRVVSVLTVVHQDWLNGKEYKCKVSNKGLP<br>APIEKTISKTKGQPREPQVYTLPPSREEMTKNQVSL<br>TCLVKGFYPSDISVEWESNGQPENNYKTTPPMLDS<br>DGSFFLYSKLTVDKSRWQQGNVFSCSVMHEALHN<br>HYTQKSLSLSPGK |
| 51 | Human IgG2 HC Constant domain (V234A G237A P238S H268A V309L A330S P331S X378S/A) (See IgGsigma SEQ ID No: 78 in WO2017079112) | ASTKGPSVFPLAPCSRSTSESTAALGCLVKDYFPEP<br>VTVSWNSGALTSGVHTFPAVLQSSGLYSLSSVVTV<br>PSSNFGTQTYTCNVDHKPSNTKVDKTVERKCCVE<br>CPPCPAPPAAASSVFLFPPKPKDTLMISRTPEVTCV<br>VVDVSAEDPEVQFNWYVDGVEVHNAKTKPREEQ<br>FNSTFRVVSVLTVLHQDWLNGKEYKCKVSNKGLP<br>SSIEKTISKTKGQPREPQVYTLPPSREEMTKNQVSL<br>TCLVKGFYPSDIXVEWESNGQPENNYKTTPPMLDS<br>DGSFFLYSKLTVDKSRWQQGNVFSCSVMHEALHN<br>HYTQKSLSLSPGK |
| 52 | Human IgG4 HC Constant domain (S228P) | ASTKGPSVFPLAPCSRSTSESTAALGCLVKDYFPEP<br>VTVSWNSGALTSGVHTFPAVLQSSGLYSLSSVVTV<br>PSSSLGTKTYTCNVDHKPSNTKVDKRVESKYGPPC<br>PPCPAPEFLGGPSVFLFPPKPKDTLMISRTPEVTCV<br>VVDVSQEDPEVQFNWYVDGVEVHNAKTKPREEQ<br>FNSTYRVVSVLTVLHQDWLNGKEYKCKVSNKGLP<br>SSIEKTISKAKGQPREPQVYTLPPSQEEMTKNQVSL<br>TCLVKGFYPSDIAVEWESNGQPENNYKTTPPVLDS<br>DGSFFLYSRLTVDKSRWQEGNVFSCSVMHEALHN<br>HYTQKSLSLSLGK |
| 53 | Human IgG4 HC Constant domain (S228P P329G) | ASTKGPSVFPLAPCSRSTSESTAALGCLVKDYFPEP<br>VTVSWNSGALTSGVHTFPAVLQSSGLYSLSSVVTV<br>PSSSLGTKTYTCNVDHKPSNTKVDKRVESKYGPPC<br>PPCPAPEFLGGPSVFLFPPKPKDTLMISRTPEVTCV<br>VVDVSQEDPEVQFNWYVDGVEVHNAKTKPREEQ<br>FNSTYRVVSVLTVLHQDWLNGKEYKCKVSNKGL<br>GSSIEKTISKAKGQPREPQVYTLPPSQEEMTKNQVS<br>LTCLVKGFYPSDIAVEWESNGQPENNYKTTPPVLD<br>SDGSFFLYSRLTVDKSRWQEGNVFSCSVMHEALH<br>NHYTQKSLSLSLGK |

TABLE of-continued

Sequences
(All amino acid positions are identified using Eu numbering)

| SEQ ID NO: | Description | Sequence |
|---|---|---|
| 54 | Human IgG4 HC Constant domain (S228P D265A) | ASTKGPSVFPLAPCSRSTSESTAALGCLVKDYFPEP VTVSWNSGALTSGVHTFPAVLQSSGLYSLSSVVTV PSSSLGTKTYTCNVDHKPSNTKVDKRVESKYGPPC PPCPAPEFLGGPSVFLFPPKPKDTLMISRTPEVTCV VVAVSQEDPEVQFNWYVDGVEVHNAKTKPREEQ FNSTYRVVSVLTVLHQDWLNGKEYKCKVSNKGLP SSIEKTISKAKGQPREPQVYTLPPSQEEMTKNQVSL TCLVKGFYPSDIAVEWESNGQPENNYKTTPPVLDS DGSFFLYSRLTVDKSRWQEGNVFSCSVMHEALHN HYTQKSLSLSLGK |
| 55 | Human IgG4 HC Constant domain (S228P D265A N297G) | ASTKGPSVFPLAPCSRSTSESTAALGCLVKDYFPEP VTVSWNSGALTSGVHTFPAVLQSSGLYSLSSVVTV PSSSLGTKTYTCNVDHKPSNTKVDKRVESKYGPPC PPCPAPEFLGGPSVFLFPPKPKDTLMISRTPEVTCV VVAVSQEDPEVQFNWYVDGVEVHNAKTKPREEQ FGSTYRVVSVLTVLHQDWLNGKEYKCKVSNKGL PSSIEKTISKAKGQPREPQVYTLPPSQEEMTKNQVS LTCLVKGFYPSDIAVEWESNGQPENNYKTTPPVLD SDGSFFLYSRLTVDKSRWQEGNVFSCSVMHEALH NHYTQKSLSLSLGK |
| 56 | Human IgG4 HC Constant domain (S228P N297X, wherein X is any amino acid other than N) | ASTKGPSVFPLAPCSRSTSESTAALGCLVKDYFPEP VTVSWNSGALTSGVHTFPAVLQSSGLYSLSSVVTV PSSSLGTKTYTCNVDHKPSNTKVDKRVESKYGPPC PPCPAPEFLGGPSVFLFPPKPKDTLMISRTPEVTCV VVDVSQEDPEVQFNWYVDGVEVHNAKTKPREEQ FXSTYRVVSVLTVLHQDWLNGKEYKCKVSNKGLP SSIEKTISKAKGQPREPQVYTLPPSQEEMTKNQVSL TCLVKGFYPSDIAVEWESNGQPENNYKTTPPVLDS DGSFFLYSRLTVDKSRWQEGNVFSCSVMHEALHN HYTQKSLSLSLGK |
| 57 | Human LC Kappa Constant domain | RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC |
| 58 | Mouse anti-CTLA-4 IgG2 HC (Mouse Modified x [CTLA-4_M] mAb (9D9 Balb/c (Igh-1a) haplotype-main a allele) IgG2a/Kappa Heavy Chain)) | EAKLQESGPVLVKPGASVKMSCKASGYTFTDYYM NWVKQSHGKSLEWIGVINPYNGDTSYNQKFKGKA TLTVDKSSSTAYMELNSLTSEDSAVYYCARYYGS WFAYWGQGTLITVSSAKTTAPSVYPLAPVCGDTTGS SVTLGCLVKGYFPEPVTLTWNSGSLSSGVHTFPAVLQS DLYTLSSSVTVTSSTWPSQSITCNVAHPASSTKVDKKIE PRGPTIKPCPPCKCPAPNLLGGPSVFIFPPKIKDVLMI SLSPIVTCVVVDVSEDDPDVQISWFVNNVEVHTAQTQ THREDYNSTLRVVSALPIQHQDWMSGKEFKCKVNNK DLPAPIERTISKPKGSVRAPQVYVLPPPEEEMTKKQVT LTCMVTDFMPEDIYVEWTNNGKTELNYKNTEPVLDS DGSYFMYSKLRVEKKNWVERNSYSCSWHEGLHNHH TTKSFSRTPGK |
| 59 | Mouse anti-CTLA-4 kappa LC (12AIL_9D9_LC) | DIVMTQTTLSLPVSLGDQASISCRSSQSIVHSNGNT YLEWYLQKPGQSPKLLIYKVSNRFSGVPDRFSGSG SGTDFTLKISRVEAEDLGVYYCFQGSHVPYTFGGG YKLEIKRTVAAPTVSIFPPSSEQLTSGGASVVCFLNNF YPKDINVKWKIDGSERQNGVLNSWTDQDSKDSTYSM SSTLTLTKDEYERHNSYTCEATHKTSTSPIVKSFNRNEC |
| 60 | Mouse anti-CTLA-4 (D265A) HC (mouse x [CTLA-4_M] mAb (9D9 mutation D265A) IgG1/ Kappa Heavy chain) | EAKLQESGPVLVKPGASVKMSCKASGYTFTDYYM NWVKQSHGKSLEWIGVINPYNGDTSYNQKFKGKA TLTVDKSSSTAYMELNSLTSEDSAVYYCARYYGS WFAYWGQGTLITVSSAKTTPPSVYPLAPGSAAQTNS MVTLGCLVKGYFPEPVTVTWNSGSLSSGVHTFPAVLQ SDLYTLSSSVTVPSSTWPSETVTCNVAHPASSTKVDKKI VPRDCGCKPCICTVPEVSSVFIFPPKPKDVLTITLTPK VTCVVVAISKDDPEVQFSWFVDDVEVHTAQTQPREE QFNSTFRSVSELPIMHQDWLNGKEFKCRVNSAAFPAP IEKTISKTKGRPKAPQVYTIPPPKEQMAKDKVSLTCMI TDFFPEDITVEWQWNGQPAENYKNTQPIMDTDGSYF VYSKLNVQKSNWEAGNTFTCSVLHEGLHNHHTEKSLS HSPGK |

TABLE of-continued

Sequences
(All amino acid positions are identified using Eu numbering)

| SEQ ID NO: | Description | Sequence |
|---|---|---|
| 61 | Mouse anti-CTLA-4 ISVD (54BBI_Llama x [CTLA4_M] [ALB_H] VHH (F023700894) (PI)) | EVQLVESGGGLVQAGGSLRLSCAASGSTPSINYMGWY RQAPGKQREFVATIRSGGATNYADSVKGRFTISRDNT KNTVYLQMNSLKPEDTAVYDCYTGGGGYEYWGQGTL VTVSSGGGGSGGGGSGGGGSGGGGSGGGGSGGGG SGGGGSEVQLVESGGGLVQAGGSLRLSCAASGSTPSI NYMGWYRQAPGKQREFVATIRSGGATNYADSVKGRF TISRDNTKNTVYLQMNSLKPEDTAVYDCYTGGGGYEY WGQGTLVTVSSGGGGSGGGGSGGGGSGGGGSGGG GSGGGGSGGGGSEVQLVESGGGLVQPGNSLRLSCAA SGFTFSSFGMSWVRQAPGKGLEWVSSISGSGSDTLYA DSVKGRFTISRDNAKTTLYLQMNSLRPEDTAVYYCTIG GSLSRSSQGTLVTVSS |
| 62 | Mouse anti-PD-1 ISVD PF023700037 | EVQLVESGGGLVQPGGSLRLSCAASGRTFSTHTMGW FRQGPGKEREFVATINRLDYTYYANSVRGRFTISRDNA KNTVYLQMNSLKPDDTAVYYCAADSERRLGVIPGLYD YWGQGTLVTVSSGGGGSGGGGSGGGGSGGGGSGG GGSGGGGSGGGGSEVQLVESGGGLVQPGGSLRLSC AASGRTFSRLAMGWFRQAPGKEREFVASISWSGGSTY YADSVKGRFTISRDNAKNTVYLQMNSLKPEDTAVYYC AASREYSGSYYYGLTLYEYDWGQGTLVTVSSGGGGS GGGGSGGGGSGGGGSGGGGSGGGGSGGGGSEVQ LVESGGGLVQPGNSLRLSCAASGFTFSSFGMSWVRQA PGKGLEWVSSISGSGSDTLYADSVKGRFTISRDNAKTT LYLQMNSLRPEDTAVYYCTIGGSLSRSSQGTLVTVSS |
| 63 | Mouse anti-PD-1 antibody clone DX400 HC | EVQLVESGGGLVQPGGSLKLSCAASGFTFSNSGLA WVRQAPEKGLEWVATITYNGTSTYYRDSVKGRFT ISRDNAKNTLYLQMSSLRSEDTATYYCARWVPGS GNFDYWGQGTLVTVSSAKTTPPSVYPLAPGSAAQTN SMVTLGCLVKGYFPEPVTVTWNSGSLSSGVHTFPAVL QSDLYTLSSSVTVPSSTWPSETVTCNVAHPASSTKVDK KIVPRDCGCKPCICTVPEVSSVFIFPPKPKDVLTITLTP KVTCVVVAISKDDPEVQFSWFVDDVEVHTAQTQPRE EQFNSTFRSVSELPIMHQDWLNGKEFKCRVNSAAFPA PIEKTISKTKGRPKAPQVYTIPPPKEQMAKDKVSLTC MTTDFFPEDITVEWQWNGQPAENYKNTQPIMDTDGS YFVYSKLNVQKSNWEAGNTFTCSVLHEGLHNHHTEK SLSHSPGK |
| 64 | Mouse anti-PD-1 antibody clone DX400 LC | DIVLTQSPASLAVSLGQRATISCRASQSVTISRYTL MHWYQQKPGQPPKLLIYRASNLASGIPARFSGSGS GTDFTLNIHPVEEDDAATYYCQQSRESPWTFGGGT KLEIKRADAAPTVSIFPPSSEQLTSGGASWCFLNNFY PKDINVKWKIDGSERQNGVLNSWTDQDSKDSTYSMS STLTLTKDEYERHNSYTCEATHKTSTSPTVKSFNRNEC |
| 65 | Residues after LC-CDR3 X is any amino acid | FGXG |
| 66 | Residues before HC-CDR1 X is any amino acid | CXXX |
| 67 | Residues before HC-CDR2 | LEWIG |
| 68 | Residues after HC-CDR3 X is any amino acid | WGXG |
| 69 | CDR-1 of anti-CTLA-4 ISVD | FYGMG |
| 70 | CDR-2 of anti-CTLA-4 ISVD | DIRTSAGRTTYADSVKG |
| 71 | CDR-3 of anti-CTLA-4 ISVD | EMSGISGWDY |
| 72 | CDR-3 of anti-CTLA-4 ISVD variant | EPSGISGWDY |
| 73 | 8D2/8D2 (RE) VH | EVKLDETGGGLVQPGRPMKLSCVASGFTFSDNWM NWVRQSPEKGLEWLAQIRNKPYNYETYYSDSVKG |

TABLE of-continued

Sequences
(All amino acid positions are identified using Eu numbering)

| SEQ ID NO: | Description | Sequence |
|---|---|---|
| | | RFTISRDDSKSSVYLQMNNLRGEDMGIYYCTAQFAYWGQGTLVTVSA |
| 74 | 8D2/8D2 (RE) VL | DIQMTQSPASLSASVGETVTITCGTSENIYGGLNWYQRKQGKSPQLLIFGATNLADGMSSRFSGSGSGRQYSLKISSLHPDDVATYYCQNVLRSPFTFGSGTKLEI |
| 75 | 8D2/8D2 RE VH VARIANT 1 M18I | EVKLDETGGGLVQPGRPIKLSCVASGFTFSDNWMNWVRQSPEKGLEWLAQIRNKPYNYETYYSDSVKGRFTISRDDSKSSVYLQMNNLRGEDMGIYYCTAQFAYWGQGTLVTVSA |
| 76 | 8D2/8D2 RE VL VARIANT 1 M18I | DIQMTQSPASLSASVGETVTITCGTSENIYGGLNWYQRKQGKSPQLLIFGATNLADGMSSRFSGSGSGRQYSLKISSLHPDDVATYYCQNVLRSPFTFGSGTKLEI |
| 77 | 8D2H1L1 VH | EVQLVESGGGLVQPGGSMRLSCAASGFTFSDNWMNWVRQAPGKGLEWLAQIRNKPYNYETYYSDSVKGRFTISRDDSKNSVYLQMNSLKTEDTGVYYCTAQFAYWGQGTLVTVSS |
| 78 | 8D2H1L1 VL | DIQMTQSPSSLSASVGDRVTITCRTSENIYGGLNWYQRKQGKSPKLLIYGATNLASGMSSRFSGSGSGTDYTLKISSLHPDDVATYYCQNVLRSPFTFGSGTKLEIK |
| 79 | 8D2H1L1 VH VARIANT 1 M18I | EVQLVESGGGLVQPGGSIRLSCAASGFTFSDNWMNWVRQAPGKGLEWLAQIRNKPYNYETYYSDSVKGRFTISRDDSKNSVYLQMNSLKTEDTGVYYCTAQFAYWGQGTLVTVSS |
| 80 | 8D2H1L1 VL VARIANT 1 M18I | DIQMTQSPSSLSASVGDRVTITCRTSENIYGGLNWYQRKQGKSPKLLIYGATNLASGMSSRFSGSGSGTDYTLKISSLHPDDVATYYCQNVLRSPFTFGSGTKLEIK |
| 81 | 8D2H2L2 VH | EVQLVESGGGLVQPGGSMRLSCAASGFTFSDNWMNWVRQAPGKGLEWLAQIRNKPYNYETYYSASVKGRFTISRDDSKNSVYLQMNSLKTEDTGVYYCTAQFAYWGQGTLVTVSS |
| 82 | 8D2H2L2 VL | DIQMTQSPSSLSASVGDRVTITCRTSENIYGGLNWYQRKPGKSPKLLIYGATNLASGVSSRFSGSGSGTDYTLTISSLQPEDVATYYCQNVLRSPFTFGSGTKLEIK |
| 83 | 8D2H2L2 VH VARIANT 1 M18I | EVQLVESGGGLVQPGGSIRLSCAASGFTFSDNWMNWVRQAPGKGLEWLAQIRNKPYNYETYYSASVKGRFTISRDDSKNSVYLQMNSLKTEDTGVYYCTAQFAYWGQGTLVTVSS |
| 84 | 8D2H2L2 VL VARIANT 1 M18I | DIQMTQSPSSLSASVGDRVTITCRTSENIYGGLNWYQRKPGKSPKLLIYGATNLASGVSSRFSGSGSGTDYTLTISSLQPEDVATYYCQNVLRSPFTFGSGTKLEIK |
| 85 | 8D3H3L3 VH | EVQLVESGGGLVQPGGSLRLSCAASGFTFSDNWMNWVRQAPGKGLEWVAQIRNKPYNYETEYAASVKGRFTISRDDSKNSAYLQMNSLKTEDTAVYYCTAQFAYWGQGTLVTVSS |
| 86 | 8D3H3L3 VL | DIQMTQSPSSLSASVGDRVTITCRASENIYGGLNWYQQKPGKAPKLLIYGATSLASGVPSRFSGSGSGTDYTLTISSLQPEDFATYYCQNVLRSPFTFGSGTKLEIK |
| 87 | 8D2H2L15 VH | EVQLVESGGGLVQPGGSMRLSCAASGFTFSDNWMNWVRQAPGKGLEWLAQIRNKPYNYETYYSASVKGRFTISRDDSKNSVYLQMNSLKTEDTGVYYCTAQFAYWGQGTLVTVSS |

TABLE of-continued

Sequences
(All amino acid positions are identified using Eu numbering)

| SEQ ID NO: | Description | Sequence |
|---|---|---|
| 88 | 8D2H2L15 VL | DIQMTQSPSSLSASVGDRVTITCRTSENIYGGLNW YQRKPGKSPKLLIYGATNLASGVSSRFSGSGSGTD YTLTISSLQPEDVATYYCQNVLSRHPGFGSGTKLEI K |
| 89 | 8D2H2L15 VH VARIANT 1 M18I | EVQLVESGGGLVQPGGSIRLSCAASGFTFSDNWM NWVRQAPGKGLEWLAQIRNKPYNYETYYSASVK GRFTISRDDSKNSVYLQMNSLKTEDTGVYYCTAQ FAYWGQGTLVTVSS |
| 90 | 8D2H2L15 VL VARIANT 1 M18I | DIQMTQSPSSLSASVGDRVTITCRTSENIYGGLNW YQRKPGKSPKLLIYGATNLASGVSSRFSGSGSGTD YTLTISSLQPEDVATYYCQNVLSRHPGFGSGTKLEI K |
| 91 | 8D2H2L17 VH | EVQLVESGGGLVQPGGSMRLSCAASGFTFSDNWM NWVRQAPGKGLEWLAQIRNKPYNYETYYSASVK GRFTISRDDSKNSVYLQMNSLKTEDTGVYYCTAQ FAYWGQGTLVTVSS |
| 92 | 8D2H2L17 VL | DIQMTQSPSSLSASVGDRVTITCRTSENIYGGLNW YQRKPGKSPKLLIYGATNLASGVSSRFSGSGSGTD YTLTISSLQPEDVATYYCQNVLSSRPGFGSGTKLEI K |
| 93 | 8D2H2L17 VH VARIANT 1 M18I | EVQLVESGGGLVQPGGSIRLSCAASGFTFSDNWM NWVRQAPGKGLEWLAQIRNKPYNYETYYSASVK GRFTISRDDSKNSVYLQMNSLKTEDTGVYYCTAQ FAYWGQGTLVTVSS |
| 94 | 8D2H2L17 VL VARIANT 1 M18I | DIQMTQSPSSLSASVGDRVTITCRTSENIYGGLNW YQRKPGKSPKLLIYGATNLASGVSSRFSGSGSGTD YTLTISSLQPEDVATYYCQNVLSSRPGFGSGTKLEI K |
| 95 | REGN4659 VH WO2019023482 | EVQLVESGGGLVQPGGSLRLSCAASGFTFSNYEMS WVRQAPGKGLEWVSSIRTSGTTKYYADSMKGRFT ISRDNAKNSLYLQMNSLRAEDTAVYYCAGGGTFL HYWGQGTLVTVSS |
| 96 | REGN4659 VL | DIQMTQSPSSVSASVGDRVTITCRASQGIASYLAW YQQKPGKAPKLLIYAASSLQTGVPSRFSGSGYGTD FTLTISSLQPEDFATYYCQQAKSFPMYTFGQGTKL EIK |
| 97 | AGEN1884w VH | EVQLVESGGGLVKPGGSLRLSCAASGFTFSSYSMN WVRQAPGKGLEWVSSISSSSSYIYYADSVKGRFTIS RDNAKNSLYLQMNSLRAEDTAVYYCARVGLMGP FDIWGQGTMVTVSS |
| 98 | AGEN1884w VL | EIVLTQSPGTLSLSPGERATLSCRASQSVSRYLGWY QQKPGQAPRLLIYGASTRATGIPDRFSGSGSGTDFT LTITRLEPEDFAVYYCQQYGSSPWTFGQGTKVEIK |
| 99 | Cemiplimab-rwlc VH | EVQLLESGGVLVQPGGSLRLSCAASGFTFSNFGMT WVRQAPGKGLEWVSGISGGGRDTYFADSVKGRFT ISRDNSKNTLYLQMNSLKGEDTAVYYCVKWGNIY FDYWGQGTLVTVSS |
| 100 | Cemiplimab-rwlc VL | DIQMTQSPSSLSASVGDSITITCRASLSINTFLNWYQ QKPGKAPNLLIYAASSLHGGVPSRFSGSGSGTDFTL TIRTLQPEDFATYYCQQSSNTPFTFGPGTVVDFR |
| 101 | Cemiplimab-rwlc HC (S228P) | EVQLLESGGVLVQPGGSLRLSCAASGFTFSNFGMT WVRQAPGKGLEWVSGISGGGRDTYFADSVKGRFT ISRDNSKNTLYLQMNSLKGEDTAVYYCVKWGNIY FDYWGQGTLVTVSS*ASTKGPSVFPLAPCSRSTSESTA ALGCLVKDYFPEPVTVSWNSGALTSGVHTFPAVLQSS GLYSLSSWTVPSSSLGTKTYTCNVDHKPSNTKVDKRV ESKYGPPCPPCPAPEFLGGPSVFLFPPKPKDTLMISR TPEVTCVVVDVSQEDPEVQFNWYVDGVEVHNAKTKP REEQFNSTYRVVSVLTVLHQDWLNGKEYKCKVSNKG LPSSIEKTISKAKGQPREPQVYTLPPSQEEMTKNQVSL* |

TABLE of-continued

Sequences
(All amino acid positions are identified using Eu numbering)

| SEQ ID NO: | Description | Sequence |
|---|---|---|
| | | TCPVKGFYPSDIAVEWESNGQPENNYKTTPPVLDSDG SFFLYSRLTVDKSRWQEGNVFSCSVMHEALHNHYTQ KSLSLSLGK |
| 102 | Cemiplimab-rwlc LC | DIQMTQSPSSLSASVGDSITITCRASLSINTFLNWYQ QKPGKAPNLLIYAASSLHGGVPSRFSGSGSGTDFTL TIRTLQPEDFATYYCQQSSNTPFTFGPGTVVDFRRT VAAPSVFIFPPSDEQLKSGTASVVCLLNNFYPREAK VQWKVDNALQSGNSQESVTEQDSKDSTYSLSSTL TLSKADYEKHKVYACEVTHQGLSSPVTKSFNRGE C |
| 103 | Durvalumab VH | EVQLVESGGGLVQPGGSLRLSCAASGFTFSRYWM SWVRQAPGKGLEWVANIKQDGSEKYYVDSVKGR FTISRDNAKNSLYLQMNSLRAEDTAVYYCAREGG WFGELAFDYWGQGTLVTVSS |
| 104 | Durvalumab VL | EIVLTQSPGTLSLSPGERATLSCRASQRVSSSYLAW YQQKPGQAPRLLIYDASSRATGIPDRFSGSGSGTDF TLTISRLEPEDFAVYYCQQYGSLPWTFGQGTKVEI K |
| 105 | Avelumab VH | QAPGKGLEWVSSIYPSGGITFYADKGRFTISRDNSK NTLYLQMNSLRAEDTAVYYCARIKLGTVTTVDY WGQGTLVTVSS |
| 106 | Avelumab VL | QSALTQPASVSGSPGQSITISCTGTSSDVGGYNYVS WYQQHPGKAPKLMIYDVSNRPSGVSNRFSGSKSG NTASLTISGLQAEDEADYYCSSYTSSSTRVFGTGTK VTVL |
| 107 | Atezolizumab VH | EVQLVESGGGLVQPGGSLRLSCAASGFTFSDSWIH WVRQAPGKGLEWVAWISPYGGSTYYADSVKGRF TISADTSKNTAYLQMNSLRAEDTAVYYCARRHWP GGFDYWGQGTLVTVSS |
| 108 | Atezolizumab VL | DIQMTQSPSSLSASVGDRVTITCRASQDVSTAVAW YQQKPGKAPKLLIYSASFLYSGVPSRFSGSGSGTDF TLTISSLQPEDFATYYCQQYLYHPATFGQGTKVEIK |
| 109 | Durvalumab HC (IgG1 L234F/L235E/P331S/ D356E/L358M) | EVQLVESGGGLVQPGGSLRLSCAASGFTFSRYWM SWVRQAPGKGLEWVANIKQDGSEKYYVDSVKGR FTISRDNAKNSLYLQMNSLRAEDTAVYYCAREGG WFGELAFDYWGQGTLVTVSSASTKGPSVFPLAPSS KSTSGGTAALGCLVKDYFPEPVTVSWNSGALTSGVHT FPAVLQSSGLYSLSSWTVPSSSLGTQTYICNVNHKPSN TKVDKRVEPKSCDKTHTCPPCPAPEFEGGPSVFLFP PKPKDTLMISRTPEVTCVVVDVSHEDPEVKFNWYVD GVEVHNAKTKPREEQYNSTYRVVSVLTVLHQDWLNG KEYKCKVSNKALPASIEKTISKAKGQPREPQVYTLPPS REEMTKNQVSLTCLVKGFYPSDIAVEWESNGQPENNY KTTPPVLDSDGSFFLYSKLTVDKSRWQQGNVFSCSVM HEALHNHYTQKSLSLSPGK |
| 110 | Durvalumab LC | EIVLTQSPGTLSLSPGERATLSCRASQRVSSSYLAW YQQKPGQAPRLLIYDASSRATGIPDRFSGSGSGTDF TLTISRLEPEDFAVYYCQQYGSLPWTFGQGTKVEI KRTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| 111 | Avelumab HC (IgG1) | EVQLLESGGGLVQPGGSLRLSCAASGFTFSSYIMM WVRQAPGKGLEWVSSIYPSGGITFYADTVKGRFTI SRDNSKNTLYLQMNSLRAEDTAVYYCARIKLGTV TTVDYWGQGTLVTVSSASTKGPSVFPLAPSSKSTSG GTAALGCLVKDYFPEPVTVSWNSGALTSGVHTFPAVL QSSGLYSLSSWTVPSSSLGTQTYICNVNHKPSNTKVD KKVEPKSCDKTHTCPPCPAPELLGGPSVFLFPPKPK DTLMISRTPEVTCVVVDVSHEDPEVKFNWYVDGVEV HNAKTKPREEQYNSTYRVVSVLTVLHQDWLNGKEYK CKVSNKALPAPIEKTISKAKGQPREPQVYTLPPSRDE LTKNQVSLTCLVKGFYPSDIAVEWESNGQPENNYKTT PPVLDSDGSFFLYSKLTVDKSRWQQGNVFSCSVMHE ALHNHYTQKSLSLSPGK |

TABLE of-continued

Sequences
(All amino acid positions are identified using Eu numbering)

| SEQ ID NO: | Description | Sequence |
|---|---|---|
| 112 | Avelumab LC | QSALTQPASVSGSPGQSITISCTGTSSDVGGYNYVS WYQQHPGKAPKLMIYDVSNRPSGVSNRFSGSKSG NTASLTISGLQAEDEADYYCSSYTSSSTRVFGTGTK NTNEGQPKANPTVTLFPPSSEELQANKATLVCLISDF YPGAVTVAWKADGSPVKAGVETTKPSKQSNNKYAASS YLSLTPEQWKSHRSYSCQVTHEGSTVEKTVAPTECS |
| 113 | Atezolizumab HC (IgG1 N297A/D235E/L358M) | EVQLVESGGGLVQPGGSLRLSCAASGFTFSDSWIH WVRQAPGKGLEWVAWISPYGGSTYYADSVKGRF TISADTSKNTAYLQMNSLRAEDTAVYYCARRHWP GGFDYWGQGTLVTVSSASTKGPSVFPLAPSSKSTSG GTAALGCLVKDYFPEPVTVSWNSGALTSGVHTFPAVL QSSGLYSLSSWTVPSSSLGTQTYICNVNHKPSNTKVD KKVEPKSCDKTHTCPPCPAPELLGGPSVFLFPPKPK DTLMISRTPEVTCVVVDVSHEDPEVKFNWYVDGVEV HNAKTKPREEQYASTYRVVSVLTVLHQDWLNGKEYK CKVSNKALPAPIEKTISKAKGQPREPQVYTLPPSREEM TKNQVSLTCLVKGFYPSDIAVEWESNGQPENNYKTTP PVLDSDGSFFLYSKLTVDKSRWQQGNVFSCSVMHEA LHNHYTQKSLSLSPGK |
| 114 | Atezolizumab LC | DIQMTQSPSSLSASVGDRVTITCRASQDVSTAVAW YQQKPGKAPKLLIYSASFLYSGVPSRFSGSGSGTDF TLTISSLQPEDFATYYCQQYLYHPATFGQGTKVEIK RTVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC |
| 115 | Human IgG1 HC Constant domain (N297A/D356E/L358M) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVDVSHEDPEVKFNWYVDGVEVHNAKTKPRE EQYASTYRVVSVLTVLHQDWLNGKEYKCKVSNK ALPAPIEKTISKAKGQPREPQVYTLPPSREEMTKNQ VSLTCLVKGFYPSDIAVEWESNGQPENNYKTTPPV LDSDGSFFLYSKLTVDKSRWQQGNVFSCSVMHEA LHNHYTQKSLSLSPGK |
| 116 | Human IgG1 HC Constant domain (L234F/L235E/P331S/ D356E/L358M) | ASTKGPSVFPLAPCSRSTSESTAALGCLVKDYFPEP VTVSWNSGALTSGVHTFPAVLQSSGLYSLSSVVTV PSSSLGTKTYTCNVDHKPSNTKVDKRVESKYGPPC PPCPAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGLP SSIEKTISKAKGQPREPQVYTLPPSLTCLVKGFYPS DIAVEWESNGQPENNYKTTPPVLDSDGSFFLYSRL TVDKSRWQEGNVFSCSVMHEALHNHYTQKSLSLS LGK |
| 117 | Human LC lambda Constant domain | GQPKANPTVTLFPPSSEELQANKATLVCLISDFYPG AVTVAWKADGSPVKAGVETTKPSKQSNNKYAAS SYLSLTPEQWKSHRSYSCQVTHEGSTVEKTVAPTE CS |

Substituted amino acids are shown in bold-faced type.
HC and LC constant domains are italicized.

REFERENCES

Azuma et al., B70 antigen is a second ligand for CTLA-4 and CD28. Nature. 1993 Nov. 4; 366(6450):76-9.

Collins et al., The interaction properties of costimulatory molecules revisited. Immunity. 2002 August; 17(2):201-10.

Hui et al., T cell costimulatory receptor CD28 is a primary target for PD-1-mediated inhibition. Science. 2017 Mar. 31; 355(6332):1428-1433.

Ingram et al., Anti-CTLA-4 therapy requires an Fc domain for efficacy. Proc Natl Acad Sci USA. 2018 Apr. 10; 115(15):3912-3917.

Kamphorst et al., Rescue of exhausted CD8 T cells by PD-1-targeted therapies is CD28– dependent. Science. 2017 Mar. 31; 355(6332):1423-1427.

Könitzer et al., Reformatting Rituximab into Human IgG2 and IgG4 Isotypes Dramatically Improves Apoptosis Induction In Vitro. PLOS One. 2015 Dec. 29; 10(12): e0145633.

Lanier et al., CD80 (B7) and CD86 (B70) provide similar costimulatory signals for T cell proliferation, cytokine production, and generation of CTL. J Immunol. 1995 Jan. 1; 154(1):97-105.

Leach et al., Enhancement of antitumor immunity by CTLA-4 blockade. Science. 1996 Mar. 22; 271(5256): 1734-6.

Pai et al., Tumor-conditional anti-CTLA4 uncouples antitumor efficacy from immunotherapy-relatedtoxicity. J Clin Invest. 2019 Jan. 2; 129(1):349-363.

Ribas &Wolchok, Cancer immunotherapy using checkpoint blockade. Science. 2018 Mar. 23; 359(6382):1350-1355.

Schneider-Merck et al., Human IgG2 antibodies against epidermal growth factor receptor effectively trigger antibody-dependent cellular cytotoxicity but, in contrast to IgG1, only by cells of myeloid lineage. J Immunol. 2010 Jan. 1; 184(1):512-20.

Selby et al., Anti-CTLA-4 antibodies of IgG$_{2a}$ isotype enhance antitumor activity through reduction of intratumoral regulatory T cells. Cancer Immunol Res. 2013 July; 1(1):32-42.

Sharma et al., Anti-CTLA-4 Immunotherapy Does Not Deplete FOXP3+ Regulatory T Cells (Tregs) in Human Cancers. Clin Cancer Res. 2018 Jul. 27.

Simpson et al., Fc-dependent depletion of tumor-infiltrating regulatory T cells co-defines the efficacy of anti-CTLA-4 therapy against melanoma. J Exp Med. 2013 Aug. 26; 210(9):1695-710.

Ullman-Culleré & Foltz, Body condition scoring: a rapid and accurate method for assessing health status in mice. Lab Anim Sci. 1999 June; 49(3):319-23.

Vargas et al., Fc Effector Function Contributes to the Activity of Human Anti-CTLA-4 Antibodies. Cancer Cell. 2018 Apr. 9; 33(4):649-663.e4.

Waight et al., Selective FcγR Co-engagement on APCs Modulates the Activity of Therapeutic Antibodies Targeting T Cell Antigens. Cancer Cell. 2018 Jun. 11; 33(6): 1033-1047.e5.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for treating a cancer in an individual with an anti-PD-1/anti-CTLA-4 antibody combination without causing moderate to severe skin or gut inflammatory immune-related toxicities, the method comprising administering a combination of:
an anti-PD-1 antibody with effector function comprising a heavy chain (HC) comprising the amino acid sequence set forth in SEQ ID NO: 27 and a light chain (LC) comprising the amino acid sequence set forth in SEQ ID NO: 28 and an effecter-silent anti-CTLA-4 antibody with reduced or no measurable effector function comprising (i) an HC having a HC variable domain (VH) comprising the amino acid sequence set forth in SEQ ID NO: 7 and an HC constant domain comprising the amino acid sequence set forth in SEQ ID NO: 38, 39, 40, 41, 42, 43, 44, 116, or 117 and (ii) a LC having an LC variable domain (VL) comprising the amino acid sequence set forth in SEQ ID NO: 8 and an LC constant domain comprising the amino acid sequence set forth in SEQ ID NO: 57, which treats the cancer in the individual without causing moderate to severe skin or gut inflammatory immune-related toxicities.

2. The method of claim 1, wherein the anti-CTLA-4 antibody is administered at a dose comprising more than 1 mg/kg or a fixed dose that does not depend on the individual's weight that is 100 mg or more.

3. The method of claim 1, wherein the anti-PD-1 antibody is administered at a dose comprising (i) 2 or 3 mg/kg or a fixed dose that does not depend on the individual's weight that is 200 mg, (ii) more than 3 mg/kg or a fixed dose that does not depend on the individual's weight that is more than 200 mg, or (iii) a fixed dose that does not depend on the individual's weight that is between about 200 mg to about 400 mg.

4. The method of claim 1, wherein the cancer is melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

5. The method of claim 1, wherein the cancer is pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

* * * * *